United States Patent
Inoue et al.

(10) Patent No.: US 7,268,128 B2
(45) Date of Patent: Sep. 11, 2007

(54) 1,3,5-TRISUBSTITUTED-5-PHENYL AND 5-PYRIDYL PYRAZOLOPYRIMIDINONE DERIVATIVES HAVING PDE7 INHIBITING ACTION

(75) Inventors: Hidekazu Inoue, Osaka (JP); Hidenobu Murafuji, Osaka (JP); Yasuhiro Hayashi, Osaka (JP)

(73) Assignee: Ausbio Pharma Co., Ltd. (JP)

( * ) Notice: Subject to any disclaimer, the term of this patent is extended or adjusted under 35 U.S.C. 154(b) by 233 days.

(21) Appl. No.: 10/866,198

(22) Filed: Jun. 14, 2004

(65) Prior Publication Data
US 2005/0148604 A1    Jul. 7, 2005

Related U.S. Application Data

(63) Continuation of application No. PCT/JP02/13083, filed on Dec. 13, 2002.

(30) Foreign Application Priority Data

Dec. 13, 2001   (JP)   .............................. 2001-380483

(51) Int. Cl.
| | |
|---|---|
| A61K 31/551 | (2006.01) |
| A61K 31/519 | (2006.01) |
| A61K 31/541 | (2006.01) |
| A61K 31/5355 | (2006.01) |
| C07D 243/08 | (2006.01) |
| C07D 487/04 | (2006.01) |
| C07D 417/12 | (2006.01) |
| C07D 413/12 | (2006.01) |

(52) U.S. Cl. ................. 514/218; 514/262.1; 514/228.5; 514/234.2; 540/553; 544/262; 544/61; 544/118; 544/231

(58) Field of Classification Search ................. 544/262, 544/61, 118, 231; 514/262.1, 228.5, 234.2, 514/218; 540/553, 231
See application file for complete search history.

(56) References Cited

U.S. PATENT DOCUMENTS

| | | | |
|---|---|---|---|
| 5,541,187 A | 7/1996 | Bacon et al. | |
| 6,100,270 A * | 8/2000 | Campbell et al. | ........... 514/258 |
| 6,407,114 B1 * | 6/2002 | Bunnage et al. | ............ 514/258 |

FOREIGN PATENT DOCUMENTS

| | | |
|---|---|---|
| EP | 0 349 239 A2 | 1/1990 |
| EP | 0 463 756 A1 | 1/1992 |
| EP | 0 526 004 A1 | 2/1993 |
| EP | 0 636 626 A1 | 2/1995 |
| EP | 0 995 751 A2 | 4/2000 |
| JP | 08-253484 A | 10/1996 |
| WO | WO 00/68230 | 11/2000 |
| WO | WO 01/29049 A2 | 4/2001 |
| WO | WO 01/32618 A1 | 5/2001 |
| WO | WO 01/34601 A2 | 5/2001 |

OTHER PUBLICATIONS

Celltech Chiroscience LTD.; PDE7 Inhibitors; Expert Opin. Ther. Patents; 2002; 12(4); 601-603.*
Castro, Ana; Cyclic Nucleotide Phosphodiesterases and Their Role in Immunomodulatory Response: Advances in the Development of Specific Phosphodiesterase Inhibitors; Med. Res. Rev.; 2005; 25(2); 229-244.*
Linsong, Li; CD3- and CD28-Dependent Induction of PDE7 Required for T cell Activation; Science; 1999; 283; 49-53.*
Lugnier, C.; Pharma & Therap.; 2006; 109; 366-398.*
Barnes, Matthew J., et al., "Synthesis and Structure—Activity Relationships of Guanine Analogues as Phosphodiesterase 7 (PDE7) Inhibitors," *Bioorganic & Medicinal Chemistry Letters*, 11:1081-1083 (2001).
Martinez, Ana, et al., "Benzyl Derivatives of 2,1,3-Benzo- and Benzothieno[3,2-a]thiadiazine 2,2-Dioxides: First Phosphodiesterase 7 Inhibitors," *J. Med. Chem.*, 43:683-689 (2000).
Castro, Ana, et al., "CoMFA of Benzyl Derivatives of 2,1,3-benzo- and Benzothieno[3,2-a]thiadiazine 2,2-dioxides: Clues for the Design of Phosphodiesterase 7 Inhibitors," *Euro. J. Med. Chem.*, 36:333-338 (2001).
Li, Linson, et al., "CD3- and CD28-Dependent Induction of PDE7 Requirement for T Cell Activation," *Science*, 283:848-851 (1999).

* cited by examiner

*Primary Examiner*—Mark L. Berch
*Assistant Examiner*—Susanna Moore
(74) *Attorney, Agent, or Firm*—Hunton & Williams LLP

(57) ABSTRACT

Pyrazolopyrimidinone derivatives expressed by the following general formula (IA) or (IB):

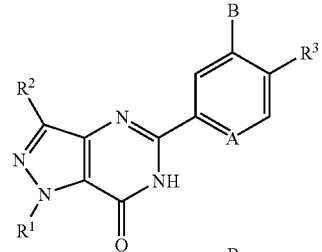

(IA)

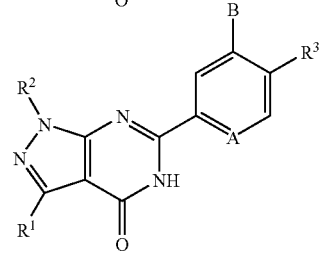

(IB)

where the symbols are as disclosed in the specification, are provided as desired compounds. These compounds selectively inhibiting PDE7, thereby increasing the intracellular cAMP level and inhibiting the activation of T cells. Thus, these compounds are useful for prevention and treatment of various allergic diseases and inflammatory or immunological diseases.

29 Claims, No Drawings

1,3,5-TRISUBSTITUTED-5-PHENYL AND 5-PYRIDYL PYRAZOLOPYRIMIDINONE DERIVATIVES HAVING PDE7 INHIBITING ACTION

CROSS-RELATED APPLICATIONS

This application is a continuation application of International Application No. PCT/JP02/13083, filed Dec. 13, 2002, which claims benefit of priority of Japanese Application No. 2001-380483, filed Dec. 13, 2001. These priority applications—including their specifications, drawings, and claims—are hereby incorporated by reference in their entirety.

FIELD OF INVENTION

This invention relates to pyrazolopyrimidinone derivatives having selective PDE7 (type VII phosphodiesterase) inhibiting action, salts or solvates thereof, and PDE7 inhibitors containing them as active ingredients. These compounds are effective in various fields for therapy, including allergic diseases, and inflammatory or immunological diseases.

BACKGROUND OF INVENTION

Cyclic AMP (cAMP) or cGMP, which is an intracellular second messenger, is decomposed by phosphodiesterases (PDE1~11) to become inactive. Of these phosphodiesterases, PDE7 selectively decomposes cAMP, and is characterized as an enzyme which is not inhibited by rolipram, a selective inhibitor of PDE4 which decomposes cAMP similarly. PDE7 is suggested to play an important role in activating T cells (Beavo et al., Science 283 (1999) 848). Activation of T cells is known to be involved in the aggravation of pathological states in various diseases, such as allergic diseases and inflammatory or immunological diseases, for example, bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, sepsis, Crohn disease, rejection reaction in transplantation, GVH disease, and restenosis after angioplasty (J Allergy Clin Immunol 2000 November; 106(5 Suppl):S221-6, Am J Respir Crit Care Med 1996 February; 153(2):629-32, Am J Respir Crit Care Med 1999 November; 160(5 Pt 2):S33-7, Clin Exp Allergy 2000 February; 30(2): 242-54, Hosp Med 1998 July: 59(7):530-3, Int Arch Allergy Immunol 1998 March; 115(3):179-90, J Immunol 1991 Feb. 15; 146(4):1169-74, Osteoarthritis Cartilage 1999 July; 7(4): 401-2, Rheum Dis Clin North Am 2001 May; 27(2):317-34, J Autoimmun 2001 May; 16(3):187-92, Curr Rheumatol Rep 2000 February; 2(1):24-31, Trends Immunol 2001 January; 22(1):21-6, Curr Opin Immunol 2000 August; 12(4):403-8, Diabetes Care 2001 September; 24(9):1661-7, J Neuroimmunol 2000 Nov. 1; 111(1-2):224-8, Curr Opin Immunol 1997 December; 9(6):793-9, JAMA 1999 Sep. 15; 282(11):1076-82, Semin Cancer Biol 1996 April; 7(2):57-64, J Interferon Cytokine Res 2001 April; 21(4):219-21). Thus, inhibitors of PDE7 are considered to be useful in dealing with various allergic diseases and inflammatory or immunological diseases which T cells are involved in.

Compounds made public as selective inhibitors of the enzyme include imidazopyridine derivatives (WO 01/34601), dihydropurine derivatives (WO 00/68203), pyrrole derivatives (WO 01/32618), and benzothiopyranoimidazolone derivatives (DE19950647), but their inhibitory activities and selectivities for other PDE's are unknown. The compounds, whose inhibitory activities are made public, include guanine derivatives (Bioorg. Med. Chem. Lett. 11(2001) 1081), benzothiadiazine, and benzothienothiadiazine derivatives (J. Med. Chem. 43(2000) 683) (Eur. J. Med. Chem. 36(2001) 333). However, their inhibitory activities are weak, and their selectivity for other PDE's is also low, so that the practical utility of these compounds as PED7 inhibitors is insufficient.

As compounds having a pyrazolopyrimidinone skeleton, the compounds described in European Patent Application No. EP463756, European Patent Application No. EP526004, European Patent Application No. EP349239, European Patent Application No. EP636626, European Patent Application No. EP995751, and Japanese Unexamined Patent Publication No. 1996-25384 are known as cGMP-specific PDE5 inhibitors, but their PDE7 inhibiting activities have not been suggested.

SUMMARY OF INVENTION

The present invention has as an object the provision of novel compounds having PDE7 inhibiting activity, and PDE7 inhibitors containing these compounds as active ingredients.

The compounds of the present invention are useful in dealing with various allergic diseases and inflammatory or immunological diseases by selectively inhibiting PDE7 to increase the intracellular cAMP level and inhibit the activation of T cells. That is, the compounds of the present invention are useful as preventive or therapeutic agents for diseases, such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, sepsis, Crohn disease, rejection reaction in transplantation, GVH disease, and restenosis after angioplasty.

We, the inventors of the present invention, conducted in-depth studies in an attempt to develop compounds having excellent PDE7 inhibiting action. As a result, we have found that compounds having a pyrazolopyrimidinone skeleton, represented by general formulas (IA), (IB), (IA') and (IB') shown below, have a potent PDE7 inhibiting action and excellent selectivity for PDE7 inhibition. This finding has led us to accomplish the present invention:

DETAILED DESCRIPTION OF PREFERRED EMBODIMENTS

According to the present invention, there can be provided a pharmaceutical composition and a PDE7 inhibitor which contain a pyrazolopyrimidinone derivative expressed by the following general formula (IA) or (IB), or a salt or solvate of the derivative, as an active ingredient:

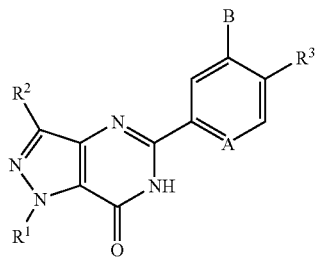

(IA)

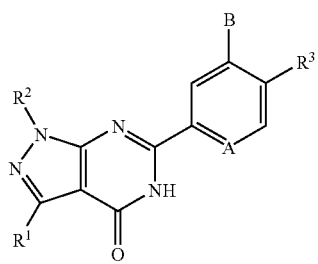

(IB)

where A represents N or CR$^4$,

B represents a hydrogen atom or a halogen atom,

R$^1$ represents optionally substituted C$_{3\sim7}$ cycloalkyl or tert-butyl,

R$^2$ represents hydrogen, methyl or ethyl,

R$^3$ represents a hydrogen, nitro, cyano or halogen atom, NR$^5$R$^6$, C(=X)R$^7$, SO$_2$NR$^5$R$^6$, OR$^8$, NR$^8$CONR$^5$R$^6$, NR$^8$SO$_2$R$^9$, a heteroaryl group, or optionally substituted C$_{1\sim3}$ alkyl, R$^4$ represents hydrogen, or C$_{1\sim3}$ alkoxy substituted, if desired, by one or more fluorine atoms, R$^5$ and R$^6$ are the same or different, and represent a hydrogen atom, optionally substituted C$_{1\sim6}$ alkyl, or optionally substituted acyl or, together with the nitrogen atom which they are bound to, form azetidinyl, pyrrolidinyl, piperidinyl, morpholino, thiomorpholino, piperazinyl or homopiperazinyl, each of these groups being optionally substituted by optionally substituted C$_{1\sim4}$ alkyl, OH, C$_{1\sim3}$ alkoxy, CO$_2$H, or NR$^5$R$^6$, R$^7$ represents optionally substituted C$_{1\sim6}$ alkyl, OH, OR$^8$, or NR$^5$R$^6$, R$^8$ represents hydrogen or an optionally substituted C$_{1\sim6}$ alkyl group, R$^9$ represents an optionally substituted C$_{1\sim6}$ alkyl group, and X represents O, S or NH.

The description shown by "C$_{o\sim o}$" herein represents the number of carbon atoms which ranges from o to o. For example, C$_{1\sim6}$ represents the number of carbon atoms ranging from 1 to 6.

In the present invention, examples of the substituent relevant to the expression "optionally substituted" include an optionally substituted linear, branched or cyclic alkyl group such as methyl, ethyl, propyl or cyclohexyl; a hydroxyl group; a cyano group; an alkoxy group such as methoxy or ethoxy; an optionally substituted amino group such as amino, methylamino or dimethylamino; an optionally substituted acyl group such as acetyl or propionyl; a carboxyl group; an optionally substituted aryl group such as phenyl or naphthyl; an optionally substituted heteroaryl group such as pyridinyl, thiazolyl, imidazolyl or pyrazyl; an optionally substituted saturated or unsaturated heterocloalkyl group such as piperazinyl or morphonyl; an optionally substituted carbamoyl group; an optionally substituted amido group; a halogen atom such as chlorine, fluorine or bromine; a nitro group; an optionally substituted sulfone group; an optionally substituted sulfonylamido group; an oxo group; a urea group; and an optionally substituted linear, branched or cyclic alkenyl group such as ethenyl, propenyl or cyclohexenyl.

In the general formulas (IA) and (IB) of the present invention, the optionally substituted C$_{3\sim7}$ cycloalkyl expressed as R$^1$ includes, for example, cyclopropyl, cyclobutyl, cyclopentyl, cyclohexyl and cycloheptyl. Preferred examples are C$_{5\sim7}$ cycloalkyls such as cyclopentyl, cyclohexyl and cycloheptyl, and particularly preferred examples are cyclohexyl and cycloheptyl.

Examples of R$^2$ are hydrogen, methyl and ethyl, and the particularly preferred example is methyl.

Examples of R$^3$ are a hydrogen, nitro, cyano or halogen atom, NR$^5$R$^6$, C(=X)R$^7$, SO$_2$NR$^5$R$^6$, OR$^8$, NR$^8$CONR$^5$R$^6$, NR$^8$SO$_2$R$^9$, a heteroaryl group, and optionally substituted C$_{1\sim3}$ alkyl. Particularly preferred examples are cyano, NR$^5$R$^6$, C(=X)R$^7$, SO$_2$NR$^5$R$^6$, OR$^8$, NR$^8$CONR$^5$R$^6$, NR$^8$SO$_2$R$^9$, a heteroaryl group, and optionally substituted C$_{1\sim3}$ alkyl. The halogen atom refers to fluorine, chlorine, bromine or iodine.

Preferred examples of the heteroaryl group as R$^3$ include a 5- to 7-membered monocyclic heteroaryl group having 2 to 8 carbon atoms and containing 1 to 4 hetero atoms consisting of oxygen atoms, nitrogen atoms or sulfur atoms, and a polycyclic heteroaryl group comprising two or more such identical or different monocyclic compounds fused together, examples of the monocyclic and polycyclic heteroaryl groups being pyrrole, furyl, thienyl, imidazolyl, thiazolyl, pyridyl, pyrazyl, indolyl, quinolyl, isoquinolyl, and tetrazolyl.

As A, N or CR$^4$ is named. As a preferred example, CR$^4$ is named.

Preferred examples of B are hydrogen or a halogen atom. The halogen atom refers to fluorine, chlorine, bromine or iodine. Particularly preferred examples of B are hydrogen and fluorine.

Preferred examples of R$^4$ are hydrogen, and C$_{1\sim3}$ alkoxy substituted, if desired, by one or more fluorine atoms, such as methoxy, ethoxy, or propyloxy. Particularly preferred examples are methoxy, ethoxy, fluoromethoxy and difluoromethoxy groups.

Examples of R$^5$ and R$^6$ are groups which are the same or different, and which represent a hydrogen atom, optionally substituted C$_{1\sim6}$ alkyl, or optionally substituted acyl or, together with the nitrogen atom which they are bound to, can form azetidinyl, pyrrolidinyl, piperidinyl, morpholino, thiomorpholino, piperazinyl or homopiperazinyl. These groups may further be optionally substituted by optionally substituted C$_{1\sim4}$ alkyl, OH, C$_{1\sim3}$ alkoxy, CO$_2$H, or NR$^5$R$^6$. Particularly preferred examples are a hydroxyl group, an alkoxy group, C$_{2\sim4}$ alkyl substituted by an optionally substituted amino group, azetidinyl, pyrrolidinyl, piperidinyl, morpholino, piperazinyl, and homopiperazinyl. Where necessary, these groups may further be substituted by optionally substituted methyl, methoxy, OH, CO$_2$H, or NR$^5$R$^6$.

Examples of R$^7$ are optionally substituted linear or branched C$_{1\sim6}$ alkyl, OH, OR$^8$, or NR$^5$R$^6$. R$^5$ and R$^6$ are as defined earlier. Particularly preferred examples are OH and NR$^5$R$^6$.

As R$^8$, hydrogen or an optionally substituted linear or branched C$_{1\sim6}$ alkyl group is named. Preferably, hydrogen and optionally substituted C$_{1\sim3}$ alkyl are quoted.

Examples of $R^9$ are an optionally substituted $C_{1\sim6}$ alkyl group and, preferably, an optionally substituted $C_{1\sim3}$ alkyl group. Particularly preferred examples are optionally substituted methyl and optionally substituted ethyl.

Examples of X are O, S and NH. A particularly preferred example is O.

According to the present invention, there can be provided a pyrazolopyrimidinone derivative expressed by the following general formula (IA') or (IB'), or a salt or solvate of the derivative:

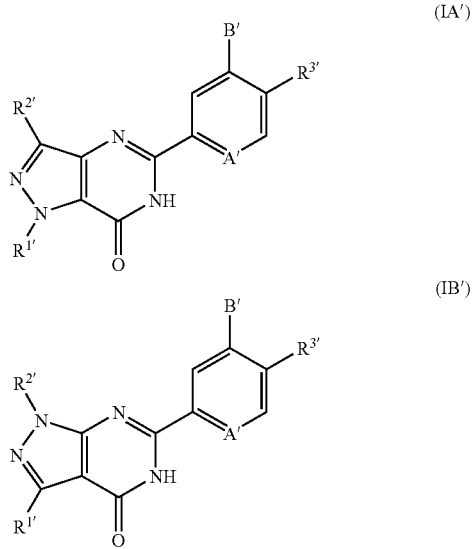

where A' represents N or $CR^{4'}$,

B' represents a hydrogen atom or a halogen atom, $R^{1'}$ represents an optionally substituted $C_{3\sim7}$ cycloalkyl or tert-butyl, $R^{2'}$ represents hydrogen, methyl or ethyl, $R^{3'}$ represents $NR^{5'}R^{6'}$, $C(=O)R^{7'}$, $SO_2NR^{5'}R^{6'}$, $OR^{8'}$, $NR^{8'}CONR^{5'}R^{6'}$, $NR^{8'}CO_2R^{9'}$, $NR^{8'}SO_2R^{9'}$, optionally substituted $C_{1\sim6}$ alkyl, optionally substituted $C_{1\sim6}$ alkenyl, or optionally substituted saturated or unsaturated heterocycloalkyl, $R^{4'}$ represents hydrogen, or $C_{1\sim3}$ alkoxy substituted, if desired, by one or more fluorine atoms, $R^{5'}$ and $R^{6'}$ are the same or different, and represent a hydrogen atom, optionally substituted $C_{1\sim6}$ alkyl, or optionally substituted heterocycloalkyl or, together with the nitrogen atom which they are bonded to, form azetidinyl, pyrrolidinyl, piperidinyl, thiomorpholino, piperazinyl or homopiperazinyl, each of these groups being further substituted by $NR^{9'}C(=O)R^{7'}$, an oxo group, or $C(=O)R^{7'}$, $R^{7'}$ represents hydrogen, optionally substituted $C_{1\sim6}$ alkyl, OH, $OR^{8'}$, or $NR^{5'}R^{6'}$, $R^{8'}$ represents hydrogen, an optionally substituted $C_{1\sim6}$ alkyl group, or optionally substituted heterocycloalkyl, and $R^{9'}$ represents an optionally substituted $C_{1\sim6}$ alkyl group.

In the general formulas (IA') and (IB') of the present invention, the optionally substituted $C_{3\sim7}$ cycloalkyl expressed as $R^{1'}$ includes, for example, cyclopropyl, cyclobutyl, cyclopentyl, cyclohexyl and cycloheptyl. Preferred examples are $C_{5\sim7}$ cycloalkyls such as cyclopentyl, cyclohexyl and cycloheptyl, and particularly preferred examples are cyclohexyl and cycloheptyl.

Examples of $R^{2'}$ are hydrogen, methyl and ethyl, and the particularly preferred example is methyl.

Examples of $R^{3'}$ are $NR^{5'}R^{6'}$, $C(=O)R^{7'}$, $SO_2NR^{5'}R^{6'}$, $OR^{8'}$, $NR^{8'}CONR^{5'}R^{6'}$, $NR^{8'}CO_2R^{9'}$, $NR^{8'}SO_2R^{9'}$, optionally substituted $C_{1\sim6}$ alkyl, optionally substituted $C_{1\sim6}$ alkenyl, and optionally substituted saturated or unsaturated heterocycloalkyl. Preferred examples are $NR^{5'}R^{6'}$, $SO_2NR^{5'}R^{6'}$, $OR^{8'}$, $NR^{8'}CONR^{5'}R^{6'}$, $NR^{8'}SO_2R^{9'}$, optionally substituted $C_{1\sim6}$ alkyl, optionally substituted $C_{1\sim6}$ alkenyl, and optionally substituted saturated or unsaturated heterocycloalkyl.

Preferred examples of the optionally substituted saturated or unsaturated heterocycloalkyl, as $R^{3'}$, include a 4- to 7-membered monocyclic saturated or unsaturated heterocycloalkyl group having 2 to 8 carbon atoms and containing 1 to 4 hetero atoms consisting of oxygen atoms, nitrogen atoms or sulfur atoms, and a polycyclic saturated or unsaturated heterocycloalkyl group comprising two or more such identical or different monocyclic compounds fused together, examples of the monocyclic and polycyclic heterocycloalkyl groups being azetidinyl, pyrrolidinyl, piperidinyl, thiomorpholino, piperazinyl, homopiperazinyl, and tetrahydropyridinyl. As A', N or $CR^{4'}$ is named. As a preferred example, $CR^{4'}$ is named.

Preferred examples of B' are hydrogen and a halogen atom. The halogen atom refers to fluorine, chlorine, bromine or iodine. Particularly preferred examples of B' are hydrogen and fluorine.

Preferred examples of $R^{4'}$ are hydrogen, and $C_{1\sim3}$ alkoxy optionally substituted, if desired, by one or more fluorine atoms, such as methoxy, ethoxy, or propyloxy. Particularly preferred examples are methoxy and ethoxy groups.

Preferred examples of $R^{5'}$ and $R^{6'}$ are groups which are the same or different, and which represent a hydrogen atom, optionally substituted $C_{1\sim6}$ alkyl, or optionally substituted heterocycloalkyl or, together with the nitrogen atom which they are bonded to, can form azetidinyl, pyrrolidinyl, piperidinyl, thiomorpholino, piperazinyl or homopiperazinyl. These groups are further substituted by $NR^{9'}C('O)R^{7'}$, an oxo group, or $C(=O)R^{7'}$. Further preferred examples are groups which include a hydrogen atom, methyl, ethyl, or optionally substituted heterocycloalkyl such as piperidinyl or pyrrolidinyl or, together with the nitrogen atom which they are bonded to, form azetidinyl, pyrrolidinyl, piperidinyl, thiomorpholino, piperazinyl or homopiperazinyl, these groups being further substituted by $NR^{9'}C(=O)R^{7'}$, an oxo group, or $C(=O)R^{7'}$.

Examples of $R^{7'}$ are a hydrogen atom, optionally substituted linear or branched $C_{1\sim6}$ alkyl, OH, $OR^{8'}$, and $NR^{5'}R^{6'}$. $R^{5'}$ and $R^{6'}$ are as defined earlier. Particularly preferred examples are OH and $NR^{5'}R^{6'}$.

As $R^{8'}$, hydrogen, an optionally substituted linear or branched $C_{1\sim6}$ alkyl group, and optionally substituted heterocycloalkyl are named. Examples of the optionally substituted linear or branched $C_{1\sim6}$ alkyl group are a carboxymethyl group, a cyanomethyl group, and a heteroarylmethyl group. Preferred examples of the heterocycloalkyl group are a 4- to 7-membered monocyclic heterocycloalkyl group having 2 to 8 carbon atoms and containing 1 to 4 hetero atoms consisting of oxygen atoms, nitrogen atoms or sulfur atoms, and a polycyclic saturated or unsaturated heterocycloalkyl group comprising two or more such identical or different monocyclic compounds fused together, examples of the monocyclic and polycyclic heterocycloalkyl groups being azetidinyl, pyrrolidinyl, piperidinyl, thiomorpholino, piperazinyl, homopiperazinyl, and tetrahydropyridinyl.

Examples of $R^{9'}$ are an optionally substituted $C_{1\sim6}$ alkyl group and, preferably, an optionally substituted $C_{1\sim3}$ alkyl group. Particularly preferred examples are optionally substituted methyl and optionally substituted ethyl.

The compounds of the general formulas (IA), (IB), (IA') and (IB') may be present in the form of tautomers, and may exist as individual tautomers, and as mixtures of individual tautomers.

Furthermore, radiolabeled derivatives of the compounds of the general formulas (IA), (IB), (IA') and (IB') are also included in the present invention.

The compounds of the present invention also include the compounds having one to a plurality of asymmetric carbon atoms, and there are (R)- and (S)-optical isomers, racemic modifications, and diastereomers based thereon. Moreover, depending on the types of the substituents, the compounds have double bonds, so that geometrical isomers, such as (Z)- and (E)-compounds, are also present. The present invention includes these isomers, whether separated or mixed.

The compounds of the present invention include those which can form salts with acids. Examples of such salts are acid adducts with mineral acids such as hydrochloric acid, hydrobromic acid, hydriodic acid, sulfuric acid, nitric acid, and phosphoric acid, and organic acids such as formic acid, acetic acid, propionic acid, oxalic acid, malonic acid, succinic acid, fumaric acid, maleic acid, lactic acid, malic acid, citric acid, tartaric acid, benzoic acid, picric acid, methanesulfonic acid, toluenesulfonic acid, benzenesulfonic acid, trichloroacetic acid, trifluoroacetic acid, aspartic acid, and glutamic acid.

The compounds of the present invention can further form pharmaceutically acceptable metal salts with metals, especially alkali metals or alkaline earth metals. Examples of these salts are sodium salts, potassium salts, and calcium salts. The compounds of the present invention further include hydrates, solvates with ethanol or isopropanol, and polymorphic substances.

Particularly preferred examples of the pyrazolopyrimidinone derivatives of the general formulas (IA), (IB), (IA') and (IB') according to the present invention are as follows: 1-cyclohexyl-3-methyl-5-phenyl-1,6-dihydro-7H-pyrazolo[4,3-d]pyrimidin-7-one; 1-cyclohexyl-3-methyl-5-(4-nitrophenyl)-1,6-dihydro-7H-pyrazolo[4,3-d]pyrimidin-7-one; 5-(4-aminophenyl)-1-cyclohexyl-3-methyl-1,6-dihydro-7H-pyrazolo[4,3-d]pyrimidin-7-one; N-[4-(1-cyclohexyl-3-methyl-7-oxo-6,7-dihydro-1H-pyrazolo[4,3-d]pyrimidin-5-yl)phenyl]acetamide; 1-cyclohexyl-5-(2-methoxyphenyl)-3-methyl-1,6-dihydro-7H-pyrazolo[4,3-d]pyrimidin-7-one; 1-cyclohexyl-3-methyl-5-(2-pyridinyl)-1,6-dihydro-7H-pyrazolo[4,3-d]pyrimidin-7-one; 1-cyclohexyl-3-methyl-5-[4-(4-methyl-1-piperazinyl)phenyl]-1,6-dihydro-7H-pyrazolo[4,3-d]pyrimidin-7-one; 1-cyclohexyl-5-(2-methoxy-4-nitrophenyl)-3-methyl-1,6-dihydro-7H-pyrazolo[4,3-d]pyrimidin-7-one; 5-(4-amino-2-methoxyphenyl)-1-cyclohexyl-3-methyl-1,6-dihydro-7H-pyrazolo[4,3-d]pyrimidin-7-one; N-[4-(1-cyclohexyl-3-methyl-7-oxo-6,7-dihydro-1H-pyrazolo[4,3-d]pyrimidin-5-yl)-3-methoxyphenyl]acetamide; 5-(5-amino-2-pyridinyl)-1-cyclohexyl-3-methyl-1,6-dihydro-7H-pyrazolo[4,3-d]pyrimidin-7-one; N-[6-(1-cyclohexyl-3-methyl-7-oxo-1H-pyrazolo[4,3-d]pyrimidin-5-yl)-3-pyridinyl]acetamide; 1-cyclohexyl-5-(2-ethoxyphenyl)-3-methyl-1,6-dihydro-7H-pyrazolo[4,3-d]pyrimidin-7-one; 1-cyclohexyl-5-[4-(4-hydroxy-1-piperidinyl)phenyl]-3-methyl-1,6-dihydro-7H-pyrazolo[4,3-d]pyrimidin-7-one; 5-(4-bromo-2-methoxyphenyl)-1-cyclohexyl-3-methyl-1,6-dihydro-7H-pyrazolo[4,3-d]pyrimidin-7-one; 1-cyclohexyl-5-[2-methoxy-4-(4-methyl-1-piperazinyl)phenyl]-3-methyl-1,6-dihydro-7H-pyrazolo[4,3-d]pyrimidin-7-one; 5-(4-chloro-2-pyridinyl)-1-cyclohexyl-3-methyl-1,6-dihydro-7H-pyrazolo[4,3-d]pyrimidin-7-one; 1-cyclohexyl-5-(5-fluoro-2-methoxyphenyl)-3-methyl-1,6-dihydro-7H-pyrazolo[4,3-d]pyrimidin-7-one; trans-5-(2-methoxyphenyl)-3-methyl-1-(4-methylcyclohexyl)-1,6-dihydro-7H-pyrazolo[4,3-d]pyrimidin-7-one; cis-5-(2-methoxyphenyl)-3-methyl-1-(4-methylcyclohexyl)-1,6-dihydro-7H-pyrazolo[4,3-d]pyrimidin-7-one; trans-3-methyl-1-(4-methylcyclohexyl)-5-[4-(4-methyl-1-piperazinyl)phenyl]-1,6-dihydro-7H-pyrazolo[4,3-d]pyrimidin-7-one; cis-3-methyl-1-(4-methylcyclohexyl)-5-[4-(4-methyl-1-piperazinyl)phenyl]-1,6-dihydro-7H-pyrazolo[4,3-d]pyrimidin-7-one; 3-cyclohexyl-1-methyl-6-phenyl-1,5-dihydro-4H-pyrazolo[3,4-d]pyrimidin-4-one; 3-cyclohexyl-6-(2-methoxypheny)-1-methyl-1,5-dihydro-4H-pyrazolo[3,4-d]pyrimidin-4-one; 3-cyclohexyl-1-methyl-6-(2-pyridinyl)-1,5-dihydro-4H-pyrazolo[3,4-d]pyrimidin-4-one; 6-(4-bromo-2-methoxyphenyl)-3-cyclohexyl-1-methyl-1,5-dihydro-4H-pyrazolo[3,4-d]pyrimidin-4-one; 3-cyclohexyl-6-[2-methoxy-4-(4-methyl-1-piperazinyl)phenyl]-1-methyl-1,5-dihydro-4H-pyrazolo[3,4-d]pyrimidin-4-one; 3-cyclohexyl-6-[4-(1,4-dioxa-8-azaspiro[4,5]deca-8-yl)-2-methoxyphenyl]-1-methyl-1,5-dihydro-4H-pyrazolo[3,4-d]pyrimidin-4-one; 3-cyclohexyl-6-[2-methoxy-4-(4-oxo-1-piperidinyl)phenyl]-1-methyl-1,5-dihydro-4H-pyrazolo[3,4-d]pyrimidin-4-one; 3-cyclohexyl-6-[4-(4-hydroxy-1-piperidinyl)-2-methoxyphenyl]-1-methyl-1,5-dihydro-4H-pyrazolo[3,4-d]pyrimidin-4-one; 3-cyclohexyl-6-[2-methoxy-4-(2-methoxyethoxy)phenyl]-1-methyl-1,5-dihydro-4H-pyrazolo[3,4-d]pyrimidin-4-one; 6-[4-(benzyloxy)-2-methoxyphenyl]-3-cyclohexyl-1-methyl-1,5-dihydro-4H-pyrazolo[3,4-d]pyrimidin-4-one; 3-cyclohexyl-6-(4-hydroxy-2-methoxyphenyl)-1-methyl-1,5-dihydro-4H-pyrazolo[3,4-d]pyrimidin-4-one; 3-cyclohexyl-6-[4-(2-hydroxyethoxy)-2-methoxyphenyl]-1-methyl-1,5-dihydro-4H-pyrazolo[3,4-d]pyrimidin-4-one; 3-cyclohexyl-6-{2-methoxy-4-[(3S)-tetrahydro-3-furanyloxy]phenyl}-1-methyl-1,5-dihydro-4H-pyrazolo[3,4-d]pyrimidin-4-one; 3-cyclohexyl-6-{2-methoxy-4-[(3R)-tetrahydro-3-furanyloxy]phenyl}-1-methyl-1,5-dihydro-4H-pyrazolo[3,4-d]pyrimidin-4-one; methyl [4-(3-cyclohexyl-1-methyl-4-oxo-4,5-dihydro-1H-pyrazolo[3,4-d]pyrimidin-6-yl)-3-methoxyphenoxy]acetate; [4-(3-cyclohexyl-1-methyl-4-oxo-4,5-dihydro-1H-pyrazolo[3,4-d]pyrimidin-6-yl)-3-methoxyphenoxy]acetic acid; 3-cyclohexyl-6-{2-methoxy-4-[(1-methyl-4-piperidinyl)oxy]phenyl}-1-methyl-1,5-dihydro-4H-pyrazolo[3,4-d]pyrimidin-4-one; 3-cyclohexyl-6-(2-methoxy-4-nitrophenyl)-1-methyl-1,5-dihydro-4H-pyrazolo[3,4-d]pyrimidin-4-one; 6-(4-amino-2-methoxyphenyl)-3-cyclohexyl-1-methyl-1,5-dihydro-4H-pyrazolo[3,4-d]pyrimidin-4-one; N-[4-(3-cyclohexyl-1-methyl-4-oxo-4,5-dihydro-1H-pyrazolo[3,4-d]pyrimidin-6-yl)-3-methoxyphenyl]acetamide; N-[4-(3-cyclohexyl-1-methyl-4-oxo-4,5-dihydro-1H-pyrazolo[3,4-d]pyrimidin-6-yl)-3-methoxyphenyl]-2-methoxyacetamide; 3-cyclohexyl-6-[2-methoxy-4-(methylamino)phenyl]-1-methyl-1,5-dihydro-4H-pyrazolo[3,4-d]pyrimidin-4-one; 4-(3-cyclohexyl-1-methyl-4-oxo-4,5-dihydro-1H-pyrazolo[3,4-d]pyrimidin-6-yl)-3-methoxybenzenesulfonyl chloride; 3-cyclohexyl-6-{2-methoxy-4-[(4-methyl-1-piperazinyl)sulfonyl]phenyl}-1-methyl-1,5-dihydro-4H-pyrazolo[3,4-d]pyrimidin-4-one; 3-cyclohexyl-6-[2-methoxy-4-(4-morpholinylsulfonyl)phenyl]-1-methyl-1,5-dihydro-4H-pyrazolo[3,4-d]pyrimidin-4-one; 3-cyclohexyl-6-{4-[(4-hydroxy-1-piperidinyl)sulfonyl]-2-methoxyphenyl}-1-methyl-1,5-dihydro-4H-pyrazolo[3,4-d]pyrimidin-4-one; ethyl 1-{[4-(3-cyclohexyl-1-methyl-4-oxo-4,5-dihydro-1H- pyrazolo[3,4-d]pyrimidin-6-yl)-3-methoxyphenyl]sulfonyl}-4-piperidinecarboxylate; 1-{[4-(3-cyclohexyl-1-methyl-4-oxo-4,5-dihydro-1H-pyrazolo[3,4-d]pyrimidin-6-yl)-3-methoxyphenyl]sulfonyl}-4-piperidinecarboxylic acid; 4-(3-cyclohexyl-1-methyl-4-oxo-4,5-dihydro-1H-pyrazolo[3,4-d]pyrimidin-6-yl)-N-[2-(dimethylamino)ethyl]-3-methoxybenzenesulfonamide; 4-(3-cyclohexyl-1-methyl-4-oxo-4,5-dihydro-1H-pyrazolo[3,4-d]pyrimidin-6-yl)-3-methoxy-N-(2-methoxyethyl)benzenesulfonamide; 4-(3-cyclohexyl-1-methyl-4-oxo-4,5-dihydro-1H-pyrazolo[3,4-d]pyrimidin-6-yl)-N-(2-hydroxyethyl)-3-methoxybenzenesulfonamide; 3-cyclohexyl-6-[2-methoxy-4-(4-morpholinyl)phenyl]-1-methyl-1,5-dihydro-4H-pyrazolo[3,4-d]pyrimidin-4-one; 3-cyclohexyl-6-[2-methoxy-4-(1-piperazinyl)phenyl]-1-methyl-1,5-dihydro-4H-pyrazolo[3,4-d]pyrimidin-4-one; 3-cyclohexyl-6-[2-methoxy-4-(4-methoxy-1-piperidinyl)phenyl]-1-methyl-1,5-dihydro-4H-pyrazolo[3,4-d]pyrimidin-4-one; 6-(4-bromo-2-methoxyphenyl)-3-cycloheptyl-1-methyl-1,5-dihydro-4H-pyrazolo[3,4-d]pyrimidin-4-one; 3-cycloheptyl-6-[2-methoxy-4-(4-methyl-1-piperazinyl)phenyl]-1-methyl-1,5-dihydro-4H-pyrazolo[3,4-d]pyrimidin-4-one; 4-(3-cyclohexyl-1-methyl-4-oxo-4,5-dihydro-1H-pyrazolo[3,4-d]pyrimidin-6-yl)-3-methoxybenzoic acid; 3-cyclohexyl-6-{2-methoxy-4-[(4-methyl-1-piperazinyl)carbonyl]phenyl}-1-methyl-1,5-dihydro-4H-pyrazolo[3,4-d]pyrimidin-4-one; 3-cyclohexyl-6-[2-methoxy-4-(4-morpholinylcarbonyl)phenyl]-1-methyl-1,5-dihydro-4H-pyrazolo[3,4-d]pyrimidin-4-one; 3-cyclohexyl-6-{4-[(4-hydroxy-1-piperidinyl)carbonyl]-2-methoxyphenyl}-1-methyl-1,5-dihydro-4H-pyrazolo[3,4-d]pyrimidin-4-one; 3-cyclohexyl-6-{2-methoxy-4-[(4-methoxy-1-piperidinyl)carbonyl]phenyl}-1-methyl-1,5-dihydro-4H-pyrazolo[3,4-d]pyrimidin-4-one; {[4-(3-cyclohexyl-1-methyl-4-oxo-4,5-dihydro-1H-pyrazolo[3,4-d]pyrimidin-6-yl)-3-methoxybenzoyl]amino}acetic acid ethyl ester; {[4-(3-cyclohexyl-1-methyl-4-oxo-4,5-dihydro-1H-pyrazolo[3,4-d]pyrimidin-6-yl)-3-methoxybenzoyl]amino}acetic acid; 3-cyclohexyl-6-{2-methoxy-4-[(2-methoxyethyl)(methyl)amino]phenyl}-1-methyl-1,5-dihydro-4H-pyrazolo[3,4-d]pyrimidin-4-one; 3-cyclohexyl-6-(5-fluoro-2-methoxyphenyl)-1-methyl-1,5-dihydro-4H-pyrazolo[3,4-d]pyrimidin-4-one; ethyl 1-[4-(3-cyclohexyl-1-methyl-4-oxo-4,5-dihydro-1H-pyrazolo[3,4-d]pyrimidin-6-yl)-3-methoxyphenyl]-4-piperazinecarboxylate; 1-[4-(3-cyclohexyl-1-methyl-4-oxo-4,5-dihydro-1H-pyrazolo[3,4-d]pyrimidin-6-yl)-3-methoxyphenyl]-4-piperazinecarboxylic acid; 3-cycloheptyl-6-[2-methoxy-4-(1-piperazinyl)phenyl]-1-methyl-1,5-dihydro-4H-pyrazolo[3,4-d]pyrimidin-4-one; benzyl 1-[4-(3-cyclohexyl-1-methyl-4-oxo-4,5-dihydro-1H-pyrazolo[3,4-d]pyrimidin-6-yl)-2-fluoro-5-methoxyphenyl]-1-piperazinecarboxylate; 3-cyclohexyl-6-[5-fluoro-2-methoxy-4-(1-piperazinyl)phenyl]-1-methyl-1,5-dihydro-4H-pyrazolo[3,4-d]pyrimidin-4-one; 3-cyclohexyl-6-[5-fluoro-2-methoxy-4-(4-methyl-1-piperazinyl)phenyl]-1-methyl-1,5-dihydro-4H-pyrazolo[3,4-d]pyrimidin-4-one; 3-cyclohexyl-6-(2-methoxy-4-{methyl[2-(methylamino)ethyl]amino}phenyl)-1-methyl-1,5-dihydro-4H-pyrazolo[3,4-d]pyrimidin-4-one; 6-(4-bromo-2-ethoxyphenyl)3-cyclohexyl-1-methyl-1,5-dihydro-4H-pyrazolo[3,4-d]pyrimidin-4-one; 3-cyclohexyl-6-[2-ethoxy-4-(4-methyl-1-piperazinyl)phenyl]-1-methyl-1,5-dihydro-4H-pyrazolo[3,4-d]pyrimidin-4-one; benzyl 1-[4-(3-cyclohexyl-1-methyl-4-oxo-4,5-dihydro-1H-pyrazolo[3,4-d]pyrimidin-6-yl)-3-ethoxyphenyl]-4-piperidinyl(methyl)carbamate; 3-cyclohexyl-6-{2-ethoxy-4-[4-(methylamino)-1-piperidinyl]phenyl}-1-methyl-1,5-dihydro-4H-pyrazolo[3,4-d]pyrimidin-4-one; benzyl 1-[4-(1-cyclohexyl-3-methyl-7-oxo-6,7-dihydro-1H-pyrazolo[4,3-d]pyrimidin-5-yl)-3-methoxyphenyl]-4-piperidinyl(methyl)carbamate; 1-cyclohexyl-5-{2-methoxy-4-[4-(methylamino)-1-piperidinyl]phenyl}-3-methyl-1,6-dihydro-7H-pyrazolo[4,3-d]pyrimidin-7-one; benzyl 1-[4-(3-cycloheptyl-1-methyl-4-oxo-4,5-dihydro-1H-pyrazolo[3,4-d]pyrimidin-6-yl)-3-methoxyphenyl]-4-piperidinyl(methyl)carbamate; 3-cycloheptyl-6-{2-methoxy-4-[4-(methylamino)-1-piperidinyl]phenyl}-1-methyl-1,5-dihydro-4H-pyrazolo[3,4-d]pyrimidin-4-one; benzyl 1-[4-(3-cyclohexyl-1-methyl-4-oxo-4,5-dihydro-1H-pyrazolo[3,4-d]pyrimidin-6-yl)-3-methoxyphenyl]-4-piperidinyl(ethyl)carbamate; 3-cyclohexyl-6-{2-methoxy-4-[4-(ethylamino)-1-piperidinyl]phenyl}-1-methyl-1,5-dihydro-4H-pyrazolo[3,4-d]pyrimidin-4-one; benzyl 1-[4-(1-cyclohexyl-3-methyl-7-oxo-6,7-dihydro-1H-pyrazolo[4,3-d]pyrimidin-5-yl)-3-methoxyphenyl]-4-piperidinyl(ethyl)carbamate; 1-cyclohexyl-5-{2-methoxy-4-[4-(ethylamino)-1-piperidinyl]phenyl}-3-methyl-1,6-dihydro-7H-pyrazolo[4,3-d]pyrimidin-7-one; 1-cyclohexyl-5-[4-(benzyloxy)-2-methoxyphenyl]-1-cyclohexyl-3-methyl-1,6-dihydro-7H-pyrazolo[4,3-d]pyrimidin-7-one; 1-cyclohexyl-5-(4-hydroxy-2-methoxyphenyl)-3-methyl-1,6-dihydro-7H-pyrazolo[4,3-d]pyrimidin-7-one; 1-cyclohexyl-5-(2-methoxy-4-{methyl[2-(methylamino)ethyl]amino}phenyl)-3-methyl-1,6-dihydro-7H-pyrazolo[4,3-d]pyrimidin-7-one; 1-cyclohexyl-5-{4-[(3R)-3-(dimethylamino)pyrrolidinyl]-2-methoxyphenyl}-3-methyl-1,6-dihydro-7H-pyrazolo[4,3-d]pyrimidin-7-one; 1-cyclohexyl-5-{4-[(3S)-3-(dimethylamino)pyrrolidinyl]-2-methoxyphenyl}-3-methyl-1,6-dihydro-7H-pyrazolo[4,3-d]pyrimidin-7-one; 5-{4-[[2-(benzyloxy)ethyl](methyl)amino]-2-methoxyphenyl}-1-cyclohexyl-3-methyl-1,6-dihydro-7H-pyrazolo[4,3-d]pyrimidin-7-one; 1-cyclohexyl-5-{4-[(2-hydroxyethyl)(methyl)amino]-2-methoxyphenyl}-3-methyl-1,6-dihydro-7H-pyrazolo[4,3-d]pyrimidin-7-one; 5-(4-{4-[(benzyloxy)methyl]-1-piperidinyl}-2-methoxyphenyl)-1-cyclohexyl-3-methyl-1,6-dihydro-7H-pyrazolo[4,3-d]pyrimidin-7-one; 1-cyclohexyl-5-{4-[4-(hydroxymethyl)-1-piperidinyl]-2-methoxyphenyl}-3-methyl-1,6-dihydro-7H-pyrazolo[4,3-d]pyrimidin-7-one; 1-cyclohexyl-5-(2-methoxy-4-{methyl[3-(methylamino)propyl]amino}phenyl)-3-methyl-1,6-dihydro-7H-pyrazolo[4,3-d]pyrimidin-7-one; 1-cyclohexyl-5-[2-methoxy-4-(4-methyl-1,4-diazepan-1-yl)phenyl]-3-methyl-1,6-dihydro-7H-pyrazolo[4,3-d]pyrimidin-7-one; 5-{4-[[2-(benzyloxy)ethyl](ethyl)amino]-2-methoxyphenyl}-1-cyclohexyl-3-methyl-1,6-dihydro-7H-pyrazolo[4,3-d]pyrimidin-7-one; 1-cyclohexyl-5-{4-[(2-hydroxyethyl)(ethyl)amino]-2-methoxyphenyl}-3-methyl-1,6-dihydro-7H-pyrazolo[4,3-d]pyrimidin-7-one; 5-(4-bromo-2-ethoxyphenyl-1-cyclohexyl-3-methyl-1,6-dihydro-7H-pyrazolo[4,3-d]pyrimidin-7-one; 3-cyclohexyl-6-{2-ethoxy-4-[(2-methoxyethyl)amino]phenyl}-1-methyl-1,5-dihydro-4H-pyrazolo[3,4-d]pyrimidin-4-one; 1-[4-(1-cyclohexyl-3-methyl-7-oxo-6,7-dihydro-1H-pyrazolo[4,3-d]pyrimidin-5-yl)-3-methoxyphenyl]-4-piperidinyl(methyl)formamide; N-{1-[4-(1-cyclohexyl-3-methyl-7-oxo-6,7-dihydro-1H-pyrazolo[4,3-d]pyrimidin-5-yl)-3-methoxyphenyl]-4-piperidinyl}-N-methylacetamide; benzyl 1-[4-(1-cyclohexyl-3-methyl-7-oxo-6,7-dihydro-1H-pyrazolo[4,3-d]pyrimidin-5-yl)-3-ethoxyphenyl]-4-piperidinyl(methyl)carbamate; 1-cyclohexyl-5-{2-ethoxy-4-[4-(methylamino)-1-piperidinyl]phenyl}-3-methyl-1,6-dihydro-7H-pyrazolo[4,3-d]pyrimidin-7-one; 1-cyclohexyl-5-[4-(4-hydroxy-1-methyl-4-piperidinyl)-2-methoxyphenyl]-3-methyl-1,6-dihydro-7H-pyrazolo[4,3-d]pyrimidin-7-one; 1-cyclohexyl-5-[2-methoxy-4-(1-methyl- 1,2,3,6-tetrahydro-4-pyridinyl)phenyl]-3-methyl-1,6-dihydro-7H-pyrazolo[4,3-d]pyrimidin-7-one; 1-cyclohexyl-5-[2-methoxy-4-(1-methyl-4-piperidinyl)phenyl]-3-methyl-1,6-dihydro-7H-pyrazolo[4,3-d]pyrimidin-7-one; 1-cyclohexyl-5-[4-(1,4-diazepan-1-yl)-2-methoxyphenyl]-3-methyl-1,6-dihydro-7H-pyrazolo[4,3-d]pyrimidin-7-one; 5-[4-(4-acetyl-1,4-diazepan-1-yl)-2-methoxyphenyl]-1-cyclohexyl-3-methyl-1,6-dihydro-7H-pyrazolo[4,3-d]pyrimidin-7-one; 1-cyclohexyl-5-[4-(4-ethyl-1,4-diazepan-1-yl)-2-methoxyphenyl]-3-methyl-1,6-dihydro-7H-pyrazolo[4,3-d]pyrimidin-7-one; benzyl 1-[4-(1-cyclohexyl-3-methyl-7-oxo-6,7-dihydro-1H-pyrazolo[4,3-d]pyrimidin-5-yl)-2-fluoro-5-methoxyphenyl]-4-piperidinyl(methyl)carbamate; 1-cyclohexyl-5-{5-fluoro-2-methoxy-4-[(methylamino)-1-piperidinyl]phenyl}-3-methyl-1,6-dihydro-7H-pyrazolo[4,3-d]pyrimidin-7-one; 1-cyclohexyl-5-[4-(4-methyl-1,4-diazepan-1-yl)-2-ethoxyphenyl]-3-methyl-1,6-dihydro-7H-pyrazolo[4,3-d]pyrimidin-7-one; 3-cyclohexyl-6-{4-[[2-(dimethylamino)ethyl](methyl)amino]-2-methoxyphenyl}-1-methyl-1,5-dihydro-4H-pyrazolo[3,4-d]pyrimidin-4-one; 3-cyclohexyl-6-[4-(1,4-diazepan-1-yl)-2-methoxyphenyl]-1-methyl-1,5-dihydro-4H-pyrazolo[3,4-d]pyrimidin-4-one; 3-cyclohexyl-6-[2-methoxy-4-(4-methyl-1,4-diazepan-1-yl)phenyl]-1-methyl-1,5-dihydro-4H-pyrazolo[3,4-d]pyrimidin-4-one; 6-[4-bromo-2-(difluoromethoxy)phenyl]-3-cyclohexyl-1-methyl-1,5-dihydro-4H-pyrazolo[3,4-d]pyrimidin-4-one; 3-cyclohexyl-6-[2-(difluoromethoxy)-4-(4-methyl-1-piperazinyl)phenyl]-1-methyl-1,5-dihydro-4H-pyrazolo[3,4-d]pyrimidin-4-one; N-[4-(3-cyclohexyl-1-methyl-4-oxo-4,5-dihydro-1H-pyrazolo[3,4-d]pyrimidin-6-yl)-3-methoxyphenyl]urea; N-[4-(3-cyclohexyl-1-methyl-4-oxo-4,5-dihydro-1H-pyrazolo[3,4-d]pyrimidin-6-yl)-3-methoxyphenyl]-N-(methylsulfonyl)methanesulfonamide; N-[4-(3-cyclohexyl-1-methyl-4-oxo-4,5-dihydro-1H-pyrazolo[3,4-d]pyrimidin-6-yl)-3-methoxyphenyl]methanesulfonamide; 3-cyclohexyl-6-[2-methoxy-4-(2-oxo-1,3-oxazolidin-3-yl)phenyl]-1-methyl-1,5-dihydro-4H-pyrazolo[3,4-d]pyrimidin-4-one; 3-cyclohexyl-6-[2-methoxy-4-(2-oxo-1-imidazolidinyl)phenyl]-1-methyl-1,5-dihydro-4H-pyrazolo[3,4-d]pyrimidin-4-one; ethyl 4-(3-cyclohexyl-1-methyl-4-oxo-4,5-dihydro-1H-pyrazolo[3,4-d]pyrimidin-6-yl)-3-methoxyphenylcarbamate; N-[4-(3-cyclohexyl-1-methyl-4-oxo-4,5-dihydro-1H-pyrazolo[3,4-d]pyrimidin-6-yl)-3-methoxyphenyl]-N-methylacetamide; N-[4-(3-cyclohexyl-1-methyl-4-oxo-4,5-dihydro-1H-pyrazolo[3,4-d]pyrimidin-6-yl)-3-methoxyphenyl]-N-methylmethanesulfonamide; N-[4-(3-cyclohexyl-1-methyl-4-oxo-4,5-dihydro-1H-pyrazolo[3,4-d]pyrimidin-6-yl)-3-methoxyphenyl]-N-morpholinecarboxamide; 3-cyclohexyl-6-{2-methoxy-4-[4-(methylamino)-1-piperidinyl]phenyl}-1-methyl-1,5-dihydro-4H-pyrazolo[3,4-d]pyrimidin-4-one; N'-[4-(3-cyclohexyl-1-methyl-4-oxo-4,5-dihydro-1H-pyrazolo[3,4-d]pyrimidin-6-yl)-3-methoxyphenyl]-N-(2-hydroxyethyl)-N-methylurea; 3-cyclohexyl-6-[2-methoxy-4-(3-methyl-2-oxo-1-imidazolidinyl)phenyl]-1-methyl-1,5-dihydro-4H-pyrazolo[3,4-d]pyrimidin-4-one; 3-cyclohexyl-6-{4-[4-(dimethylamino)-1-piperidinyl]-2-methoxyphenyl}-1-methyl-1,5-dihydro-4H-pyrazolo[3,4-d]pyrimidin-4-one; 3-cyclohexyl-6-[4-(1,1-dioxido-2-isothiazolidinyl)-2-methoxyphenyl]-1-methyl-1,5-dihydro-4H-pyrazolo[3,4-d]pyrimidin-4-one; 4-(3-cyclohexyl-1-methyl-4-oxo-4,5-dihydro-1H-pyrazolo[3,4-d]pyrimidin-6-yl)-N-(2-hydroxyethyl)-3-methoxy-N-methylbenzenesulfonamide; 4-(3-cyclohexyl-1-methyl-4-oxo-4,5-dihydro-1H-pyrazolo[3,4-d]pyrimidin-6-yl)-N-[2-(dimethylamino)ethyl]-3-methoxy-N-methylbenzenesulfonamide; 4-(3-cyclohexyl-1-methyl-4-oxo-4,5-dihydro-1H-pyrazolo[3,4-d]pyrimidin-6-yl)-N-(3-hydroxypropyl)-3-methoxybenzenesulfonamide; 3-cyclohexyl-6-[4-(1,4-diazepan-1-ylsulfonyl)-2-methoxyphenyl]-1-methyl-1,5-dihydro-4H-pyrazolo[3,4-d]pyrimidin-4-one; 3-cyclohexyl-6-{2-methoxy-4-[(4-methyl-1,4-diazepan-1-yl)sulfonyl]phenyl}-1-methyl-1,5-dihydro-4H-pyrazolo[3,4-d]pyrimidin-4-one; 3-cyclohexyl-6-{4-[(3-hydroxy-1-pyrrolidinyl)sulfonyl]-2-methoxyphenyl}-1-methyl-1,5-dihydro-4H-pyrazolo[3,4-d]pyrimidin-4-one; 3-cyclohexyl-6-[2-methoxy-4-(4-thiomorpholinylsulfonyl)phenyl]-1-methyl-1,5-dihydro-4H-pyrazolo[3,4-d]pyrimidin-4-one; 3-cyclohexyl-6-[4-(1,4-dioxa-8-azaspiro[4.5]deca-8-ylsulfonyl)-2-methoxyphenyl]-1-methyl-1,5-dihydro-4H-pyrazolo[3,4-d]pyrimidin-4-one; 3-cyclohexyl-6-{2-methoxy-4-[(4-oxo-1-piperidinyl)sulfonyl]phenyl}-1-methyl-1,5-dihydro-4H-pyrazolo[3,4-d]pyrimidin-4-one; 3-cyclohexyl-6-(2-methoxy-4-{[4-(methylamino)-1-piperidinyl]sulfonyl}phenyl)-1-methyl-1,5-dihydro-4H-pyrazolo[3,4-d]pyrimidin-4-one; benzyl 1-{[4-(3-cyclohexyl-1-methyl-4-oxo-4,5-dihydro-1H-pyrazolo[3,4-d]pyrimidin-6-yl)-3-methoxyphenyl]sulfonyl}-3-pyrrolidinylcarbamate; 6-{4-[(3-amino-1-pyrrolidinyl)sulfonyl]-2-methoxyphenyl}-3-cyclohexyl-1-methyl-1,5-dihydro-4H-pyrazolo[3,4-d]pyrimidin-4-one; benzyl 1-{[4-(3-cyclohexyl-1-methyl-4-oxo-4,5-dihydro-1H-pyrazolo[3,4-d]pyrimidin-6-yl)-3-methoxyphenyl]sulfonyl}-4-piperidinylcarbamate; 6-{4-[(4-amino-1-piperidinyl)sulfonyl]-2-methoxyphenyl}-3-cyclohexyl-1-methyl-1,5-dihydro-4H-pyrazolo[3,4-d]pyrimidin-4-one; 3-cyclohexyl-6-[2-methoxy-4-(4-thiomorpholinyl)phenyl]-1-methyl-1,5-dihydro-4H-pyrazolo[3,4-d]pyrimidin-4-one; 6-(4-bromophenyl)-3-cyclohexyl-1-methyl-1,5-dihydro-4H-pyrazolo[3,4-d]pyrimidin-4-one; 3-cyclohexyl-1-methyl-6-[4-(4-methyl-1-piperazinyl)phenyl]-1,5-dihydro-4H-pyrazolo[3,4-d]pyrimidin-4-one; 6-(4-aminophenyl)-3-cyclohexyl-1-methyl-1,5-dihydro-4H-pyrazolo[3,4-d]pyrimidin-4-one; 4-(3-cyclohexyl-1-methyl-4-oxo-4,5-dihydro-1H-pyrazolo[3,4-d]pyrimidin-6-yl)benzenesulfonyl chloride; 3-cyclohexyl-6-{4-[(4-hydroxy-1-piperidinyl)sulfonyl]phenyl}-1-methyl-1,5-dihydro-4H-pyrazolo[3,4-d]pyrimidin-4-one; 6-{4-[4-(benzylamino)-1-piperidinyl]-2-methoxyphenyl}-3-cyclohexyl-1-methyl-1,5-dihydro-4H-pyrazolo[3,4-d]pyrimidin-4-one; 6-[4-(4-amino-1-piperidinyl)-2-methoxyphenyl]-3-cyclohexyl-1-methyl-1,5-dihydro-4H-pyrazolo[3,4-d]pyrimidin-4-one; 3-cyclohexyl-1-methyl-6-{4-[(4-methyl-1,4-diazepan-1-yl)sulfonyl]phenyl}-1,5-dihydro-4H-pyrazolo[3,4-d]pyrimidin-4-one; benzyl 1-[4-(3-cyclohexyl-1-methyl-4-oxo-4,5-dihydro-1H-pyrazolo[3,4-d]pyrimidin-6-yl)phenyl]-4-piperidinyl(methyl)carbamate; 3-cyclohexyl-1-methyl-6-{4-[4-(methylamino)-1-piperidinyl]phenyl}-1,5-dihydro-4H-pyrazolo[3,4-d]pyrimidin-4-one; 3-cyclohexyl-6-[4-(1,4-diazepan-1-ylsulfonyl)phenyl]-1-methyl-1,5-dihydro-4H-pyrazolo[3,4-d]pyrimidin-4-one; 3-cyclohexyl-6-{4-[(1,1-dioxido-4-thiomorpholinyl)sulfonyl]-2-methoxyphenyl}-1-methyl-1,5-dihydro-4H-pyrazolo[3,4-d]pyrimidin-4-one; 3-cyclohexyl-6-[4-(1,1-dioxido-4-thiomorpholinyl)-2-methoxyphenyl]-1-methyl-1,5-dihydro-4H-pyrazolo[3,4-d]pyrimidin-4-one; 6-(4-bromo-2-methoxyphenyl)-3-cyclohexyl-1-ethyl-1,5-dihydro-4H-pyrazolo[3,4-d]pyrimidin-4-one; 3-cyclohexyl-1-ethyl-6-[2-methoxy-4-(4-methyl-1-piperazinyl)phenyl]-1,5-dihydro-4H-pyrazolo[3,4-d]pyrimidin-4-one; benzyl 1-[4-(3-cyclohexyl-1-ethyl-4-oxo-4,5-dihydro-1H-pyrazolo[3,4-d]pyrimidin-6-yl)-3-methoxyphenyl]-4-piperidinyl(methyl) carbamate; 3-cyclohexyl-1-ethyl-6-{2-methoxy-4-[4-(methylamino)-1-piperidinyl]phenyl}-1,5-dihydro-4H-pyrazolo[3,4-d]pyrimidin-4-one; 4-(1-cyclohexyl-3-methyl- 7-oxo-6,7-dihydro-1H-pyrazolo[3,4-d]pyrimidin-5-yl)-3-methoxybenzenesulfonyl chloride; 1-cyclohexyl-5-{2-methoxy-4-[(4-methyl-1,4-diazepan-1-yl)sulfonyl]phenyl}-3-methyl-1,6-dihydro-7H-pyrazolo[4,3-d]pyrimidin-7-one; 1-cyclohexyl-5-{4-[(4-hydroxy-1-piperidinyl)sulfonyl]-2-methoxyphenyl}-3-methyl-1,6-dihydro-7H-pyrazolo[4,3-d]pyrimidin-7-one; 4-(1-cyclohexyl-3-methyl-7-oxo-6,7-dihydro-1H-pyrazolo[4,3-d]pyrimidin-5-yl)-N-(2-hydroxyethyl)-3-methoxybenzenesulfonamide; 4-(1-cyclohexyl-3-methyl-7-oxo-6,7-dihydro-1H-pyrazolo[4,3-d]pyrimidin-5-yl)-3-methoxy-N-methylbenzenesulfonamide; 1-cyclohexyl-5-[4-(1,4-diazepan-1-ylsulfonyl)-2-methoxyphenyl]-3-methyl-1,6-dihydro-7H-pyrazolo[4,3-d]pyrimidin-7-one; 4-(3-cyclohexyl-1-methyl-4-oxo-4,5-dihydro-1H-pyrazolo[3,4-d]pyrimidin-6-yl)-3-methoxy-N-methylbenzenesulfonamide; 6-(4-amino-2-methoxyphenyl)-3-cyclohexyl-1-ethyl-1,5-dihydro-4H-pyrazolo[3,4-d]pyrimidin-4-one; 4-(3-cyclohexyl-1-ethyl-4-oxo-4,5-dihydro-1H-pyrazolo[3,4-d]pyrimidin-6-yl)-3-methoxybenzenesulfonyl chloride; 3-cyclohexyl-1-ethyl-6-{4-[(4-hydroxy-1-piperidinyl)sulfonyl]-2-methoxyphenyl}-1,5-dihydro-4H-pyrazolo[3,4-d]pyrimidin-4-one; 3-cyclohexyl-1-ethyl-6-{2-methoxy-4-[(4-methyl-1,4-diazepan-1-yl)sulfonyl]phenyl}-1,5-dihydro-4H-pyrazolo[3,4-d]pyrimidin-4-one; 3-cyclohexyl-6-[4-(1,4-diazepan-1-ylsulfonyl)-2-methoxyphenyl]-1-ethyl-1,5-dihydro-4H-pyrazolo[3,4-d]pyrimidin-4-one; N-(2-aminoethyl)-4-(1-cyclohexyl-3-methyl-7-oxo-6,7-dihydro-1H-pyrazolo[4,3-d]pyrimidin-5-yl)-3-methoxy-N-methylbenzenesulfonamide; 4-(1-cyclohexyl-3-methyl-7-oxo-6,7-dihydro-1H-pyrazolo[4,3-d]pyrimidin-5-yl)-3-methoxy-N-[2-(methylamino)ethyl]benzenesulfonamide; 4-(1-cyclohexyl-3-methyl-7-oxo-6,7-dihydro-1H-pyrazolo[4,3-d]pyrimidin-5-yl)-N-[2-(dimethylamino)ethyl]-3-methoxybenzenesulfonamide; 4-(1-cyclohexyl-3-methyl-7-oxo-6,7-dihydro-1H-pyrazolo[4,3-d]pyrimidin-5-yl)-3-methoxy-N-methyl-N-[2-(methylamino)ethyl]benzenesulfonamide; 4-(1-cyclohexyl-3-methyl-7-oxo-6,7-dihydro-1H-pyrazolo[4,3-d]pyrimidin-5-yl)-N-(2-hydroxyethyl)-3-methoxy-N-methylbenzenesulfonamide; 1-cyclohexyl-5-{2-methoxy-4-[(4-methyl-1-piperazinyl)sulfonyl]phenyl}-3-methyl-1,6-dihydro-7H-pyrazolo[4,3-d]pyrimidin-7-one; 4-(1-cyclohexyl-3-methyl-7-oxo-6,7-dihydro-1H-pyrazolo[4,3-d]pyrimidin-5-yl)-3-methoxy-N-methyl-N-[3-(methylamino)propyl]benzenesulfonamide; 1-cyclohexyl-5-(4-{[4-(2-hydroxyethyl)-1-piperazinyl]sulfonyl}-2-methoxyphenyl)-3-methyl-1,6-dihydro-7H-pyrazolo[4,3-d]pyrimidin-7-one; 1-cyclohexyl-5-[2-methoxy-4-(1-piperazinylsulfonyl)phenyl]-3-methyl-1,6-dihydro-7H-pyrazolo[4,3-d]pyrimidin-7-one; 1-cyclohexyl-5-{4-[(4-ethyl-1-piperazinyl)sulfonyl]-2-methoxyphenyl}-3-methyl-1,6-dihydro-7H-pyrazolo[4,3-d]pyrimidin-7-one; N-(1-benzyl-4-piperidinyl)-4-(1-cyclohexyl-3-methyl-7-oxo-6,7-dihydro-1H-pyrazolo[4,3-d]pyrimidin-5-yl)-3-methoxybenzenesulfonamide; 4-(1-cyclohexyl-3-methyl-7-oxo-6,7-dihydro-1H-pyrazolo[4,3-d]pyrimidin-5-yl)-3-methoxy-N-(4-piperidinyl)benzenesulfonamide; benzyl 1-{[4-(1-cyclohexyl-3-methyl-7-oxo-6,7-dihydro-1H-pyrazolo[4,3-d]pyrimidin-5-yl)-3-methoxyphenyl]sulfonyl}-4-piperidinyl(methyl)carbamate; 1-cyclohexyl-5-(2-methoxy-4-{[4-(methylamino)-1-piperidinyl]sulfonyl}phenyl)-3-methyl-1,6-dihydro-7H-pyrazolo[4,3-d]pyrimidin-7-one; 5-{4-[(1-benzyl-4-piperidinyl)amino]-2-methoxyphenyl}-1-cyclohexyl-3-methyl-1,6-dihydro-7H-pyrazolo[4,3-d]pyrimidin-7-one; 1-cyclohexyl-5-[2-methoxy-4-(4-piperidinylamino)phenyl]-3-methyl-1,6-dihydro-7H-pyrazolo[4,3-d]pyrimidin-7-one; 1-cyclohexyl-5-{2-methoxy-4-[(2-methoxyethyl)amino]phenyl}-3-methyl-1,6-dihydro-7H-pyrazolo[4,3-d]pyrimidin-7-one; methyl (2E)-3-[4-(1-cyclohexyl-3-methyl-7-oxo-6,7-dihydro-1H-pyrazolo[4,3-d]pyrimidin-5-yl)-3-methoxyphenyl]-2-propenate; (2E)-3-[4-(1-cyclohexyl-3-methyl-7-oxo-6,7-dihydro-1H-pyrazolo[4,3-d]pyrimidin-5-yl)-3-methoxyphenyl]-2-propenic acid; methyl 3-[4-(1-cyclohexyl-3-methyl-7-oxo-6,7-dihydro-1H-pyrazolo[4,3-d]pyrimidin-5-yl)-3-methoxyphenyl]propanate; 3-[4-(1-cyclohexyl-3-methyl-7-oxo-6,7-dihydro-1H-pyrazolo[4,3-d]pyrimidin-5-yl)-3-methoxyphenyl]propanic acid; 1-cyclohexyl-5-(4-{[2-(dimethylamino)ethyl]amino}-2-methoxyphenyl)-3-methyl-1,6-dihydro-7H-pyrazolo[4,3-d]pyrimidin-7-one; 5-{4-[(1-acetyl-4-piperidinyl)amino]-2-methoxyphenyl}-1-cyclohexyl-3-methyl-1,6-dihydro-7H-pyrazolo[4,3-d]pyrimidin-7-one; 1-cyclohexyl-5-{2-methoxy-4-[(1-methyl-4-piperidinyl)amino]phenyl}-3-methyl-1,6-dihydro-7H-pyrazolo[4,3-d]pyrimidin-7-one; 4-(1-cyclohexyl-3-methyl-7-oxo-6,7-dihydro-1H-pyrazolo[4,3-d]pyrimidin-5-yl)-3-methoxybenzaldehyde; 1-cyclohexyl-5-{2-methoxy-4-[(4-methyl-1-piperazinyl)methyl]phenyl}-3-methyl-1,6-dihydro-7H-pyrazolo[4,3-d]pyrimidin-7-one; 1-cyclohexyl-5-[2-methoxy-4-(4-morpholinylmethyl)phenyl]-3-methyl-1,6-dihydro-7H-pyrazolo[4,3-d]pyrimidin-7-one; 1-cyclohexyl-5-{4-[(4-hydroxy-1-piperidinyl)methyl]-2-methoxyphenyl}-3-methyl-1,6-dihydro-7H-pyrazolo[4,3-d]pyrimidin-7-one; 1-cyclohexyl-5-(2-methoxy-4-{[(2-methoxyethyl)amino]methyl}phenyl)-3-methyl-1,6-dihydro-7H-pyrazolo[4,3-d]pyrimidin-7-one; ethyl 1-[4-(1-cyclohexyl-3-methyl-7-oxo-6,7-dihydro-1H-pyrazolo[4,3-d]pyrimidin-5-yl)-3-methoxybenzyl]-4-piperidinecarboxylate; 1-[4-(1-cyclohexyl-3-methyl-7-oxo-6,7-dihydro-1H-pyrazolo[4,3-d]pyrimidin-5-yl)-3-methoxybenzyl]-4-piperidinecarboxylic acid; benzyl 1-[4-(1-cyclohexyl-3-methyl-7-oxo-6,7-dihydro-1H-pyrazolo[4,3-d]pyrimidin-5-yl)-3-methoxybenzyl]-4-piperidinyl(methyl)carbamate; 1-cyclohexyl-5-(2-methoxy-4-{[4-(methylamino)-1-piperidinyl]methyl}phenyl)-3-methyl-1,6-dihydro-7H-pyrazolo[4,3-d]pyrimidin-7-one; 1-cyclohexyl-5-[2-methoxy-4-(tetrahydro-2H-pyran-4-ylamino)phenyl]-3-methyl-1,6-dihydro-7H-pyrazolo[4,3-d]pyrimidin-7-one; 1-cyclohexyl-5-[4-(1,4-dioxa-8-azaspiro[4.5]deca-8-yl)-2-methoxyphenyl]-3-methyl-1,6-dihydro-7H-pyrazolo[4,3-d]pyrimidin-7-one; 1-cyclohexyl-5-[2-methoxy-4-(4-oxo-1-piperidinyl)phenyl]-3-methyl-1,6-dihydro-7H-pyrazolo[4,3-d]pyrimidin-7-one; 1-cyclohexyl-5-{4-[4-(dimethylamino)-1-piperidinyl]-2-methoxyphenyl}-3-methyl-1,6-dihydro-7H-pyrazolo[4,3-d]pyrimidin-7-one; 5-{4-[4-(benzylamino)-1-piperidinyl]-2-methoxyphenyl}-1-cyclohexyl-3-methyl-1,6-dihydro-7H-pyrazolo[4,3-d]pyrimidin-7-one; 5-[4-(4-amino-1-piperidinyl)-2-methoxyphenyl]-1-cyclohexyl-3-methyl-1,6-dihydro-7H-pyrazolo[4,3-d]pyrimidin-7-one; 1-cyclohexyl-5-[4-(1,4-dioxa-8-azaspiro[4.5]deca-8-yl)-2-ethoxyphenyl]-3-methyl-1,6-dihydro-7H-pyrazolo[4,3-d]pyrimidin-7-one; 1-cyclohexyl-5-[2-ethoxy-4-(4-oxo-1-piperidinyl)phenyl]-3-methyl-1,6-dihydro-7H-pyrazolo[4,3-d]pyrimidin-7-one; 1-cyclohexyl-5-{4-[4-(dimethylamine)-1-piperidinyl]-2-ethoxyphenyl}-3-methyl-1,6-dihydro-7H-pyrazolo[4,3-d]pyrimidin-7-one; 5-{4-[4-(benzylamino)-1-piperidinyl]-2-ethoxyphenyl}-1-cyclohexyl-3-methyl-1,6-dihydro-7H-pyrazolo[4,3-d]pyrimidin-7-one; benzyl 1-[4-(1-cyclohexyl-3-methyl-7-oxo-6,7-dihydro-1H-pyrazolo[4,3-d]pyrimidin-5-yl)-3-ethoxyphenyl]-4-piperidinyl(ethyl)carbamate; 1-cyclohexyl-5-{2-ethoxy-4-[(ethylamino)-1-piperidinyl]phenyl}-3-methyl-1,6-dihydro-7H-pyrazolo[4,3-d]pyrimidin-7-one; 5-(4-amino-2-ethoxyphenyl)-1-cyclohexyl-3-methyl-1,6-dihydro-7H-pyrazolo[4,3-d]pyrimidin-7-one; 4-(1-cyclohexyl-3-methyl-7-oxo-6,7-dihydro-1H-pyrazolo[4,3-d]pyrimidin-5-yl)-3-ethoxybenzenesulfonyl chloride; 1-cyclohexyl-5-{2-ethoxy-4-[(4-methyl-1,4-diazepan-1-yl)sulfonyl]phenyl}-3-methyl-1,6-dihydro-7H-pyrazolo[4,3-d]pyrimidin-7-one; 1-cyclohexyl-5-{2-ethoxy-4-[(4-hydroxy-1-piperidinyl)sulfonyl]phenyl}-3-methyl-1,6-dihydro-7H-pyrazolo[4,3-d]pyrimidin-7-one; 1-cyclohexyl-5-[4-[(4-hydroxy-1-piperidinyl)-2-methoxyphenyl]-3-methyl-1,6-dihydro-7H-pyrazolo[4,3-d]pyrimidin-7-one; (2E)-3-[4-(1-cyclohexyl-3-methyl-7-oxo-6,7-dihydro-1H-pyrazolo[4,3-d]pyrimidin-5-yl)-3-methoxyphenyl]-2-propenenitrile; 5-[4-(4-amino-1-piperidinyl)-2-ethoxyphenyl]-1-cyclohexyl-3-methyl-1,6-dihydro-7H-pyrazolo[4,3-d]pyrimidin-7-one; 1-cyclohexyl-5-[2-ethoxy-4-(4-hydroxy-1-piperidinyl)phenyl]-3-methyl-1,6-dihydro-7H-pyrazolo[4,3-d]pyrimidin-7-one; 1-cyclohexyl-5-[4-(1,4-diazepan-1-yl)-2-ethoxyphenyl]-3-methyl-1,6-dihydro-7H-pyrazolo[4,3-d]pyrimidin-7-one; 1-cyclohexyl-5-{2-ethoxy-4-[(2-methoxyethyl)amino]phenyl}-3-methyl-1,6-dihydro-7H-pyrazolo[4,3-d]pyrimidin-7-one; 1-cyclohexyl-5-[2-ethoxy-4-(4-methyl-1-piperazinyl)phenyl]-3-methyl-1,6-dihydro-7H-pyrazolo[4,3-d]pyrimidin-7-one; benzyl 4-[4-(1-cyclohexyl-3-methyl-7-oxo-6,7-dihydro-1H-pyrazolo[4,3-d]pyrimidin-5-yl)-2-fluoro-5-methoxyphenyl]-1,4-diazepane-1-carboxylate; 1-cyclohexyl-5-[4-(1,4-diazepan-1-yl)-5-fluoro-2-methoxyphenyl]-3-methyl-1,6-dihydro-7H-pyrazolo[4,3-d]pyrimidin-7-one; 1-cyclohexyl-5-{2-methoxy-4-[methyl(1-methyl-piperidinyl)amino]phenyl}-3-methyl-1,6-dihydro-7H-pyrazolo[4,3-d]pyrimidin-7-one; 1-cyclohexyl-5-[2-ethoxy-4-(1-piperazinyl)phenyl]-3-methyl-1,6-dihydro-7H-pyrazolo[4,3-d]pyrimidin-7-one; 5-[4-((3R)-3-{[tert-butyl(dimethyl)silyl]oxy}pyrrolidinyl)-2-methoxyphenyl]-1-cyclohexyl-3-methyl-1,6-dihydro-7H-pyrazolo[4,3-d]pyrimidin-7-one; 1-cyclohexyl-5-{4-[(3R)-3-hydroxypyrrolidinyl]-2-methoxyphenyl}-3-methyl-1,6-dihydro-7H-pyrazolo[4,3-d]pyrimidin-7-one; 5-[4-(1-benzyl-4-hydroxy-4-piperidinyl)-2-methoxyphenyl]-1-cyclohexyl-3-methyl-1,6-dihydro-7H-pyrazolo[4,3-d]pyrimidin-7-one; 5-[4-(1-benzyl-1,2,3,6-tetrahydro-4-pyridinyl)-2-methoxyphenyl]-1-cyclohexyl-3-methyl-1,6-dihydro-7H-pyrazolo[4,3-d]pyrimidin-7-one; 1-cyclohexyl-5-[2-methoxy-4-(1,2,3,6-tetrahydro-4-pyridinyl)phenyl]-3-methyl-1,6-dihydro-7H-pyrazolo[4,3-d]pyrimidin-7-one monohydrochloride; 1-cyclohexyl-5-{2-methoxy-4-[methyl(tetrahydro-2H-pyran-4-yl)amino]phenyl}-3-methyl-1,6-dihydro-7H-pyrazolo[4,3-d]pyrimidin-7-one; and 1-cyclohexyl-5-[4-(ethylamino)-2-methoxyphenyl]-3-methyl-1,6-dihydro-7H-pyrazolo[4,3-d]pyrimidin-7-one.

The compounds of the formula (IA) according to the present invention can be synthesized, for example, by the methods shown below.

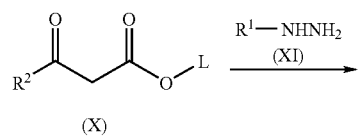

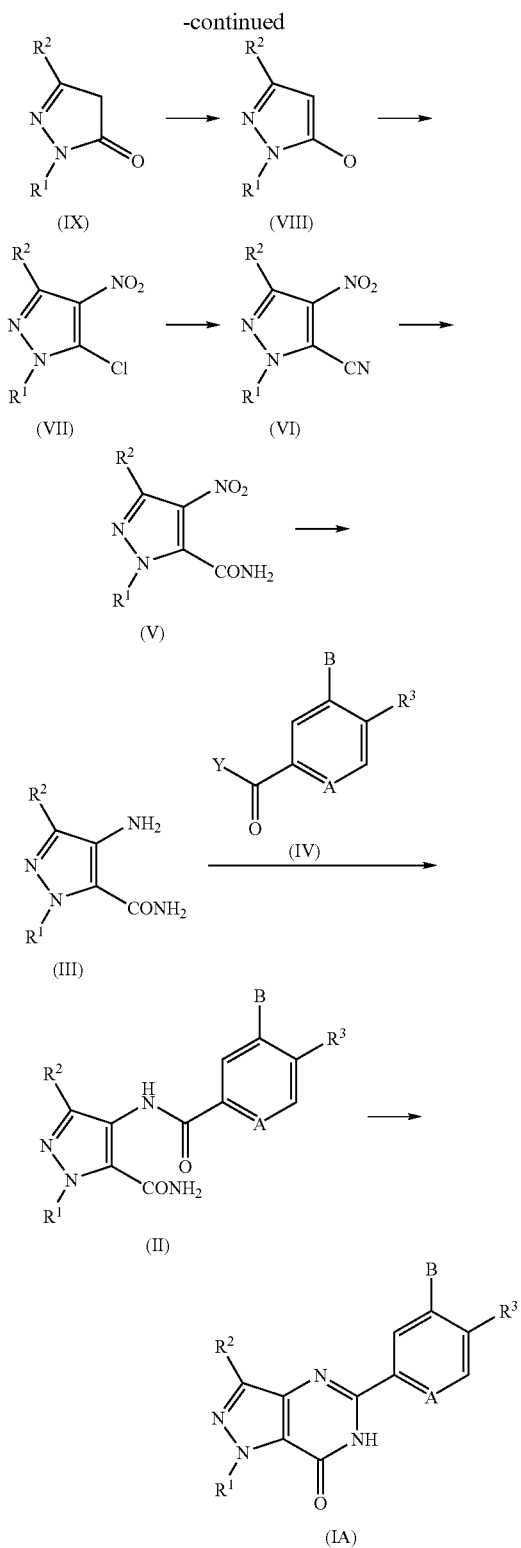

where A, B, $R^1$, $R^2$ and $R^3$ are as defined earlier, L represents a $C_{1-3}$ lower alkyl group, and Y represents a hydroxyl group or a halogen atom, preferably, a chlorine atom.

To carry out the above methods, the compound (IX) is obtained from the compound (X) according to a publicly known method. According this reaction, the compound (XI) in an amount of 1 to 2 equivalents, preferably about 1 equivalent, relative to the compound (X), is reacted with the compound (X) at room temperature to a temperature of up to 120° C. in an aqueous solution of an inorganic acid, such as hydrochloric acid or sulfuric acid, an aromatic hydrocarbon such as benzene or toluene, an organic acid such as acetic acid, an alcohol such as methanol or ethanol, or a mixture of these substances, or in the absence of a solvent. After completion of the reaction, an aqueous solution of an inorganic base, e.g. sodium hydroxide, is added, and the mixture is extracted with an organic solvent immiscible with water. The entire organic matter is washed with water and a saturated aqueous solution of sodium chloride in this order, and then the solvent is distilled off to obtain the desired compound (IX). If desired, the product can be purified, for example, by recrystallization. As the compound (X), the starting material, a commercially available or publicly known compound can be used. The compound (XI) used in this reaction may be a commercially available or publicly known compound, but it is possible to use a compound which is easily synthesized by a publicly known method (for example, J. Org. Chem., 1981, 46, 5414-5415).

From the compound (IX), the compound (VIII) can be obtained in accordance with a publicly known method. A halogenation reagent, such as phosphorus oxychloride or thionyl chloride, in an amount of 1 to 5 equivalents, relative to the compound (IX), is caused to act on the compound (IX) at room temperature to reflux temperature in an aromatic hydrocarbon such as toluene or benzene, or in the absence of a solvent. After completion of the reaction, the solvent is distilled off, whereby the desired compound (VIII) can be obtained.

The resulting compound (VIII) can be led to the compound (VII) in accordance with a publicly known method without being purified. Nitric acid is used at −20° C. to room temperature in concentrated sulfuric acid or acetic anhydride. After completion of the reaction, the reaction mixture is poured over ice, and precipitated solids are collected by filtration, whereby the desired compound (VII) can be obtained. If desired, this compound can be purified by recrystallization or the like.

From the compound (VII), the compound (VI) can be obtained in accordance with a publicly known method. A metal cyanide, such as potassium cyanide or sodium cyanide, is used in an amount of 1 to 3 equivalents at room temperature to 120° C. in a polar solvent such as N,N-dimethylformamide. After completion of the reaction, water is added, and the mixture is extracted with an organic solvent immiscible with water. Then, the entire extract is washed with water and a saturated aqueous solution of sodium chloride in this order. By distilling off the solvent, the desired compound (VI) can be obtained. If desired, this compound can be purified by, say, column chromatography.

From the compound (VI), the compound (V) can be obtained in accordance with a publicly known method. This reaction is a method for synthesizing an acid amide by hydrolysis of the nitrile group, and many methods are available for this purpose. For example, hydrogen peroxide is caused to act at 0° C. to room temperature in water, an alcohol such as methanol or ethanol, an ether such as 1,4-dioxane or tetrahydrofuran, or a mixture of these substances in the presence of a base such as sodium hydroxide or potassium carbonate. After completion of the reaction, the reaction mixture is diluted with an organic solvent immiscible with water. Then, the dilution is washed with water and a saturated aqueous solution of sodium chloride in this order. By distilling off the solvent, the desired compound (V) can be obtained. If desired, this compound can be purified by, say, recrystallization.

From the compound (V), the compound (III) can be obtained in accordance with a publicly known method. This reaction is a method for converting the nitro group into an amino group by a reduction reaction, and many methods are available for this purpose. For example, tin dichloride in an amount of 2 to 10 equivalents, relative to the compound (V), is caused to act on the compound (V) at 0° C. to reflux temperature in an inorganic acid such as hydrochloric acid. After completion of the reaction, the reaction mixture is neutralized with an inorganic base such as sodium hydroxide, and filtered through Celite. Then, the filtrate is extracted with an organic solvent immiscible with water. The extracted organic solvent layer is washed with water and a saturated aqueous solution of sodium chloride in this order. By distilling off the solvent, the desired compound (III) can be obtained. If desired, this compound can be purified, for example, by column chromatography.

From the compound (III), the compound (II) can be obtained in accordance with a publicly known method. This reaction is a method for synthesizing an acid amide from the amine compound (III) and a carboxylic acid component (IV), and many methods are available for this purpose. For example, if Y is a halogen atom (preferably, a chlorine atom), the compound (IV) in an amount of 1 to 1.5 equivalents, preferably 1.2 equivalents, relative to the compound (III), is used at 0° C. to room temperature in an inert solvent, for example dichloromethlane, in the presence of 1 to 5 equivalents, preferably 2.5 equivalents, relative to the compound (III), of a tertiary amine, for example triethylamine, where necessary, with the use of a catalyst, for example, 4-dimethylaminopyridine. If Y is a hydroxyl group, the reaction is performed using the compound (IV) in an amount of 1 to 1.5 equivalents, preferably 1.2 equivalents, relative to the compound (III), at 0° C. to room temperature in an inert solvent, for example dichloromethane, in the presence of 1 to 1.5 equivalents, preferably 1.2 equivalents, relative to the compound (III), of a condensation agent, for example 1-ethyl-3-(3-dimethylaminopropyl)carbodiimide hydrochloride, where necessary, with the use of a catalyst, for example, 4-dimethylaminopyridine. After completion of the reaction, the reaction mixture is diluted with an organic solvent immiscible with water. Then, the dilution is washed with water and a saturated aqueous solution of sodium chloride in this order. By distilling off the solvent, the desired compound (II) can be obtained. If desired, this compound can be purified, for example, by column chromatography.

From the compound (II), the compound (IA) can be obtained by use of a cyclization method publicly known in connection with the formation of a pyrimidine ring (for example, Bioorg. Med. Chem. Lett., 6, 1996, 1819-1824). For example, cyclization can be performed by reacting the compound (II) at room temperature to reflux temperature in an ethanol-water solvent with the use of a base, such as sodium hydroxide or potassium carbonate, where necessary, in the presence of hydrogen peroxide. After completion of the reaction, the reaction mixture is diluted with an organic solvent immiscible with water. Then, the dilution is washed with water and a saturated aqueous solution of sodium chloride in this order. By distilling off the solvent, the desired compound (IA) can be obtained. If desired, this compound can be purified, for example, by column chromatography or recrystallization.

As an alternative method for synthesizing the compound (IA), this compound can be synthesized, for example, by the methods shown below.

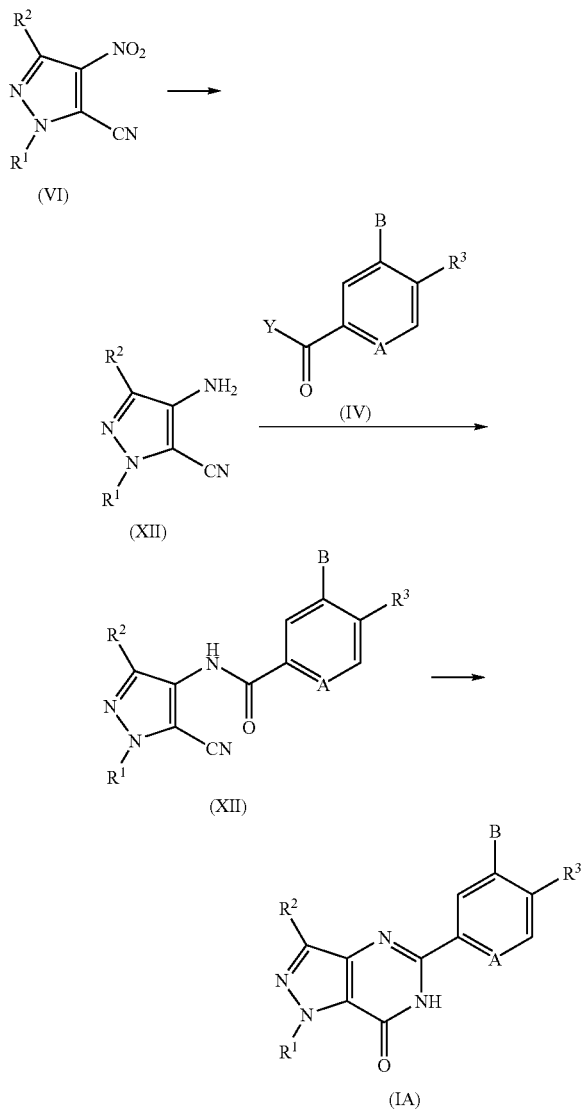

where A, B, $R^1$, $R^2$ and $R^3$ are as defined earlier, and Y represents a hydroxyl group or a halogen atom, preferably, a chlorine atom.

From the compound (VI), the compound (XIII) can be obtained in accordance with a publicly known method. This reaction is a method for converting the nitro group into an amino group by a reduction reaction, and many methods are available for this purpose. For example, tin dichloride in an amount of 2 to 10 equivalents, relative to the compound (VI), is caused to act on the compound (VI) at 0° C. to reflux temperature in an inorganic acid such as hydrochloric acid. After completion of the reaction, the reaction mixture is neutralized with an inorganic base such as sodium hydroxide, and filtered through Celite. Then, the filtrate is extracted with an organic solvent immiscible with water. The extracted organic solvent is washed with water and a saturated aqueous solution of sodium chloride in this order. By distilling off the solvent, the desired compound (XIII) can be obtained. If desired, this compound can be purified, for example, by column chromatography.

From the compound (XIII), the compound (XII) can be obtained in accordance with a publicly known method. This reaction is a method for synthesizing an acid amide from the amine compound (XIII) and a carboxylic acid component (IV), and many methods are available for this purpose. For example, if Y is a halogen atom (preferably, a chlorine atom), the compound (IV) in an amount of 1 to 1.5 equivalents, preferably 1.2 equivalents, relative to the compound (XIII), is used at 0° C. to room temperature in an inert solvent, for example dichloromethane, in the presence of 1 to 5 equivalents, preferably 2.5 equivalents, relative to the compound (XIII), of a tertiary amine, for example triethylamine, where necessary, with the use of a catalyst, for example, 4-dimethylaminopyridine. Pyridine may be used as a solvent in place of the tertiary amine. If Y is a hydroxyl group, the reaction is performed using the compound (IV) in an amount of 1 to 1.5 equivalents, preferably 1.2 equivalents, relative to the compound (XIII), at 0° C. to room temperature in an inert solvent, for example dichloromethane, in the presence of 1 to 1.5 equivalents, preferably 1.2 equivalents, relative to the compound (XIII), of a condensation agent, for example 1-ethyl-3-(3-dimethylaminopropyl)carbodiimide hydrochloride, where necessary, with the use of a catalyst, for example, 4-dimethylaminopyridine. After completion of the reaction, the reaction mixture is diluted with an organic solvent immiscible with water. Then, the dilution is washed with water and a saturated aqueous solution of sodium chloride in this order. By distilling off the solvent, the desired compound (XII) can be obtained. If desired, this compound can be purified, for example, by column chromatography.

From the resulting compound (XII), the compound (IA) can be obtained by use of a cyclization method publicly known in connection with the formation of a pyrimidine ring (for example, J. Med. Chem., 30, 1987, 91-96). For example, cyclization can be performed by reacting the compound (XII) at room temperature to reflux temperature in water or an alcohol such as ethanol, an ether such as 1,4-dioxane, or a solvent mixture of these solvents with the use of a base, such as sodium hydroxide or potassium carbonate, where necessary, in the presence of hydrogen peroxide. After completion of the reaction, the reaction mixture is diluted with an organic solvent immiscible with water. Then, the dilution is washed with water and a saturated aqueous solution of sodium chloride in this order. By distilling off the solvent, the desired compound (IA) can be obtained. If desired, this compound can be purified, for example, by column chromatography or recrystallization.

The above-described reactions are all completely general, and suitable reagents and conditions for execution of these reactions can be immediately established by reference to standard textbooks and the Examples to be described later. Alternative methods and modified methods, which can prepare all the compounds defined as the compounds (IA), are clear to any one of ordinary skill in the art.

The compounds of the formula (IB) according to the present invention can be synthesized, for example, by the methods shown below.

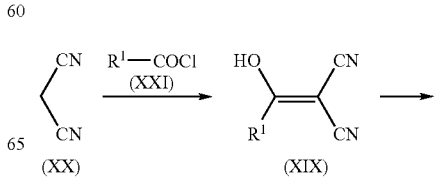

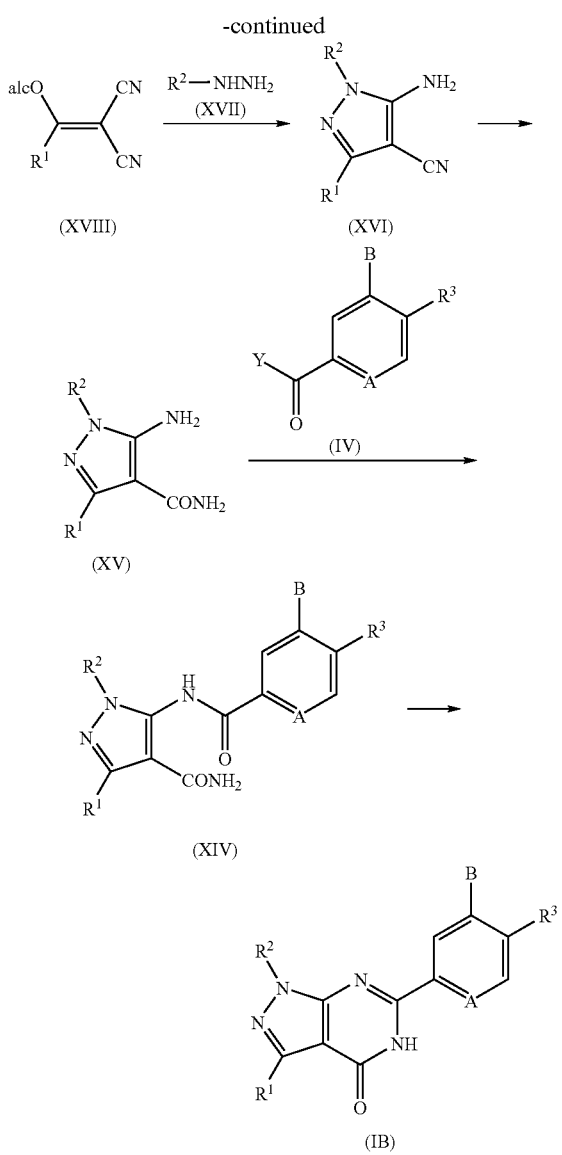

where A, B, $R^1$, $R^2$ and $R^3$ are as defined earlier, and Y represents a hydroxyl group or a halogen atom, preferably, a chlorine atom.

To carry out the above methods, the compound (XIX) can be obtained from the compound (XX) in accordance with a publicly known method (for example, J. Chem. Soc., Perkin Trans. 1, 1996, 1545-1552). The compound (XXI) in an amount of 1 to 1.5 equivalents, relative to the compound (XX), is caused to act thereon at 0° C. to room temperature in a halogenated hydrocarbon such as methylene chloride, an aromatic hydrocarbon such as toluene or benzene, an ether such as diethyl ether or tetrahydrofuran, or a mixture of these substances, in the presence of 2 to 2.5 equivalents, relative to the compound (XX), of an alkali metal hydride, such as sodium hydride or potassium hydride, or the same amount of a tertiary amine such as triethylamine. After completion of the reaction, the reaction mixture is diluted with an organic solvent immiscible with water. Then, the dilution is washed with water and a saturated aqueous solution of sodium chloride in this order. By distilling off the solvent, the desired compound (XIX) can be obtained. If desired, the product can be purified, for example, by column chromatography.

From the resulting compound (XIX), the compound (XVIII) can be obtained in accordance with a publicly known method (for example, J. Chem. Soc., Perkin Trans. 1, 1996, 1545-1552). A methylation reagent, such as dimethylsulfuric acid, in an amount of 5 to 10 equivalents, relative to the compound (XIX), is used therefor at room temperature to reflux temperature in an aromatic hydrocarbon such as toluene or benzene, an ether such as tetrahydrofuran or 1,4-dioxane, or a mixture of these substances. After completion of the reaction, the reaction mixture is diluted with an organic solvent immiscible with water. Then, the dilution is washed with water and a saturated aqueous solution of sodium chloride in this order. By distilling off the solvent, the desired compound (XVIII) can be obtained. If desired, the product can be purified, for example, by column chromatography.

From the resulting compound (XVIII), the compound (XVI) can be obtained in accordance with a publicly known method (for example, J. Chem. Soc., Perkin Trans. 1, 1996, 1545-1552). The compound (XVII) in an amount of 1 to 1.5 equivalents, relative to the compound (XVIII), is used therefor at room temperature to reflux temperature in an alcohol such as ethanol, an ether such as tetrahydrofuran or 1,4-dioxane, or a mixture of these substances. After completion of the reaction, the solvent is distilled off, whereby the desired compound (XVI) can be obtained. If desired, the product can be purified, for example, by column chromatography.

From the compound (XVI), the compound (XV) can be obtained in accordance with a publicly known method. This reaction is a method for synthesizing an acid amide by hydrolysis of the nitrile group, and many methods are available for this purpose. For example, a catalyst such as sulfuric acid or hydrochloric acid is caused to act at room temperature to 100° C. in water, an alcohol such as ethanol or methanol, an ether such as diethyl ether, tetrahydrofuran or dioxane, or a mixture of these substances. After completion of the reaction, the reaction mixture is rendered weakly alkaline, and diluted with an organic solvent immiscible with water. Then, the dilution is washed with water and a saturated aqueous solution of sodium chloride in this order. By distilling off the solvent, the desired compound (XV) can be obtained. If desired, this compound can be purified by, say, recrystallization.

From the resulting compound (XV), the compound (XIV) can be obtained in accordance with a publicly known method. Generally, if Y is a halogen atom (preferably, a chlorine atom), the compound (IV) in an amount of 1 to 2 equivalents, preferably about 1.4 equivalents, relative to the compound (XV), is used at 0° C. to room temperature in an inert solvent, for example dichloromethane, in the presence of 1 to 5 equivalents, preferably about 2.5 equivalents, relative to the compound (XV), of a tertiary amine, for example triethylamine, where necessary, with the use of a catalyst, for example, 4-dimethylaminopyridine. Pyridine may be used as a solvent in place of the tertiary amine. If Y is a hydroxyl group, the reaction is performed using the compound (IV) in an amount of 1 to 1.5 equivalents, preferably about 1.2 equivalents, relative to the compound (XV), at 0° C. to room temperature in an inert solvent, for example dichloromethane, in the presence of 1 to 1.5 equivalents, preferably about 1.2 equivalents, relative to the compound (XV), of a condensation agent, for example 1-ethyl-3-(3-dimethylaminopropyl)carbodiimide hydrochloride, where necessary, with the use of a catalyst, for example, 4-dimethylaminopyridine. After completion of the reaction, the reaction mixture is diluted with an organic solvent immiscible with water. Then, the dilution is washed with water and a saturated aqueous solution of sodium chloride in this order. By distilling off the solvent, the desired compound (XIV) can be obtained.

The resulting compound (XIV) is used without being purified, and the compound (IB) can be obtained by use of a cyclization method publicly known in connection with the formation of a pyrimidine ring (for example, J. Med. Chem., 39, 1996, 1635-1644). Hence, cyclization can be performed by reacting the compound (XIV) at reflux temperature in an ethanol-water solvent with the use of a base, such as sodium hydroxide or potassium carbonate, where necessary, in the presence of hydrogen peroxide. After completion of the reaction, the reaction mixture is diluted with an organic solvent immiscible with water. Then, the dilution is washed with water and a saturated aqueous solution of sodium chloride in this order. By distilling off the solvent, the desired compound (IB) can be obtained. If desired, this compound can be purified, for example, by column chromatography or recrystallization.

The above-described reactions are all completely general, and suitable reagents and conditions for execution of these reactions can be immediately established by reference to standard textbooks and the Examples to be described later. Alternative methods and modified methods, which can prepare all the compounds defined as the compounds (IB), are clear to any one of ordinary skill in the art.

The present invention will be described in further detail by reference to Test Examples, Examples, and Production Examples.

Synthesis of the compounds of the present invention, and intermediates for use therein will be described in detail by the Examples and the Production Examples to be offered later. The chemical structures of and identification data on the compounds of the present invention and their intermediates, which were produced in the Examples and the Production Examples, are listed in Tables presented behind the Examples. The respective compounds in the Examples and the Production Examples are described as the corresponding Example Nos. and Production Example Nos. in the Tables.

It goes without saying that the scope of the present invention is not restricted by these Test Examples, Examples, and Production Examples.

EXAMPLES

The inhibitory activity, against PDE7 (type VII phosphodiesterase), of the compounds of the present invention produced in the following Production Examples and the following Examples was confirmed by the Test Examples shown below.

Test Example 1

Method of Measuring PDE7 Inhibiting Activity

To evaluate the compounds of the present invention for the ability to suppress PDE7 (type VII phosphodiesterase), the method of Biochemical Pharmacol. 48(6), 1219-1223 (1994) was partially modified to perform the following assay:

1) PDE7 (type VII phosphodiesterase) active fraction was obtained. That is, human acute lymphoblastoid lymphoma T cell strain MOLT-4 (purchasable from ATCC under ATCC No. CRL-1582) was cultured in RPMI1640 medium containing 10% fetal bovine serum to obtain $5 \times 10^8$ MOLT4 cells. The cells were harvested by centrifugation, and suspended in 10 ml of buffer A (25 mM tris-HCl, 5 mM 2-mercaptoethanol, 2 mM benzamidine, 2 mM EDTA, 0.1 mM 4-(2-aminoethyl)benzenesulfonyl hydrochloride, pH 7=7.5). The cells were homogenized in a Polytoron homogenizer, and centrifuged (4° C., 25,000 G, 10 min). The supernatant was further ultracentrifuged (4° C., 100,000 G, 60 min), and the resulting supernatant was filtered through a 0.2 μm filter to obtain a soluble fraction.

2) HiTrapQ column (5 ml×2) equilibrated with buffer A was charged with the resulting soluble fraction. Phosphodiesterase was eluted using 300 ml of buffer A containing a linear gradient solution of 0 to 0.8M sodium chloride to collect sixty 5 ml fractions. Each fraction was tested for cAMP metabolizing phosphodiesterase activity. O f the respective fractions, those fractions were selected which had the activity of metabolizing cAMP and whose metabolic activity was not eliminated by 10 μM rolipram (selective inhibitor of type IV phosphodiesterase) or 10 μM milrinone (selective inhibitor of type III phosphodiesterase). Of these selected fractions, fractions eluted as active peaks mainly around 350 mM sodium chloride were combined, and used as a stored solution for testing PDE7 inhibiting activity.

3) The test compounds at desired concentrations were each reacted for 2 hours at 25° C. in a reactant mixture containing 20 mM tris-HCl (pH 7.5), 1 mM $MgCl_2$, 100 μM EDTA, 330 μg/ml bovine serum albumin, 4 μg/ml 5'-nucleotidase, 0.1 μ$Ci^3$H-cAMP (0.064 μM cAMP), 10 μM rolipram, and the type VII phosphodiesterase stored solution. QAE-Sephadex suspended in 10 mM HEPES-Na (pH 7.0) was added to the reaction mixture, and the mixture was allowed to stand for 5 minutes. Then, the supernatant was recovered, and QAE-Sephadex was further added, followed by allowing the mixture to stand for 5 minutes. Then, the resulting supernatant was measure for radioactivity.

4) $IC_{50}$, as the concentration of the test compound that inhibited 50% of the metabolic activity of PDE7, was calculated for each of the compounds.

PDE7 Inhibiting Activity of each Compound

The following are the Example Nos. of the compounds whose $IC_{50}$ values for phosphodiesterase inhibiting activities measured by the above-described method were 1 μM or less:

1, 2, 3, 4, 5, 6, 7, 8, 9, 10, 11, 12, 13, 14, 16, 17, 18, 24, 25, 27, 28, 29, 31, 32, 34, 37, 38, 39, 41, 42, 44, 45, 46, 47, 50, 51, 52, 54, 56, 57, 58, 59, 60, 62, 64, 65, 67, 68, 69, 70, 72, 73, 74, 76, 78, 81, 82, 84, 87, 90, 92, 95, 97, 99, 103, 104, 105, 107, 109, 111, 112, 115, 117, 118, 119, 121, 123, 124, 125, 126, 127, 129, 130, 132, 134, 136, 139, 140, 142, 143, 144, 145, 146, 147, 148, 150, 152, 154, 155, 156, 158, 159, 161, 163, 164, 165, 169, 172, 175, 176, 179, 185, 189, 191, 192, 194, 196, 198, 199, 200, 201, 203, 204, 207, 208, 209, 210-1, 210-2, 211, 212, 213, 214, 215, 216, 217, 218, 220, 222, 224, 225, 227, 229, 230, 231, 232, 234, 235, 236, 237, 239, 241, 242, 245, 247, 250, 253, 256, 257, 258, 260, 261, 262, 263, 264, 266, 267, 268, 270, 272, 273, 275

Of these compounds, the compounds with the following Example Nos. showed $IC_{50}$ values of 0.01 μM or less:

27, 28, 31, 32, 38, 44, 46, 47, 51, 52, 60, 62, 73, 76, 78, 81, 82, 84, 87, 90, 92, 95, 97, 103, 104, 107, 109, 111, 117, 121, 125, 132, 134, 136, 140, 142, 143, 144, 145, 148, 150, 152, 154, 155, 163, 185, 192, 224, 225, 227, 230, 232, 250, 260, 261, 262, 263

The above phosphodiesterase inhibiting activity tests confirmed the pyrazolopyrimidinone derivatives of the present invention to show a very satisfactory effect of inhibiting PDE7.

The compounds of the present invention were inhibitors selective for PDE7, and showed selectivities 10 times or more that for other phosphodiesterase isozymes. From these findings, few side effects due to other isozymes are expected.

As an example, the inhibitory activity, against PDE4 (type IV phosphodiesterase), of the compounds of the present invention was confirmed by the test shown below.

Test Example 2

Method of Measuring PDE4 Inhibiting Activity

To evaluate the compounds of the present invention, which suppress PDE7, for the ability to suppress PDE4, the method of Biochemical Pharmacol. 48(6), 1219-1223 (1994) was partially modified to perform the following assay:

1) PDE4 active fraction was obtained. That is, livers obtained from three Balb/c mice (female, 12-week-old) (purchasable from CLEA JAPAN) were suspended in 30 ml of buffer B (20 mM bis-tris, 5 mM 2-mercaptoethanol, 2 mM benzamidine, 2 mM EDTA, 0.1 mM 4-(2-aminoethyl)benzenesulfonyl hydrochloride, 50 mM sodium acetate, pH=6.5). The livers were homogenized in a Polytoron homogenizer, and centrifuged (4° C., 25,000 G, 10 min). Then, the supernatant was further ultracentrifuged (4° C., 100,000 G, 60 min), and the resulting supernatant was filtered through a 0.2 μm filter to obtain a soluble fraction.

2) 1×10 cm DEAE Sepharose column equilibrated with buffer B was charged with the resulting soluble fraction. Phosphodiesterase was eluted using 120 ml of buffer B containing a linear gradient solution of 0.05 to 1M sodium acetate to collect twenty-four 5 ml fractions. Each fraction was tested for cAMP metabolizing phosphodiesterase activity. Of the respective fractions, those fractions were selected which had the activity of metabolizing cAMP and whose metabolic activity was eliminated by 30 μM rolipram (selective inhibitor of PDE4). Of these selected fractions, fractions eluted as active peaks mainly around 620 mM sodium acetate were combined, and used as a stored solution for testing PDE4 inhibiting activity.

3) The test compounds at desired concentrations were each reacted for 2 hours at 25° C. in a reactant mixture containing 20 mM tris-HCl (pH 7.5), 1 mM $MgCl_2$, 100 μM EDTA, 330 μg/ml bovine serum albumin, 4 μg/ml 5'-nucleotidase, 0.1 μCi$^3$H-cAMP (0.064 μM cAMP), and the PDE4 stored solution. QAE-Sephadex suspended in 10 mM HEPES-Na (pH 7.0) was added to the reaction mixture, and the mixture was allowed to stand for 5 minutes. Then, the supernatant was recovered, and QAE-Sephadex was further added, followed by allowing the mixture to stand for 5 minutes. Then, the resulting supernatant was measure for radioactivity.

4) $IC_{50}$, as the concentration of the test compound that inhibited 50% of the metabolic activity of PDE4, was calculated for each of the compounds.

The above tests showed that the $IC_{50}$ values of the compounds of the present invention against PDE4 were 10 times or more as weak as the inhibitory activities of the same compounds against PDE7.

The compounds of the present invention selectively inhibit PDE7 to increase the intracellular cAMP level and further inhibit the activation of T cells. Thus, these compounds are useful in dealing with various allergic diseases and inflammatory or immunological diseases. That is, they are useful as agents for prevention or treatment of diseases, such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, sepsis, Crohn disease, rejection reaction in transplantation, GVH disease, and restenosis after angioplasty.

To use the active ingredients of the present invention as pharmaceutical compositions or PDE7 inhibitors, it is recommendable to prepare compositions containing one or more of the compounds of the present invention and process them into dosage forms suitable for the mode of administration in accordance with customary methods. For example, dosage forms such as capsules, tablets, granules, fine granules, syrups, and dry syrups are exemplified for oral administration. Not only injections, but suppositories including vaginal suppositories, transnasal preparations such as sprays, and percutaneously absorbable preparations such as ointments and transdermally absorbable tapes are exemplified for parenteral administration.

The dose of the compound of the present invention for clinical use differs according to the symptoms of the patient to receive administration, the severity of the disease, the age of the patient, and the presence or absence of complication of the disease. The dose also differs according to the type of the preparation. For oral administration, the compound as the active ingredient may be administered usually in a daily dose, for adults, of 0.1 to 1,000 mg, preferably 0.1 to 500 mg, more preferably 1 to 100 mg. For parenteral administration, the dose may be a tenth or a half of the oral dose. These doses can be increased or decreased, as desired, depending on the patient's age and symptoms.

Furthermore, the compounds of the present invention are expected to be low in toxicity and high in safety.

Examples and Production Examples

Synthesis of the compounds of the present invention, and intermediates for use therein will be described by the Examples and the Production Examples to be offered below. The chemical structures of and identification data on the compounds in the following Examples and Production Examples will be summarized in Tables presented later. The compounds in the Examples and the Production Examples are described as Example Nos. and Production Example Nos. in the Tables.

Production Example 1

2-Cyclohexyl-5-methyl-2,4-dihydro-3H-pyrazol-3-one

A mixture of 14.5 ml (0.134 mol) of methyl acetoacetate and 20.2 g (0.134 mol) of cyclohexylhydrazine hydrochloride was stirred at 120° C. for 2 hours, and then cooled. The reaction mixture was neutralized with 30 ml of a 4M aqueous solution of sodium hydroxide, and extracted with ethyl acetate. The organic layer was washed with water and a saturated aqueous solution of sodium chloride, dried over anhydrous sodium sulfate, and distilled under reduced pressure to remove the solvent. Hexane was added to the residue, and precipitated crystals were collected by filtration to obtain 19.0 g (79%) of the captioned compound.

Production Example 2

5-Chloro-1-cyclohexyl-3-methyl-4-nitro-1H-pyrazole

To 9.3 g (51.6 mmol) of the compound obtained in Production Example 1, 10 ml (107 mmol) of phosphorus oxychloride was added, and the mixture was stirred for 10 hours at 120° C. Then, the reaction mixture was brought to room temperature, and the excess phosphorus oxychloride was distilled off under reduced pressure. The residue was dissolved by addition of 45 ml of acetic anhydride and, to this solution, 9 ml of fuming nitric acid was slowly added dropwise with cooling with ice. After the mixture was stirred for 2 hours at the same temperature, the reaction mixture was poured over ice, and solids were collected by filtration. The solids were dissolved in dichloromethane, and the solution was washed with an aqueous solution of sodium hydrogen carbonate, water, and a saturated aqueous solution of sodium chloride. Then, the washed solution was dried over anhydrous sodium sulfate, and the solvent was distilled off under reduced pressure. The residue was recrystallized (hexane) from hexane for purification to obtain 6.28 g (50%) of the captioned compound. Also, the filtrate was distilled under reduced pressure, and the residue was purified by silica gel column chromatography (hexane/ethyl acetate=6/1) to obtain 4.21 g (33%) of the captioned compound.

Production Example 3

1-Cyclohexyl-3-methyl-4-nitro-1H-pyrazole-5-carbonitrile

To a 90 ml N,N-dimethylformamide solution of 10.3 g (42.4 mmol) of the compound obtained in Production Example 2, 4.2 g (84.9 mmol) of sodium cyanide was added, followed by stirring the mixture for 1.5 hours at 80° C. Then, the reaction mixture was brought to room temperature, water was added thereto, and the mixture was extracted with dichloromethane. The organic layer was washed with water and a saturated aqueous solution of sodium chloride. Then, the washed solution was dried over anhydrous sodium sulfate, and the solvent was distilled off under reduced pressure. The residue was purified by silica gel column chromatography (hexane/ethyl acetate=6/1) to obtain 9.18 g (93%) of the captioned compound.

Production Example 4

4-Amino-1-cyclohexyl-3-methyl-1H-pyrazole-5-carbonitrile

To a mixed suspension, in 10 ml of methanol and 10 ml of concentrated hydrochloric acid, of 1.0 g (4.27 mmol) of the compound obtained in Production Example 3, 1.2 g (21.4 mmol) of iron powder was added, followed by heating the mixture under reflux for 2 hours. Then, the reaction mixture was brought to room temperature, neutralized with an aqueous solution of sodium hydrogen carbonate, and then filtered through Celite. The filtrate was extracted with dichloromethane, and the organic layer was washed with water and a saturated aqueous solution of sodium chloride. Then, the washed layer was dried over anhydrous sodium sulfate, and the solvent was distilled off under reduced pressure. The residue was purified by silica gel column chromatography (hexane/ethyl acetate=7/1) to obtain 0.75 g (87%) of the captioned compound.

Production Example 5

1-Cyclohexyl-3-methyl-4-nitro-1H-pyrazole-5-carboxamide

To a 25 ml methanol solution of 9.0 g (38.5 mmol) of the compound obtained in Production Example 3, 12 ml of a 30% aqueous solution of hydrogen peroxide and 30 ml of a 3M aqueous solution of sodium hydroxide were added, followed by stirring the mixture for 1.5 hours at room temperature. Then, the reaction mixture was diluted with water, and extracted with dichloromethane. The organic layer was washed with water and a saturated aqueous solution of sodium chloride, and dried over anhydrous sodium sulfate. Then, the solvent was distilled off under reduced pressure to obtain 7.8 g (80%) of the captioned compound.

Production Example 6

4-Amino-1-cyclohexyl-3-methyl-1H-pyrazole-5-carboxamide

To a 180 ml concentrated hydrochloric acid suspension of 7.7 g (30.6 mmol) of the compound obtained in Production Example 5, 27.6 g (122 mmol) of tin dichloride dihydrate was added, and the mixture was stirred for 1.5 hours at 80° C. Then, the reaction mixture was brought to room temperature, neutralized with an aqueous solution of sodium hydroxide, and then filtered through Celite. The filtrate was extracted with dichloromethane, and the organic layer was washed with water and a saturated aqueous solution of sodium chloride. Then, the washed layer was dried over anhydrous sodium sulfate, and the solvent was distilled off under reduced pressure. The residue was purified by silica gel column chromatography (ethyl acetate) to obtain 6.05 g (89%) of the captioned compound.

Production Example 7

N-(5-cyano-1-cyclohexyl-3-methyl-1H-pyrazol-4-yl)benzamide

To a 2 ml pyridine solution of 188 mg (0.92 mmol) of the compound obtained in Production Example 4, 0.13 ml (1.11 mmol) of benzoyl chloride was added at 0° C., and the mixture was stirred for 3 hours at the same temperature. Then, an aqueous solution of sodium hydrogen carbonate was added to the reaction mixture, and the mixture was extracted with ethyl acetate. The organic layer was washed with water and a saturated aqueous solution of sodium chloride, and dried over anhydrous sodium sulfate. Then, the solvent was distilled off under reduced pressure, and the residue was purified by recrystallization (ethanol) to obtain 141 mg (50%) of the captioned compound.

Production Example 8

N-(5-cyano-1-cyclohexyl-3-methyl-1H-pyrazol-4-yl)-4-nitrobenzamide

The same reaction as in Production Example 7 was performed, except that p-nitrobenzoyl chloride was used in place of benzoyl chloride. In this manner, 389 mg (55%) of the captioned compound was obtained.

Production Example 9

1-Cyclohexyl-4-[(2-methoxybenzoyl)amino]-3-methyl-1H-pyrazole-5-carboxamide

A 1 ml (13.7 mmol) thionyl chloride solution of 136 mg (0.89 mmol) of o-anisic acid was heated under reflux for 2 hours. Then, the excess thionyl chloride was distilled off under reduced pressure to obtain o-anisic acid chloride.

To the above acid chloride, a 5 ml anhydrous dichloromethane suspension of 180 mg (0.81 mmol) of the compound obtained in Production Example 6, and 0.28 ml (2.03 mmol) of triethylamine were added, and the mixture was stirred for 30 minutes at room temperature. Then, an aqueous solution of sodium hydrogen carbonate was added to the reaction mixture, and the mixture was extracted with dichloromethane. The organic layer was washed with water and a saturated aqueous solution of sodium chloride, and dried over anhydrous sodium sulfate. Then, the solvent was distilled off under reduced pressure, and the residue was purified by silica gel column chromatography (hexane/ethyl acetate=1/1~1/2) to obtain 267 mg (93%) of the captioned compound.

Production Example 10

1-Cyclohexyl-4-[(2-ethoxybenzoyl)amino]-3-methyl-1H-pyrazole-5-carboxamide

The same reaction as in Production Example 9 was performed, except that 2-ethoxybenzoic acid was used in place of o-anisic acid. In this manner, 200 mg (99%) of the captioned compound was obtained.

Production Example 11

N-[5-(aminocarbonyl)-1-cyclohexyl-3-methyl-1H-pyrazol-4-yl]-2-pyridinecarboxamide To a 2 ml anhydrous dichloromethane suspension of 150 mg (0.68 mmol) of the compound obtained in Production Example 6, 144 mg (0.81 mmol) of 2-picolinic acid chloride and 0.21 ml (1.49 mmol) of triethylamine were added, and the mixture was stirred for 30 minutes at room temperature. Then, an aqueous solution of sodium hydrogen carbonate was added to the reaction mixture, and the mixture was extracted with dichloromethane. The organic layer was washed with water and a saturated aqueous solution of sodium chloride, and dried over anhydrous sodium sulfate. Then, the solvent was distilled off under reduced pressure. The residue was purified by recrystallization (ethyl acetate) to obtain 178 mg (80%) of the captioned compound.

Production Example 12

1-Cyclohexyl-3-methyl-4-{[4-(4-methyl-1-piperazinyl)benzoyl]amino}-1H-pyrazole-5-carboxamide To a 3 ml anhydrous dichloromethane suspension of 150 mg (0.68 mmol) of the compound obtained in Production Example 6, 214 mg (0.81 mmol) of 4-(4-methyl-1-piperazinyl)benzoic acid, 143 mg (0.743 mmol) of 1-ethyl-3-(3-dimethylaminopropyl)carbodiimide hydrochloride, and a catalytic amount of 4-dimethylaminopyridine were added, followed by stirring the mixture for 20 hours at room temperature. Then, water was added to the reaction mixture, and the mixture was extracted with dichloromethane. The organic layer was washed with water and a saturated aqueous solution of sodium chloride, and dried over anhydrous sodium sulfate. Then, the solvent was distilled off under reduced pressure. The residue was purified by recrystallization (ethyl acetate-hexane) to obtain 119 mg (42%) of the captioned compound.

Production Example 13

1-Cyclohexyl-4-[(2-methoxy-4-nitrobenzoyl)amino]-3-methyl-1H-pyrazole-5-carboxamide The same reaction as in Production Example 9 was performed, except that 2-methoxy-4-nitrobenzoic acid was used in place of o-anisic acid. In this manner, 301 mg (67%) of the captioned compound was obtained.

Production Example 14

N-[5-(aminocarbonyl)-1-cyclohexyl-3-methyl-1H-pyrazol-4-yl]-5-nitro-2-pyridinecarboxamide To a 5 ml anhydrous dichloromethane suspension of 500 mg (2.25 mmol) of the compound obtained in Production Example 6, 453 mg (2.70 mmol) of 5-nitro-2-pyridinecarboxylic acid and 518 mg (2.70 mmol) of 1-ethyl-3-(3-dimethylaminopropyl)carbodiimide hydrochloride were added, and the mixture was stirred for 20 hours at room temperature. Then, precipitated solids were collected by filtration, washed with water, and then dried to obtain 588 mg (70%) of the captioned compound.

Production Example 15

N-[5-(aminocarbonyl)-1-cyclohexyl-3-methyl-1H-pyrazol-4-yl]-4-chloro-2-pyridinecarboxamide To a 3 ml anhydrous dichloromethane suspension of 500 mg (2.25 mmol) of the compound obtained in Production Example 6, 426 mg (2.70 mmol) of 4-chloropicolinic acid and 518 mg (2.70 mmol) of 1-ethyl-3-(3-dimethylaminopropyl)carbodiimide hydrochloride were added while cooled with ice, followed by stirring the mixture for 3 hours at the same temperature. Then, water was added to the reaction mixture, and the mixture was extracted with dichloromethane. The organic layer was washed with water and a saturated aqueous solution of sodium chloride, and dried over anhydrous sodium sulfate. Then, the solvent was distilled off under reduced pressure. The residue was purified by silica gel column chromatography (hexane/ethyl acetate=1/1) to obtain 741 mg (91%) of the captioned compound.

Production Example 16

1-Cyclohexyl-4-[(5-fluoro-2-methoxybenzoyl)amino]-3-methyl-1H-pyrazole-5-carboxamide The same reaction as in Production Example 15 was performed, except that 5-fluoro-2-methoxybenzoic acid was used in place of 4-chloropicolinic acid. In this manner, 272 mg (81%) of the captioned compound was obtained.

Production Example 17 t-Butyl 2-(4-methylcyclohexylidene)hydrazinecarboxylate

To a 230 ml hexane solution of 23.6 ml (192 mmol) of 4-methylcyclohexanone, 25.5 g (192 mg) of t-butyl carbazate was added, followed by heating the mixture under reflux for 20 minutes. Then, the reaction mixture was brought to room temperature, and precipitated solids were collected by filtration to obtain 38.7 g (89%) of the captioned compound.

Production Example 18

5-Methyl-2-(4-methylcyclohexyl)-2,4-dihydro-3H-pyrazol-3-one (cis/trans mixture)

To 35.8 g (158 mmol) of the compound obtained in Production Example 17, 147 ml of borane-tetrahydrofuran complex (1.08 mol/l in tetrahydrofuran 158 mmol) was added, followed by stirring the mixture for 15 minutes at room temperature. Then, 79 ml of 6M hydrochloric acid was added dropwise, and the mixture was heated under reflux for 20 minutes. The reaction mixture was brought to room temperature, and then distilled under reduced pressure. Then, tetrahydrofuran was added to the residue, and the insolubles were filtered off. The filtrate was distilled under reduced pressure to obtain crude crystals of 1-(4-methylcyclohexyl)hydrazine hydrochloride. These crude crystals were not further purified, but used unchanged, and their mixture with methyl acetoacetate was stirred for 1 hour at 120° C. Then, the reaction mixture was brought to room temperature, neutralized with an aqueous solution of sodium hydroxide, and then extracted with ethyl acetate. The organic layer was washed with water and a saturated aqueous solution of sodium chloride, and dried over anhydrous sodium sulfate. Then, the solvent was distilled off under reduced pressure. The residue was purified by silica gel column chromatography (ethyl acetate) to obtain 13.0 mg (42%) of the captioned compound as a cis-trans mixture (cis/trans=1/2).

Production Example 19

5-Chloro-3-methyl-1-(4-methylcyclohexyl)-4-nitro-1H-pyrazole (cis/trans mixture)

The same reaction procedure as in Production Example 2 was performed, except that the compound obtained in Production Example 18 was used in place of the compound obtained in Production Example 1. In this manner, 7.15 g (77%) of the captioned compound was obtained as a cis-trans mixture (cis/trans=1/2).

Production Example 20

3-Methyl-1-(4-methylcyclohexyl)-4-nitro-1H-pyrazole-5-carbonitrile (cis/trans mixture)

The same reaction procedure as in Production Example 3 was performed, except that the compound obtained in Production Example 19 was used in place of the compound obtained in Production Example 2. In this manner, 5.62 g (88%) of the captioned compound was obtained as a cis-trans mixture (cis/trans=1/2).

Production Example 21

Trans-3-methyl-1-(4-methylcyclohexyl)-4-nitro-1H-pyrazole-5-carboxamide

Production Example 22

Cis-3-methyl-1-(4-methylcyclohexyl)-4-nitro-1H-pyrazole-5-carboxamide

The same reaction procedure as in Production Example 5 was performed, except that the compound obtained in Production Example 20 was used in place of the compound obtained in Production Example 3. In this manner, 2.03 g (36%) of the compound of Production Example 21, and 1.31 g (23%) of the compound of Production Example 22 were obtained.

Production Example 23

Trans-4-amino-3-methyl-1-(4-methylcyclohexyl)-1H-pyrazole-5-carboxamide

The same reaction procedure as in Production Example 6 was performed, except that the compound obtained in Production Example 21 was used in place of the compound obtained in Production Example 5. In this manner, 1.41 g (57%) of the captioned compound was obtained.

Production Example 24

Cis-4-amino-3-methyl-1-(4-methylcyclohexyl)-1H-pyrazole-5-carboxamide

The same reaction procedure as in Production Example 6 was performed, except that the compound obtained in Production Example 22 was used in place of the compound obtained in Production Example 5. In this manner, 0.78 g (49%) of the captioned compound was obtained.

Production Example 25

Trans-3-methyl-1-(4-methylcyclohexyl)-4-{[4-(4-methyl-1-piperazinyl)benzoyl]amino}-1H-pyrazole-5-carboxamide The same reaction procedure as in Production Example 12 was performed, except that the compound obtained in Production Example 23 was used in place of the compound obtained in Production Example 6. In this manner, 211 mg (57%) of the captioned compound was obtained.

Production Example 26

Cis-3-methyl-1-(4-methylcyclohexyl)-4-{[4-(4-methyl-1-piperazinyl)benzoyl]amino}-1H-pyrazole-5-carboxamide The same reaction procedure as in Production Example 12 was performed, except that the compound obtained in Production Example 24 was used in place of the compound obtained in Production Example 6. In this manner, 196 mg (53%) of the captioned compound was obtained.

Production Example 27

Trans-4-[(2-methoxybenzoyl)amino]-3-methyl-1-(4-methylcyclohexyl)-1H-pyrazole-5-carboxamide The same reaction procedure as in Production Example 9 was performed, except that the compound obtained in Production Example 23 was used in place of the compound obtained in Production Example 6. In this manner, 192 mg (82%) of the captioned compound was obtained.

Production Example 28

Cis-4-[(2-methoxybenzoyl)amino]-3-methyl-1-(4-methylcyclohexyl)-1H-pyrazole-5-carboxamide The same reaction procedure as in Production Example 9 was performed, except that the compound obtained in Production Example 24 was used in place of the compound obtained in Production Example 6. In this manner, 143 mg (61%) of the captioned compound was obtained.

Production Example 29

2-[Cyclohexyl(hydroxy)methylene]malononitrile

To a 60 ml tetrahydrofuran solution of 3.96 g (0.06 mol) of malononitrile, 4.8 g (60% in oil, 0.12 mol) of sodium hydride was added at 0° C. in four divided portions, and the mixture was stirred for 30 minutes at 0° C. Then, cyclohexanecarboxylic acid chloride was added dropwise, and the mixture was stirred for 30 minutes at room temperature. Then, 150 ml of 1M hydrochloric acid was slowly added, and the mixture was extracted with ethyl acetate. Then, the extract was dried over anhydrous sodium sulfate, and the solvent was distilled off under reduced pressure. Recrystallization of the residue from diisopropyl ether gave 8.16 g (77%) of the captioned compound.

Production Example 30

2-[Cyclohexyl(methoxy)methylene]malononitrile

To a solution of 2.64 g (15 mmol) of the compound, obtained in Production Example 29, in a mixture of 24 ml of 1,4-dioxane and 4 ml of water, 10 g of sodium hydrogen carbonate was added at room temperature. Further, 10 ml of dimethylsulfuric acid was added dropwise over 5 minutes. After the mixture was heated for 2.5 hours at 85° C., the reaction mixture was returned to room temperature. Water was added, and the mixture was extracted with diethyl ether. The extract was dried over sodium sulfate, and then the solvent was distilled off under reduced pressure. The residue was purified by silica gel column chromatography (hexane/ethyl acetate=3/1) to obtain 2.35 g (82%) of the captioned compound.

Production Example 31-1

5-Amino-3-cyclohexyl-1-methyl-1H-pyrazole-4-carbonitrile

To a 20 ml ethanol solution of 2.3 g (12.1 mmol) of the compound obtained in Production Example 30, 0.643 ml (12.1 mmol) of methylhydrazine was added at room temperature. The mixture was heated under reflux for 5 hours. The reaction mixture was returned to room temperature, and the solvent was distilled off under reduced pressure. The residue was purified by silica gel column chromatography (methylene chloride/methanol=50/1) to obtain 1.48 g (60%) of the captioned compound.

Production Example 31-2

5-Amino-3-cyclohexyl-1-methyl-1H-pyrazole-4-carbonitrile

In a stream of nitrogen, 20.8 g (abt. 60% oil suspension 520 mmol) of sodium hydride was slowly added at 0° C. to a 260 ml tetrahydrofuran solution of 17.2 g (260 mmol) of malononitrile. Then, 35 ml (260 mmol) of cyclohexanecarbonyl chloride was added dropwise at the same temperature. After the dropwise addition, the reactant mixture was brought to room temperature, and stirred for 1.5 hours. Then, 30 ml (312 mmol) of dimethylsulfuric acid was added to the reaction mixture, and the mixture was heated under reflux for 3 hours. Then, 17.4 ml (125 mmol) of triethylamine and 13.8 ml (260 mmol) of methylhydrazine were added with ice cooling, and the mixture was heated under reflux for 1 hour. The reaction mixture was brought to room temperature, and distilled under reduced pressure. Then, water was added to the residue, and the mixture was extracted with ethyl acetate. The organic layer was washed with water and a saturated aqueous solution of sodium chloride, and dried over sodium sulfate. Then, the solvent was distilled off under reduced pressure. The residue was purified by silica gel column chromatography (chloroform/methanol=30/1~20/1) to obtain crude crystals. The crude crystals were further purified by recrystallization (hexane-ethyl acetate) to obtain 20.7 g (39%) of the captioned compound. Also, the mother liquor was purified by silica gel column chromatography (hexane/ethyl acetate=2/1) to obtain 11.3 g (21%) of the captioned compound.

Production Example 32

5-Amino-3-cyclohexyl-1-methyl-1H-pyrazole-4-carboxamide

To 25.3 g (124 mmol) of the compound obtained in Production Example 31, 75 ml of concentrated hydrochloric acid was added with ice cooling. The mixture was stirred for 15 minutes at room temperature, and further stirred for 1 hour at 60° C. Then, the reaction mixture was poured over ice, neutralized with an aqueous solution of sodium hydroxide, and then extracted with dichloromethane. The organic layer was washed with water and a saturated aqueous solution of sodium chloride, and dried over anhydrous sodium sulfate. Then, the solvent was distilled off under reduced pressure. The residue was purified by recrystallization (ethyl acetate) to obtain 20.0 g (73%) of the captioned compound.

Production Example 33

Ethyl 4-(4-hydroxy-1-piperidinyl)benzoate

To a 20 ml N,N-dimethylformamide solution of 1.0 g (5.95 mmol) of ethyl 4-fluorobenzoate, 662 mg (6.54 mmol) of 4-hydroxypiperidine and 1.23 g (8.92 mmol) of potassium carbonate were added, and the mixture was stirred for 24 hours at 120° C. The reaction mixture was returned to room temperature, and the solvent was distilled off under reduced pressure. Then, water was added to the residue, and the mixture was extracted with ethyl acetate. The organic layer was washed with a saturated aqueous solution of sodium chloride, and dried over sodium sulfate. Then, the solvent was distilled off under reduced pressure. Diethyl ether was added to the residue, and precipitated crystals were collected to obtain 234 mg (16%) of the captioned compound.

Production Example 34

4-(4-Hydroxy-1-piperidinyl)benzoic acid monohydrochloride

To a 1 ml 1,4-dioxane solution of 200 mg (0.802 mmol) of the compound obtained in Production Example 33, 2 ml of 6M hydrochloric acid was added, and the mixture was stirred at 90° C. for 1.5 hours. The reaction mixture was returned to room temperature, and the solvent was distilled off under reduced pressure to obtain 190 mg (92%) of the captioned compound.

Production Example 35

Methyl 2-hydroxy-4-(2-methoxyethoxy)benzoate

To a 50 ml tetrahydrofuran solution of 4.0 g (23.8 mmol) of methyl 2,4-dihydroxybenzoate, 7.49 g (28.5 mmol) of triphenylphosphine, 2.25 ml (28.5 mmol) of 2-methoxyethanol, and 4.5 ml (28.5 mmol) of diethyl azodicarboxylate were slowly added at 0° C. The mixture was brought to room temperature, and stirred for 1 hour. Then, the reaction mixture was diluted with ethyl acetate, and washed with water and a saturated aqueous solution of sodium chloride. The washed system was dried over sodium sulfate, and then the solvent was distilled off under reduced pressure. To the residue, 100 ml of a solution of ethyl acetate/hexane (=1/4) was added, and insoluble solids were removed by filtration. Then, the mother liquor was concentrated under reduced pressure, and the residue was purified by silica gel column chromatography (hexane/ethyl acetate=6/1) to obtain 4.71 g (87%) of the captioned compound.

Production Example 36

Methyl 2-methoxy-4-(2-methoxyethoxy)benzoate

To a 35 ml N,N-dimethylformamide solution of 4.51 g (19.9 mmol) of the compound obtained in Production Example 35, 2.48 ml (39.9 mmol) of methyl iodide and 877 mg (abt. 60% oil suspension 21.9 mmol) of sodium hydride were gradually added at 0° C. The mixture was stirred at room temperature for 2 hours. Then, 10 ml of methanol was added to the reaction mixture, and the mixture was diluted with ethyl acetate. The dilution was washed with water and a saturated aqueous solution of sodium chloride. The washed system was dried over sodium sulfate, and then the solvent was distilled off under reduced pressure. The residue was purified by silica gel column chromatography (hexane/ethyl acetate=3/1~2/1) to obtain 4.53 g (95%) of the captioned compound.

Production Example 37

2-Methoxy-4-(2-methoxyethoxy)benzoic acid

To a 41 ml methanol solution of 4.11 g (17.11 mmol) of the compound obtained in Production Example 36, 20.5 ml (20.5 mmol) of a 1M aqueous solution of sodium hydroxide was added at room temperature. The mixture was stirred at room temperature for 1 hour, and at 60° C. for 2 hours. Then, the reaction mixture was concentrated, and water was added. The aqueous layer was washed with diethyl ether, and then 21 ml of 2M hydrochloric acid was slowly added to the aqueous layer. Precipitated solids were collected by filtration to obtain 3.42 g (88%) of the captioned compound.

Production Example 38

N-benzoyl-N-(4-cyano-3-cyclohexyl-1-methyl-1H-pyrazol-5-yl)benzamide

To a 10 ml methylene chloride solution of 400 mg (1.96 mmol) of the compound obtained in Production Example 31, 409 μl (2.94 mmol) of triethylamine, 250 μl (2.15 mmol) of benzoyl chloride, and 5 mg of 4-dimethylaminopyridine were added at room temperature, and the mixture was stirred at 50° C. for 4 hours. Then, the reaction mixture was diluted with ethyl acetate, and washed with water. The washed system was dried over sodium sulfate, and then the solvent was distilled off under reduced pressure. The residue was purified by silica gel column chromatography (hexane/ethyl acetate=2/1) to obtain 333 mg (41%) of the captioned compound.

Production Example 39

Benzyl 4-methoxy-1-piperidinecarboxylate

To a 20 ml tetrahydrofuran solution of 1.87 g (7.95 mmol) of benzyl 4-hydroxy-1-piperidinecarboxylate, 413 mg (60% in oil, 10.33 mmol) of sodium hydride and 792 μl (12.72 mmol) of methyl iodide were added at 0° C., and the mixture was stirred at room temperature for 16.5 hours. Then, the reaction mixture was diluted with ethyl acetate, and washed with water. The washed system was dried over sodium sulfate, and then the solvent was distilled off under reduced pressure. The residue was purified by silica gel column chromatography (hexane/ethyl acetate=2/1) to obtain 2.08 g (94%) of the captioned compound.

Production Example 40

4-Methoxypiperidine p-toluenesulfonate

To a 40 ml methanol solution of 2.0 g (8.02 mmol) of the compound obtained in Production Example 39, 1.556 g (8.18 mmol) of p-toluenesulfonic acid and 400 mg of 5% palladium carbon were added. The mixture was stirred at room temperature in an atmosphere of hydrogen for 3 hours. Then, the catalyst was filtered off, and the solvent was distilled off under reduced pressure to obtain 2.36 g (quantitative) of the captioned compound.

Production Example 41

5-Amino-3-cycloheptyl-1-methyl-1H-pyrazole-4-carbonitrile

The same reaction procedure as in Production Example 31-2 was performed, except that cycloheptanecarbonyl chloride was used in place of cyclohexanecarbonyl chloride. In this manner, 20.83 g (55%) of the captioned compound was obtained.

Production Example 42

5-Amino-3-cycloheptyl-1-methyl-1H-pyrazole-4-carboxamide

The same reaction procedure as in Production Example 32 was performed, except that the compound obtained in Production Example 41 was used in place of the compound obtained in Production Example 31. In this manner, 16.93 g (92%) of the captioned compound was obtained.

Production Example 43

Methyl 4-(4-benzyl-1-piperazinyl)-2,5-difluorobenzoate

To a 30 ml tetrahydrofuran solution of 4.25 g (22.35 mmol) of methyl 2,4,5-trifluorobenzoate, 3.89 ml (22.35 mmol) of N-benzylpiperazine was added with ice cooling. The mixture was stirred at 0° C. for 0.5 hour, and at room temperature for 2.5 hours. Then, the reaction mixture was diluted with ethyl acetate, and the dilution was washed with water and a saturated aqueous solution of sodium chloride in this order. The washed system was dried over sodium sulfate, and then the solvent was distilled off under reduced pressure. The residue was purified by silica gel column chromatography (hexane/ethyl acetate=2/1) to obtain 2.61 g (34%) of the captioned compound.

Production Example 44

Methyl 4-(4-benzyl-1-piperazinyl)-5-fluoro-2-methoxybenzoate

To a 20 ml tetrahydrofuran solution of 2.46 g (7.10 mmol) of the compound obtained in Production Example 43, 2.06 g (28% in MeOH, 10.65 mmol) of sodium methylate was added with ice cooling. The mixture was stirred at room temperature for 13.5 hours. Then, the reaction mixture was diluted with ethyl acetate, and the dilution was washed with water and a saturated aqueous solution of sodium chloride in this order. The washed system was dried over sodium sulfate, and then the solvent was distilled off under reduced pressure. The residue was purified by silica gel column chromatography (hexane/ethyl acetate=1.5/1~1/1) to obtain 2.06 g (81%) of a 4:1 mixture of the captioned compound and methyl 2-(4-benzyl-1-piperazinyl)-5-fluoro-4-methoxybenzoate.

Production Example 45

Benzyl 4-[2-fluoro-5-methoxy-4-(methoxycarbonyl)phenyl]-1-piperazinecarboxylate To a 20 ml 1,2-dichloroethane solution of 1.37 g (3.82 mmol) of the compound obtained in Production Example 44, 818 μl (5.73 mmol) of benzyloxycarbonyl chloride was added, and the mixture was heated under reflux for 2 hours. Then, 273 μl (1.91 mmol) of benzyloxycarbonyl chloride was added, and the mixture was heated under reflux for 1 hour. Further, 273 μl (1.91 mmol) of benzyloxycarbonyl chloride was added, and the mixture was heated under reflux for 0.5 hour. Then, the reaction mixture was returned to room temperature, and the solvent was distilled off under reduced pressure. The residue was purified by silica gel column chromatography (hexane/ethyl acetate=2/1~1.5/1) to obtain 1.20 g (78%) of the captioned compound.

Production Example 46

4-{4-[(Benzyloxy)carbonyl]-1-piperazinyl}-5-fluoro-2-methoxybenzoic acid

The same reaction procedure as in Production Example 37 was performed, except that the compound obtained in Production Example 45 was used in place of the compound obtained in Production Example 36. In this manner, 1.02 g (99%) of the captioned compound was obtained.

Production Example 47 tert-Butyl 4-[(benzyloxy)methyl]-1-piperidinecarboxylate

To a 30 ml N,N-dimethylformamide solution of 2.4 g (11.15 mmol) of tert-butyl 4-hydroxymethyl-1-piperidinecarboxylate, 557 mg (60% in oil, 13.9 mmol) of sodium hydride and 1.86 ml (15.6 mmol) of benzyl bromide were added with ice cooling. The mixture was stirred at room temperature for 23 hours. Then, the reaction mixture was diluted with ethyl acetate, and the dilution was washed with water and a saturated aqueous solution of sodium chloride in this order. The washed system was dried over sodium sulfate, and then the solvent was distilled off under reduced pressure. The residue was purified by silica gel column chromatography (hexane/ethyl acetate=4/1) to obtain 3.5 g (quantitative) of the captioned compound.

Production Example 48

4-[(Benzyloxy)methyl]piperidine monohydrochloride

To 3.4 g (11.1 mmol) of the compound obtained in Production Example 47, 11.3 ml of a 4N-hydrochloric acid/1,4-dioxane solution was added, and the mixture was stirred at room temperature for 1.5 hours. Then, ether was gradually added, and precipitated solids were collected by filtration to obtain 1.26 g (84%) of the captioned compound.

Production Example 49

N-[2-(benzyloxy)ethyl]-N-ethylamine

To 7.0 g (30 mmol) of 2-(benzyloxy)ethyl methanesulfonate, a 75 ml methanol solution of 2M ethylamine was added, and the mixture was heated at 110° C. in a sealed tube for 2 hours. Then, the reaction mixture was returned to room temperature, and then diluted with methylene chloride. The dilution was washed with a saturated aqueous solution of sodium hydride. The washed system was dried over sodium sulfate, and then the solvent was distilled off under reduced pressure. The residue was purified by silica gel column chromatography (hexane/ethyl acetate=4/1) to obtain 3.85 g (72%) of the captioned compound.

Production Example 50

N-[2-(benzyloxy)ethyl]-N-ethylamine hydrochloride

To a 100 ml ether solution of 3.72 g (20.75 mmol) of the compound obtained in Production Example 49, 6.2 ml of a 4N-hydrochloric acid/1,4-dioxane solution was added. Precipitated solids were collected by filtration to obtain 4.09 g (91%) of the captioned compound.

Production Example 51

Methyl 4-{4-[[(benzyloxy)carbonyl](methyl)amino]-1-piperidinyl}-2,5-difluorobenzoate The same reaction procedure as in Production Example 43 was performed, except that benzyl methyl(4-piperidinyl)carbamate hydrochloride was used in place of N-benzylpiperazine. In this manner, 2.0 g (68%) of the captioned compound was obtained.

Production Example 52

Methyl 4-{4-[[(benzyloxy)carbonyl](methyl)amino]-1-piperidinyl}-5-fluoro-2-methoxybenzoate The same reaction procedure as in Production Example 44 was performed, except that the compound obtained in Production Example 51 was used in place of the compound obtained in Production Example 43. In this manner, 0.46 g (24%) of the captioned compound was obtained.

Production Example 53

4-{4-[[(Benzyloxy)carbonyl](methyl)amino]-1-piperidinyl}-5-fluoro-2-methoxybenzoic acid The same reaction procedure as in Production Example 37 was performed, except that the compound obtained in Production Example 52 was used in place of the compound obtained in Production Example 36. In this manner, 0.41 g (quantitative) of the captioned compound was obtained.

Production Example 54

Methyl 4-bromo-2-(difluoromethoxy)benzoate

To a 70 ml dimethylformamide solution of 5.0 g (21.7 mmol) of methyl 4-bromo-2-hydroxybenzoate, 3.4 ml (32.6 mmol) of methyl chlorodifluoroacetate and 3.0 g (21.7 mmol) of potassium carbonate were added. The mixture was stirred at 60° C. for 6 hours and at room temperature for 60 hours. Then, water was added to the reaction mixture, and the mixture was extracted with ether. The organic layer was washed with water and a saturated aqueous solution of sodium chloride. The washed system was dried over anhydrous sodium sulfate, and then the solvent was distilled off under reduced pressure. The residue was purified by silica gel column chromatography (hexane/ethyl acetate=8/1) to obtain 1.4 g (23%) of the captioned compound.

Production Example 55

4-Bromo-2-(difluoromethoxy)benzoic acid

To a 10 ml methanol/lo ml tetrahydrofuran mixed solution of 1.36 g (4.84 mmol) of the compound obtained in Production Example 54, a 2M aqueous solution of sodium hydroxide was added, and the mixture was stirred at room temperature for 3 hours. Then, the solvent was distilled off under reduced pressure, and the residue was dissolved by addition of water. A 6M aqueous solution of hydrochloric acid was added to the solution. Precipitated solids were collected by filtration to obtain 1.17 g (91%) of the captioned compound.

Production Example 56

5-Amino-3-cyclohexyl-1-ethyl-1H-pyrazole-4-carbonitrile

The same reaction procedure as in Production Example 31-2 was performed, except that ethylhydrazine was used in place of methylhydrazine. In this manner, 2.0 g (18%) of the captioned compound was obtained.

Production Example 57

5-Amino-3-cyclohexyl-1-ethyl-1H-pyrazole-4-carboxamide

The same reaction procedure as in Production Example 32 was performed, except that the compound obtained in Production Example 56 was used in place of the compound obtained in Production Example 31. In this manner, 1.93 g (99%) of the captioned compound was obtained.

Production Example 58

Methyl 2-fluoro-4-(4-thiomorpholinyl)benzoate

To a 30 ml dimethyl sulfoxide solution of 3.44 g (20 mmol) of methyl 2,4-difluorobenzoate, 1.9 ml (20 mmol) of thiomorpholine and 2.76 g (20 mmol) of potassium carbonate were added, and the mixture was stirred at 80° C. Then, the reaction mixture was cooled to room temperature, water was added, and the mixture was extracted with ethyl acetate. The organic layer was washed with water and a saturated aqueous solution of sodium chloride. The washed system was dried over anhydrous sodium sulfate, and then the solvent was distilled off. The residue was purified by silica gel column chromatography (hexane/ethyl acetate=5/1) to obtain 2.96 g (58%) of the captioned compound.

Production Example 59

Methyl 2-methoxy-4-(4-thiomorpholinyl)benzoate

To a 30 ml tetrahydrofuran solution of 2.5 g (9.8 mmol) of the compound obtained in Production Example 59, 12.3 ml (11.8 mmol) of sodium methoxide (28% methanol solution) was added, and the mixture was stirred at 80° C. for 4 hours. Then, the reaction mixture was distilled under reduced pressure, water was added to the residue, and the mixture was extracted with ethyl acetate. The organic layer was washed with water and a saturated aqueous solution of sodium chloride. The washed system was dried over anhydrous sodium sulfate, and then the solvent was distilled off. The residue was purified by silica gel column chromatography (hexane/ethyl acetate=5/1~3/1) to obtain 2.59 g (99%) of the captioned compound.

Production Example 60

2-Methoxy-4-(4-thiomorpholinyl)benzoic acid

To a 30 ml methanol solution of 2.47 g (9.3 mmol) of the compound obtained in Production Example 59, 15 ml of a 1M aqueous solution of sodium hydroxide was added, and the mixture was stirred at room temperature for 3 hours. Further, 2 ml of a 4M aqueous solution of sodium hydroxide was added, and the mixture was stirred at room temperature for 12 hours and at 50° C. for 7 hours. Then, the reaction mixture was cooled to room temperature, and the solvent was distilled off under reduced pressure. The residue was dissolved by addition of water, and the solution was washed with ether. The aqueous layer was acidified with a 1M aqueous solution of hydrochloric acid. Precipitated solids were collected by filtration, and dried to obtain 2.2 g (94%) of the captioned compound.

Production Example 61

Benzyl 4-[2,5-difluoro-4-(methoxycarbonyl)phenyl]-1,4-diazepane-1-carboxylate

The same reaction procedure as in Production Example 43 was performed, except that benzyl 1-homopiperazinecarboxylate was used in place of N-benzylpiperazine. In this manner, 1.31 g (32%) of the captioned compound was obtained.

Production Example 62

Benzyl 4-[2-fluoro-5-methoxy-4-(methoxycarbonyl)phenyl]-1,4-diazepane-1-carboxylate The same reaction procedure as in Production Example 44 was performed, except that the compound obtained in Production Example 61 was used in place of the compound obtained in Production Example 43. In this manner, 0.31 g (27%) of the captioned compound was obtained.

Production Example 63

4-{4-[(Benzyloxy)carbonyl]-1,4-diazepan-1-yl}-5-fluoro-2-methoxybenzoic acid

The same reaction procedure as in Production Example 37 was performed, except that the compound obtained in Production Example 62 was used in place of the compound obtained in Production Example 36. In this manner, 0.28 g (97%) of the captioned compound was obtained.

Example 1

1-Cyclohexyl-3-methyl-5-phenyl-1,6-dihydro-7H-pyrazolo[4,3-d]pyrimidin-7-one

To a 4 ml dioxane/4.6 ml water mixed solution of 150 mg (0.49 mmol) of the compound obtained in Production Example 7, 0.12 ml of a 30% aqueous solution of hydrogen peroxide and 30 mg (0.75 mmol) of sodium hydroxide were added, and the mixture was stirred at 80° C. for 2 hours. Then, the reaction mixture was brought to room temperature, and the solvent was distilled off under reduced pressure. Then, the residue was acidified by addition of acetic acid. Precipitated solids were collected by filtration to obtain 103 mg (68%) of the captioned compound.

Example 2

1-Cyclohexyl-3-methyl-5-(4-nitrophenyl)-1,6-dihydro-7H-pyrazolo[4,3-d]pyrimidin-7-one The same reaction procedure as in Example 1 was performed, except that the compound obtained in Production Example 8 was used in place of the compound obtained in Production Example 7. In this manner, 273 mg (44%) of the captioned compound was obtained.

Example 3

5-(4-Aminophenyl)-1-cyclohexyl-3-methyl-1,6-dihydro-7H-pyrazolo[4,3-d]pyrimidin-7-one To a mixed solution, in 4 ml of methanol and 2 ml of N,N-dimethylformamide, of 222 mg (0.63 mmol) of the compound obtained in Example 2, 25 mg of 10% palladium carbon was added. After substitution by hydrogen, the mixture was stirred for 2 hours. Then, the reaction mixture was filtered through Celite, and the filtrate was distilled under reduced pressure. The residue was dissolved in 6M hydrochloric acid, and the solution was washed with ether. The aqueous layer was neutralized with 28% aqueous ammonia, and then extracted with dichloromethane. The organic layer was washed with water and a saturated aqueous solution of sodium chloride. Then, the washed layer was dried over anhydrous sodium sulfate, and the solvent was distilled off under reduced pressure. The residue was purified by recrystallization (ethanol) to obtain 77 mg (38%) of the captioned compound.

Example 4

N-[4-(1-cyclohexyl-3-methyl-7-oxo-6,7-dihydro-1H-pyrazolo[4,3-d]pyrimidin-5-yl)phenyl]acetamide To a 4 ml pyridine solution of 110 mg (0.34 mmol) of the compound obtained in Example 3, 39 μl (0.41 mmol) of acetic anhydride was added with ice cooling. The mixture was stirred at the same temperature for 30 minutes. Then, an aqueous solution of sodium hydrogen carbonate was added to the reaction mixture, and the mixture was extracted with dichloromethane. The organic layer was washed with water and a saturated aqueous solution of sodium chloride. Then, the washed layer was dried over anhydrous sodium sulfate, and the solvent was distilled off under reduced pressure. The residue was purified by recrystallization (ethanol) to obtain 43.7 mg (35%) of the captioned compound.

Example 5

1-Cyclohexyl-5-(2-methoxyphenyl)-3-methyl-1,6-dihydro-7H-pyrazolo[4,3-d]pyrimidin-7-one To a 2 ml ethanol solution of 100 mg (0.28 mmol) of the compound obtained in Example 9, 1 ml of a 1M aqueous solution of sodium hydroxide was added, and the mixture was stirred at 90° C. for 10 hours. Then, the reaction mixture was brought to room temperature, water was added, and the mixture was extracted with ethyl acetate. The organic layer was washed with water and a saturated aqueous solution of sodium chloride. After the washed layer was dried over anhydrous sodium sulfate, the solvent was distilled off under reduced pressure. The residue was purified by silica gel column chromatography (hexane/ethyl acetate=2/1) to obtain 68.5 mg (72%) of the captioned compound.

Example 6

1-Cyclohexyl-3-methyl-5-(2-pyridinyl)-1,6-dihydro-7H-pyrazolo[4,3-d]pyrimidin-7-one The same reaction procedure as in Example 5 was performed, except that the compound obtained in Production Example 11 was used in place of the compound obtained in Production Example 9. In this manner, 77.8 mg (59%) of the captioned compound was obtained.

Example 7

1-Cyclohexyl-3-methyl-5-[4-(4-methyl-1-piperazinyl)phenyl]-1,6-dihydro-7H-pyrazolo[4,3-d]pyrimidin-7-one The same reaction procedure as in Example 5 was performed, except that the compound obtained in Production Example 12 was used in place of the compound obtained in Production Example 9. In this manner, 59 mg (63%) of the captioned compound was obtained.

Example 8

1-Cyclohexyl-5-(2-methoxy-4-nitrophenyl)-3-methyl-1,6-dihydro-7H-pyrazolo[4,3-d]pyrimidin-7-one The same reaction procedure as in Example 5 was performed, except that the compound obtained in Production Example 13 was used in place of the compound obtained in Production Example 9. In this manner, 171 mg (45%) of the captioned compound was obtained.

Example 9

5-(4-Amino-2-methoxyphenyl)-1-cyclohexyl-3-methyl-1,6-dihydro-7H-pyrazolo[4,3-d]pyrimidin-7-one The same reaction procedure as in Example 3 was performed, except that the compound obtained in Example 8 was used in place of the compound obtained in Example 2. In this manner, 52 mg (41%) of the captioned compound was obtained.

Example 10

N-[4-(1-cyclohexyl-3-methyl-7-oxo-6,7-dihydro-1H-pyrazolo[4,3-d]pyrimidin-5-yl)-3-methoxyphenyl]acetamide The same reaction procedure as in Example 4 was performed, except that the compound obtained in Example 9 was used in place of the compound obtained in Example 3. In this manner, 61 mg (quant.) of the captioned compound was obtained.

Example 11

5-(5-Amino-2-pyridinyl)-1-cyclohexyl-3-methyl-1,6-dihydro-7H-pyrazolo[4,3-d]pyrimidin-7-one To a 6 ml ethanol suspension of 500 mg (1.34 mmol) of the compound obtained in Production Example 14, 3 ml of a 1M aqueous solution of sodium hydroxide was added, and the mixture was stirred at 90° C. for 4 hours. Then, the reaction mixture was brought to room temperature, diluted with water, and then extracted with chloroform. The organic layer was washed with water and a saturated aqueous solution of sodium chloride, and dried over anhydrous sodium sulfate. Then, the solvent was distilled off under reduced pressure to obtain crude crystals of 1-cyclohexyl-3-methyl-5-(5-nitro-2-pyridinyl)-1,6-dihydro-7H-pyrazolo[4,3-d]-7-one. The crude crystals were not purified, but dissolved in 6 ml of methanol and 5 ml of N,N-dimethylformamide. Then, 10% palladium carbon was added, and the mixture was substituted by hydrogen, followed by stirring for 14 hours. Then, the reaction mixture was filtered through Celite, and the filtrate was distilled under reduced pressure. The residue was purified by silica gel column chromatography (chloroform/methanol=50/1) to obtain 78.8 mg (18%) of the captioned compound.

Example 12

N-[6-(1-cyclohexyl-3-methyl-7-oxo-1H-pyrazolo[4,3-d]pyrimidin-5-yl)-3-pyridinyl]acetamide The same reaction procedure as in Example 4 was performed, except that the compound obtained in Example 11 was used in place of the compound obtained in Example 3. In this manner, 40 mg (74%) of the captioned compound was obtained.

Example 13

1-Cyclohexyl-5-(2-ethoxyphenyl)-3-methyl-1,6-dihydro-7H-pyrazolo[4,3-d]pyrimidin-7-one The same reaction procedure as in Example 5 was performed, except that the compound obtained in Production Example 10 was used in place of the compound obtained in Production Example 9. In this manner, 145 mg (90%) of the captioned compound was obtained.

Example 14

1-Cyclohexyl-5-[4-(4-hydroxy-1-piperidinyl)phenyl]-3-methyl-1,6-dihydro-7H-pyrazolo[4,3-d]pyrimidin-7-one To a 4 ml anhydrous dichloromethane/2 ml N,N-dimethylformamide solution of 150 mg (0.675 mmol) of the compound obtained in Production Example 6, 174 mg (0.675 mmol) of the compound obtained in Production Example 34, 155 mg (0.810 mmol) of 1-ethyl-3-(3-dimethylaminopropyl)carbodiimide hydrochloride, and 68 mg (0.675 mmol) of triethylamine were added. The mixture was stirred at room temperature for 2 hours. Then, the mixture was diluted with water, and then extracted with methylene chloride. The extract was dried over anhydrous sodium sulfate, and then the solvent was distilled off under reduced pressure to obtain a carboxamide intermediate.

Further, the carboxamide intermediate synthesized above was dissolved in 4 ml of ethanol, 2 ml of a 1M aqueous solution of sodium hydroxide was added, and the mixture was stirred for 24 hours at 90° C. Then, the reaction mixture was brought to room temperature, diluted with water, and then extracted with methylene chloride. The extract was dried over anhydrous sodium sulfate, and then the solvent was distilled off under reduced pressure. The residue was recrystallized from ethanol to obtain 19 mg (7%) of the captioned compound.

Example 15

5-(4-Bromo-2-methoxyphenyl)1-cyclohexyl-3-methyl-1,6-dihydro-7H-pyrazolo[4,3-d]pyrimidin-7-one The same reaction procedure as in Example 14 was performed, except that 4-bromo-2-methoxybenzoic acid was used in place of the compound obtained in Production Example 34. In this manner, 545 mg (48%) of the captioned compound was obtained.

Example 16

1-Cyclohexyl-5-[2-methoxy-4-(4-methyl-1-piperazinyl)phenyl]-3-methyl-1,6-dihydro-7H-pyrazolo[4,3-d]pyrimidin-7-one In a stream of argon, 166 µl (1.50 mmol) of N-methylpiperazine, 72 mg (0.75 mmol) of sodium tert-butoxide, 166 mg (0.01 mmol) of tri-tert-butylphosphine, and 1.6 mg (0.008 mmol) of palladium(II) acetate were added to a 2 ml toluene solution of 209 mg (0.50 mmol) of the compound obtained in Example 15, and the mixture was stirred at 110° C. for 2 hours. Further, 166 mg (0.01 mmol) of tri-tert-butylphosphine and 1.6 mg (0.008 mmol) of palladium(II) acetate were added, and the mixture was stirred at 110° C. for 8 hours. Then, the reaction mixture was brought to room temperature, diluted with water, and then extracted with ethyl acetate. The extract was dried over anhydrous sodium sulfate, and then the solvent was distilled off under reduced pressure. The residue was purified by silica gel column chromatography (chloroform/methanol=20/1) to obtain 82 mg (38%) of the captioned compound.

Example 17

5-(4-Chloro-2-pyridinyl)-1-cyclohexyl-3-methyl-1,6-dihydro-7H-pyrazolo[4,3-d]pyrimidin-7-one The same reaction procedure as in Example 5 was performed, except that the compound obtained in Production Example 15 was used in place of the compound obtained in Production Example 9. In this manner, 496 mg (75%) of the captioned compound was obtained.

Example 18

1-Cyclohexyl-5-(5-fluoro-2-methoxyphenyl)-3-methyl-1,6-dihydro-7H-pyrazolo[4,3-d]pyrimidin-7-one The same reaction procedure as in Example 5 was performed, except that the compound obtained in Production Example 16 was used in place of the compound obtained in Production Example 9. In this manner, 118 mg (63%) of the captioned compound was obtained.

Example 19

Trans-5-(2-methoxyphenyl)-3-methyl-1-(4-methylcyclohexyl)-1,6-dihydro-7H-pyrazolo[4,3-d]pyrimidin-7-one The same reaction procedure as in Example 5 was performed, except that the compound obtained in Production Example 27 was used in place of the compound obtained in Production Example 9. In this manner, 123 mg (86%) of the captioned compound was obtained.

Example 20

Cis-5-(2-methoxyphenyl)-3-methyl-1-(4-methylcyclohexyl)-1,6-dihydro-7H-pyrazolo[4,3-d]pyrimidin-7-one The same reaction procedure as in Example 5 was performed, except that the compound obtained in Production Example 28 was used in place of the compound obtained in Production Example 9. In this manner, 88 mg (84%) of the captioned compound was obtained.

Example 21

Trans-3-methyl-1-(4-methylcyclohexyl)-5-[4-(4-methyl-1-piperazinyl)phenyl]-1,6-dihydro-7H-pyrazolo[4,3-d]pyrimidin-7-one The same reaction procedure as in Example 5 was performed, except that the compound obtained in Production Example 25 was used in place of the compound obtained in Production Example 9. In this manner, 116 mg (81%) of the captioned compound was obtained.

Example 22

Cis-3-methyl-1-(4-methylcyclohexyl)-5-[4-(4-methyl-1-piperazinyl)phenyl]-1,6-dihydro-7H-pyrazolo[4,3-d]pyrimidin-7-one The same reaction procedure as in Example 5 was performed, except that the compound obtained in Production Example 26 was used in place of the compound obtained in Production Example 9. In this manner, 132 mg (92%) of the captioned compound was obtained.

Example 23

3-Cyclohexyl-1-methyl-6-phenyl-1,5-dihydro-4H-pyrazolo[3,4-d]pyrimidin-4-one

To a 5 ml 1,4-dioxane solution of 292 mg (0.708 mmol) of the compound obtained in Example 38, 1.9 ml (1.9 mmol) of a 1M aqueous solution of sodium hydroxide and 0.5 ml of a 30% aqueous solution of hydrogen peroxide were added, and the mixture was stirred at 85° C. for 3.5 hours. Then, the reaction mixture was returned to room temperature, and diluted with water. Then, 1 ml of 2M hydrochloric acid was added, and the mixture was extracted with ethyl acetate. The extract was dried over anhydrous sodium sulfate, and then the solvent was distilled off under reduced pressure. The residue was purified by silica gel column chromatography (hexane/ethyl acetate=2/1) to obtain 176 mg (81%) of the captioned compound.

Example 24

3-Cyclohexyl-6-(2-methoxyphenyl)-1-methyl-1,5-dihydro-4H-pyrazolo[3,4-d]pyrimidin-4-one To a 3 ml 1,2-dichloroethane suspension of 181 mg (1.19 mmol) of o-anisic acid, 158 µl (2.16 mmol) of thionyl chloride was added, and the mixture was stirred at 85° C. for 1.5 hours. Then, the solvent was distilled off under reduced pressure to obtain an acid chloride as colorless oily matter.

To a 2 ml pyridine solution of the acid chloride synthesized above, a 2 ml pyridine solution of 240 mg (1.08 mmol) of the compound obtained in Production Example 32 was added. The mixture was stirred at 60° C. for 18 hours and at room temperature for 2 days. Then, the reaction mixture was concentrated under reduced pressure, diluted with water, and extracted with ethyl acetate. The organic layer was washed with a saturated aqueous solution of sodium chloride, and dried over anhydrous sodium sulfate, followed by distilling off the solvent under reduced pressure. The residue was purified by silica gel column chromatography (methylene chloride/methanol=30/1) to obtain 246 mg (64%) of a carboxamide intermediate (3-cyclohexyl-5-[(2-methoxybenzoyl)amino]-1-methyl-1H-pyrazole-4-carboxamide).

To a 2.2 ml ethanol solution of 130 mg (0.365 mmol) of the carboxamide intermediate synthesized above, 1.1 ml (1.1 mmol) of a 1M aqueous solution of sodium hydroxide was added, and the mixture was stirred at 90° C. for 20 hours. Then, the reaction mixture was brought to room temperature, diluted with water, and extracted with methylene chloride. The extract was dried over anhydrous sodium sulfate, and then the solvent was distilled off under reduced pressure. The residue was purified by silica gel column chromatography (methylene chloride/methanol=30/1) to obtain 91 mg (74%) of the captioned compound.

Example 25

3-Cyclohexyl-1-methyl-6-(2-pyridinyl)-1,5-dihydro-4H-pyrazolo[3,4-d]pyrimidin-4-one To an 8 ml chloroform solution of 261 mg (1.17 mmol) of the compound obtained in Production Example 32, 409 µl (2.94 mmol) of triethylamine, 14 mg (0.117 mmol) of 4-dimethylaminopyridine, and 251 mg (1.41 mmol) of picolinic acid chloride were added, and the mixture was stirred at 50° C. for 20 hours. Then, water was added to the reaction mixture, and the mixture was extracted with methylene chloride. The extract was dried over anhydrous sodium sulfate, and then the solvent was distilled off under reduced pressure to obtain 315 mg of a carboxamide intermediate as crude crystals.

To a 2 ml ethanol suspension of the carboxamide intermediate synthesized above, 2 ml (2.0 mmol) of a 1M aqueous solution of sodium hydroxide was added, and the mixture was stirred at 80° C. for 20 hours. Then, the reaction mixture was brought to room temperature, diluted with water, and extracted with methylene chloride. The extract was dried over anhydrous sodium sulfate, and then the solvent was distilled off under reduced pressure. The residue was purified by silica gel column chromatography (methylene chloride/methanol=50/1) to obtain 109 mg of crude crystals. These crude crystals were further recrystallized from chloroform/hexane to obtain 72 mg (20%) of the captioned compound.

Example 26

6-(4-Bromo-2-methoxyphenyl)-3-cyclohexyl-1-methyl-1,5-dihydro-4H-pyrazolo[3,4-d]pyrimidin-4-one To a 5 ml 1,2-dichloroethane suspension of 500 mg (2.25 mmol) of 4-bromo-2-methoxybenzoic acid, 328 µl (4.50 mmol) of thionyl chloride was added, and the mixture was stirred at 85° C. for 1.5 hours. Then, the solvent was distilled off under reduced pressure to obtain an acid chloride as yellow solids.

To a 1 ml pyridine solution of the acid chloride synthesized above, a 4 ml pyridine solution of 500 mg (2.25 mmol) of the compound obtained in Production Example 32 was added. The mixture was stirred at room temperature for 1 hour and at 60° C. for 2 hours. Then, the reaction mixture was concentrated under reduced pressure, diluted with water, and extracted with ethyl acetate. The organic layer was washed with a saturated aqueous solution of sodium chloride, and dried over anhydrous sodium sulfate, followed by distilling off the solvent under reduced pressure. A carboxamide intermediate (3-cyclohexyl-5-[(4-bromo-2-methoxybenzoyl)amino]-1-methyl-1H-pyrazole-4-carboxamide) was obtained by this measure.

To a 13.5 ml ethanol solution of the carboxamide intermediate synthesized above, 6.75 ml (6.75 mmol) of a 1M aqueous solution of sodium hydroxide was added, and the mixture was stirred with heating under reflux for 12 hours. Then, the reaction mixture was brought to room temperature, and diluted with water. Then, 3.38 ml of 2M hydrochloric acid was added, and the mixture was extracted with methylene chloride. The extract was dried over anhydrous sodium sulfate, and then the solvent was distilled off under reduced pressure. The residue was purified by silica gel column chromatography (methylene chloride/methanol=40/1), and further crystallized by addition of diisopropyl ether to obtain 320 mg (34%) of the captioned compound.

Example 27

3-Cyclohexyl-6-[2-methoxy-4-(4-methyl-1-piperazinyl)phenyl]-1-methyl-1,5-dihydro-4H-pyrazolo[3,4-d]pyrimidin-4-one In a stream of argon, 207 µl (1.87 mmol) of N-methylpiperazine, 120 mg (1.25 mmol) of sodium tert-butoxide, 12.6 mg (0.062 mmol) of tri-tert-butylphosphine, and 7.0 mg (0.031 mmol) of palladium(II) acetate were added to an 8 ml toluene solution of 260 mg (0.623 mmol) of the compound obtained in Example 26, and the mixture was heated under reflux for 5 hours. Then, the reaction mixture was brought to room temperature, diluted with water, and then extracted with ethyl acetate. The extract was dried over anhydrous sodium sulfate, and then the solvent was distilled off under reduced pressure. The residue was purified by silica gel column chromatography (chloroform/methanol=20/1) to obtain 230 mg (85%) of the captioned compound.

Example 28

3-Cyclohexyl-6-[2-methoxy-4-(4-methyl-1-piperazinyl)phenyl]-1-methyl-1,5-dihydro-4H-pyrazolo[3,4-d]pyrimidin-4-one monomethanesulfonate To a 3 ml tetrahydrofuran/4 ml dioxane mixed solution of 450 mg (1.03 mmol) of the compound obtained in Example 27, 68.6 µl (1.05 mmol) of methanesulfonic acid was added, and precipitated solids were collected by filtration. The solids were purified by recrystallization (ethanol) to obtain 364 mg (66%) of the captioned compound.

Example 29

3-Cyclohexyl-6-[4-(1,4-dioxa-8-azaspiro[4,5]deca-8-yl)-2-methoxyphenyl]-1-methyl-1,5-dihydro-4H-pyrazolo[3,4-d]pyrimidin-4-one The same reaction procedure as in Example 27 was performed, except that 1,4-dioxa-8-azaspiro[4,5]decane was used in place of N-methylpiperazine. In this manner, 140 mg (81%) of the captioned compound was obtained.

Example 30

3-Cyclohexyl-6-[2-methoxy-4-(4-oxo-1-piperidinyl)phenyl]-1-methyl-1,5-dihydro-4H-pyrazolo[3,4-d]pyrimidin-4-one To a 50 ml acetone/5 ml water mixed solution of 850 mg (1.77 mmol) of the compound obtained in Example 29, 405 mg (2.13 mmol) of p-toluenesulfonic acid monohydrate was added, and the mixture was heated under reflux for 5 hours. Then, the reaction mixture was returned to room temperature, and concentrated under reduced pressure. A saturated aqueous solution of sodium hydrogen carbonate was added to the residue, and the mixture was extracted with methylene chloride. The extract was dried over anhydrous sodium sulfate, and then the solvent was distilled off under reduced pressure to obtain 827 mg of the captioned compound as crude crystals.

Example 31

3-Cyclohexyl-6-[4-(4-hydroxy-1-piperidinyl)-2-methoxyphenyl]-1-methyl-1,5-dihydro-4H-pyrazolo[3,4-d]pyrimidin-4-one To a 30 ml ethanol suspension of 780 mg (1.79 mmol) of the compound obtained in Example 30, 81 mg (2.15 mmol) of sodium borohydride was added, and the mixture was stirred at room temperature for 1.5 hours. Then, acetone was added to the reaction mixture, and the mixture was concentrated under reduced pressure. Water was added to the residue, and the mixture was extracted with methylene chloride. The organic layer was washed with water and a saturated aqueous solution of sodium chloride in this order. Then, the washed layer was dried over anhydrous sodium sulfate, and then the solvent was distilled off under reduced pressure. The residue was purified by silica gel column chromatography (chloroform/methanol=40/1) to obtain 606 mg (77%) of the captioned compound.

Example 32

3-Cyclohexyl-6-[4-(4-hydroxy-1-piperidinyl)-2-methoxyphenyl]-1-methyl-1,5-dihydro-4H-pyrazolo[3,4-d]pyrimidin-4-one monomethanesulfonate A 3 ml ethanol suspension of 100 mg (0.23 mmol) of the compound obtained in Example 31 was heated to 50° C. to form a solution. To this solution, 15 µM (0.23 mmol) of methanesulfonic acid was added, and the mixture was heated under reflux for 10 minutes. Then, the reaction mixture was brought to room temperature, and the solvent was distilled off under reduced pressure. Ether was added to the residue, and solids were collected by filtration to obtain 101 mg (83%) of the captioned compound.

Example 33

3-Cyclohexyl-6-[4-(4-hydroxy-1-piperidinyl)-2-methoxyphenyl]-1-methyl-1,5-dihydro-4H-pyrazolo[3,4-d]pyrimidin-4-one monohydrochloride A 2 ml tetrahydrofuran suspension of 100 mg (0.23 mmol) of the compound obtained in Example 31 was heated to 50° C. to form a solution. To this solution, 68 µl (0.27 mmol) of a 4M dioxane hydrochloride solution was added. Then, the reaction mixture was brought to room temperature, and ether was added. Precipitated solids were collected by filtration to obtain 96 mg (88%) of the captioned compound.

Example 34

3-Cyclohexyl-6-[2-methoxy-4-(2-methoxyethoxy)phenyl]-1-methyl-1,5-dihydro-4H-pyrazolo[3,4-d]pyrimidin-4-one The same reaction procedure as in Example 26 was performed, except that the compound obtained in Production Example 37 was used in place of 4-bromo-2-methoxybenzoic acid. In this manner, 90 mg (24%) of the captioned compound was obtained.

Example 35

6-[4-(Benzyloxy)-2-methoxyphenyl]-3-cyclohexyl-1-methyl-1,5-dihydro-4H-pyrazolo[3,4-d]pyrimidin-4-one The same reaction procedure as in Example 26 was performed, except that 4-benzyloxy-2-methoxybenzoic acid was used in place of 4-bromo-2-methoxybenzoic acid. In this manner, 1.3 g (87%) of the captioned compound was obtained.

Example 36

3-Cyclohexyl-6-(4-hydroxy-2-methoxyphenyl)-1-methyl-1,5-dihydro-4H-pyrazolo[3,4-d]pyrimidin-4-one To a 50 ml methanol/50 ml tetrahydrofuran mixed solution of 1.16 g (2.61 mmol) of the compound obtained in Example 35, 300 mg of 5% palladium carbon was added. The mixture was stirred for 3 hours at room temperature at atmospheric pressure in an atmosphere of hydrogen. Then, the catalyst was removed by filtration to obtain 0.92 g (99%) of the captioned compound.

Example 37

3-Cyclohexyl-6-[4-(2-hydroxyethoxy)-2-methoxyphenyl]-1-methyl-1,5-dihydro-4H-pyrazolo[3,4-d]pyrimidin-4-one To a 5 ml N,N-dimethylformamide solution of 150 mg (0.423 mmol) of the compound obtained in Example 36, 87.7 mg (0.635 mmol) of potassium carbonate and 33 µl (0.466 mmol) of 2-bromoethanol were added. The mixture was stirred at 100° C. for 1 hour and at 120° C. for 2 hours. Further, 16 µl (0.233 mmol) of 2-bromoethanol was added, and the mixture was stirred at 120° C. for 1 hour. Then, the reaction mixture was concentrated under reduced pressure. Water was added to the residue, and the mixture was extracted with ethyl acetate. The extract was dried over anhydrous sodium sulfate, and then the solvent was distilled off under reduced pressure. The residue was purified by silica gel column chromatography (ethyl acetate), and further recrystallized (toluene) to obtain 60 mg (36%) of the captioned compound.

Example 38

3-Cyclohexyl-6-{2-methoxy-4-[(3S)-tetrahydro-3-furanyloxy]phenyl}-1-methyl-1,5-dihydro-4H-pyrazolo[3,4-d]pyrimidin-4-one To a 10 ml tetrahydrofuran suspension of 150 ml (0.423 mmol) of the compound obtained in Example 36, 133 mg (0.508 mmol) of triphenylphosphine, 51 µl (0.635 mmol) of (R)-(−)-3-hydroxytetrahydrofuran, and 80 µl (0.508 mmol) of diethyl azodicarboxylate were slowly added at room temperature, and the mixture was stirred at room temperature for 1 hour. Further, 44 mg (0.169 mmol) of triphenylphosphine, 17 µl (0.212 mmol) of (R)-(−)-3-hydroxytetrahydrofuran, and 27 µl (0.169 mmol) of diethyl azodicarboxylate were added, and the mixture was stirred at room temperature for 1.5 hours. Then, the reaction mixture was diluted with ethyl acetate, and the dilution was washed with water and a saturated aqueous solution of sodium chloride in this order. The washed system was dried over sodium sulfate, and then the solvent was distilled off under reduced pressure. The residue was purified by silica gel column chromatography (hexane/ethyl acetate=1/1~1/2) to obtain 124 mg (69%) of the captioned compound.

Example 39

3-Cyclohexyl-6-{2-methoxy-4-[(3R)-tetrahydro-3-furanyloxy]phenyl}-1-methyl-1,5-dihydro-4H-pyrazolo[3,4-d]pyrimidin-4-one The same reaction procedure as in Example 38 was performed, except that (S)-(+)-3-hydroxytetrahydrofuran was used in place of (R)-(–)-3-hydroxytetrahydrofuran. In this manner, 77 mg (64%) of the captioned compound was obtained.

Example 40

Methyl [4-(3-cyclohexyl-1-methyl-4-oxo-4,5-dihydro-1H-pyrazolo[3,4-d]pyrimidin-6-yl)-3-methoxyphenoxy]acetate The same reaction procedure as in Example 37 was performed, except that methyl bromoacetate was used in place of 2-bromoethanol. In this manner, 160 mg (89%) of the captioned compound was obtained.

Example 41

[4-(3-cyclohexyl-1-methyl-4-oxo-4,5-dihydro-1H-pyrazolo[3,4-d]pyrimidin-6-yl)-3-methoxyphenoxy]acetic acid To a 2 ml methanol solution of 127 mg (0.298 mmol) of the compound obtained in Example 40, 372 µl (0.372 mmol) of 1M sodium hydroxide was added, and the mixture was stirred at 50° C. for 1 hour. The reaction mixture was returned to room temperature, and diluted with 5 ml of water. Then, 0.4 ml of 1M hydrochloric acid was slowly added. Precipitated solids were collected by filtration to obtain 85 mg (69%) of the captioned compound.

Example 42

3-Cyclohexyl-6-{2-methoxy-4-[(-methyl-4-piperidinyl)oxy]phenyl}-1-methyl-1,5-dihydro-4H-pyrazolo[3,4-d]pyrimidin-4-one monomaleate The same reaction procedure as in Example 38 was performed, except that 4-hydroxy-1-methylpiperidine was used in place of (R)-(–)-3-hydroxytetrahydrofuran. In this manner, 62 mg (44%) of 3-cyclohexyl-6-{2-methoxy-4-[(1-methyl-4-piperidinyl)oxy]phenyl}-1-methyl-1,5-dihydro-4H-pyrazolo[3,4-d]pyrimidin-4-one was obtained as a free compound. Then, 9.6 mg (0.082 mmol) of maleic acid was added to a 1 ml ethanol suspension of 62 mg (0.137 mmol) of the free compound, and the mixture was heated under reflux. Then, the temperature was gradually lowered to room temperature, and precipitated solids were collected by filtration. By this procedure, 32 mg (41%) of the captioned compound was obtained.

Example 43

3-Cyclohexyl-6-(2-methoxy-4-nitrophenyl)-1-methyl-1,5-dihydro-4H-pyrazolo[3,4-d]pyrimidin-4-one The same reaction procedure as in Example 26 was performed, except that 2-methyl-4-nitrobenzoic acid was used in place of 4-bromo-2-methoxybenzoic acid. In this manner, 2.33 g (40%) of the captioned compound was obtained.

Example 44

6-(4-Amino-2-methoxyphenyl)-3-cyclohexyl-1-methyl-1,5-dihydro-4H-pyrazolo[3,4-d]pyrimidin-4-one The same reaction procedure as in Example 3 was performed, except that the compound obtained in Example 43 was used in place of the compound obtained in Example 2. In this manner, 0.97 g (48%) of the captioned compound was obtained.

Example 45

N-[4-(3-cyclohexyl-1-methyl-4-oxo-4,5-dihydro-1H-pyrazolo[3,4-d]pyrimidin-6-yl)-3-methoxyphenyl] acetamide The same reaction procedure as in Example 4 was performed, except that the compound obtained in Example 44 was used in place of the compound obtained in Example 3. In this manner, 79 mg (quant.) of the captioned compound was obtained.

Example 46

N-[4-(3-cyclohexyl-1-methyl-4-oxo-4,5-dihydro-1H-pyrazolo[3,4-d]pyrimidin-6-yl)-3-methoxyphenyl]-2-methoxyacetamide The same reaction procedure as in Example 12 was performed, except that the compound obtained in Example 45 was used in place of the compound obtained in Example 6, and methoxyacetic acid was used in place of 4-(4-methyl-1-piperazinyl)benzoic acid. In this manner, 82 g (96%) of the captioned compound was obtained.

Example 47

3-Cyclohexyl-6-[2-methoxy-4-(methylamino)phenyl]-1-methyl-1,5-dihydro-4H-pyrazolo[3,4-d]pyrimidin-4-one The same reaction procedure as in Example 26 was performed, except that 4-{[(benzyloxy)carbonyl](methyl)amino}-2-methoxybenzoic acid was used in place of 4-bromo-2-methoxybenzoic acid. In this manner, 500 g (36%) of the captioned compound was obtained.

Example 48

4-(3-Cyclohexyl-1-methyl-4-oxo-4,5-dihydro-1H-pyrazolo[3,4-d]pyrimidin-6-yl)-3-methoxybenzenesulfonyl chloride To a 2.5 ml concentrated hydrochloric acid/8.5 ml acetic acid mixed solution of 750 mg (2.12 mmol) of the compound obtained in Example 44, a solution of 220 mg (3.2 mmol) of sodium nitrite in 1.5 ml of water was added with ice cooling. The mixture was stirred for 30 minutes at the same temperature. To the resulting solution, 87 mg (0.65 mmol) of copper dichloride and 4.5 ml of a 22% acetic acid solution of sulfur dioxide were added, and the mixture was stirred at room temperature for 6 hours. Then, water was added to the reaction mixture, and precipitated solids were collected by filtration. The collected solids were dissolved in dichloromethane again, and the solution was washed with water and a saturated aqueous solution of sodium chloride. The washed solution was dried over anhydrous sodium sulfate, and then the solvent was distilled off under reduced pressure. Ether was added to the residue, and the cake was collected by filtration to obtain 673 mg (73%) of the captioned compound.

Example 49

3-Cyclohexyl-6-{2-methoxy-4-[(4-methyl-1-piperazinyl)sulfonyl]phenyl}-1-methyl-1,5-dihydro-4H-pyrazolo[3,4-d]pyrimidin-4-one To a 2 ml anhydrous dichloromethane solution of 87.2 mg (0.2 mmol) of the compound obtained in Example 48, 26.6 µl (0.24 mmol) of N-methylpiperazine and 70 µl (0.5 mmol) of triethylamine were added, and the mixture was stirred at room temperature for 20 hours. Then, water was added to the reaction mixture, and the mixture was extracted with dichloromethane. The organic layer was washed with water and a saturated aqueous solution of sodium chloride. After the washed layer was dried over anhydrous sodium sulfate, the solvent was distilled off under reduced pressure. The residue was purified by silica gel column chromatography (chloroform/methanol=50/1~30/1) to obtain 87 mg (87%) of the captioned compound.

Example 50

3-Cyclohexyl-6-{2-methoxy-4-[(4-methyl-1-piperazinyl)sulfonyl]phenyl}-1-methyl-1,5-dihydro-4H-pyrazolo[3,4-d]pyrimidin-4-one monochloride To a 2 ml dioxane solution of 87 mg (0.17 mmol) of the compound obtained in Example 49, 0.1 ml (0.4 mmol) of a 4M dioxane hydrochloride solution was added. Ether was added to the resulting solution, and precipitated solids were collected by filtration. The solids were purified by recrystallization (ethanol) to obtain 52.1 mg (56%) of the captioned compound.

Example 51

3-Cyclohexyl-6-[2-methoxy-4-(4-morpholinylsulfonyl)phenyl]-1-methyl-1,5-dihydro-4H-pyrazolo[3,4-d]pyrimidin-4-one The same reaction procedure as in Example 49 was performed, except that morpholine was used in place of N-methylpiperazine. In this manner, 66.6 mg (72%) of the captioned compound was obtained.

Example 52

3-Cyclohexyl-6-{4-[(4-hydroxy-1-piperidinyl)sulfonyl]-2-methoxyphenyl}-1-methyl-1,5-dihydro-4H-pyrazolo[3,4-d]pyrimidin-4-one The same reaction procedure as in Example 49 was performed, except that 4-hydroxylpiperidine was used in place of N-methylpiperazine. In this manner, 84 mg (84%) of the captioned compound was obtained.

Example 53

Ethyl 1-{[4-(3-cyclohexyl-1-methyl-4-oxo-4,5-dihydro-1H-pyrazolo[3,4-d]pyrimidin-6-yl)-3-methoxyphenyl]sulfonyl}-4-piperidinecarboxylate The same reaction procedure as in Example 49 was performed, except that isonipecotic acid ethyl ester was used in place of N-methylpiperazine. In this manner, 104 mg (75%) of the captioned compound was obtained.

Example 54

1-{[4-(3-Cyclohexyl-1-methyl-4-oxo-4,5-dihydro-1H-pyrazolo[3,4-d]pyrimidin-6-yl)-3-methoxyphenyl]sulfonyl}-4-piperidinecarboxylic acid To a 2 ml methanol/3 ml tetrahydrofuran mixed solution of 82 mg (0.15 mmol) of the compound obtained in Example 53, 1 ml (1 mmol) of a 1M aqueous solution of sodium hydroxide was added, and the mixture was stirred at room temperature for 1 hour. Then, the solvent was distilled off under reduced pressure, and the residue was diluted with water. The aqueous layer was washed with ether, then acidified with a 2M aqueous solution of hydrochloric acid, and extracted with dichloromethane. The organic layer was washed with water and a saturated aqueous solution of sodium chloride. After the washed layer was dried over anhydrous sodium sulfate, the solvent was distilled off under reduced pressure to obtain 77 mg (99%) of the captioned compound.

Example 55

4-(3-Cyclohexyl-1-methyl-4-oxo-4,5-dihydro-1H-pyrazolo[3,4-d]pyrimidin-6-yl)-N-[2-(dimethylamino)ethyl]-3-methoxybenzenesulfonamide The same reaction procedure as in Example 49 was performed, except that N,N-dimethylethylenediamine was used in place of N-methylpiperazine. In this manner, 85 mg (87%) of the captioned compound was obtained.

Example 56

4-(3-Cyclohexyl-1-methyl-4-oxo-4,5-dihydro-1H-pyrazolo[3,4-d]pyrimidin-6-yl)-N-[2-(dimethylamino)ethyl]-3-methoxybenzenesulfonamide monochloride The same reaction procedure as in Example 50 was performed, except that the compound obtained in Example 55 was used in place of the compound obtained in Example 49. In this manner, 57.5 mg (64%) of the captioned compound was obtained.

Example 57

4-(3-Cyclohexyl-1-methyl-4-oxo-4,5-dihydro-1H-pyrazolo[3,4-d]pyrimidin-6-yl)-3-methoxy-N-(2-methoxyethyl) benzenesulfonamide The same reaction procedure as in Example 49 was performed, except that methoxyethylamine was used in place of N-methylpiperazine. In this manner, 79.8 mg (84%) of the captioned compound was obtained.

Example 58

4-(3-Cyclohexyl-1-methyl-4-oxo-4,5-dihydro-1H-pyrazolo[3,4-d]pyrimidin-6-yl)-N-(2-hydroxyethyl)-3-methoxybenzenesulfonamide The same reaction procedure as in Example 49 was performed, except that ethanolamine was used in place of N-methylpiperazine. In this manner, 65.4 mg (71%) of the captioned compound was obtained.

Example 59

3-Cyclohexyl-6-[2-methoxy-4-(4-morpholinyl)phenyl]-1-methyl-1,5-dihydro-4H-pyrazolo[3,4-d]pyrimidin-4-one The same reaction procedure as in Example 27 was performed, except that morpholine was used in place of N-methylpiperazine. In this manner, 49 mg (32%) of the captioned compound was obtained.

Example 60

3-Cyclohexyl-6-[2-methoxy-4-(1-piperazinyl)phenyl]-1-methyl-1,5-dihydro-4H-pyrazolo[3,4-d]pyrimidin-4-one The same reaction procedure as in Example 27 was performed, except that piperazine was used in place of N-methylpiperazine. In this manner, 81 mg (53%) of the captioned compound was obtained.

Example 61

3-Cyclohexyl-6-[2-methoxy-4-(4-methoxy-1-piperidinyl)phenyl]-1-methyl-1,5-dihydro-4H-pyrazolo[3,4-d]pyrimidin-4-one The same reaction procedure as in Example 27 was performed, except that the compound obtained in Production Example 40 was used in place of N-methylpiperazine. In this manner, 145 mg (89%) of the captioned compound was obtained.

Example 62

3-Cyclohexyl-6-[2-methoxy-4-(4-methoxy-1-piperidinyl)phenyl]-1-methyl-1,5-dihydro-4H-pyrazolo[3,4-d]pyrimidin-4-one monomethanesulfonate A 1.15 ml ethanol suspended solution of 115 mg (0.255 mmol) of the compound obtained in Example 61 was heated to 60° C. To the system, 17.4 μl (0.267 mmol) of methanesulfonic acid was added, and the temperature of the mixture was gradually lowered to room temperature. Precipitated solids were collected by filtration to obtain 108 mg (77%) of the captioned compound.

Example 63

6-(4-Bromo-2-methoxyphenyl)-3-cycloheptyl-1-methyl-1,5-dihydro-4H-pyrazolo[3,4-d]pyrimidin-4-one The same reaction procedure as in Example 26 was performed, except that the compound obtained in Production Example 42 was used in place of the compound obtained in Production Example 32. In this manner, 2.28 g (80%) of the captioned compound was obtained.

Example 64

3-Cycloheptyl-6-[2-methoxy-4-(4-methyl-1-piperazinyl)phenyl]-1-methyl-1,5-dihydro-4H-pyrazolo[3,4-d]pyrimidin-4-one The same reaction procedure as in Example 27 was performed, except that the compound obtained in Example 63 was used in place of the compound obtained in Example 26. In this manner, 188 mg (90%) of the captioned compound was obtained.

Example 65

4-(3-Cyclohexyl-1-methyl-4-oxo-4,5-dihydro-1H-pyrazolo[3,4-d]pyrimidin-6-yl)-3-methoxybenzoic acid In a stream of nitrogen, 1.6 ml of n-butyl lithium (1.56M hexane solution 2.5 mmol) was added dropwise at −78° C. to a 10 ml tetrahydrofuran solution of 500 mg (1.20 mmol) of the compound obtained in Example 26. The mixture was stirred at the same temperature for 30 minutes, and then a carbon dioxide gas was blown into the reaction mixture for 45 minutes. Further, the reaction mixture was stirred at −78° C. for 2 hours, and then brought to room temperature. The reaction mixture was alkalinized by addition of a 1M aqueous solution of sodium hydroxide, and washed with dichloromethane. The aqueous layer was acidified with a 6M aqueous solution of hydrochloric acid, and precipitated solids were collected by filtration, obtaining 200 mg (44%) of the captioned compound.

Example 66

3-Cyclohexyl-6-{2-methoxy-4-[(4-methyl-1-piperazinyl)carbonyl]phenyl}-1-methyl-1,5-dihydro-4H-pyrazolo[3,4-d]pyrimidin-4-one To a 2 ml dichloromethane suspension of 86 mg (0.23 mmol) of the compound obtained in Example 65, 31 μl (0.28 mmol) of N-methylpiperazine and 53 mg (0.28 mmol) of 1-ethyl-3-(3-dimethylaminopropyl)carbodiimide hydrochloride were added, and the mixture was stirred at room temperature for 18 hours. Then, an aqueous solution of sodium hydrogen carbonate was added to the reaction mixture, and the mixture was extracted with dichloromethane. The organic layer was washed with water and a saturated aqueous solution of sodium chloride. After the washed layer was dried over anhydrous sodium sulfate, the solvent was distilled off under reduced pressure. The residue was purified by silica gel column chromatography (chloroform/methanol=20/1~10/1) to obtain 80 mg (75%) of the captioned compound.

Example 67

3-Cyclohexyl-6-{2-methoxy-4-[(4-methyl-1-piperazinyl)carbonyl]phenyl}-1-methyl-1,5-dihydro-4H-pyrazolo[3,4-d]pyrimidin-4-one monomethanesulfonate To a 1 ml methanol/1 ml tetrahydrofuran mixed solution of 45 mg (0.097 mmol) of the compound obtained in Example 66, 6.4 μl (0.098 mmol) of methanesulfonic acid was added, and the mixture was stirred at room temperature

Example 68

3-Cyclohexyl-6-[2-methoxy-4-(4-morpholinylcarbonyl)phenyl]-1-methyl-1,5-dihydro-4H-pyrazolo[3,4-d]pyrimidin-4-one The same reaction procedure as in Example 66 was performed, except that morpholine was used in place of N-methylpiperazine. In this manner, 84.3 mg (85%) of the captioned compound was obtained.

Example 69

3-Cyclohexyl-6-{4-[(4-hydroxy-1-piperidinyl)carbonyl]-2-methoxyphenyl}-1-methyl-1,5-dihydro-4H-pyrazolo[3,4-d]pyrimidin-4-one The same reaction procedure as in Example 66 was performed, except that 4-hydroxylpiperidine was used in place of N-methylpiperazine. In this manner, 57 mg (47%) of the captioned compound was obtained.

Example 70

3-Cyclohexyl-6-{2-methoxy-4-[(4-methoxy-1-piperidinyl)carbonyl]phenyl}-1-methyl-1,5-dihydro-4H-pyrazolo[3,4-d]pyrimidin-4-one The same reaction procedure as in Example 66 was performed, except that the compound obtained in Production Example 40 was used in place of N-methylpiperazine. In this manner, 68.7 mg (65%) of the captioned compound was obtained.

Example 71

{[4-(3-Cyclohexyl-1-methyl-4-oxo-4,5-dihydro-1H-pyrazolo[3,4-d]pyrimidin-6-yl)-3-methoxybenzoyl]amino}acetic acid ethyl ester The same reaction procedure as in Example 66 was performed, except that glycine ethyl ester hydrochloride was used in place of N-methylpiperazine. In this manner, 75 mg (73%) of the captioned compound was obtained.

Example 72

{[4-(3-Cyclohexyl-1-methyl-4-oxo-4,5-dihydro-1H-pyrazolo[3,4-d]pyrimidin-6-yl)-3-methoxybenzoyl]amino}acetic acid To a 1 ml methanol/3 ml 1,4-dioxane mixed solution of 60 mg (0.13 mmol) of the compound obtained in Example 71, 1 ml of a 1M aqueous solution of sodium hydroxide was added at room temperature, and the mixture was stirred at the same temperature for 1 hour. Then, the solvent was distilled off under reduced pressure, and the residue was diluted with water, followed by washing the dilution with ether. The aqueous layer was acidified with a 2M aqueous solution of hydrochloric acid, and then extracted with chloroform. The organic layer was washed with water and a saturated aqueous solution of sodium chloride. After the washed layer was dried over anhydrous sodium sulfate, the solvent was distilled off under reduced pressure to obtain 53 mg (93%) of the captioned compound.

Example 73

3-Cyclohexyl-6-{2-methoxy-4-[(2-methoxyethyl)(methyl)amino]phenyl}-1-methyl-1,5-dihydro-4H-pyrazolo[3,4-d]pyrimidin-4-one The same reaction procedure as in Example 27 was performed, except that N-(2-methoxyethyl)methylamine was used in place of N-methylpiperazine. In this manner, 182 mg (86%) of the captioned compound was obtained.

Example 74

3-Cyclohexyl-6-(5-fluoro-2-methoxyphenyl)-1-methyl-1,5-dihydro-4H-pyrazolo[3,4-d]pyrimidin-4-one The same reaction procedure as in Example 26 was performed, except that 5-fluoro-2-methoxybenzoic acid was used in place of 4-bromo-2-methoxybenzoic acid. In this manner, 244 mg (76%) of the captioned compound was obtained.

Example 75

Ethyl 1-[4-(3-cyclohexyl-1-methyl-4-oxo-4,5-dihydro-1H-pyrazolo[3,4-d]pyrimidin-6-yl)-3-methoxyphenyl]-4-piperazinecarboxylate The same reaction procedure as in Example 27 was performed, except that ethyl 4-piperidinecarboxylate was used in place of N-methylpiperazine. In this manner, 28 mg (14%) of the captioned compound was obtained.

Example 76

1-[4-(3-Cyclohexyl-1-methyl-4-oxo-4,5-dihydro-1H-pyrazolo[3,4-d]pyrimidin-6-yl)-3-methoxyphenyl]-4-piperazinecarboxylic acid The same reaction procedure as in Example 41 was performed, except that the compound obtained in Example 75 was used in place of the compound obtained in Example 40. In this manner, 40 mg (quant.) of the captioned compound was obtained.

Example 77

3-Cycloheptyl-6-[2-methoxy-4-(1-piperazinyl)phenyl]-1-methyl-1,5-dihydro-4H-pyrazolo[3,4-d]pyrimidin-4-one The same reaction procedure as in Example 27 was performed, except that the compound obtained in Example 63 was used in place of the compound obtained in Example 26, and piperazine was used in place of N-methylpiperazine. In this manner, 156 mg (77%) of the captioned compound was obtained.

Example 78

3-Cycloheptyl-6-[2-methoxy-4-(1-piperazinyl)phenyl]-1-methyl-1,5-dihydro-4H-pyrazolo[3,4-d]pyrimidin-4-one monomethanesulfonate The same reaction procedure as in Example 62 was performed, except that the compound obtained in Example 77 was used in place of the compound obtained in Example 61. In this manner, 108 mg (72%) of the captioned compound was obtained.

--- for 10 minutes. Ether was added to the resulting solution, and precipitated solids were collected by filtration, thereby obtaining 43.9 mg (81%) of the captioned compound.

Example 79

Benzyl 1-[4-(3-cyclohexyl-1-methyl-4-oxo-4,5-di-hydro-1H-pyrazolo[3,4-d]pyrimidin-6-yl)-2-fluoro-5-methoxyphenyl]-1-piperazinecarboxylate The same reaction procedure as in Example 26 was performed, except that the compound obtained in Production Example 46 was used in place of 4-bromo-2-methoxybenzoic acid. In this manner, 366 mg (40%) of the captioned compound was obtained.

Example 80

3-Cycloheptyl-6-[5-fluoro-2-methoxy-4-(1-piperazinyl)phenyl]-1-methyl-1,5-dihydro-4H-pyrazolo[3,4-d]pyrimidin-4-one The same reaction procedure as in Example 36 was performed, except that the compound obtained in Example 79 was used in place of the compound obtained in Example 35. In this manner, 144 mg (63%) of the captioned compound was obtained.

Example 81

3-Cycloheptyl-6-[5-fluoro-2-methoxy-4-(1-piperazinyl)phenyl]-1-methyl-1,5-dihydro-4H-pyrazolo[3,4-d]pyrimidin-4-one monomethanesulfonate The same reaction procedure as in Example 62 was performed, except that the compound obtained in Example 80 was used in place of the compound obtained in Example 61. In this manner, 62 mg (85%) of the captioned compound was obtained.

Example 82

3-Cyclohexyl-6-[5-fluoro-2-methoxy-4-(4-methyl-1-piperazinyl)phenyl]-1-methyl-1,5-dihydro-4H-pyrazolo[3,4-d]pyrimidin-4-one To a 2 ml ethanol/1 ml water solution of 65 mg (0.15 mmol) of the compound obtained in Example 80, 500 µl of formalin and 1 ml of formic acid were added, and the mixture was heated under reflux for 4 hours. Then, an aqueous solution of sodium hydrogen carbonate was added to the reaction mixture, and the mixture was extracted with dichloromethane. The organic layer was washed with a saturated aqueous solution of sodium chloride. After the washed layer was dried over anhydrous sodium sulfate, the solvent was distilled off under reduced pressure. The residue was purified by silica gel column chromatography (chloroform/methanol=30/1~20/1) to obtain 37 mg (55%) of the captioned compound.

Example 83

3-Cyclohexyl-6-(2-methoxy-4-{methyl[2-(methylamino)ethyl]amino}phenyl)-1-methyl-1,5-dihydro-4H-pyrazolo[3,4-d]pyrimidin-4-one The same reaction procedure as in Example 27 was performed, except that N,N'-dimethylethylenediamine was used in place of N-methylpiperazine. In this manner, 123 mg (71%) of the captioned compound was obtained.

Example 84

3-Cyclohexyl-6-(2-methoxy-4-{methyl[2-(methylamino)ethyl]amino}phenyl)-1-methyl-1,5-dihydro-4H-pyrazolo[3,4-d]pyrimidin-4-one monomethanesulfonate The same reaction procedure as in Example 62 was performed, except that the compound obtained in Example 83 was used in place of the compound obtained in Example 61. In this manner, 93 mg (71%) of the captioned compound was obtained.

Example 85

6-(4-Bromo-2-ethoxyphenyl)-3-cyclohexyl-1-methyl-1,5-dihydro-4H-pyrazolo[3,4-d]pyrimidin-4-one The same reaction procedure as in Example 26 was performed, except that 4-bromo-2-ethoxybenzoic acid was used in place of 4-bromo-2-methoxybenzoic acid. In this manner, 3.79 g (93%) of the captioned compound was obtained.

Example 86

3-Cyclohexyl-6-[2-ethoxy-4-(4-methyl-1-piperazinyl)phenyl]-1-methyl-1,5-dihydro-4H-pyrazolo[3,4-d]pyrimidin-4-one The same reaction procedure as in Example 27 was performed, except that the compound obtained in Example 85 was used in place of the compound obtained in Example 26. In this manner, 159 mg (76%) of the captioned compound was obtained.

Example 87

3-Cyclohexyl-6-[2-ethoxy-4-(4-methyl-1-piperazinyl)phenyl]-1-methyl-1,5-dihydro-4H-pyrazolo[3,4-d]pyrimidin-4-one monomethanesulfonate The same reaction procedure as in Example 62 was performed, except that the compound obtained in Example 86 was used in place of the compound obtained in Example 61. In this manner, 83 mg (50%) of the captioned compound was obtained.

Example 88

Benzyl 1-[4-(3-cyclohexyl-1-methyl-4-oxo-4,5-di-hydro-1H-pyrazolo[3,4-d]pyrimidin-6-yl)-3-ethoxyphenyl]-4-piperidinyl(methyl)carbamate The same reaction procedure as in Example 27 was performed, except that the compound obtained in Example 85 was used in place of the compound obtained in Example 26, and benzyl methyl(4-piperidinyl)carbamate hydrochloride was used in place of N-methylpiperazine. In this manner, 234 mg (77%) of the captioned compound was obtained.

Example 89

3-Cyclohexyl-6-{2-ethoxy-4-[4-(methylamino)-1-piperidinyl]phenyl}-1-methyl-1,5-dihydro-4H-pyrazolo[3,4-d]pyrimidin-4-one The same reaction procedure as in Example 36 was performed, except that the compound obtained in Example 88 was used in place of the compound obtained in Example 35. In this manner, 46 mg (32%) of the captioned compound was obtained.

Example 90

3-Cyclohexyl-6-{2-ethoxy-4-[4-(methylamino)-1-piperidinyl]phenyl}-1-methyl-1,5-dihydro-4H-pyrazolo[3,4-d]pyrimidin-4-one monomethanesulfonate The same reaction procedure as in Example 62 was performed, except that the compound obtained in Example 89 was used in place of the compound obtained in Example 61. In this manner, 18 mg (38%) of the captioned compound was obtained.

Example 91

Benzyl 1-[4-(1-cyclohexyl-3-methyl-7-oxo-6,7-dihydro-1H-pyrazolo[4,3-d]pyrimidin-5-yl)-3-methoxyphenyl]-4-pyridinyl(methyl)carbamate The same reaction procedure as in Example 16 was performed, except that benzyl methyl(4-piperidinyl)carbamate hydrochloride was used in place of N-methylpiperazine. In this manner, 330 mg (94%) of the captioned compound was obtained.

Example 92

1-Cyclohexyl-5-{2-methoxy-4-[4-(methylamino)-1-piperidinyl]phenyl}-3-methyl-1,6-dihydro-7H-pyrazolo[4,3-d]pyrimidin-7-one The same reaction procedure as in Example 36 was performed, except that the compound obtained in Example 91 was used in place of the compound obtained in Example 35. In this manner, 322 mg (89%) of the captioned compound was obtained.

Example 93

Benzyl 1-[4-(3-cycloheptyl-1-methyl-4-oxo-4,5-dihydro-1H-pyrazolo[3,4-d]pyrimidin-6-yl)-3-methoxyphenyl]-4-piperidinyl(methyl)carbamate The same reaction procedure as in Example 27 was performed, except that the compound obtained in Example 63 was used in place of the compound obtained in Example 26, and benzyl methyl(4-piperidinyl)carbamate hydrochloride was used in place of N-methylpiperazine. In this manner, 179 mg (52%) of the captioned compound was obtained.

Example 94

3-Cycloheptyl-6-{2-methoxy-4-[4-(methylamino)-1-piperidinyl]phenyl}-1-methyl-1,5-dihydro-4H-pyrazolo[3,4-d]pyrimidin-4-one The same reaction procedure as in Example 36 was performed, except that the compound obtained in Example 93 was used in place of the compound obtained in Example 35. In this manner, 124 mg (quant.) of the captioned compound was obtained.

Example 95

3-Cycloheptyl-6-{2-methoxy-4-[4-(methylamino)-1-piperidinyl]phenyl}-1-methyl-1,5-dihydro-4H-pyrazolo[3,4-d]pyrimidin-4-one monomethanesulfonate The same reaction procedure as in Example 62 was performed, except that the compound obtained in Example 94 was used in place of the compound obtained in Example 61. In this manner, 112 mg (81%) of the captioned compound was obtained.

Example 96

Benzyl 1-[4-(3-cyclohexyl-1-methyl-4-oxo-4,5-dihydro-1H-pyrazolo[3,4-d]pyrimidin-6-yl)-3-methoxyphenyl]-4-piperidinyl(ethyl)carbamate The same reaction procedure as in Example 27 was performed, except that benzyl ethyl(4-piperidinyl)carbamate hydrochloride was used in place of N-methylpiperazine. In this manner, 195 mg (54%) of the captioned compound was obtained.

Example 97

3-Cyclohexyl-6-{2-methoxy-4-[4-(ethylamino)-1-piperidinyl]phenyl}-1-methyl-1,5-dihydro-4H-pyrazolo[3,4-d]pyrimidin-4-one The same reaction procedure as in Example 36 was performed, except that the compound obtained in Example 96 was used in place of the compound obtained in Example 35. In this manner, 108 mg (79%) of the captioned compound was obtained.

Example 98

Benzyl 1-[4-(1-cyclohexyl-3-methyl-7-oxo-6,7-dihydro-1H-pyrazolo[4,3-d]pyrimidin-5-yl)-3-methoxyphenyl]-4-piperidinyl(ethyl)carbamate The same reaction procedure as in Example 16 was performed, except that benzyl ethyl(4-piperidinyl)carbamate hydrochloride was used in place of N-methylpiperazine. In this manner, 272 mg (76%) of the captioned compound was obtained.

Example 99

1-Cyclohexyl-5-{2-methoxy-4-[4-(ethylamino)-1-piperidinyl]phenyl}-3-methyl-1,6-dihydro-7H-pyrazolo[4,3-d]pyrimidin-7-one The same reaction procedure as in Example 36 was performed, except that the compound obtained in Example 98 was used in place of the compound obtained in Example 35. In this manner, 131 mg (72%) of the captioned compound was obtained.

Example 100

1-Cyclohexyl-5-[4-(benzyloxy)-2-methoxyphenyl]-1-cyclohexyl-3-methyl-1,6-dihydro-7H-pyrazolo[4,3-d]pyrimidin-7-one The same reaction procedure as in Example 14 was performed, except that 4-(benzyloxy)-2-methoxybenzoic acid was used in place of the compound obtained in Production Example 34. In this manner, 1.37 g (77%) of the captioned compound was obtained.

Example 101

1-Cyclohexyl-5-(4-hydroxy-2-methoxyphenyl)-3-methyl-1,6-dihydro-7H-pyrazolo[4,3-d]pyrimidin-7-one The same reaction procedure as in Example 36 was performed, except that the compound obtained in Example 100 was used in place of the compound obtained in Example 35. In this manner, 1.08 g (99%) of the captioned compound was obtained.

Example 102

1-Cyclohexyl-5-(2-methoxy-4-{methyl[2-(methylamino)ethyl]amino}phenyl)-3-methyl-1,6-dihydro-7H-pyrazolo[4,3-d]pyrimidin-7-one The same reaction procedure as in Example 16 was performed, except that N,N'-dimethylethylenediamine was used in place of N-methylpiperazine. In this manner, 107 mg (62%) of the captioned compound was obtained.

Example 103

1-Cyclohexyl-5-(2-methoxy-4-{methyl[2-(methylamino)ethyl]amino}phenyl)-3-methyl-1,6-dihydro-7H-pyrazolo[4,3-d]pyrimidin-7-one monofumarate The same reaction procedure as in Example 62 was performed, except that the compound obtained in Example 102 was used in place of the compound obtained in Example 61, and fumaric acid was used in place of methanesulfonic acid. In this manner, 96 mg (75%) of the captioned compound was obtained.

Example 104

1-Cyclohexyl-5-{4-[(3R)-3-(dimethylamino)pyrrolidinyl]-2-methoxyphenyl}-3-methyl-1,6-dihydro-7H-pyrazolo[4,3-d]pyrimidin-7-one The same reaction procedure as in Example 16 was performed, except that (3R)-(dimethylamino)pyrrolidine was used in place of N-methylpiperazine. In this manner, 244 mg (75%) of the captioned compound was obtained.

Example 105

1-Cyclohexyl-5-{4-[(3S)-3-(dimethylamino)pyrrolidinyl]-2-methoxyphenyl}-3-methyl-1,6-dihydro-7H-pyrazolo[4,3-d]pyrimidin-7-one The same reaction procedure as in Example 16 was performed, except that (3S)-(dimethylamino)pyrrolidine was used in place of N-methylpiperazine. In this manner, 80 mg (49%) of the captioned compound was obtained.

Example 106

5-{4-[[2-(Benzyloxy)ethyl](methyl)amino]-2-methoxyphenyl}-1-cyclohexyl-3-methyl-1,6-dihydro-7H-pyrazolo[4,3-d]pyrimidin-7-one The same reaction procedure as in Example 16 was performed, except that N-[2-(benzyloxy)ethyl]-N-methylamine was used in place of N-methylpiperazine. In this manner, 80 mg (49%) of the captioned compound was obtained.

Example 107

1-Cyclohexyl-5-{4-[(2-hydroxyethyl)(methyl)amino]-2-methoxyphenyl}-3-methyl-1,6-dihydro-7H-pyrazolo[4,3-d]pyrimidin-7-one The same reaction procedure as in Example 36 was performed, except that the compound obtained in Example 106 was used in place of the compound obtained in Example 35. In this manner, 82 mg (64%) of the captioned compound was obtained.

Example 108

5-(4-{4-[(Benzyloxy)methyl]-1-piperidinyl}-2-methoxyphenyl)-1-cyclohexyl-3-methyl-1,6-dihydro-7H-pyrazolo[4,3-d]pyrimidin-7-one The same reaction procedure as in Example 16 was performed, except that the compound obtained in Production Example 48 was used in place of N-methylpiperazine. In this manner, 150 mg (66%) of the captioned compound was obtained.

Example 109

1-Cyclohexyl-5-{4-[4-(hydroxymethyl)-1-piperidinyl]-2-methoxyphenyl}-3-methyl-1,6-dihydro-7H-pyrazolo[4,3-d]pyrimidin-7-one The same reaction procedure as in Example 36 was performed, except that the compound obtained in Example 108 was used in place of the compound obtained in Example 35. In this manner, 75 mg (77%) of the captioned compound was obtained.

Example 110

1-Cyclohexyl-5-(2-methoxy-4-{methyl[3-(methylamino)propyl]amino}phenyl)-3-methyl-1,6-dihydro-7H-pyrazolo[4,3-d]pyrimidin-7-one The same reaction procedure as in Example 16 was performed, except that N,N'-dimethyl-1,3-propanediamine was used in place of N-methylpiperazine. In this manner, 95 mg (53%) of the captioned compound was obtained.

Example 111

1-Cyclohexyl-5-(2-methoxy-4-{methyl[3-(methylamino)propyl]amino}phenyl)-3-methyl-1,6-dihydro-7H-pyrazolo[4,3-d]pyrimidin-7-one monofumarate The same reaction procedure as in Example 62 was performed, except that the compound obtained in Example 110 was used in place of the compound obtained in Example 61, and fumaric acid was used in place of methanesulfonic acid. In this manner, 92 mg (84%) of the captioned compound was obtained.

Example 112

1-Cyclohexyl-5-[2-methoxy-4-(4-methyl-1,4-diazepan-1-yl)phenyl]-3-methyl-1,6-dihydro-7H-pyrazolo[4,3-d]pyrimidin-7-one The same reaction procedure as in Example 16 was performed, except that N-methylhomopiperazine was used in place of N-methylpiperazine. In this manner, 159 mg (98%) of the captioned compound was obtained.

Example 113

5-{4-[[2-(Benzyloxy)ethyl](ethyl)amino]-2-methoxyphenyl}-1-cyclohexyl-3-methyl-1,6-dihydro-7H-pyrazolo[4,3-d]pyrimidin-7-one The same reaction procedure as in Example 16 was performed, except that the compound obtained in Production Example 50 was used in place of N-methylpiperazine. In this manner, 188 mg (87%) of the captioned compound was obtained.

Example 114

1-Cyclohexyl-5-{4-[(2-hydroxyethyl)(ethyl)amino]-2-methoxyphenyl}-3-methyl-1,6-dihydro-7H-pyrazolo[4,3-d]pyrimidin-7-one The same reaction procedure as in Example 36 was performed, except that the compound obtained in Example 113 was used in place of the compound obtained in Example 35. In this manner, 120 mg (81%) of the captioned compound was obtained.

Example 115

1-Cyclohexyl-5-{4-[(2-hydroxyethyl)(ethyl)amino]-2-methoxyphenyl}-3-methyl-1,6-dihydro-7H-pyrazolo[4,3-d]pyrimidin-7-one monohydrochloride The same reaction procedure as in Example 62 was performed, except that the compound obtained in Example 114 was used in place of the compound obtained in Example 61, and a 4N-hydrochloric acid/1,4-dioxane solution was used in place of methanesulfonic acid. In this manner, 104 mg (87%) of the captioned compound was obtained.

Example 116

5-(4-Bromo-2-ethoxyphenyl-1-cyclohexyl-3-methyl-1,6-dihydro-7H-pyrazolo[4,3-d]pyrimidin-7-one The same reaction procedure as in Example 14 was performed, except that 4-bromo-2-ethoxybenzoic acid was used in place of the compound obtained in Production Example 34. In this manner, 2.16 g (quant.) of the captioned compound was obtained.

Example 117

3-Cyclohexyl-6-{2-ethoxy-4-[(2-methoxyethyl)amino]phenyl}-1-methyl-1,5-dihydro-4H-pyrazolo[3,4-d]pyrimidin-4-one The same reaction procedure as in Example 27 was performed, except that the compound obtained in Example 85 was used in place of the compound obtained in Example 26, and 2-methoxyethylamine was used in place of N-methylpiperazine. In this manner, 46 mg (31%) of the captioned compound was obtained.

Example 118

1-[4-(1-Cyclohexyl-3-methyl-7-oxo-6,7-dihydro-1H-pyrazolo[4,3-d]pyrimidin-5-yl)-3-methoxyphenyl]-4-piperidiny(methyl)formamide To a 3 ml methylene chloride solution of 96 mg (0.21 mmol) of the compound obtained in Example 92, 16 µl (0.43 mmoml) of formic acid, 119 µl (0.85 mmoml) of triethylamine, and 100 µl of propanephosphonic acid anhydride (25% ethyl acetate solution) were added, and the mixture was stirred at room temperature for 1 hour. Further, 16 µl (0.43 mmoml) of formic acid, 119 µl (0.85 mmoml) of triethylamine, and 100 µl of propanephosphonic acid anhydride (25% ethyl acetate solution) were added three times, and then the mixture was stirred at room temperature for 14.5 hours. Then, water was added to the reaction mixture, and the mixture was extracted with dichloromethane. The extract was dried over anhydrous sodium sulfate, and then the solvent was distilled off under reduced pressure. The residue was purified by silica gel column chromatography (chloroform/methanol=60/1) to obtain 92 mg (90%) of the captioned compound.

Example 119

N-{1-[4-(1-cyclohexyl-3-methyl-7-oxo-6,7-dihydro-1H-pyrazolo[4,3-d]pyrimidin-5-yl)-3-methoxyphenyl]-4-piperidinyl}-N-methylacetamide To a 4 ml methylene chloride solution of 105 mg (0.23 mmol) of the compound obtained in Example 92, 33 µl (0.35 mmoml) of acetic anhydride and 33.7 µl (0.47 mmoml) of pyridine were added, and the mixture was stirred at room temperature for 1 hour. Then, water was added to the reaction mixture, and the mixture was extracted with dichloromethane. The extract was dried over anhydrous sodium sulfate, and then the solvent was distilled off under reduced pressure. The residue was purified by silica gel column chromatography (chloroform/methanol=60/1) to obtain 92 mg (80%) of the captioned compound.

Example 120

Benzyl 1-[4-(1-cyclohexyl-3-methyl-7-oxo-6,7-dihydro-1H-pyrazolo[4,3-d]pyrimidin-5-yl)-3-ethoxyphenyl]-4-piperidiny(methyl)carbamate The same reaction procedure as in Example 16 was performed, except that the compound obtained in Example 116 was used in place of the compound obtained in Example 15, and benzyl methyl(4-piperidinyl)carbamate hydrochloride was used in place of N-methylpiperazine. In this manner, 176 mg (75%) of the captioned compound was obtained.

Example 121

1-Cyclohexyl-5-{2-ethoxy-4-[4-(methylamino)-1-piperidinyl]phenyl}-3-methyl-1,6-dihydro-7H-pyrazolo[4,3-d]pyrimidin-7-one The same reaction procedure as in Example 36 was performed, except that the compound obtained in Example 120 was used in place of the compound obtained in Example 35. In this manner, 97 mg (82%) of the captioned compound was obtained.

Example 122

1-Cyclohexyl-5-[4-(4-hydroxy-1-methyl-4-piperidinyl)-2-methoxyphenyl]-3-methyl-1,6-dihydro-7H-pyrazolo[4,3-d]pyrimidin-7-one In an atmosphere of argon, 0.95 ml of n-butyl lithium (1.59M/hexane solution, 1.51 mmol) was added dropwise at −78° C. to a 10 ml anhydrous tetrahydrofuran solution of 300 mg (0.72 mmol) of the compound obtained in Example 15. The mixture was stirred at −78° C. for 30 minutes, and then 133 µl (1.08 mmol) of 1-methyl-4-piperidone was added, followed by heating the mixture gradually to 0° C. over the course of 1 hour. Then, water was added to the reaction mixture, and then the mixture was extracted with ethyl acetate. The extract was dried over anhydrous sodium sulfate, and then the solvent was distilled off under reduced pressure. The residue was purified by silica gel column chromatography (chloroform/methanol=100/1) to obtain 179 mg (55%) of the captioned compound.

Example 123

1-Cyclohexyl-5-[2-methoxy-4-(1-methyl-1,2,3,6-tetrahydro-4-pyridinyl)phenyl]-3-methyl-1,6-dihydro-7H-pyrazolo[4,3-d]pyrimidin-7-one To a 10 ml toluene solution of 160 mg (0.35 mmol) of the compound obtained in Example 122, 135 mg (0.71 mmol) of p-toluenesulfonic acid monohydrate was added, and the mixture was heated under reflux for 22 hours with the use of a Dean-Stark dehydrator. The reaction mixture was returned to room temperature, and washed with a saturated aqueous solution of sodium hydrogen carbonate. The system was dried over anhydrous sodium sulfate, and then the solvent was distilled off under reduced pressure. The residue was purified by silica gel column chromatography (chloroform/methanol=30/1) to obtain 78 mg (51%) of the captioned compound.

Example 124

1-Cyclohexyl-5-[2-methoxy-4-(1-methyl-4-piperidinyl)phenyl]-3-methyl-1,6-dihydro-7H-pyrazolo[4,3-d]pyrimidin-7-one The same reaction procedure as in Example 36 was performed, except that the compound obtained in Example 123 was used in place of the compound obtained in Example 35. In this manner, 32 mg (62%) of the captioned compound was obtained.

Example 125

1-Cyclohexyl-5-[4-(1,4-diazepan-1-yl)-2-methoxyphenyl]-3-methyl-1,6-dihydro-7H-pyrazolo[4,3-d]pyrimidin-7-one The same reaction procedure as in Example 16 was performed, except that homopiperazine was used in place of N-methylpiperazine. In this manner, 286 mg (91%) of the captioned compound was obtained.

Example 126

5-[4-(4-Acetyl-1,4-diazepan-1-yl)-2-methoxyphenyl]-1-cyclohexyl-3-methyl-1,6-dihydro-7H-pyrazolo[4,3-d]pyrimidin-7-one The same reaction procedure as in Example 119 was performed, except that the compound obtained in Example 125 was used in place of the compound obtained in Example 92. In this manner, 286 mg (91%) of the captioned compound was obtained.

Example 127

1-Cyclohexyl-5-[4-(4-ethyl-1,4-diazepan-1-yl)-2-methoxyphenyl]-3-methyl-1,6-dihydro-7H-pyrazolo[4,3-d]pyrimidin-7-one To a 4 ml N,N-dimethylformamide solution of 102 mg (0.23 mmol) of the compound obtained in Example 125, 49 µl (0.35 mmol) of triethylamine and 23 µl (0.29 mmol) of ethyl iodide were added at room temperature, and the mixture was stirred for 3 hours. Ethyl acetate was added to the reaction mixture, and the mixture was washed with water and a saturated aqueous solution of sodium chloride in this order. The washed system was dried over anhydrous sodium sulfate, and then the solvent was distilled off under reduced pressure. The residue was purified by silica gel column chromatography (methylene chloride/methanol=20/1~10/1) to obtain 65 mg (60%) of the captioned compound.

Example 128

Benzyl 1-[4-(1-cyclohexyl-3-methyl-7-oxo-6,7-dihydro-1H-pyrazolo[4,3-d]pyrimidin-5-yl)-2-fluoro-5-methoxyphenyl]-4-piperidiny(methyl)carbamate The same reaction procedure as in Example 14 was performed, except that the compound obtained in Production Example 53 was used in place of the compound obtained in Production Example 34. In this manner, 257 mg (48%) of the captioned compound was obtained.

Example 129

1-Cyclohexyl-5-{5-fluoro-2-methoxy-4-[4-(methylamino)-1-piperidinyl]phenyl}-3-methyl-1,6-dihydro-7H-pyrazolo[4,3-d]pyrimidin-7-one The same reaction procedure as in Example 36 was performed, except that the compound obtained in Example 128 was used in place of the compound obtained in Example 35. In this manner, 129 mg (71%) of the captioned compound was obtained.

Example 130

1-Cyclohexyl-5-[4-(4-methyl-1,4-diazepan-1-yl)-2-ethoxyphenyl]-3-methyl-1,6-dihydro-7H-pyrazolo[4,3-d]pyrimidin-7-one The same reaction procedure as in Example 16 was performed, except that the compound obtained in Example 116 was used in place of the compound obtained in Example 15, and methylhomopiperazine was used in place of N-methylpiperazine. In this manner, 94 mg (58%) of the captioned compound was obtained.

Example 131

3-Cyclohexyl-6-{4-[[2-(dimethylamino)ethyl](methyl)amino]-2-methoxyphenyl}-1-methyl-1,5-dihydro-4H-pyrazolo[3,4-d]pyrimidin-4-one The same reaction procedure as in Example 27 was performed., except that N,N,N'-trimethylethylenediamine was used in place of N-methylpiperazine. In this manner, 174 mg (79%) of the captioned compound was obtained.

Example 132

3-Cyclohexyl-6-{4-[[2-(dimethylamino)ethyl](methyl)amino]-2-methoxyphenyl}-1-methyl-1,5-dihydro-4H-pyrazolo[3,4-d]pyrimidin-4-one monomethanesulfonate A 2 ml methanol suspended solution of 130 mg (0.30 mmol) of the compound obtained in Example 131 was heated to 50° C. To the system, 20 µl (0.30 mmol) of methanesulfonic acid was added, and the temperature of the mixture was gradually lowered to room temperature. Then, the solvent was distilled off under reduced pressure, and the residue was dissolved by addition of ethyl acetate. Ether was added to the resulting solution, and precipitated solids were collected by filtration to obtain 89 mg (55%) of the captioned compound.

Example 133

3-Cyclohexyl-6-[4-(1,4-diazepan-1-yl)-2-methoxyphenyl]-1-methyl-1,5-dihydro-4H-pyrazolo[3,4-d]pyrimidin-4-one The same reaction procedure as in Example 27 was performed, except that homopiperazine was used in place of N-methylpiperazine. In this manner, 165 mg (76%) of the captioned compound was obtained.

Example 134

3-Cyclohexyl-6-[4-(1,4-diazepan-1-yl)-2-methoxyphenyl]-1-methyl-1,5-dihydro-4H-pyrazolo[3,4-d]pyrimidin-4-one monomethanesulfonate To a 2 ml methanol solution of 74 mg (0.17 mmol) of the compound obtained in Example 133, 11.2 µl (0.17 mmol) of methanesulfonic acid was added, and the mixture was heated under reflux for 10 minutes. Then, the temperature of the reaction mixture was gradually lowered to room temperature. Ether was added to the resulting solution, and precipitated solids were collected by filtration to obtain 62 mg (69%) of the captioned compound.

Example 135

3-Cyclohexyl-6-[2-methoxy-4-(4-methyl-1,4-diazepan-1-yl)phenyl]-1-methyl-1,5-dihydro-4H-pyrazolo[3,4-d]pyrimidin-4-one To a 2 ml ethanol/2 ml water mixed solution of 60 mg (0.14 mmol) of the compound obtained in Example 133, 30 mg of paraformaldehyde and 1 ml of formic acid were added, and the mixture was heated under reflux for 24 hours. Then, the reaction mixture was brought to room temperature, an aqueous solution of sodium hydrogen carbonate was added, and the mixture was extracted with dichloromethane. The organic layer was washed with water and a saturated aqueous solution of sodium chloride. After the washed layer was dried over anhydrous sodium sulfate, the solvent was distilled off under reduced pressure. The residue was purified by silica gel column chromatography (chloroform/methanol=10/1) to obtain 53 mg (84%) of the captioned compound.

Example 136

3-Cyclohexyl-6-[2-methoxy-4-(4-methyl-1,4-diazepan-1-yl)phenyl]-1-methyl-1,5-dihydro-4H-pyrazolo[3,4-d]pyrimidin-4-one monomethanesulfonate The same reaction procedure as in Example 134 was performed, except that the compound obtained in Example 135 was used in place of the compound obtained in Example 133. In this manner, 31 mg (60%) of the captioned compound was obtained.

Example 137

6-[4-Bromo-2-(difluoromethoxy)phenyl]-3-cyclohexyl-1-methyl-1,5-dihydro-4H-pyrazolo[3,4-d]pyrimidin-4-one The same reaction procedure as in Example 26 was performed, except that the compound obtained in Production Example 55 was used in place of 4-bromo-2-methoxybenzoic acid. In this manner, 231 mg (16%) of the captioned compound was obtained.

Example 138

3-Cyclohexyl-6-[2-(difluoromethoxy)-4-(4-methyl-1-piperazinyl)phenyl]-1-methyl-1,5-dihydro-4H-pyrazolo[3,4-d]pyrimidin-4-one The same reaction procedure as in Example 27 was performed, except that the compound obtained in Example 137 was used in place of the compound obtained in Example 26. In this manner, 90 mg (58%) of the captioned compound was obtained.

Example 139

3-Cyclohexyl-6-[2-(difluoromethoxy)-4-(4-methyl-1-piperazinyl)phenyl]-1-methyl-1,5-dihydro-4H-pyrazolo[3,4-d]pyrimidin-4-one monomethanesulfonate A 2 ml methanol suspended solution of 65 mg (0.138 mmol) of the compound obtained in Example 138 was heated to 50° C. To the system, 9.1 µl (0.14 mmol) of methanesulfonic acid was added, and then the mixture was heated under reflux for 15 minutes. Then, the reaction mixture was brought to room temperature, and the solvent was distilled off under reduced pressure. The residue was recrystallized from ethyl acetate-ethanol to obtain 16 mg (20%) of the captioned compound.

Example 140

N-[4-(3-cyclohexyl-1-methyl-4-oxo-4,5-dihydro-1H-pyrazolo[3,4-d]pyrimidin-6-yl)-3-methoxyphenyl]urea To a 2 ml water/4 ml acetic acid solution of 200 mg (0.567 mmol) of the compound obtained in Example 44, 377 mg (4.65 mmol) of potassium cyanate was added, and the mixture was stirred at room temperature for 3 hours. Then, water was added to the reaction mixture, and the mixture was extracted with chloroform. The organic layer was washed with water and a saturated aqueous solution of sodium chloride. After the washed layer was dried over anhydrous sodium sulfate, the solvent was distilled off under reduced pressure. The residue was purified by silica gel column chromatography (chloroform/methanol=10/1) to obtain 126 mg (56%) of the captioned compound.

Example 141

N-[4-(3-cyclohexyl-1-methyl-4-oxo-4,5-dihydro-1H-pyrazolo[3,4-d]pyrimidin-6-yl)-3-methoxyphenyl]-N-(methylsulfonyl)methanesulfonamide To a 6 ml tetrahydrofuran solution of 114 mg (0.323 mmol) of the compound obtained in Example 44, 49 µl (0.63 mmol) of methanesulfonyl chloride and 90 µl (0.65 mmol)

of triethylamine were added, and the mixture was stirred at room temperature for 1 hour. Then, 23 µl (0.3 mmol) of methanesulfonyl chloride was further added to the reaction mixture, and the mixture was stirred at room temperature for 1 hour. Then, an aqueous solution of sodium hydrogen carbonate was added to the reaction mixture, and the mixture was extracted with chloroform. The organic layer was washed with water and a saturated aqueous solution of sodium chloride. After the washed layer was dried over anhydrous sodium sulfate, the solvent was distilled off under reduced pressure. The residue was purified by silica gel column chromatography (chloroform/methanol=30/1) to obtain 123 mg (75%) of the captioned compound.

Example 142

N-[4-(3-cyclohexyl-1-methyl-4-oxo-4,5-dihydro-1H-pyrazolo[3,4-d]pyrimidin-6-yl)-3-methoxyphenyl]methanesulfonamide To a 2 ml methanol solution of 100 mg (0.20 mg) of the compound obtained in Example 141, 1 ml of a 1M aqueous solution of sodium hydroxide was added, and the mixture was stirred at room temperature for 3 hours. Then, the reaction mixture was diluted with water, and the dilution was washed with dichloromethane. The aqueous layer was acidified with a 2M aqueous solution of hydrochloric acid, and precipitated solids were collected by filtration, followed by drying and recrystallization to obtain 19 mg (22%) of the captioned compound.

Example 143

3-Cyclohexyl-6-[2-methoxy-4-(2-oxo-1,3-oxazolidin-3-yl)phenyl]-1-methyl-1,5-dihydro-4H-pyrazolo[3,4-d]pyrimidin-4-one To a 6 ml tetrahydrofuran solution of 150 mg (0.425 mmol) of the compound obtained in Example 44, 79 µl (0.765 mmol) of 2-chloroethyl chloroformate and triethylamine were added, and the mixture was stirred at room temperature for 20 hours. Further, 30 µl (0.29 mmol) of 2-chloroethyl chloroformate was added, and the mixture was stirred at room temperature for 4 hours. Then, an aqueous solution of sodium hydrogen carbonate was added to the reaction mixture, and the mixture was extracted with chloroform. The organic layer was washed with water and a saturated aqueous solution of sodium chloride. After the washed layer was dried over anhydrous sodium sulfate, the solvent was distilled off under reduced pressure. To a 2 ml ethanol solution of the residue, 1 ml of a 1M aqueous solution of sodium hydroxide was added, and the mixture was stirred at room temperature for 5 hours. Then, the reaction mixture was neutralized with a 1M aqueous solution of hydrochloric acid, and extracted with chloroform. The organic layer was washed with water and a saturated aqueous solution of sodium chloride. After the washed layer was dried over anhydrous sodium sulfate, the solvent was distilled off under reduced pressure. The residue was recrystallized from ethanol to obtain 116 mg (65%) of the captioned compound.

Example 144

3-Cyclohexyl-6-[2-methoxy-4-(2-oxo-1-imidazolidinyl)phenyl]-1-methyl-1,5-dihydro-4H-pyrazolo[3,4-d]pyrimidin-4-one To a 4 ml tetrahydrofuran solution of 150 mg (0.425 mmol) of the compound obtained in Example 44, 71 µl (0.829 mmol) of 2-chloroethyl isocyanate was added, and the mixture was stirred at room temperature for 20 hours. Then, water was added to the reaction mixture, and the mixture was extracted with chloroform. The organic layer was washed with a saturated aqueous solution of sodium chloride, and then dried over anhydrous sodium sulfate, followed by distilling off the solvent under reduced pressure. To the residue, 4 ml of ethanol and 2 ml of a 1M aqueous solution of sodium hydroxide were added, and the mixture was stirred at room temperature for 15 hours. Then, the reaction mixture was neutralized with a 1M aqueous solution of hydrochloric acid, and extracted with chloroform. The organic layer was washed with water and a saturated aqueous solution of sodium chloride. After the washed layer was dried over anhydrous sodium sulfate, the solvent was distilled off under reduced pressure. The residue was purified by silica gel column chromatography (chloroform/methanol=1/1) to obtain 95 mg (53%) of the captioned compound.

Example 145

Ethyl 4-(3-cyclohexyl-1-methyl-4-oxo-4,5-dihydro-1H-pyrazolo[3,4-d]pyrimidin-6-yl)-3-methoxyphenylcarbamate To a 6 ml tetrahydrofuran suspension of 100 mg (0.283 mmol) of the compound obtained in Example 44, 48 µl (0.50 mmol) of ethyl chlorocarbonate and 98 µl (0.707 mmol) of triethylamine were added, and the mixture was stirred at room temperature for 3 hours. Further, 48 µl (0.50 mmol) of ethyl chlorocarbonate and 1 ml of pyridine were added, and the mixture was stirred at room temperature for 18 hours. Then, a 1M aqueous solution of sodium hydroxide was added to the reaction mixture, and the mixture was extracted with dichloromethane. The organic layer was washed with water and a saturated aqueous solution of sodium chloride. After the washed layer was dried over anhydrous sodium sulfate, the solvent was distilled off under reduced pressure. The residue was purified by silica gel column chromatography (ethyl acetate/hexane=1/1~2/1) to obtain 68 mg (57%) of the captioned compound.

Example 146

N-[4-(3-cyclohexyl-1-methyl-4-oxo-4,5-dihydro-1H-pyrazolo[3,4-d]pyrimidin-6-yl)-3-methoxyphenyl]-N-methylacetamide The same reaction procedure as in Example 4 was performed, except that the compound obtained in Example 47 was used in place of the compound obtained in Example 3. In this manner, 94 mg (92%) of the captioned compound was obtained.

Example 147

N-[4-(3-cyclohexyl-1-methyl-4-oxo-4,5-dihydro-1H-pyrazolo[3,4-d]pyrimidin-6-yl)-3-methoxyphenyl]-N-methylmethanesulfonamide To a 3 ml pyridine solution of 91.8 mg (0.25 mmol) of the compound obtained in Example 47, 23.2 µl (0.3 mmol) of methanesulfonyl chloride was added, and the mixture was stirred at room temperature for 20 hours. Then, an aqueous solution of sodium hydrogen carbonate was added to the reaction mixture, and the mixture was extracted with dichloromethane. The organic layer was washed with water and a saturated aqueous solution of sodium chloride. After the washed layer was dried over anhydrous sodium sulfate, the solvent was distilled off under reduced pressure. The residue was purified by silica gel column chromatography (ethyl acetate/hexane=2/1˜only ethyl acetate) to obtain 97.2 mg (87%) of the captioned compound.

Example 148

N-[4-(3-cyclohexyl-1-methyl-4-oxo-4,5-dihydro-1H-pyrazolo[3,4-d]pyrimidin-6-yl)-3-methoxyphenyl]-4-morpholinecarboxamide To a 3 ml dichloromethane suspension of 100 mg (0.283 mmol) of the compound obtained in Example 44, 28 mg (0.0944 mmol) of triphosgene and 79 μl (0.566 mmol) of triethylamine were added, and the mixture was stirred at room temperature for 15 minutes. Then, 25 μl (0.283 mmol) of morpholine was added to the reaction mixture, and the mixture was stirred at room temperature for 4 hours. Water was added to the reaction mixture, and the mixture was extracted with dichloromethane. The organic layer was washed with water and a saturated aqueous solution of sodium chloride. After the washed layer was dried over anhydrous sodium sulfate, the solvent was distilled off under reduced pressure. The residue was purified by silica gel column chromatography (chloroform/methanol=15/1) to obtain 95 mg (72%) of the captioned compound.

Example 149

3-Cyclohexyl-6-{2-methoxy-4-[4-(methylamino)-1-piperidinyl]phenyl}-1-methyl-1,5-dihydro-4H-pyrazolo[3,4-d]pyrimidin-4-one To a 4 ml 1,2-dichloroethane solution of 200 mg (0.46 mmol) of the compound obtained in Example 30, 100 μl (0.92 mmol) of methylamine (30% methanol solution), 146 mg (0.69 mmol) of sodium triacetoxyborohydride, and 26 μl of acetic acid were added, and the mixture was stirred at room temperature for 6 hours. Then, water was added to the reaction mixture, and the mixture was extracted with chloroform. The organic layer was washed with water and a saturated aqueous solution of sodium chloride. After the washed layer was dried over anhydrous sodium sulfate, the solvent was distilled off under reduced pressure. The residue was purified by silica gel column chromatography (ethyl acetate/chloroform/methanol=10/10/1) to obtain 176 mg (85%) of the captioned compound.

Example 150

3-Cyclohexyl-6-{2-methoxy-4-[4-(methylamino)-1-piperidinyl]phenyl}-1-methyl-1,5-dihydro-4H-pyrazolo[3,4-d]pyrimidin-4-one monomethanesulfonate The same reaction procedure as in Example 62 was performed, except that the compound obtained in Example 149 was used in place of the compound obtained in Example 61. In this manner, 38 mg (55%) of the captioned compound was obtained.

Example 151

N'-[4-(3-cyclohexyl-1-methyl-4-oxo-4,5-dihydro-1H-pyrazolo[3,4-d]pyrimidin-6-yl)-3-methoxyphenyl]-N-(2-hydroxyethyl)-N-methylurea The same reaction procedure as in Example 148 was performed, except that 2-(methylamino)ethanol was used in place of morpholine. In this manner, 162 mg (42%) of the captioned compound was obtained.

Example 152

3-Cyclohexyl-6-[2-methoxy-4-(3-methyl-2-oxo-1-imidazolidinyl)phenyl]-1-methyl-1,5-dihydro-4H-pyrazolo[3,4-d]pyrimidin-4-one To a 3 ml tetrahydrofuran suspension of 114 mg (0.25 mmol) of the compound obtained in Example 151, 52 mg (0.30 mmol) of 1,1'-azobis(N,N-dimethylformamide) and 75 μl (0.30 mmol) of n-tributylphosphine were added, and the mixture was stirred at room temperature for 20 hours. Then, water was added to the reaction mixture, and the mixture was extracted with ethyl acetate. The organic layer was washed with water and a saturated aqueous solution of sodium chloride. After the washed layer was dried over anhydrous sodium sulfate, the solvent was distilled off under reduced pressure. The residue was purified by silica gel column chromatography (ethyl acetate) to obtain 71.6 mg (66%) of the captioned compound.

Example 153

3-Cyclohexyl-6-{4-[4-(dimethylamino)-1-piperidinyl]-2-methoxyphenyl}-1-methyl-1,5-dihydro-4H-pyrazolo[3,4-d]pyrimidin-4-one The same reaction procedure as in Example 135 was performed, except that the compound obtained in Example 149 was used in place of the compound obtained in Example 133. In this manner, 68.3 mg (74%) of the captioned compound was obtained.

Example 154

3-Cyclohexyl-6-{4-[4-(dimethylamino)-1-piperidinyl]-2-methoxyphenyl}-1-methyl-1,5-dihydro-4H-pyrazolo[3,4-d]pyrimidin-4-one monomethanesulfonate To a 1 ml ethanol solution of 50 mg (0.108 mmol) of the compound obtained in Example 153, 7.1 ml (0.110 mmol) of methanesulfonic acid was added, and the mixture was heated under reflux for 10 minutes. Then, the reaction mixture was cooled to room temperature, and the solvent was distilled off under reduced pressure. The residue was purified by recrystallization (ethyl acetate-ethanol) to obtain 28 mg (46%) of the captioned compound.

Example 155

3-Cyclohexyl-6-[4-(1,1-dioxido-2-isothiazolidinyl)-2-methoxyphenyl]-1-methyl-1,5-dihydro-4H-pyrazolo[3,4-d]pyrimidin-4-one To a 2 ml pyridine solution of 100 mg (0.280 mmol) of the compound obtained in Example 44, 85.2 μl (0.700 mmol) of 3-chloropropanesulfonyl chloride was added, and the mixture was stirred at room temperature for 8 hours. Then, an aqueous solution of sodium hydrogen carbonate was added to the reaction mixture, and the mixture was extracted with ethyl acetate. The organic layer was washed with water and a saturated aqueous solution of sodium chloride, and then dried over anhydrous sodium sulfate, followed by distilling off the solvent under reduced pressure. To the residue, 2 ml of ethanol and a 1M aqueous solution of sodium hydroxide were added, and the mixture was stirred at room temperature for 48 hours. Then, the reaction mixture was neutralized with a 1M aqueous solution of hydrochloric acid, and extracted with ethyl acetate. The organic layer was washed with water and a saturated aqueous solution of sodium chloride. After the washed layer was dried over anhydrous sodium sulfate, the solvent was distilled off under reduced pressure. The residue was purified by silica gel column chromatography (ethyl acetate) to obtain 68 mg (53%) of the captioned compound.

Example 156

4-(3-Cyclohexyl-1-methyl-4-oxo-4,5-dihydro-1H-pyrazolo[3,4-d]pyrimidin-6-yl)-N-(2-hydroxyethyl)-3-methoxy-N-methylbenzenesulfonamide The same reaction procedure as in Example 49 was performed, except that 2-(methylamino)ethanol was used in place of N-methylpiperazine. In this manner, 54 mg (57%) of the captioned compound was obtained.

Example 157

4-(3-Cyclohexyl-1-methyl-4-oxo-4,5-dihydro-1H-pyrazolo[3,4-d]pyrimidin-6-yl)-N-(2-(dimethylamino)ethyl)-3-methoxy-N-methylbenzenesulfonamide The same reaction procedure as in Example 49 was performed, except that N,N,N'-trimethylethylenediamine was used in place of N-methylpiperazine. In this manner, 56 mg (56%) of the captioned compound was obtained.

Example 158

4-(3-Cyclohexyl-1-methyl-4-oxo-4,5-dihydro-1H-pyrazolo[3,4-d]pyrimidin-6-yl)-N-(2-(dimethylamino)ethyl)-3-methoxy-N-methylbenzenesulfonamide monomethanesulfonate To a 1 ml ethanol solution of 44 mg (0.0876 mmol) of the compound obtained in Example 157, 5.8 μl (0.0894 mmol) of methanesulfonic acid was added, and the mixture was heated under reflux for 10 minutes. Then, the reaction mixture was cooled to room temperature, and ether was added to the reaction mixture. Precipitated solids were collected by filtration. The solids were purified by recrystallization (ethyl acetate-ethanol) to obtain 22 mg (42%) of the captioned compound.

Example 159

4-(3-Cyclohexyl-1-methyl-4-oxo-4,5-dihydro-1H-pyrazolo[3,4-d]pyrimidin-6-yl)-N-(3-hydroxypropyl)-3-methoxybenzenesulfonamide The same reaction procedure as in Example 49 was performed, except that n-propanolamine was used in place of N-methylpiperazine. In this manner, 148 mg (54%) of the captioned compound was obtained.

Example 160

3-Cyclohexyl-6-[4-(1,4-diazepan-1-ylsulfonyl)-2-methoxyphenyl]-1-methyl-1,5-dihydro-4H-pyrazolo[3,4-d]pyrimidin-4-one The same reaction procedure as in Example 49 was performed, except that homopiperazine was used in place of N-methylpiperazine. In this manner, 115 mg (50%) of the captioned compound was obtained.

Example 161

3-Cyclohexyl-6-[4-(1,4-diazepan-1-ylsulfonyl)-2-methoxyphenyl]-1-methyl-1,5-dihydro-4H-pyrazolo[3,4-d]pyrimidin-4-one monomethanesulfonate The same reaction procedure as in Example 62 was performed, except that the compound obtained in Example 160 was used in place of the compound obtained in Example 61. In this manner, 15 mg (36%) of the captioned compound was obtained.

Example 162

3-Cyclohexyl-6-{2-methoxy-4-[(4-methyl-1,4-diazepan-1-yl)sulfonyl]phenyl}-1-methyl-1,5-dihydro-4H-pyrazolo[3,4-d]pyrimidin-4-one The same reaction procedure as in Example 135 was performed, except that the compound obtained in Example 160 was used in place of the compound obtained in Example 133. In this manner, 47.6 mg (77%) of the captioned compound was obtained.

Example 163

3-Cyclohexyl-6-{2-methoxy-4-[(4-methyl-1,4-diazepan-1-yl)sulfonyl]phenyl}-1-methyl-1,5-dihydro-4H-pyrazolo[3,4-d]pyrimidin-4-one monomethanesulfonate The same reaction procedure as in Example 154 was performed, except that the compound obtained in Example 162 was used in place of the compound obtained in Example 153. In this manner, 20 mg (46%) of the captioned compound was obtained.

Example 164

3-Cyclohexyl-6-{4-[(3-hydroxy-1-pyrrolidinyl)sulfonyl]-2-methoxyphenyl}-1-methyl-1,5-dihydro-4H-pyrazolo[3,4-d]pyrimidin-4-one The same reaction procedure as in Example 49 was performed, except that 3-pyrrolidinol was used in place of N-methylpiperazine. In this manner, 85 mg (76%) of the captioned compound was obtained.

Example 165

3-Cyclohexyl-6-[2-methoxy-4-(4-thiomorpholinylsulfonyl)phenyl]-1-methyl-1,5-dihydro-4H-pyrazolo[3,4-d]pyrimidin-4-one The same reaction procedure as in Example 49 was performed, except that thiomorpholine was used in place of N-methylpiperazine. In this manner, 86.3 mg (75%) of the captioned compound was obtained.

Example 166

3-Cyclohexyl-6-[4-(1,4-dioxa-8-azaspiro[4,5]deca-8-ylsulfonyl)-2-methoxyphenyl]-1-methyl-1,5-dihydro-4H-pyrazolo[3,4-d]pyrimidin-4-one The same reaction procedure as in Example 49 was performed, except that 1,4-dioxa-8-azaspiro[4,5]decane was used in place of N-methylpiperazine. In this manner, 254 mg (68%) of the captioned compound was obtained.

Example 167

3-Cyclohexyl-6-{2-methoxy-4-[(4-oxo-1-piperidinyl)sulfonyl]phenyl}-1-methyl-1,5-dihydro-4H-pyrazolo[3,4-d]pyrimidin-4-one The same reaction procedure as in Example 30 was performed, except that the compound obtained in Example 166 was used in place of the compound obtained in Example 29. In this manner, 182 mg (99%) of the captioned compound was obtained.

Example 168

3-Cyclohexyl-6-(2-methoxy-4-{[4-(methylamino)-1-piperidinyl]sulfonyl}phenyl)-1-methyl-1,5-dihydro-4H-pyrazolo[3,4-d]pyrimidin-4-one The same reaction procedure as in Example 149 was performed, except that the compound obtained in Example 167 was used in place of the compound obtained in Example 30. In this manner, 92 mg (60%) of the captioned compound was obtained.

Example 169

3-Cyclohexyl-6-(2-methoxy-4-{[4-(methylamino)-1-piperidinyl]sulfonyl}phenyl)-1-methyl-1,5-dihydro-4H-pyrazolo[3,4-d]pyrimidin-4-one monomethanesulfonate The same reaction procedure as in Example 154 was performed, except that the compound obtained in Example 168 was used in place of the compound obtained in Example 153. In this manner, 30.5 mg (43%) of the captioned compound was obtained.

Example 170

Benzyl 1-{[4-(3-cyclohexyl-1-methyl-4-oxo-4,5-dihydro-1H-pyrazolo[3,4-d]pyrimidin-6-yl)-3-methoxyphenyl]sulfonyl}-3-pyrrolidinylcarbamate The same reaction procedure as in Example 49 was performed, except that benzyl 3-pyrrolidinylcarbamate monohydrochloride was used in place of N-methylpiperazine. In this manner, 108 mg (76%) of the captioned compound was obtained.

Example 171

6-{4-[(3-Amino-1-pyrrolidinyl)sulfonyl]-2-methoxyphenyl}-3-cyclohexyl-1-methyl-1,5-dihydro-4H-pyrazolo[3,4-d]pyrimidin-4-one The same reaction procedure as in Example 36 was performed, except that the compound obtained in Example 170 was used in place of the compound obtained in Example 35. In this manner, 48 mg (76%) of the captioned compound was obtained.

Example 172

6-{4-[(3-Amino-1-pyrrolidinyl)sulfonyl]-2-methoxyphenyl}-3-cyclohexyl-1-methyl-1,5-dihydro-4H-pyrazolo[3,4-d]pyrimidin-4-one monomethanesulfonate The same reaction procedure as in Example 154 was performed, except that the compound obtained in Example 171 was used in place of the compound obtained in Example 153. In this manner, 37 mg (90%) of the captioned compound was obtained.

Example 173

Benzyl 1-{[4-(3-cyclohexyl-1-methyl-4-oxo-4,5-dihydro-1H-pyrazolo[3,4-d]pyrimidin-6-yl)-3-methoxyphenyl]sulfonyl}-4-piperidinylcarbamate The same reaction procedure as in Example 49 was performed, except that benzyl 3-piperidinylcarbamate monohydrochloride was used in place of N-methylpiperazine. In this manner, 202 mg (93%) of the captioned compound was obtained.

Example 174

6-{4-[(4-Amino-1-piperidinyl)sulfonyl]-2-methoxyphenyl}-3-cyclohexyl-1-methyl-1,5-dihydro-4H-pyrazolo[3,4-d]pyrimidin-4-one The same reaction procedure as in Example 36 was performed, except that the compound obtained in Example 173 was used in place of the compound obtained in Example 35. In this manner, 94 mg (78%) of the captioned compound was obtained.

Example 175

6-{4-[(4-Amino-1-piperidinyl)sulfonyl]-2-methoxyphenyl}-3-cyclohexyl-1-methyl-1,5-dihydro-4H-pyrazolo[3,4-d]pyrimidin-4-one monomethanesulfonate The same reaction procedure as in Example 62 was performed, except that the compound obtained in Example 174 was used in place of the compound obtained in Example 61. In this manner, 60 mg (63%) of the captioned compound was obtained.

Example 176

3-Cyclohexyl-6-[2-methoxy-4-(4-thiomorpholinyl) phenyl]-1-methyl-1,5-dihydro-4H-pyrazolo[3,4-d] pyrimidin-4-one The same reaction procedure as in Example 26 was performed, except that the compound obtained in Production Example 60 was used in place of 4-bromo-2-methoxybenzoic acid. In this manner, 126 mg (18%) of the captioned compound was obtained.

Example 177

6-(4-Bromophenyl)-3-cyclohexyl-1-methyl-1,5-dihydro-4H-pyrazolo[3,4-d]pyrimidin-4-one To a 30 ml pyridine solution of 2.2 g (10 mmol) of the compound obtained in Example 32, 2.8 g (13 mmol) of p-bromobenzoyl chloride was added, and the mixture was stirred at room temperature for 3 hours. Further, 1.0 g (4.5 mmol) of p-bromobenzoyl chloride was added, and the mixture was stirred at room temperature for 4 hours. Then, an aqueous solution of sodium hydrogen carbonate was added to the reaction mixture, and the mixture was extracted with ethyl acetate. The organic layer was washed with water and a saturated aqueous solution of sodium chloride, and then dried over anhydrous sodium sulfate, followed by distilling off the solvent under reduced pressure. To the residue, 80 ml of ethanol and 40 ml of a 1M aqueous solution of sodium hydroxide were added, and the mixture was heated under reflux for 8 hours. Then, the reaction mixture was cooled to room temperature, and acetic acid was added. Precipitated solids were collected by filtration, the solids obtained were dissolved in chloroform, and the solution was washed with sodium hydrogen carbonate, water and a saturated aqueous solution of sodium chloride in this order. After the organic layer was dried over anhydrous sodium sulfate, the solvent was distilled off under reduced pressure. The residue was recrystallized (ethanol) to obtain 590 mg (15%) of the captioned compound.

Example 178

3-Cyclohexyl-1-methyl-6-[4-(4-methyl-1-piperazinyl)phenyl]-1,5-dihydro-4H-pyrazolo[3,4-d]pyrimidin-4-one The same reaction procedure as in Example 27 was performed, except that the compound obtained in Example 177 was used in place of the compound obtained in Example 26. In this manner, 143 mg (77%) of the captioned compound was obtained.

Example 179

3-Cyclohexyl-1-methyl-6-[4-(4-methyl-1-piperazinyl)phenyl]-1,5-dihydro-4H-pyrazolo[3,4-d]pyrimidin-4-one monomethanesulfonate The same reaction procedure as in Example 62 was performed, except that the compound obtained in Example 178 was used in place of the compound obtained in Example 61. In this manner, 106 mg (86%) of the captioned compound was obtained.

Example 180

6-(4-Aminophenyl)-3-cyclohexyl-1-methyl-1,5-dihydro-4H-pyrazolo[3,4-d]pyrimidin-4-one To a pyridine solution of 2.2 g (10 mmol) of the compound obtained in Example 32, 2.2 g (13 mmol) of p-nitrobenzoyl chloride was added, and the mixture was stirred at room temperature for 1.5 hours. Then, the reaction mixture was distilled under reduced pressure, and an aqueous solution of sodium hydrogen carbonate was added to the residue, followed by extracting the mixture with ethyl acetate. The organic layer was washed with water and a saturated aqueous solution of sodium chloride, and then dried over anhydrous sodium sulfate, followed by distilling off the solvent under reduced pressure. To the residue, 30 ml of methanol and 400 mg of 10% palladium carbon were added. The mixture was stirred for 8 hours in an atmosphere of hydrogen at room temperature and atmospheric pressure. Then, the catalyst was removed by filtration, and the filtrate was distilled under reduced pressure. To the residue, 80 ml of ethanol and 40 ml of a 1M aqueous solution of sodium hydroxide were added, followed by heating the mixture under reflux for 5 hours. Then, the reaction mixture was cooled to room temperature, diluted with water, and extracted with chloroform. The organic layer was washed with water and a saturated aqueous solution of sodium chloride, and then dried over anhydrous sodium sulfate, followed by distilling off the solvent under reduced pressure. The residue was purified by silica gel column chromatography (chloroform/methanol=30/1) to obtain 960 mg (30%) of the captioned compound.

Example 181

4-(3-Cyclohexyl-1-methyl-4-oxo-4,5-dihydro-1H-pyrazolo[3,4-d]pyrimidin-6-yl)benzenesulfonyl chloride The same reaction procedure as in Example 48 was performed, except that the compound obtained in Example 180 was used in place of the compound obtained in Example 44. In this manner, 743 mg (65%) of the captioned compound was obtained.

Example 182

3-Cyclohexyl-6-{4-[(4-hydroxy-1-piperidinyl)sulfonyl]phenyl}-1-methyl-1,5-dihydro-4H-pyrazolo[3,4-d]pyrimidin-4-one The same reaction procedure as in Example 49 was performed, except that the compound obtained in Example 181 was used in place of the compound obtained in Example 48, and 4-hydroxypiperidine was used in place of N-methylpiperazine. In this manner, 72 mg (62%) of the captioned compound was obtained.

Example 183

6-{4-[4-(Benzyamino)-1-piperidinyl]-2-methoxyphenyl}-3-cyclohexyl-1-methyl-1,5-dihydro-4H-pyrazolo[3,4-d]pyrimidin-4-one The same reaction procedure as in Example 149 was performed, except that benzylamine was used in place of methylamine. In this manner, 236 mg (90%) of the captioned compound was obtained.

Example 184

6-[4-(4-amino-1-piperidinyl)-2-methoxyphenyl]-3-cyclohexyl-1-methyl-1,5-dihydro-4H-pyrazolo[3,4-d]pyrimidin-4-one The same reaction procedure as in Example 36 was performed, except that the compound obtained in Example 183 was used in place of the compound obtained in Example 35. In this manner, 126 mg (76%) of the captioned compound was obtained.

Example 185

6-[4-(4-Amino-1-piperidinyl)-2-methoxyphenyl]-3-cyclohexyl-1-methyl-1,5-dihydro-4H-pyrazolo[3,4-d]pyrimidin-4-one monomethanesulfonate The same reaction procedure as in Example 154 was performed, except that the compound obtained in Example 184 was used in place of the compound obtained in Example 153. In this manner, 53 mg (43%) of the captioned compound was obtained.

Example 186

3-Cyclohexyl-1-methyl-6-{4-[(4-methyl-1,4-diazepan-1-yl)sulfonyl]phenyl}-1,5-dihydro-4H-pyrazolo[3,4-d]pyrimidin-4-one The same reaction procedure as in Example 49 was performed, except that the compound obtained in Example 181 was used in place of the compound obtained in Example 48, and N-methyl-1,4-diazacycloheptane was used in place of N-methylpiperazine. In this manner, 110 mg (45%) of the captioned compound was obtained.

Example 187

3-Cyclohexyl-1-methyl-6-{4-[(4-methyl-1,4-diazepan-1-yl)sulfonyl]phenyl}-1,5-dihydro-4H-pyrazolo[3,4-d]pyrimidin-4-one monomethanesulfonate The same reaction procedure as in Example 154 was performed, except that the compound obtained in Example 186 was used in place of the compound obtained in Example 153. In this manner, 75 mg (72%) of the captioned compound was obtained.

Example 188

Benzyl 1-[4-(3-cyclohexyl-1-methyl-4-oxo-4,5-dihydro-1H-pyrazolo[3,4-d]pyrimidin-6-yl)phenyl]-4-piperidinyl(methyl)carbamate The same reaction procedure as in Example 27 was performed, except that the compound obtained in Example 177 was used in place of the compound obtained in -Example 26, and benzyl methyl(4-piperidinyl)carbamate was used in place of N-methylpiperazine. In this manner, 255 mg (71%) of the captioned compound was obtained.

Example 189

3-Cyclohexyl-1-methyl-6-{4-[4-(methylamino)-1-piperidinyl]phenyl}-1,5-dihydro-4H-pyrazolo[3,4-d]pyrimidin-4-one monomethanesulfonate To a 5 ml methanol suspension of the compound obtained in Example 188, 10% palladium carbon and 27 μl (0.41 mmol) of methanesulfonic acid were added. The mixture was stirred for 72 hours in an atmosphere of hydrogen at room temperature and atmospheric pressure. Then, the catalyst was removed by filtration to obtain 221 mg (quant.) of the captioned compound.

Example 190

3-Cyclohexyl-6-[4-(1,4-diazepan-1-ylsulfonyl)phenyl]-1-methyl-1,5-dihydro-4H-pyrazolo[3,4-d]pyrimidin-4-one The same reaction procedure as in Example 49 was performed, except that the compound obtained in Example 181 was used in place of the compound obtained in Example 48, and homopiperazine was used in place of N-methylpiperazine. In this manner, 64 mg (37%) of the captioned compound was obtained.

Example 191

3-Cyclohexyl-6-{4-[(1,1-dioxido-4-thiomorpholinyl)sulfonyl]-2-methoxyphenyl}-1-methyl-1,5-dihydro-4H-pyrazolo[3,4-d]pyrimidin-4-one The same reaction procedure as in Example 49 was performed, except that thiomorpholine 1,1-dioxide monohydrochloride was used in place of N-methylpiperazine. In this manner, 124 mg (67%) of the captioned compound was obtained.

Example 192

3-Cyclohexyl-6-[4-(1,1-dioxido-4-thiomorpholinyl)-2-methoxyphenyl]-1-methyl-1,5-dihydro-4H-pyrazolo[3,4-d]pyrimidin-4-one The same reaction procedure as in Example 27 was performed, except that thiomorpholine 1,1-dioxide monohydrochloride was used in place of N-methylpiperazine. In this manner, 69 mg (41%) of the captioned compound was obtained.

Example 193

6-(4-Bromo-2-methoxyphenyl)-3-cyclohexyl-1-ethyl-1,5-dihydro-4H-pyrazolo[3,4-d]pyrimidin-4-one The same reaction procedure as in Example 26 was performed, except that the compound obtained in Production Example 57 was used in place of the compound obtained in Production Example 32. In this manner, 523 mg (53%) of the captioned compound was obtained.

Example 194

3-Cyclohexyl-1-ethyl-6-[2-methoxy-4-(4-methyl-1-piperazinyl)phenyl]-1,5-dihydro-4H-pyrazolo[3,4-d]pyrimidin-4-one The same reaction procedure as in Example 27 was performed, except that the compound obtained in Example 193 was used in place of the compound obtained in Example 26. In this manner, 62 mg (41%) of the captioned compound was obtained.

Example 195

Benzyl 1-[4-(3-cyclohexyl-1-ethyl-4-oxo-4,5-dihydro-1H-pyrazolo[3,4-d]pyrimidin-6-yl)-3-methoxyphenyl]-4-piperidinyl(methyl)carbamate The same reaction procedure as in Example 27 was performed, except that the compound obtained in Example 193 was used in place of the compound obtained in Example 26, and benzyl methyl (4-piperidinyl) carbamate monohydrochloride was used in place of N-methylpiperazine. In this manner, 215 mg (90%) of the captioned compound was obtained.

Example 196

3-Cyclohexyl-1-ethyl-6-{2-methoxy-4-(4-methylamino)-1-piperidinyl}phenyl}-1,5-dihydro-4H-pyrazolo[3,4-d]pyrimidin-4-one The same reaction procedure as in Example 36 was performed, except that the compound obtained in Example 195 was used in place of the compound obtained in Example 35. In this manner, 130 mg (quant.) of the captioned compound was obtained.

Example 197

4-(1-Cyclohexyl-3-methyl-7-oxo-6,7-dihydro-1H-pyrazolo[4,3-d]pyrimidin-5-yl)-3-methoxybenzenesulfonyl chloride The same reaction procedure as in Example 48 was performed, except that the compound obtained in Example 9 was used in place of the compound obtained in Example 44. In this manner, 1.01 g (91%) of the captioned compound was obtained.

Example 198

1-Cyclohexyl-5-{2-methoxy-4-[(4-methyl-1,4-diazepan-1-yl)sulfonyl]phenyl}-3-methyl-1,6-dihydro-7H-pyrazolo[4,3-d]pyrimidin-7-one The same reaction procedure as in Example 49 was performed, except that the compound obtained in Example 197 was used in place of the compound obtained in Example 48, and N-methyl-1,4-diazacycloheptane was used in place of N-methylpiperazine. In this manner, 146 mg (83%) of the captioned compound was obtained.

Example 199

1-Cyclohexyl-5-{4-[(4-hydroxy-1-piperidinyl)sulfonyl]-2-methoxyphenyl}-3-methyl-1,6-dihydro-7H-pyrazolo[4,3-d]pyrimidin-7-one The same reaction procedure as in Example 49 was performed, except that the compound obtained in Example 197 was used in place of the compound obtained in Example 48, and 4-hydroxypiperidine was used in place of N-methylpiperazine. In this manner, 145 mg (84%) of the captioned compound was obtained.

Example 200

4-(1-Cyclohexyl-3-methyl-7-oxo-6,7-dihydro-1H-pyrazolo[4,3-d]pyrimidin-5-yl)-N-(2-hydroxyethyl)-3-methoxybenzenesulfonamide The same reaction procedure as in Example 49 was performed, except that the compound obtained in Example 197 was used in place of the compound obtained in Example 48, and ethanolamine was used in place of N-methylpiperazine. In this manner, 113 mg (71%) of the captioned compound was obtained.

Example 201

4-(1-Cyclohexyl-3-methyl-7-oxo-6,7-dihydro-1H-pyrazolo[4,3-d]pyrimidin-5-yl)-3-methoxy-N-methylbenzenesulfonamide The same reaction procedure as in Example 49 was performed, except that the compound obtained in Example 197 was used in place of the compound obtained in Example 48, and methylamine (30% ethanol solution) was used in place of N-methylpiperazine. In this manner, 88 mg (60%) of the captioned compound was obtained.

Example 202

1-Cyclohexyl-5-[4-(1,4-diazepan-1-ylsulfonyl)-2-methoxyphenyl]-3-methyl-1,6-dihydro-7H-pyrazolo[4,3-d]pyrimidin-7-one The same reaction procedure as in Example 49 was performed, except that the compound obtained in Example 197 was used in place of the compound obtained in Example 48, and homopiperazine was used in place of N-methylpiperazine. In this manner, 141 mg (82%) of the captioned compound was obtained.

Example 203

1-Cyclohexyl-5-[4-(1,4-diazepan-1-ylsulfonyl)-2-methoxyphenyl]-3-methyl-1,6-dihydro-7H-pyrazolo[4,3-d]pyrimidin-7-one monomethanesulfonate The same reaction procedure as in Example 154 was performed, except that the compound obtained in Example 202 was used in place of the compound obtained in Example 153. In this manner, 24 mg (40%) of the captioned compound was obtained.

Example 204

4-(3-Cyclohexyl-1-methyl-4-oxo-4,5-dihydro-1H-pyrazolo[3,4-d]pyrimidin-6-yl)-3-methoxy-N-methylbenzenesulfonamide The same reaction procedure as in Example 49 was performed, except that methylamine (30% ethanol solution) was used in place of N-methylpiperazine. In this manner, 102 mg (69%) of the captioned compound was obtained.

Example 205

6-(4-Amino-2-methoxyphenyl)-3-cyclohexyl-1-ethyl-1,5-dihydro-4H-pyrazolo[3,4-d]pyrimidin-4-one To a 10 ml 1,2-dichloroethane suspension of 1.2 g (6.06 mmol) of 2-methoxy-4-nitrobenzoic acid, 0.88 ml (12.1 mmol) of thionyl chloride was added, and the mixture was heated under reflux for 1.5 hours. The reaction mixture was cooled to room temperature, and then distilled under reduced pressure to obtain an acid chloride.

To a 10 ml pyridine solution of the acid chloride synthesized above, 1.1 g (4.66 mmol) of the compound obtained in Production Example 57 was added. The mixture was stirred at room temperature for 5 hours. Then, the reaction mixture was distilled under reduced pressure, an aqueous solution of sodium hydrogen carbonate was added to the residue, and the mixture was extracted with ethyl acetate. The organic layer was washed with water and a saturated aqueous solution of sodium chloride, and dried over anhydrous sodium sulfate, followed by distilling off the solvent under reduced pressure. A carboxamide intermediate was obtained by this procedure.

To a 30 ml methanol/10 ml N,N-dimethylformamide mixed solution of the above carboxamide intermediate, 170 mg of 5% palladium carbon was added, and the mixture was stirred for 18 hours in an atmosphere of hydrogen at room temperature and atmospheric pressure. Then, the catalyst was removed by filtration, and the filtrate was distilled under reduced pressure to obtain an amine intermediate.

To the above amine intermediate, 19 ml of ethanol and 38 ml of a 1M aqueous solution of sodium hydroxide were added, and the mixture was heated under reflux for 24 hours. Then, the reaction mixture was cooled to room temperature, diluted with water, and extracted with dichloromethane. The organic layer was washed with water and a saturated aqueous solution of sodium chloride, and dried over anhydrous sodium sulfate, whereafter the solvent was distilled off under reduced pressure. The residue was purified by silica gel column chromatography (chloroform/methanol=30/1) to obtain 996 mg (58%) of the captioned compound.

Example 206

4-(3-Cyclohexyl-1-ethyl-4-oxo-4,5-dihydro-1H-pyrazolo[3,4-d]pyrimidin-6-yl)-3-methoxybenzenesulfonyl chloride The same reaction procedure as in Example 48 was performed, except that the compound obtained in Example 205 was used in place of the compound obtained in Example 44. In this manner, 940 g (83%) of the captioned compound- was obtained.

Example 207

3-Cyclohexyl-1-ethyl-6-{4-[(4-hydroxy-1-piperidinyl)sulfonyl]-2-methoxyphenyl}-1,5-dihydro-4H-pyrazolo[3,4-d]pyrimidin-4-one The same reaction procedure as in Example 49 was performed, except that the compound obtained in Example 206 was used in place of the compound obtained in Example 48, and 4-hydroxypiperidine was used in place of N-methylpiperazine. In this manner, 155 mg (91%) of the captioned compound was obtained.

Example 208

3-Cyclohexyl-1-ethyl-6-{2-methoxy-4-[(4-methyl-1,4-diazepan-1-yl)sulfonyl]phenyl}-1,5-dihydro-4H-pyrazolo[3,4-d]pyrimidin-4-one The same reaction procedure as in Example 49 was performed, except that the compound obtained in Example 206 was used in place of the compound obtained in Example 48, and N-methyl-1,4-diazacycloheptane was used in place of N-methylpiperazine. In this manner, 129 mg (74%) of the captioned compound was obtained.

Example 209

3-Cyclohexyl-6-[4-(1,4-diazepan-1-ylsulfonyl)-2-methoxyphenyl]-1-ethyl-1,5-dihydro-4H-pyrazolo[3,4-d]pyrimidin-4-one The same reaction procedure as in Example 49 was performed, except that the compound obtained in Example 206 was used in place of the compound obtained in Example 48, and homopiperazine was used in place of N-methylpiperazine. In this manner, 100 mg (59%) of the captioned compound was obtained.

Example 210

N-(2-aminoethyl)-4-(1-cyclohexyl-3-methyl-7-oxo-6,7-dihydro-1H-pyrazolo[4,3-d]pyrimidin-5-yl)-3-methoxy-N-methylbenzenesulfonamide (210-1)

4-(1-Cyclohexyl-3-methyl-7-oxo-6,7-dihydro-1H-pyrazolo[4,3-d]pyrimidin-5-yl)-3-methoxy-N-[2-(methylamino)ethyl]benzenesulfonamide (210-2)

The same reaction procedure as in Example 49 was performed, except that the compound obtained in Example 197 was used in place of the compound obtained in Example 48, and N-methylethylenediamine was used in place of N-methylpiperazine. In this manner, there were obtained 139 mg (59%) of N-(2-aminoethyl)-4-(1-cyclohexyl-3-methyl-7-oxo-6,7-dihydro-1H-pyrazolo[4,3-d]pyrimidin-5-yl)-3-methoxy-N-methylbenzenesulfonamide, and 39 mg (16%) of 4-(1-cyclohexyl-3-methyl-7-oxo-6,7-dihydro-1H-pyrazolo[4,3-d]pyrimidin-5-yl)-3-methoxy-N-[2-(methylamino)ethyl]benzenesulfonamide.

Example 211

4-(1-Cyclohexyl-3-methyl-7-oxo-6,7-dihydro-1H-pyrazolo[4,3-d]pyrimidin-5-yl)-N-[2-(dimethylamino)ethyl]-3-methoxybenzenesulfonamide The same reaction procedure as in Example 49 was performed, except that the compound obtained in Example 197 was used in place of the compound obtained in Example 48, and N,N-dimethylethylenediamine was used in place of N-methylpiperazine. In this manner, 95.4 mg (85%) of the captioned compound was obtained.

Example 212

4-(1-Cyclohexyl-3-methyl-7-oxo-6,7-dihydro-1H-pyrazolo[4,3-d]pyrimidin-5-yl)-3-methoxy-N-methyl-N-[2-(methylamino)ethyl]benzenesulfonamide The same reaction procedure as in Example 49 was performed, except that the compound obtained in Example 197 was used in place of the compound obtained in Example 48, and N,N'-dimethylethylenediamine was used in place of N-methylpiperazine. In this manner, 82 mg (73%) of the captioned compound was obtained.

Example 213

4-(1-Cyclohexyl-3-methyl-7-oxo-6,7-dihydro-1H-pyrazolo[4,3-d]pyrimidin-5-yl)-N-(2-hydroxyethyl)-3-methoxy-N-methylbenzenesulfonamide The same reaction procedure as in Example 49 was performed, except that the compound obtained in Example 197 was used in place of the compound obtained in Example 48, and 2-(methylamino)ethanol was used in place of N-methylpiperazine. In this manner, 70 mg (64%) of the captioned compound was obtained.

Example 214

1-Cyclohexyl-5-{2-methoxy-4-[(4-methyl-1-piperazinyl)sulfonyl]phenyl}-3-methyl-1,6-dihydro-7H-pyrazolo[4,3-d]pyrimidin-7-one The same reaction procedure as in Example 49 was performed, except that the compound obtained in Example

Example 215

4-(1-Cyclohexyl-3-methyl-7-oxo-6,7-dihydro-1H-pyrazolo[4,3-d]pyrimidin-5-yl)-3-methoxy-N-methyl-N-[3-(methylamino)propyl]benzenesulfonamide The same reaction procedure as in Example 49 was performed, except that the compound obtained in Example 197 was used in place of the compound obtained in Example 48, and N,N'-dimethyl-1,3-propanediamine was used in place of N-methylpiperazine. In this manner, 36 mg (31%) of the captioned compound was obtained.

Example 216

1-Cyclohexyl-5-(4-{[4-(2-hydroxyethyl)-1-piperazinyl]sulfonyl}-2-methoxyphenyl)-3-methyl-1,6-dihydro-7H-pyrazolo[4,3-d]pyrimidin-7-one The same reaction procedure as in Example 49 was performed, except that the compound obtained in Example 197 was used in place of the compound obtained in Example 48, and 1-piperazineethanol was used in place of N-methylpiperazine. In this manner, 79 mg (65%) of the captioned compound was obtained.

Example 217

1-Cyclohexyl-5-[2-methoxy-4-(1-piperazinylsulfonyl)phenyl]-3-methyl-1,6-dihydro-7H-pyrazolo[4,3-d]pyrimidin-7-one The same reaction procedure as in Example 49 was performed, except that the compound obtained in Example 197 was used in place of the compound obtained in Example 48, and piperazine was used in place of N-methylpiperazine. In this manner, 34 mg (30%) of the captioned compound was obtained.

Example 218

1-Cyclohexyl-5-{4-[(4-ethyl-1-piperazinyl)sulfonyl]-2-methoxyphenyl}-3-methyl-1,6-dihydro-7H-pyrazolo[4,3-d]pyrimidin-7-one The same reaction procedure as in Example 49 was performed, except that the compound obtained in Example 197 was used in place of the compound obtained in Example 48, and N-ethylpiperazine was used in place of N-methylpiperazine. In this manner, 90 mg (76%) of the captioned compound was obtained.

Example 219

N-(1-benzyl-4-piperidinyl)-4-(1-cyclohexyl-3-methyl-7-oxo-6,7-dihydro-1H-pyrazolo[4,3-d]pyrimidin-5-yl)-3-methoxybenzenesulfonamide The same reaction procedure as in Example 49 was performed, except that the compound obtained in Example 197 was used in place of the compound obtained in Example 48, and 4-amino-1-benzylpiperidine was used in place of N-methylpiperazine. In this manner, 39 mg (29%) of the captioned compound was obtained.

Example 220

4-(1-Cyclohexyl-3-methyl-7-oxo-6,7-dihydro-1H-pyrazolo[4,3-d]pyrimidin-5-yl)-3-methoxy-N-(4-piperidinyl)benzenesulfonamide monohydrochloride To a 2 ml dichloromethane solution of 30 mg (0.05 mmol) of the compound obtained in Example 219, 11 µl (0.101 mmol) of 1-chloroethyl chloroformate was added, and the mixture was stirred at room temperature for 3 hours. Then, the reaction mixture was distilled under reduced pressure, 2 ml of methanol was added to the residue, and the mixture was heated under reflux for 3 hours. The reaction mixture was cooled to room temperature, and the solvent was distilled off under reduced pressure. The residue was recrystallized from ethanol to obtain 12 mg (45%) of the captioned compound.

Example 221

Benzyl 1-{[4-(1-cyclohexyl-3-methyl-7-oxo-6,7-dihydro-1H-pyrazolo[4,3-d]pyrimidin-5-yl)-3-methoxyphenyl]sulfonyl}-4-piperidinyl(methyl)carbamate The same reaction procedure as in Example 49 was performed, except that the compound obtained in Example 197 was used in place of the compound obtained in Example 48, and benzyl methyl(4-piperidinyl)carbamate monohydrochloride was used in place of N-methylpiperazine. In this manner, 125 mg (84%) of the captioned compound was obtained.

Example 222

1-Cyclohexyl-5-(2-methoxy-4-{[4-(methylamino)-1-piperidinyl]sulfonyl}phenyl)-3-methyl-1,6-dihydro-7H-pyrazolo[4,3-d]pyrimidin-7-one The same reaction procedure as in Example 36 was performed, except that the compound obtained in Example 221 was used in place of the compound obtained in Example 35. In this manner, 62 mg (86%) of the captioned compound was obtained.

Example 223

5-{4-[(1-Benzyl-4-piperidinyl)amino]-2-methoxyphenyl}-1-cyclohexyl-3-methyl-1,6-dihydro-7H-pyrazolo[4,3-d]pyrimidin-7-one The same reaction procedure as in Example 16 was performed, except that 4-amino-1-benzylpiperidine was used in place of N-methylpiperazine. In this manner, 148 mg (78%) of the captioned compound was obtained.

Example 224

1-Cyclohexyl-5-[2-methoxy-4-(4-piperidinylamino)phenyl]-3-methyl-1,6-dihydro-7H-pyrazolo[4,3-d]pyrimidin-7-one To a 3 ml dichloromethane solution of 120 mg (0.228 mmol) of the compound obtained in Example 223, 50 µl (0.456 mmol) of 1-chloroethyl chloroformate was added, and the mixture was stirred at room temperature for 4 hours. Further, 50 µl (0.456 mmol) of 1-chloroethyl chloroformate and 3 ml of 1,2-dichloroethane were added, and the mixture was heated under reflux for 5 hours. Then, the reaction mixture was distilled under reduced pressure, 3 ml of methanol was added to the residue, and the mixture was heated under reflux for 1.5 hours. The reaction mixture was cooled to room temperature, and the solvent was distilled off under reduced pressure. An aqueous solution of sodium hydrogen carbonate was added to the residue, and the mixture was extracted with dichloromethane. The organic layer was washed with water and a saturated aqueous solution of sodium chloride, and dried over anhydrous sodium sulfate, whereafter the solvent was distilled off under reduced pressure. The residue was purified by basic silica gel column chromatography (dichloromethane/methanol=20/1) to obtain 62 mg (62%) of the captioned compound.

Example 225

1-Cyclohexyl-5-{2-methoxy-4-[(2-methoxyethyl) amino]phenyl}-3-methyl-1,6-dihydro-7H-pyrazolo [4,3-d]pyrimidin-7-one The same reaction procedure as in Example 16 was performed, except that methoxyethylamine was used in place of N-methylpiperazine. In this manner, 63 mg (43%) of the captioned compound was obtained.

Example 226

Methyl (2E)-3-[4-(1-cyclohexyl-3-methyl-7-oxo-6, 7-dihydro-1H-pyrazolo[4,3-d]pyrimidin-5-yl)-3-methoxyphenyl]-2-propenate To a 2 ml N,N-dimethylformamide solution of 150 mg (0.36 mmol) of the compound obtained in Example 15, 8 mg (0.036 mmol) of palladium acetate, 22 mg (0.072 mmol) of tri-o-tolylphosphine, 0.15 ml (1.08 mmol) of triethylamine, and 97 µl (1.08 mmol) of methyl acrylate were added, and the mixture was stirred at 115° C. in a sealed tube for 15 hours. Then, the reaction mixture was cooled to room temperature, water was added, and the mixture was extracted with ethyl acetate. The organic layer was washed with water and a saturated aqueous solution of sodium chloride, and dried over anhydrous sodium sulfate, whereafter the solvent was distilled off under reduced pressure. The residue was purified by silica gel column chromatography (hexane/ethyl acetate=2/1) to obtain 130 mg (85%) of the captioned compound.

Example 227

(2E)-3-[4-(1-cyclohexyl-3-methyl-7-oxo-6,7-dihydro-1H-pyrazolo[4,3-d]pyrimidin-5-yl)-3-methoxyphenyl]-2-propenic acid To a 1 ml methanol suspension of 45 mg (0.107 mmol) of the compound obtained in Example 226, 1 ml of a 1M aqueous solution of sodium hydroxide was added, and the mixture was stirred at room temperature for 2 hours. Then, the reaction mixture was diluted with water, and the aqueous layer was washed with ether. The aqueous layer was acidified with a 2M aqueous solution of hydrochloric acid, and precipitated solids were collected by filtration to obtain 39 mg (89%) of the captioned compound.

Example 228

Methyl 3-[4-(1-cyclohexyl-3-methyl-7-oxo-6,7-dihydro-1H-pyrazolo[4,3-d]pyrimidin-5-yl)-3-methoxyphenyl]propanate To a 2 ml tetrahydrofuran solution of 63 mg (0.15 mmol) of the compound obtained in Example 226, 6 mg of platinum oxide was added, and the mixture was stirred for 3.5 hours in an atmosphere of hydrogen at room temperature and atmospheric pressure. Then, the catalyst was removed by filtration, and the filtrate was distilled under reduced pressure. The residue was purified by silica gel column chromatography (ethyl acetate/hexane=1/1) to obtain 52 mg (82%) of the captioned compound.

Example 229

3-[4-(1-Cyclohexyl-3-methyl-7-oxo-6,7-dihydro-1H-pyrazolo[4,3-d]pyrimidin-5-yl)-3-methoxyphenyl] propanic acid The same reaction procedure as in Example 227 was performed, except that the compound obtained in Example 228 was used in place of the compound obtained in Example 226. In this manner, 32 mg (71%) of the captioned compound was obtained.

Example 230

1-Cyclohexyl-5-(4-{[2-(dimethylamino)ethyl] amino}-2-methoxyphenyl)-3-methyl-1,6-dihydro-7H-pyrazolo[4,3-d]pyrimidin-7-one The same reaction procedure as in Example 16 was performed, except that N,N-dimethylethylenediamine was used in place of N-methylpiperazine. In this manner, 91 mg (50%) of the captioned compound was obtained.

Example 231

5-{4-[(1-Acetyl-4-piperidinyl)amino]-2-methoxyphenyl}-1-cyclohexyl-3-methyl-1,6-dihydro-7H-pyrazolo[4,3-d]pyrimidin-7-one The same reaction procedure as in Example 16 was performed, except that 1-acetyl-4-piperidinylamine was used in place of N-methylpiperazine. In this manner, 69 mg (60%) of the captioned compound was obtained.

Example 232

1-Cyclohexyl-5-{2-methoxy-4-[(1-methyl-4-piperidinyl)amino]phenyl}-3-methyl-1,6-dihydro-7H-pyrazolo[4,3-d]pyrimidin-7-one The same reaction procedure as in Example 16 was performed, except that 1-methyl-4-piperidinylamine was used in place of N-methylpiperazine. In this manner, 76 mg (70%) of the captioned compound was obtained.

Example 233

4-(1-Cyclohexyl-3-methyl-7-oxo-6,7-dihydro-1H-pyrazolo[4,3-d]pyrimidin-5-yl)-3-methoxybenzaldehyde To a 3 ml tetrahydrofuran solution of 150 mg (0.36 mmol) of the compound obtained in Example 15, 0.45 ml of n-butyl lithium (1.59M hexane solution 0.72 mmol) was added dropwise at −78° C. After the mixture was stirred at the same temperature for 30 minutes, 33.4 µl (0.43 mmol) of N,N- dimethylformamide was added dropwise to the reaction mixture, followed by stirring the mixture at −78° C. for 2 hours. Then, an aqueous solution of ammonium chloride was added to the reaction mixture, and the mixture was extracted with ethyl acetate. The organic layer was washed with water and a saturated aqueous solution of sodium chloride, and dried over anhydrous sodium sulfate, whereafter the solvent was distilled off under reduced pressure. The residue was purified by silica gel column chromatography (hexane/ethyl acetate=2/1) to obtain 73 mg (55%) of the captioned compound.

Example 234

1-Cyclohexyl-5-{2-methoxy-4-[(4-methyl-1-piperazinyl)methyl]phenyl}-3-methyl-1,6-dihydro-7H-pyrazolo[4,3-d]pyrimidin-7-one To a 2 ml 1,2-dichloroethane solution of 61 mg (0.166 mmol) of the compound obtained in Example 233, 37 μl (0.332 mmol) of N-methylpiperazine, 10 μl of acetic acid, and 53 mg (0.252 mmol) of sodium triacetoxyborohydride were added, and the mixture was stirred at room temperature for 1 hour. Then, an aqueous solution of sodium hydrogen carbonate was added to the reaction mixture, and the mixture was extracted with dichloromethane. The organic layer was washed with water and a saturated aqueous solution of sodium chloride, and dried over anhydrous sodium sulfate, whereafter the solvent was distilled off under reduced pressure. The residue was purified by silica gel column chromatography (dichloromethane/methanol=10/1) to obtain 57 mg (76%) of the captioned compound.

Example 235

1-Cyclohexyl-5-[2-methoxy-4-(4-morpholinylmethyl)phenyl]-3-methyl-1,6-dihydro-7H-pyrazolo[4,3-d]pyrimidin-7-one The same reaction procedure as in Example 234 was performed, except that morpholine was used in place of N-methylpiperazine. In this manner, 72 mg (quant.) of the captioned compound was obtained.

| Ex. No. | Chemical Structure | Properties Melting Point (° C.) (Solvent for Recrystallization) | $^1$H—NMR | MS(FAB) $(M + 1)^+$ |
|---|---|---|---|---|
| 1 | 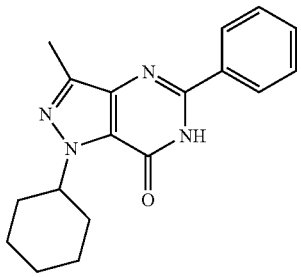 | Colorless solid 236-237 | CDCl$_3$ 1.25-1.37(1H, m), 1.42-1.55(2H, m), 1.72-1.80(1H, m), 1.89-2.14(6H, m), 2.57(3H, s), 4.99-5.10(1H, m), 7.51-7.59(3H, m), 8.06-8.13(2H, m), 10.69-10.88(1H, brm) | 309 |
| 2 | 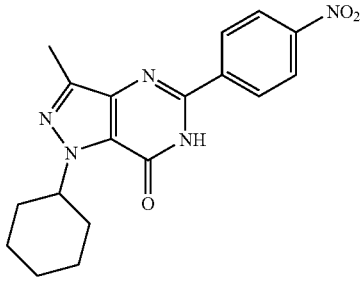 | Yellow solid >300 (Ethanol) | CDcl$_3$ 1.21-1.37(1H, m), 1.39-1.56(2H, m), 1.78-1.88(1H, m), 1.92-2.12(6H, m), 2.60(3H, s), 5.00-5.11(1H, m), 8.38-8.50(4H, m), 12.12(1H, brs) | 354 |
| 3 | 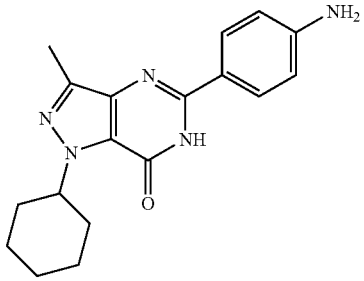 | Light yellow solid 260.3-262.8 (Ethanol) | DMDO-d6 1.16-1.30(1H, m), 1.32-1.49(2H, m), 1.65-1.74(1H, m), 1.80-2.00(6H, m), 2.38(3H, s), 4.86-4.99(1H, m), 5.67(2H, s), 6.57-6.63(2H, m), 7.78-7.84(2H,m) | 324 |

-continued

| Ex. No. | Chemical Structure | Properties Melting Point (° C.) (Solvent for Recrystallization) | $^1$H—NMR | MS(FAB) $(M + 1)^+$ |
|---|---|---|---|---|
| 4 | 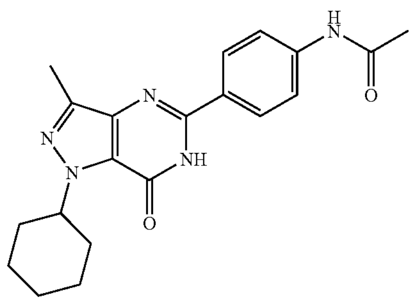 | Light yellow solid >300 (Ethanol) | DMDO d6 1.18-1.30(1H, m), 1.32-1.48(2H, m), 1.62-1.73(1H, m), 1.79-2.00(6H, m), 2.09(3H, s), 2.41(3H, s)4.88-4.99(1 H, m), 7.66-7.75(2H, m), 8.00-8.09(2H, m), 10.18(1H, brs), 12.27(1H, brs) | 366 |
| 5 | 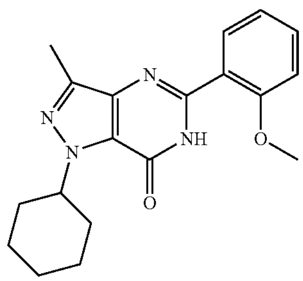 | Colorless solid 169.5-170.8 (Ethyl acetate-Hexane) | CDCl$_3$ 1.24-1.40(1H, m), 1.45-1.59(2H, m), 1.70-1.79(1H, m), 1.87-2.12(6H, m), 2.56(3H, s), 4.04(3H, s), 4.98-5.08(1H, m), 7.01-7.08(1H, m), 7.11-7.18(1H, m), 7.44-7.51(1H, m), 8.42-8.49(1H, m), 10.79(1H, brs) | 339 |
| 6 | 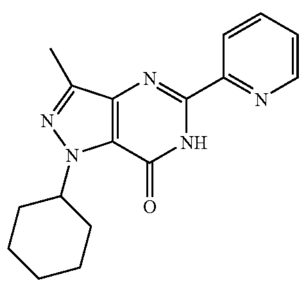 | Colorless solid 191-192 (Ethyl acetate-Hexane) | CDCl$_3$ 1.24-1.39(1H, m), 1.43-1.60(2H, m), 1.69-1.79(1H, m), 1.86-2.12(6H, m), 2.57(3H, s), 5.02-5.13(1H, m), 7.40-7.47(1H, m), 7.82-7.91(1H, m). 8.49-8.54(1H, m), 8.60-8.65(1H, m), 10.86(1H, brs) | 310 |
| 7 | 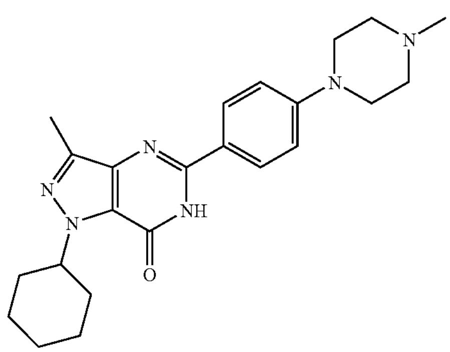 | Colorless solid 280.1-282.3 (Ethanol-Ethyl acetate) | CDCl$_3$ 1.26-1.39(1H, m), 1.42-1.58(2H, m), 1.69-1.79(1H, m), 1.88-2.13(6H, m), 2.36(3H, s), 2.55(3H, s), 2.56-2.67(4H, m), 3.30-3.40(4H, m), 5.49-5.09(1H, m), 6.98-7.06(2H, m), 7.94-8.01(2H, m), 10.26(1H, brs) | 407 |
| 8 | 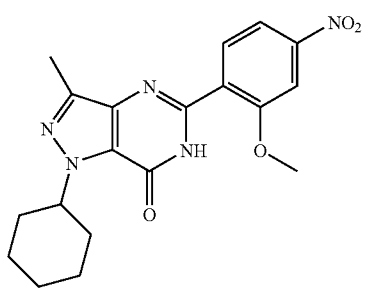 | Yellow solid 245-246 (Ethyl acetate-Hexane) | CDCl$_3$ 1.23-1.39(1H, m), 1.45-1.61(2H, m), 1.70-1.80(1H, m), 1.87-2.11(6H, m), 2.57(3H, s), 4.17(3H, s), 4.94-5.08(1H, m), 7.91-7.95(1H, m), 7.97-8.03(1H, m), 8.65-8.71(1H, m), 10.66(1H, brs) | 384 |

-continued

| Ex. No. | Chemical Structure | Properties Melting Point (° C.) (Solvent for Re-crystallization) | ¹H—NMR | MS(FAB) (M + 1)⁺ |
|---|---|---|---|---|
| 9 | 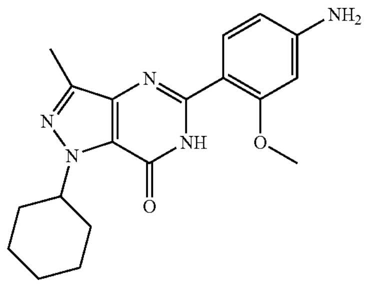 | Colorless solid 223-225.8 (Ethyl acetate-Hexane) | CDCl₃ 1.22-1.38(1H, m), 1.42-1.60(2H, m), 1.69-1.79(1H, m), 1.85-2.12(6H, m), 2.53(3H, s), 3.98(3H, s), 4.03(2H, s), 4.95-5.06(1H, m), 6.27-6.31(1H, m), 6.41-6.48(1H, m), 8.28-8.33(1H, m), 10.77(1H, brs) | 354 |
| 10 | 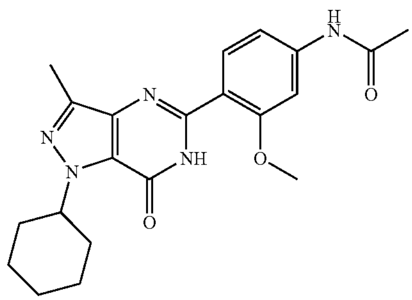 | Colorless solid 294.8-295.9 (Ethanol-Ethyl acetate) | CDCl₃ 1.21-1.38(1H, m), 1.41-1.60(2H, m), 1.68-1.78(1H, m), 1.84-2.11(6H, m), 2.22(3H, s), 2.54(3H, s), 4.05(3H, s), 4.97-5.08(1H, m), 6.82-6.89(1H, m), 7.36(1H, s), 7.90(1H, s), 8.39-8.45(1H, m), 10.80(1H, brs) | 396 |
| 11 | 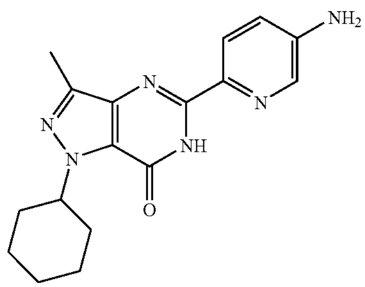 | Light yellow solid 202-203 | CDCl₃ 1.23-1.38(1H, m), 1.42-1.61(2H, m), 1.69-1.79(1H, m), 1.85-2.11(6H, m), 2.54(3H, s), 4.03(2H, s), 5.01-5.11(1H, m), 7.04-7.11(1H, m), 8.00-8.05(1H, m), 8.24-8.29(1H, m), 10.68(1H, brs) | 325 |
| 12 | 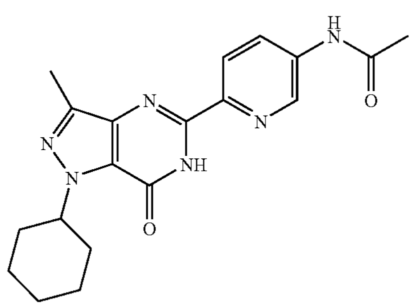 | Colorless solid 259.5-260.5 (Ethyl acetate) | CDCl₃ 1.23-1.39(1H, m), 1.42-1.62(2H, m), 1.69-1.80(1H, m), 1.86-2.12(6H, m), 2.27(3H, s), 2.56(3H, s), 5.01-5.11(1H, m), 7.49(1H, brs), 8.23-8.32(1H, m), 8.46-8.51(1H, m), 8.64-8.69(1H, m), 10.72(1H, brs) | 367 |
| 13 | 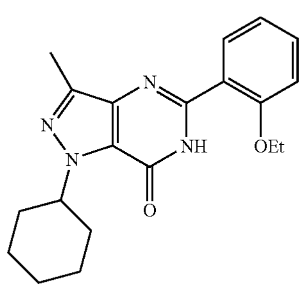 | Colorless solid 160-162 | CDCl₃ 1.23-1.38(1H, m), 1.42-1.56(2H. m). 1.61(3H, t, J=7.0Hz), 1.68-1.77(1H, m), 1.85-2.10(6H, m), 2.56(3H, s), 4.29(2H, q, J=7.0Hz), 4.97-5.07(1H, m), 7.00-7.05(1H, m), 7.10-7.16(1H, m). 7.40-7.48(1H, m), 8.46-8.51(1H, m), 11.13(1H, brs) | 353 |

-continued

| Ex. No. | Chemical Structure | Properties Melting Point (° C.) (Solvent for Recrystallization) | ¹H—NMR | MS(FAB) (M + 1)⁺ |
|---|---|---|---|---|
| 14 | 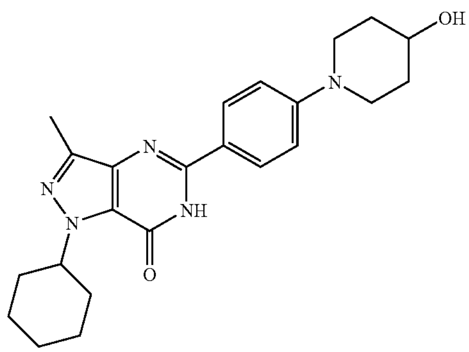 | Colorless solid | DMSO-d₆ 1.17-1.30(1H, m), 1.35-1.49(4H, m), 1.64-1.72(1H, m), 1.77-1.98(8H, m), 2.39(3H, s), 2.94-3.04(2H, m), 3.64-3.72(3H, m), 4.68-4.71(1H, m), 4.87-4.97(1H, m), 6.95-7.01(2H, m), 7.94-7.99(2H, m) | 408 |
| 15 | 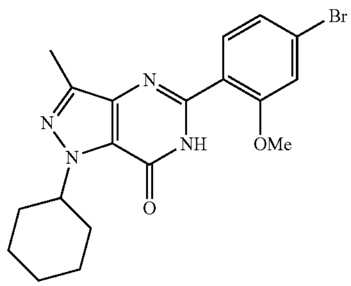 | Colorless solid 218-223 (Ethyl acetate) | CDCl₃ 1.23-1.38(1H, m), 1.42-1.60(2H, m), 1.69-1.78(1H, m), 1.85-2.8(6H, m), 2.55(3H, s), 4.05(3H, s), 4.96-5.06(1H, m), 7.19-7.32(2H, m), 8.31-8.36(1H, m), 10.64(1H, brs) | 417 |
| 16 | 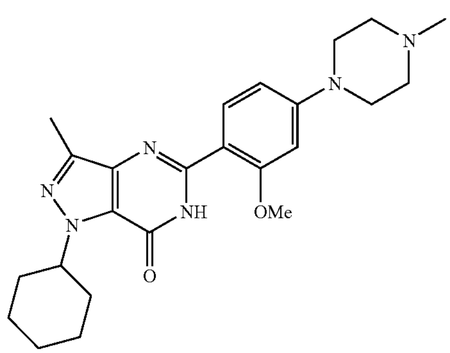 | Faint yellow solid | CDCl₃ 1.21-1.39(1H, m), 1.42-1.61(2H, m), 1.67-1.76(1H, m), 1.83-2.09(6H. m), 2.37(3H, s), 2.53(3H, s), 2.55-2.61(4H, m), 3.30-3.37(4H, m), 4.02(3H, s), 4.96-5.06(1H, m), 6.43-6.46(1H, m), 6.63-6.68(1H, m), 8.31-8.36(1H, m), 10.82(1H, brs) | 437 |
| 17 | 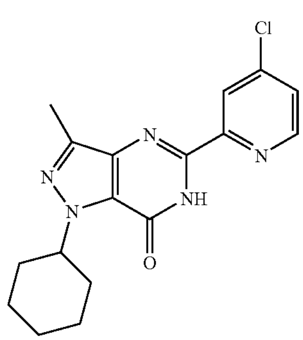 | Colorless solid 240-241 (Ethyl acetate-Ethanol) | CDCl₃ 1.23-1.39(1H, m), 1.44-1.61(2H, m), 1.70-1.79(1H, m), 1.88-2.10(6H, m), 2.57(3H, s), 5.03-5.12(1H, m), 7.40-7.43(1H, m), 8.51-8.55(2H, m), 10.72(1H, brs) | 344 |

-continued

| Ex. No. | Chemical Structure | Properties Melting Point (° C.) (Solvent for Recrystallization) | ¹H—NMR | MS(FAB) (M + 1)⁺ |
|---|---|---|---|---|
| 18 | 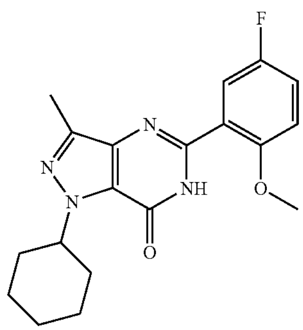 | Colorless solid 205.5-207 (Hexane-Ethyl acetate) | CDCl₃ 1.23-1.39(1H, m), 1.43-1.58(2H, m). 1.69-1.78(1H, m), 1.85-2.10(6H, m), 2.56(3H, s), 4.04(3H, s), 4.97-5.08(1H, m), 6.94-7.02(1H, m), 7.11-7.19(1H, m), 8.18-8.25(1H, m), 10.88(1H, brd) | 357 |
| 19 | 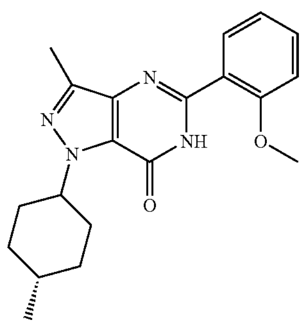 | Colorless solid 158.5-159 (Hexane-Ethyl acetate) | CDCl₃ 0.96(3H, d, J=6.5Hz), 1.13-1.28(2H, m), 1.44-1.59(1H, m), 1.80-1.90(2H, m), 2.00-2.12(4H, m), 2.56(3H, s), 4.04(3H, s), 4.97-5.08(1H, m), 7.03-7.08(1H, m), 7.11-7.20(1H, m), 7.43-7.52(1H, m), 8.42-8.49(1H, m), 10.80(1H, brs) | 353 |
| 20 | 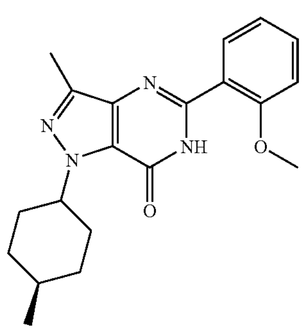 | Colorless solid 152-152.5 (Hexane-Ethyl acetate) | CDCl₃ 1.16(3H, d, J=7.1Hz), 1.61-1.88(6H, m), 1.90-2.01(1H, m), 2.21-2.35(2H, m), 2.56(3H, s), 4.04(3H, s), 4.92-5.03(1H, m), 7.00-7.07(1H, m), 7.11-7.19(1H, m), 7.43-7.51(1H, m), 8.42-8.49(1H, m), 10.81(1H, brs) | 353 |
| 21 | 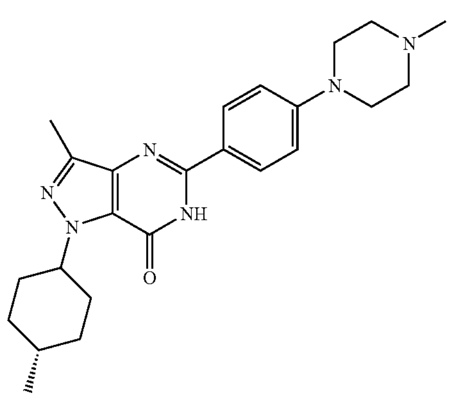 | Colorless solid 296-298 (Ethanol) | CDCl₃ 0.96(3H, d, J=6.5Hz), 1.14-1.29(2H, m), 1.47-1.59(1H, m), 1.82-1.92(2H, m), 2.01-2.12(4H, m), 2.36(3H, s), 2.55(3H, s), 2.56-2.62(4H, m), 3.31-3.38(4H, m), 4.97-5.08(1H, m), 6.98-7.01(2H, m), 7.93-8.01(2H, m), 10.33(1H, brs) | 421 |

-continued

| Ex. No. | Chemical Structure | Properties Melting Point (° C.) (Solvent for Recrystallization) | ¹H—NMR | MS(FAB) (M + 1)⁺ |
|---|---|---|---|---|
| 22 | 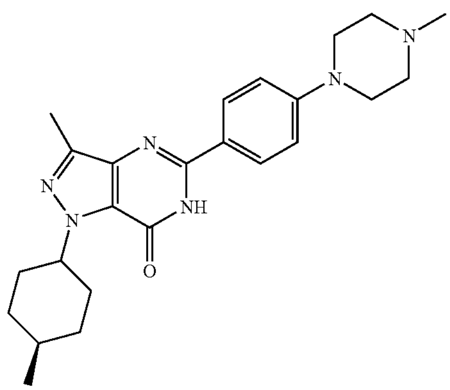 | Colorless solid 265-266 (Ethanol-Ethyl acetate) | CDCl₃ 1.10(3H, d, J=7.1Hz), 1.66-1.90(6H, m). 1.91-2.01(1H, m), 2.18-2.32(2H, m), 2.37(3H, s), 2.56(3H, m), 2.57-2.65(4H, m), 3.30-3.41(4H, m), 4.98-5.08(1H, m), 6.97-7.03(2H, m), 7.94-8.01(2H, m), 10.81(1H, brs) | 421 |
| 23 | 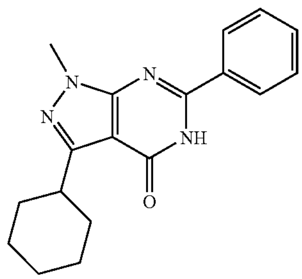 | Pale yellow solid 190-191.5 | CDCl₃ 1.21-1.45(3H, m), 1.50-1.66(2H, m), 1.68-1.77(1H, m), 1.80-1.88(2H, m). 1.92-2.00(2H, m), 2.68-2.77(1H, m), 3.75(3H, s), 7.48-7.56(2H, m), 7.59-7.66(1H, m). 7.89-7.96(2H, m), 8.11(1H, brs) | 309 |
| 24 | 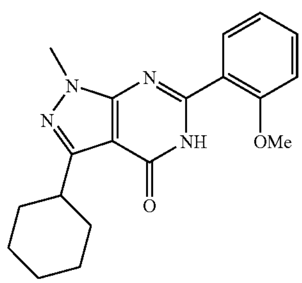 | Colorless solid 188.5-190 | CDCl₃ 1.26-1.51(3H, m), 1.69-1.88(5H, m), 1.97-2.04(2H, m), 3.02-3.13(1H, m), 3.98(3H, s), 4.06(3H, s), 7.05-7.10(1H, m), 7.14-7.20(1H, m), 7.48-7.57(1H, m), 8.48-8.52(1 H, m), 10.74(1H, brs) | 339 |
| 25 | 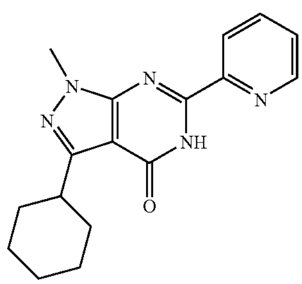 | Colorless solid 217-219 (CHCl₃-hexane) | CDCl₃ 1.28-1.53(3H, m), 1.68-1.90(5H, m), 1.99-2.07(2H, m), 3.08-3.18(1H, m), 4.01(3H, s), 7.45-7.51(1H, m). 7.87-7.93(1H, m), 8.49-8.53(1H, m), 8.65-8.69(1H, m), 10.66(1H, brs) | 310 |
| 26 | 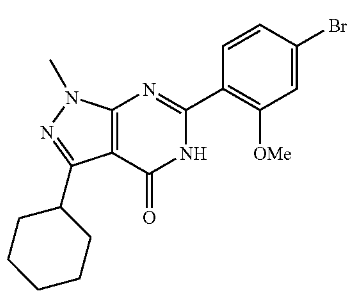 | Colorless solid 194-196 (EtOH) | CDCl₃ 1.30-1.58(3H, m), 1.68-1.89(5H, m), 1.96-2.04(2H, m), 3.04-3.14(1H, m), 3.97(3H, s), 4.07(3H, s), 7.21-7.25(1H, m), 7.28-7.36(1H, m), 8.35-8.40(1H, m), 10.59(1H, brs) | 417 |

-continued

| Ex. No. | Chemical Structure | Properties Melting Point (° C.) (Solvent for Recrystallization) | ¹H—NMR | MS(FAB) (M + 1)⁺ |
|---|---|---|---|---|
| 27 | 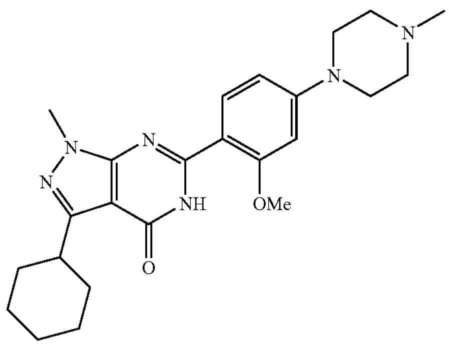 | Faint yellow solid 188-190 | CDCl₃ 1.28-1.51(3H, m), 1.62-1.88(5H, m), 1.96-2.04(2H, m), 2.37(3H, s), 2.55-2.60(4H, m), 3.01-3.10(1H, m), 3.95(3H, s), 4.03(3H, s), 6.40-6.45(1H, m), 6.61-6.66(1H, m), 8.37-8.41(1H, m), 10.73(1H, brs) | 437 |
| 28 | 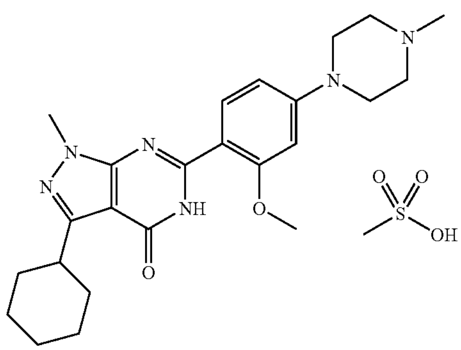 | Colorless solid 270 Decomposition (Ethanol) | CDCl₃ 1.28-1.53(3H, m), 1.60-2.11(7H, m), 2.83(3H, s), 2.98(3H, s), 3.01-3.93(9H, m), 3.95(3H, s), 4.04(3H, s), 6.46-6.49(1H, m), 6.62-6.69(1H, m), 8.41-8.47(1H, m), 10.66(1H, brs) | 437(free) |
| 29 | 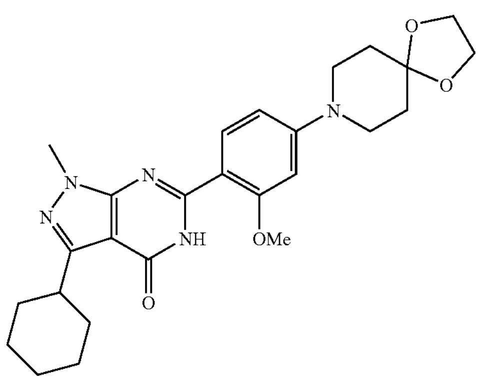 | Faint yellow oil | CDCl₃ 1.27-1.50(3H, m), 1.68-1.92(9H, m), 1.97-2.05(2H, m), 3.02-3.12(1H, m), 3.48-3.54(4H, m), 3.95(3H, m), 3.97-4.04(7H, m), 6.42-6.45(1H, m), 6.62-6.67(1H, m), 8.37-8.41(1H, m), 10.73(1H, brs) | 480 |
| 30 | 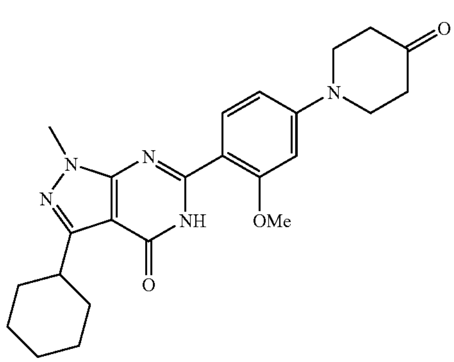 | Faint yellow solid 128-133 | CDCl₃ 1.32-1.55(3H, m), 1.70-1.92(5H, m), 1.96-2.04(2H, m), 2.60-2.66(4H, m), 3.03-3.14(4H, m), 3.96(3H, s), 4.06(3H, m), 6.44-6.47(1H, m), 6.65-6.70(1H, m), 8.43-8.48(1H, m), 10.70(1H, brs) | 436 |

-continued

| Ex. No. | Chemical Structure | Properties Melting Point (° C.) (Solvent for Re-crystallization) | ¹H—NMR | MS(FAB) (M + 1)⁺ |
|---|---|---|---|---|
| 31 | 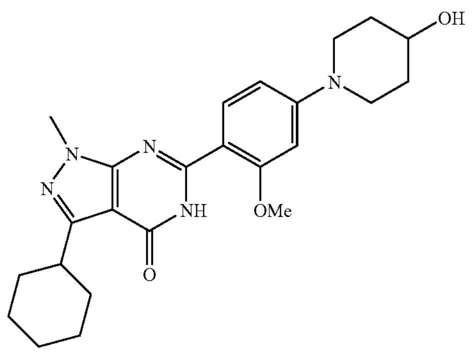 | Colorless solid 243-246 | CDCl₃ 1.24-1.50(3H, m), 1.63-1.86(7H, m), 1.93-2.05(4H, m), 3.03-3.18(3H, m), 3.68-3.76(2H, m), 3.94(3H, s), 4.02(3H, s), 6.40-6.43(1H, m), 6.62-6.67(1H, m), 8.38-8.42(1H, m), 10.75(1H, brs) | 438 |
| 32 | 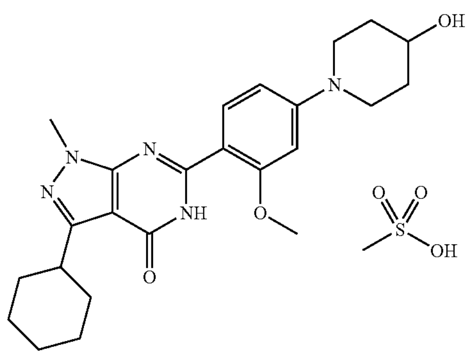 | Light yellow solid 230 Decomposition | CDCL₃ 1.29-1.54(3H, m), 1.70-2.67(11H, m), 2.89(3H, s), 3.06-3.18(1H, m), 3.42-3.58(2H, s), 3.78-3.91(2H, s), 4.00(3H, s), 4.19(3H, s), 4.23-4.35(1H, m), 7.18-7.24(1H, m), 7.70-7.85(1H, m), 8.58-8.68(1H, m), 10.67(1H, brs) | 438(free) |
| 33 | 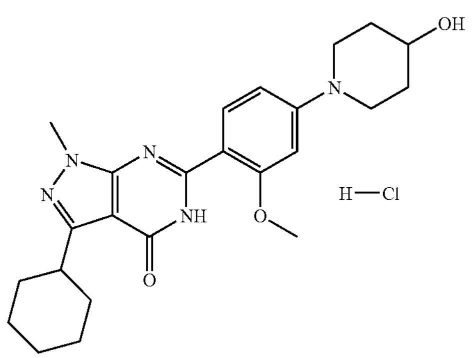 | Light yellow solid 247-249 | CDCl₃ 1.28-1.54(3H, m), 1.69-1.90(5H, m), 1.98-2.18(4H, m), 2.71-2.88(2H, m), 3.03-3.18(1H, m), 3.40-3.51(2H, m). 3.79-3.92(2H, m), 3.99(3H, s), 4.16(3H, s), 4.27-4.35(1H, m), 7.26-7.32(1H, m), 8.09-8.20(1H, m), 8.57-8.67(1H, m), 10.60(1H, brs) | 438(free) |
| 34 | 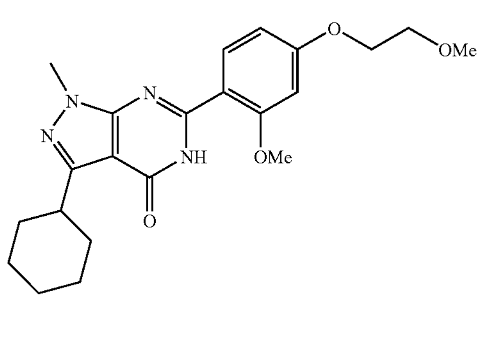 | Colorless solid 162-163 (iPr₂O/EtOH) | CDCl₃ 1.28-1.51(3H, m), 1.69-1.98(5H, m), 1.96-2.05(2H, m), 3.03-3.12(1H, m), 3.47(3H, s), 3.76-3.80(2H, m), 3.96(3H, m), 4.02(3H, s), 4.19-4.23(2H, m), 6.64(1H, d, J=2.2Hz), 6.69(1H, dd, J=2.2 and 8.9Hz), 8.47(1H, d, J=8.9Hz), 10.69(1H, brs) | 413 |

| Ex. No. | Chemical Structure | Properties Melting Point (° C.) (Solvent for Re-crystallization) | ¹H—NMR | MS(FAB) (M + 1)⁺ |
|---|---|---|---|---|
| 35 | 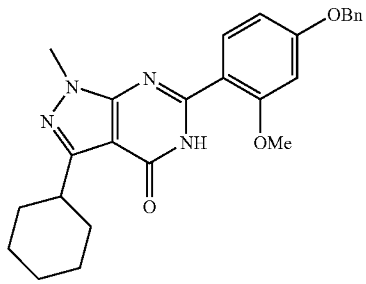 | Colorless solid 182-184 | CDCl₃ 1.30-1.50(3H, m), 1.69-1.88(5H, m), 1.97-2.04(2H, m), 3.03-3.12(1H, m), 3.96(3H, s), 4.01(3H, s), 5.16(2H, s), 6.65(1H, d, J = 2.1Hz), 6.75(1H, dd, J=2.1 and 8.9Hz), 7.33-7.45(5H, m), 8.47(1H, d, J=8.9Hz), 10.68(1H, brs) | 445 |
| 36 | 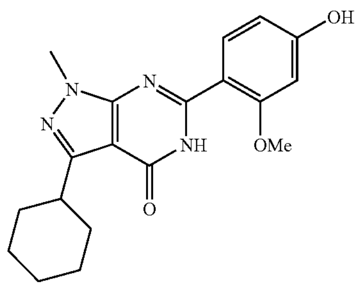 | Colorless solid >300 | DMSO-d₆ 1.20-1.39(3H, m), 1.58-1.81(5H, m), 1.86-1.94(2H, m), 2.86-2.97(1H, m), 3.83(3H, s), 3.86(3H, s), 6.49-6.55(2H, m), 7.79(1H, d, J=8.4Hz), 11.29(1H, brs) | 355 |
| 37 | 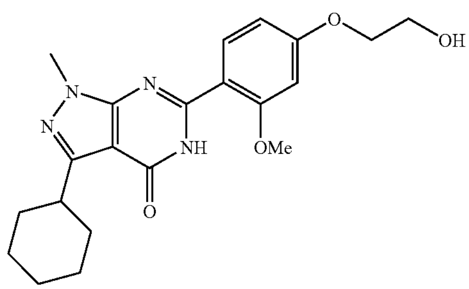 | Colorless solid 215-216.5 (toluene) | DMSO-d₆ 1.17-1.41(3H, m), 1.59-1.80(5H, m), 1.85-1.93(2H, m), 2.88-2.97(1H, m), 3.71-7.77(2H, m), 3.83(3H, s), 3.90(3H, s), 4.05-4.11(2H, m), 4.88-4.93(1H, m), 6.66-6.73(2H, m), 7.81(1H, d, J=8.6Hz), 11.44(1H, brs) | 399 |
| 38 | 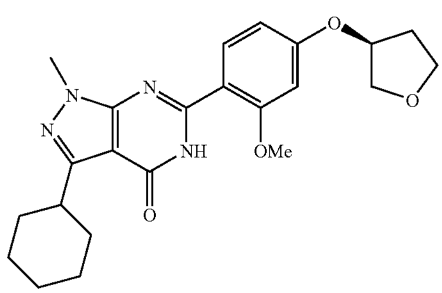 | Colorless solid 220-221 | CDCl₃ 1.30-1.50(3H, m), 1.69-1.88(5H, m), 1.97-2.04(2H, m), 2.12-2.32(2H, m), 3.03-3.12(1H, m), 3.91-4.06(4H, m), 3.96(3H, s), 4.03(3H, s), 5.00-5.05(1H, m), 6.56(1H, d, J=2.1Hz), 6.62(1H, dd, J=2.1 and 9.0Hz), 8.47(1H, d, J=9.0Hz), 10.66(1H, brs) | 425 |
| 39 | 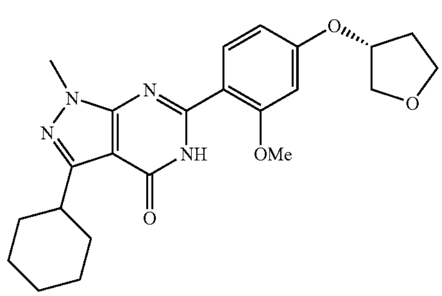 | Colorless solid 216-218 | CDCl₃ 1.30-1.50(3H, m), 1.70-1.88(5H, m), 1.98-2.04(2H, m), 2.13-2.32(2H, m), 3.03-3.12(1H, m), 3.90-4.05(4H, m), 3.96(3H, s), 4.02(3H, s), 5.00-5.05(1H, m), 6.56(1H, d, J=2.1Hz), 6.62(1H, dd, J=2.1 and 9.0Hz), 8.47(1H, d, J=9.0Hz), 10.67(1H, brs) | 425 |

-continued

| Ex. No. | Chemical Structure | Properties Melting Point (° C.) (Solvent for Re-crystallization) | $^1$H—NMR | MS(FAB) (M + 1)$^+$ |
|---|---|---|---|---|
| 40 | 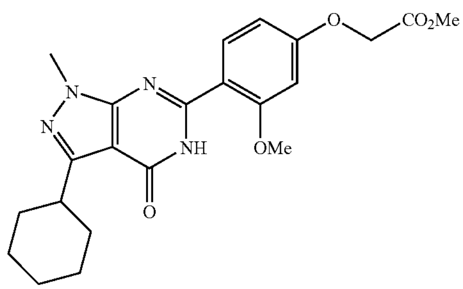 | Colorless solid 200-201.5 | CDCl$_3$ 1.30-1.50(3H, m), 1.70-1.88(5H, m), 1.97-2.04(2H, m), 3.03-3.12(1H, m), 3.84(3H, s), 3.96(3H, s), 4.03(3H, s), 4.72(2H, s), 6.61(1H, dd, J = 2.2 and 9.0Hz), 6.67(1H, d, J=2.2Hz). 8.48(1H, d, J=9.0Hz), 10.65(1H, brs) | 427 |
| 41 | 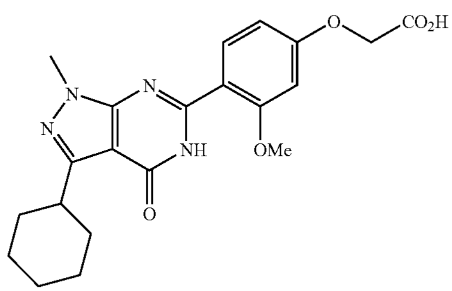 | Colorless solid >250 | DMSO-d$_6$ 1.18-1.42(3H, m), 1.60-1.82(5H, m), 1.88-1.96(2H, m), 2.88-3.00(1H, m), 3.83(3H, s), 3.88(3H, s), 4.79(2H, s), 6.65(1H, dd, J=2.2 and 8.8Hz), 6.63(1H, d, J=2.2Hz), 7.76(1H, d, J=8.8Hz), 11.50(1H, brs) | 413 |
| 42 | maleate | Colorless solid 203.5-205 (EtOH/iPrOH) | CD$_3$OD 1.28-1.52(3H, m), 1.68-1.89(5H, m), 1.93-2.00(2H, m), 2.07-2.28(4H, m), 2.89(3H, brs), 3.00-3.10(1H, m). 3.27-3.47(4H, m), 3.92(3H, s), 4.05(3H, s), 6.25(2H, s), 6.81-6.65(2H, m), 8.29(1H, d, J = 8.6Hz) | 452(free) |
| 43 | 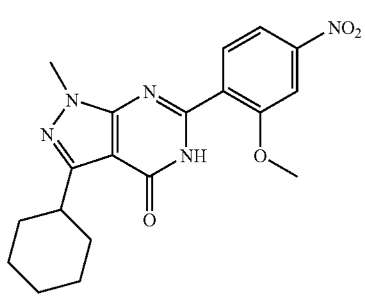 | Light yellow crystal 249-250 (Ethyl acetate) | CDCl$_3$ 1.29-1.51(3H, m), 1.69-1.89(5H, m), 1.97-2.07(2H, m), 3.03-3.16(1H, m), 4.01(3H, s), 4.18(3H, s), 7.92-7.96(1H, m), 7.99-8.04(1H, m), 8.68-8.72(1H, m), 10.62(1H, brs) | 384 |
| 44 | 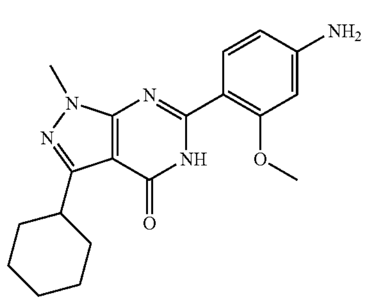 | Orange crystal 259-261 (Ethyl acetate-Ethanol) | CDCl$_3$ 1.27-1.50(3H, m), 1.68-1.88(5H, m), 1.94-2.06(2H, m), 3.00-3.12(1H, m), 3.94(3H, s), 3.99(3H, s), 4.15(2H, s). 6.26-6.30(1H, m), 6.40-6.46(1H, m), 8.31-8.35(1H, m), 10.70(1H, brs) | 354 |

-continued

| Ex. No. | Chemical Structure | Properties Melting Point (° C.) (Solvent for Recrystallization) | ¹H—NMR | MS(FAB) (M + 1)⁺ |
|---|---|---|---|---|
| 45 | 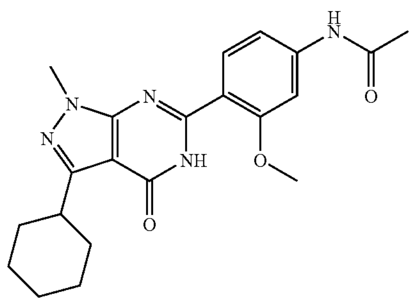 | Colorless crystal >300 (Ethanol-Ethyl acetate) | DMSO-$d_6$ 1.16-1.43(3H, m), 1.60-1.82(5H, m), 1.86-1.98(2H, m), 2.09(3H, s), 2.88-2.99(1H, m), 3.84(3H, s), 3.85(3H, s). 7.20-7.28(1H, m), 7.57-7.60(1H, m), 7.75-7.80(1H, m), 10.24(1H, brs), 11.50(1H, brs) | 396 |
| 46 | 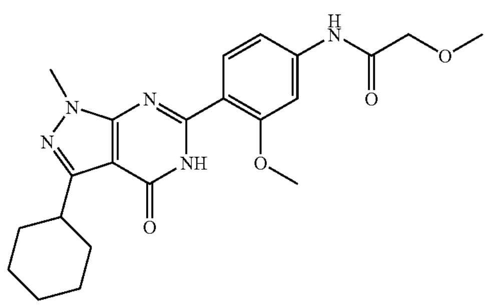 | Colorless crystal 257-258 (Ethanol-Ethyl acetate) | $CDCl_3$ 1.29-1.52(3H, m), 1.70-1.91(5H, m), 1.98-2.08(2H, m), 3.02-3.14(1H, m), 3.54(3H, s), 3.97(3H, s), 4.06(2H, s). 4.08(3H, s), 6.99-7.05(1H, m), 7.85-7.90(1H, m), 8.41-8.53(2H, m), 10.75(1H, brs) | 426 |
| 47 | 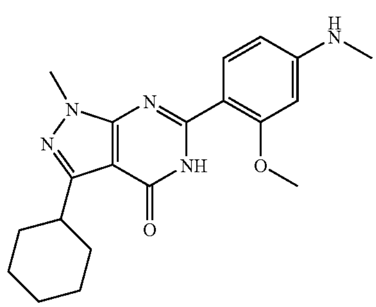 | Colorless solid 227-228 (Ethyl acetate) | $CDCl_3$ 1.28-1.51(3H, m), 1.68-1.88(5H, m), 196-2.07(2H, m), 2.93(3H, d, J=5.0Hz), 3.00-3.11(1H, m), 3.94(3H, s), 4.02(3H, s), 4.30(1H, brd, J=5.0Hz), 6.10-6.15(1H, m), 6.31-6.37(1H, m), 8.32-8.39(1H, m), 10.74(1H, brs) | 368 |
| 48 | 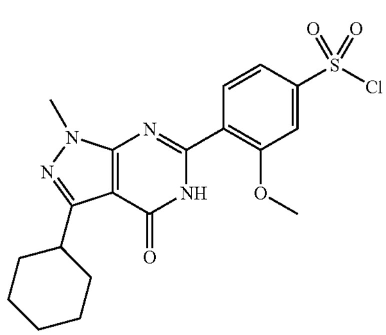 | Light yellow solid 227-230.1 | $CDCl_3$ 1.32-1.53(3H, m), 1.69-1.91(5H, m), 1.97-2.08(2H, m), 3.04-3.16(1H, m), 4.01(3H, s), 4.19(3H, s), 7.65-7.70(1H, m), 7.78-7.86(1H, m), 8.68-8.75(1H, m), 10.57(1H, brs) | |

-continued

| Ex. No. | Chemical Structure | Properties Melting Point (° C.) (Solvent for Recrystallization) | ¹H—NMR | MS(FAB) (M + 1)⁺ |
|---|---|---|---|---|
| 49 | 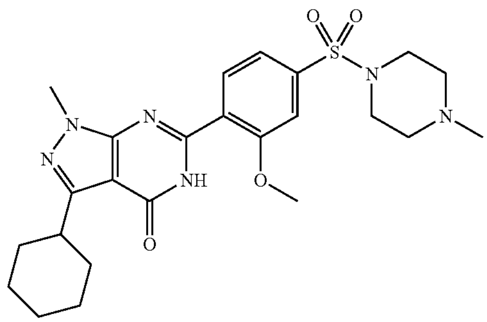 | Colorless solid 211-213 (Ethanol) | CDCl₃ 1.22-1.52(3H, m), 1.69-1.91(5H, m), 1.97-2.09(2H, m), 2.28(3H, s), 2.45-2.57(4H, m), 3.08-3.20(4H, m), 4.00(3H, s), 4.13(3H, s), 7.39-7.43(1H, m), 7.48-7.53(1H, m), 8.60-8.68(1H, m), 10.58(1H, brs) | |
| 50 | 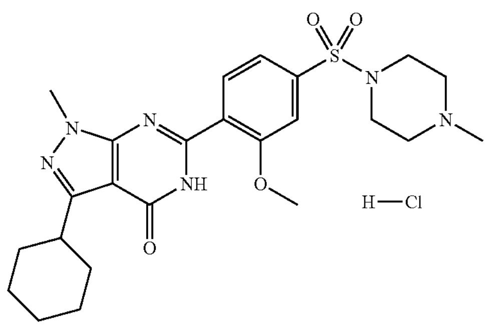 | Colorless solid 238-239 (Ethanol) | CDCl₃ 1.29-1.91(8H, m), 1.97-2.11(2H, m), 2.81(3H, s), 2.91-3.99(9H, m), 4.00(3H, s), 4.14(3H, s), 7.39-7.42(1H, m), 7.47-7.52(1H, m), 8.61-8.68(1H, m), 10.56(1H, brs) | 501(free) |
| 51 | 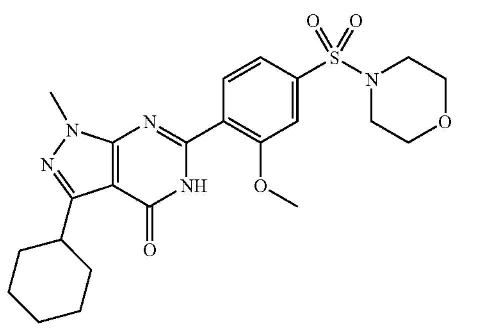 | Light yellow solid 224-224.5 (Ethyl acetate-Hexane) | CDCl₃ 1.32-1.53(3H, m), 1.70-1.93(5H, m), 2.00-2.08(2H, m), 3.05-3.18(5H, m), 3.74-3.81(3H, m), 4.00(3H, s), 4.14(3H, s), 7.41-7.44(1H, m), 7.50-7.54(1H, m), 8.65-8.70(1H, m). 10.58(1H, brs) | 488 |
| 52 | 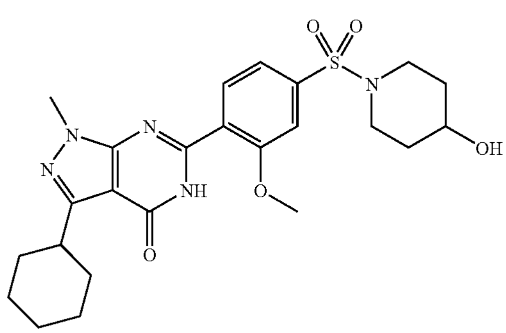 | Colorless solid 210-212 (Ethyl acetate) | CDCl₃ 1.30-1.52(4H, m), 1.63-1.90(7H, m). 1.92-2.08(4H, m), 2.08-3.15(3H, m), 3.29-3.39(2H, m), 3.80-3.91(1H, m). 4.00(3H, s), 4.13(3H, s), 7.41-7.44(1H, m), 7.50-7.55(1H, m), 8.60-8.67(1H, m), 10.58(1H, brs) | 502 |

-continued

| Ex. No. | Chemical Structure | Properties Melting Point (° C.) (Solvent for Recrystallization) | $^1$H—NMR | MS(FAB) $(M + 1)^+$ |
|---|---|---|---|---|
| 53 | 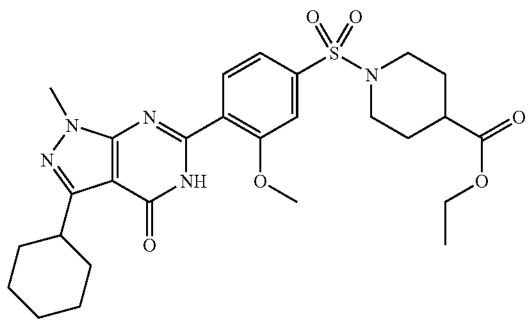 | Colorless solid 183.2-184.5 | CDCl$_3$ 1.23(3H, t, J=7.1Hz), 1.30-1.51(3H, m), 1.68-1.90(7H, m), 1.94-2.06(4H, m), 2.23-2.36(1H, m), 2.58-2.67(2H, m), 3.03-3.15(1H, m), 3.62-3.71(2H, m), 4.00(3H, s), 4.12(2H, q, J=7.1Hz), 4.13(3H, s), 7.41-7.45(1H, s), 7.47-7.52(1H, m), 8.59-8.66(1H, m), 10.58(1H, brs) | 558 |
| 54 | 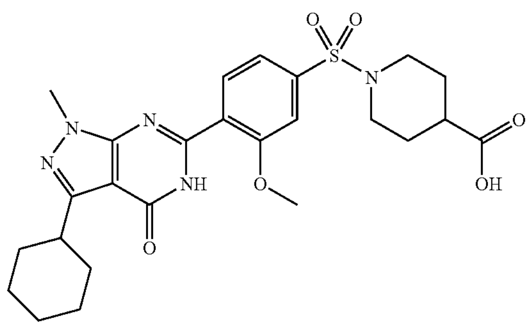 | Colorless solid 268-269 (Ethyl acetate-Ethanol) | CDCl$_3$ 1.28-1.54(3H, m), 1.69-2.12(11H, m). 2.31-2.42(1H, m), 2.60-2.73(2H, m), 3.05-3.18(1H, m), 3.61-3.71(2H, m), 3.99(3H, s), 4.10(3H, s), 7.40-7.45(1H, s), 7.47-7.53(1H, m), 8.50-8.58(1H, m), 10.85(1H, brs) | 530 |
| 55 | 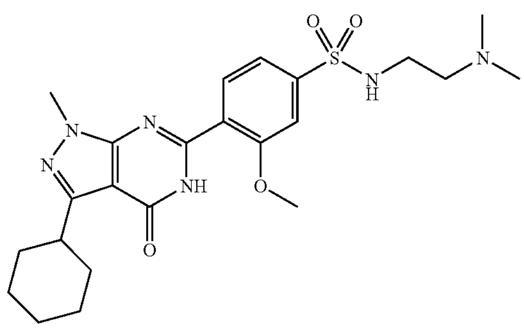 | Colorless solid 169-170.5 (Ethanol) | CDCl$_3$ 1.28-1.52(3H, m), 1.69-1.93(5H, m), 1.99-2.08(2H, m), 2.12(6H, s), 2.38(2H, t, J = 5.9Hz), 3.00-3.15(3H, m), 4.00(3H, s), 4.14(3H, s), 7.57-7.68(2H, m), 8.62-8.70(1H, m), 10.64(1H, brs) | 489 |
| 56 | 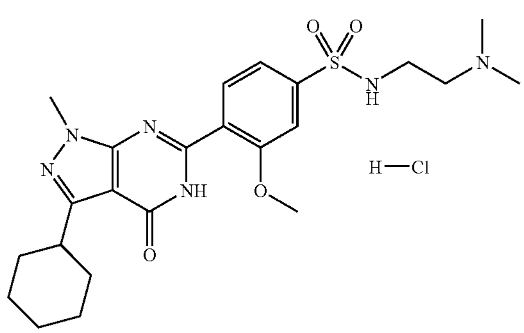 | Colorless solid 203.5-205 (Ethanol) | CDCl$_3$ 1.28-1.52(3H, m), 1.70-1.91(5H, m), 1.97-2.09(2H, m), 2.93(6H, s), 3.01-3.15(1H, m), 3.30-3.43(4H, m), 3.99(3H, s), 4.20(3H, s), 7.65-7.71(1H, m), 7.80-7.83(1H, s), 8.55-8.63(1H, m), 10.64(1H, brs) | 489 |

| Ex. No. | Chemical Structure | Properties Melting Point (° C.) (Solvent for Recrystallization) | ¹H—NMR | MS(FAB) (M + 1)⁺ |
|---|---|---|---|---|
| 57 | 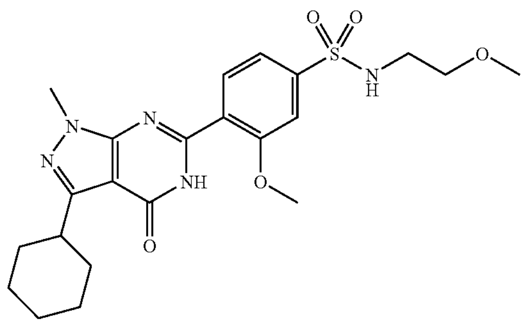 | Colorless solid 175-176 (Ethyl acetate-Hexane) | CDCl₃ 1.30-1.53(3H, m), 1.68-1.90(5H, m), 1.97-2.07(2H, m), 3.02-3.14(1H, m), 3.16-3.22(2H, m), 3.30(3H, s), 3.45(2H, t, J=5.0Hz), 4.00(3H, s), 4.13(3H, s), 5.03(1H, t, J=5.8Hz), 7.53-7.57(1H, m), 7.58-7.64(1H, m), 8.61-8.67(1H, m), 10.61(1H, brs) | 476 |
| 58 | 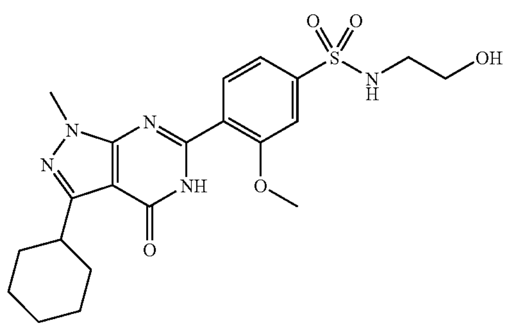 | Colorless solid 211-222 (Ethyl acetate) | CDCl₃ 1.27-1.50(3H, m), 1.68-1.90(5H, m), 1.97-2.07(3H, m), 3.03-3.14(1H, m), 3.16-3.23(2H, m), 3.71-3.79(2H, m), 3.99(3H, s), 4.13(3H, s), 5.29(1H, t, J=5.9Hz), 7.58-7.68(2H, m), 8.59-8.66(1H, m), 10.63(1H, brs) | 462 |
| 59 | 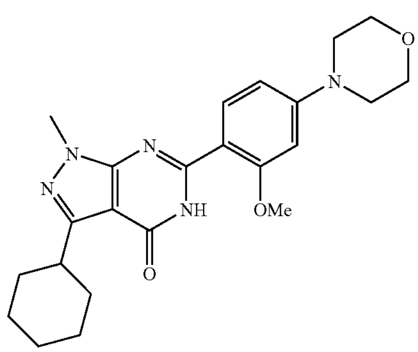 | Colorless solid 249-250.5 (Toluene) | CDCl₃ 1.32-1.51(3H, m), 1.72-1.78(5H, m), 1.97-2.05(2H, m), 3.03-3.13(1H, m), 3.31-3.36(4H, m), 3.87-3.91(4H, m), 3.95(3H, s), 4.04(3H, m), 6.44(1H, d, J=2.0Hz), 6.65(1H, dd, J=2.0 and 9.0Hz), 8.43(1H, d, J=9.0Hz), 10.73(1H, brs) | 424 |
| 60 | 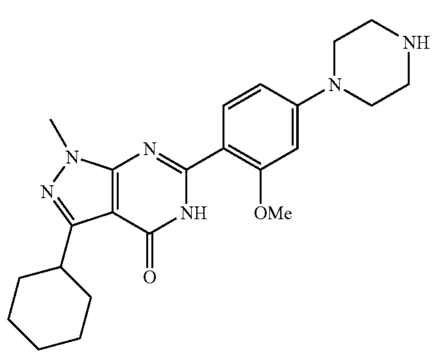 | Faint brown solid 187-190 | CDCl₃ 1.28-1.51(3H, m), 1.68-1.87(5H, m), 1.97-2.05(2H, m), 3.03-3.13(5H, m), 3.31-3.37(4H, m), 3.95(3H, s), 4.03(3H, s), 6.42(1H, d, J=2.0Hz), 6.65(1H, dd; J=2.0 and 9.0Hz), 8.40(1H, d, J=9.0Hz), 10.74(1H, brs) | 423 |

| Ex. No. | Chemical Structure | Properties Melting Point (° C.) (Solvent for Recrystallization) | ¹H—NMR | MS(FAB) (M + 1)⁺ |
|---|---|---|---|---|
| 61 | 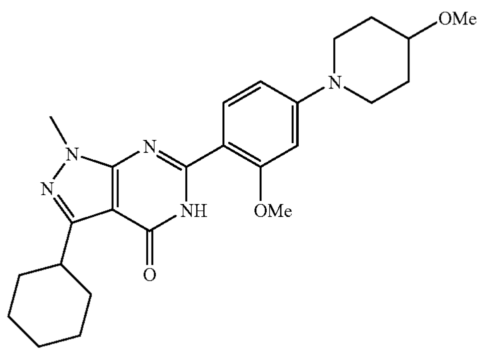 | Faint yellow solid 179-182 | CDCl₃ 1.23-1.50(3H, m), 1.65-1.88(7H, m), 1.95-2.03(4H, m), 3.01-3.12(1H, m), 3.14-3.21(2H, m), 3.39(3H, s), 3.42-3.51(1H, m), 3.62-3.71(2H, m), 3.95(3H, s), 4.03(3H, s), 6.42(1H, d, J=2.3Hz), 6.64(1H, dd, J=2.3 and 9.0Hz), 8.38(1H, d, J=9.0Hz), 10.74(1H, brs) | 452 |
| 62 | 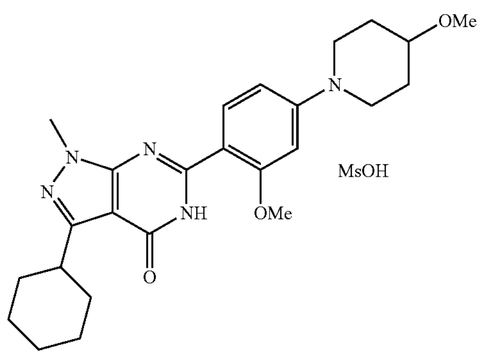 | Colorless solid 209 (Decomposition) (Toluene) MsOH | DMSO-d₆ 1.20-1.42(3H, m), 1.47-1.56(2H, m), 1.60-1.82(5H, m), 1.87-1.96(4H, m), 2.33(3H, s), 2.87-2.96(1H, m), 3.08-3.17(2H, m), 3.29(3H, s), 3.37-3.48(1H, m), 3.65-3.73(2H, m), 3.83(3H, s), 3.95(3H, s), 6.61-6.63(1H, m), 6.68-6.73(1H, m), 7.94(1H, d, J=9.0Hz), 11.12(1H, brs) | 452(free) |
| 63 | 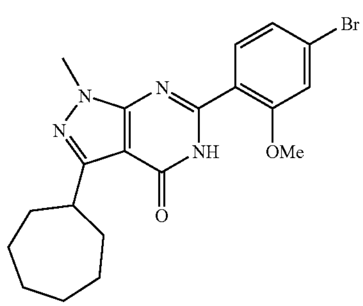 | Faint yellow solid 180-190 | CDCl₃ 1.57-1.74(6H, m), 1.78-1.87(2H, m), 192-2.06(4H, m), 3.21-3.30(1H, m), 3.97(3H, s), 4.06(3H, s), 7.22(1H, d, J=1.5Hz), 7.30(1H, dd, J=1.5 and 8.6Hz), 8.38(1H, d, J = 8.6Hz), 10.60(1H, brs) | 431 |
| 64 | 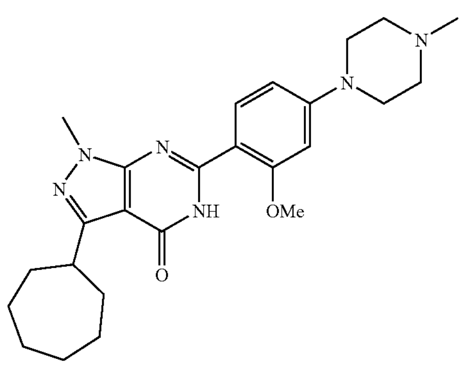 | Faint yellow solid 180-181.5 (Ethanol) | CDCl₃ 1.57-1.73(6H, m), 1.77-1.87(2H, m), 1.92-2.06(4H, m), 2.37(3H, s), 2.55-2.61(4H, m), 3.19-3.27(1H, m), 3.34-3.40(4H, m), 3.94(3H, s), 4.03(3H, s), 6.42(1H, d, J=2.0Hz), 6.64(1H, dd, J=2.0 and 9.0Hz), 8.40(1H, d, J=9.0Hz), 10.75(1H, brs) | 451 |

-continued

| Ex. No. | Chemical Structure | Properties Melting Point (° C.) (Solvent for Recrystallization) | ¹H—NMR | MS(FAB) (M + 1)⁺ |
|---|---|---|---|---|
| 65 | 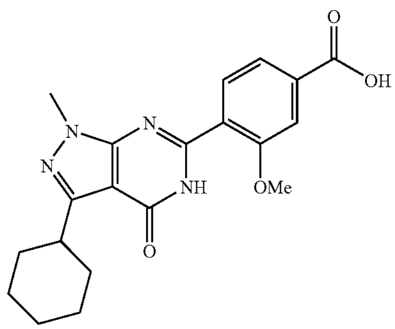 | Colorless solid 290 (Decomposition) (Ethyl acetate-Ethanol) | DMSO-$d_6$ 1.16-1.43(3H, m), 1.60-1.99(7H, m), 2.90-3.02(1H, m), 3.84(3H, s), 3.91(3H, s), 4.03(3H, s), 7.59-7.69(2H, m), 7.72-7.80(1H, m), 11.97(1H, brs), 13.34(1H, brs) | 383 |
| 66 | 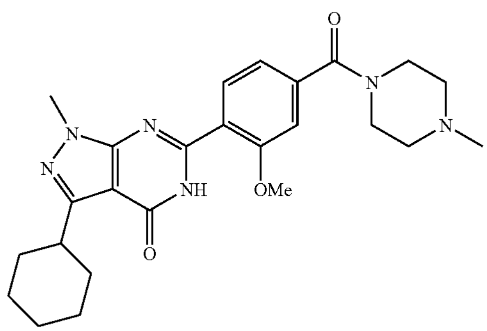 | Colorless solid 224-225 (Ethanol) | CDCl$_3$ 1.24-1.52(3H, m), 1.69-1.91(5H, m), 1.98-2.09(2H, m), 2.31-2.60(7H, m), 3.03-3.17(1H, m), 3.38-3.56(2H, m), 3.74-3.90(2H, m), 3.99(3H, s), 4.09(3H, s), 7.09-7.19(2H, m), 8.54(1H, d, J=8.0Hz), 10.67(1H. brs) | 465 |
| 67 | 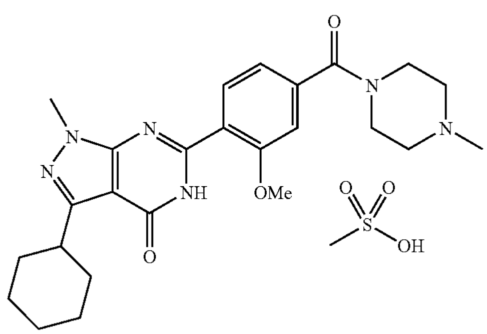 | Colorless solid 235-240 | DMSO-$d_6$ 1.19-1.43(3H, m), 1.60-1.85(5H, m), 1.89-1.99(2H, m), 2.33(3H, s), 2.84(3H, s), 2.90-3.01(1H, m), 3.03-3.63(8H, m), 3.84(3H, s), 3.89(3H, s), 7.10-7.24(2H, m), 7.74(1H, d, J=7.8Hz), 9.81(1H, brs), 11.90(1H, brs) | 465(free) |
| 68 | 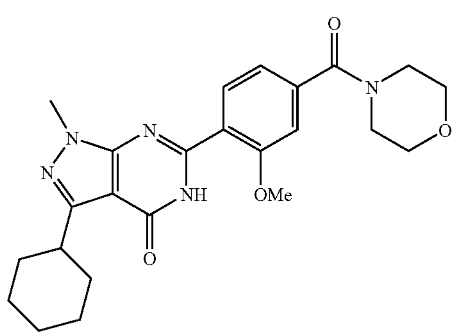 | Colorless solid 225-226 (Ethanol) | CDCl$_3$ 1.29-1.55(3H, m), 1.70-1.91(5H, m), 1.98-2.10(2H, m), 3.03-3.17(1H, m), 3.39-3.91(8H, m), 3.99(3H, s), 4.09(3H, s), 7.11-7.21(2H, m), 8.55(1H, d, J=8.1Hz), 10.66(1H, brs) | 452 |

-continued

| Ex. No. | Chemical Structure | Properties Melting Point (° C.) (Solvent for Re-crystallization) | ¹H—NMR | MS(FAB) (M + 1)⁺ |
|---|---|---|---|---|
| 69 | 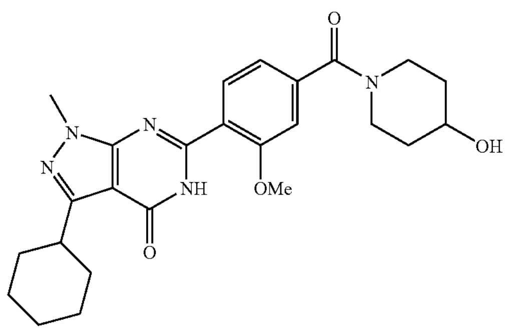 | Colorless solid 225.5-227 (Ethyl acetate) | CDCl₃ 1.30-2.15(15H, m), 3.03-3.15(1H, m), 3.18-3.35(1H, m), 3.40-3.54(1H, m), 3.62-3.79(1H, m), 3.97-4.28(8H, m), 7.10-7.19(2H, m), 8.54(1H, d, J=8.4Hz), 10.68(1H, brs) | 466 |
| 70 | 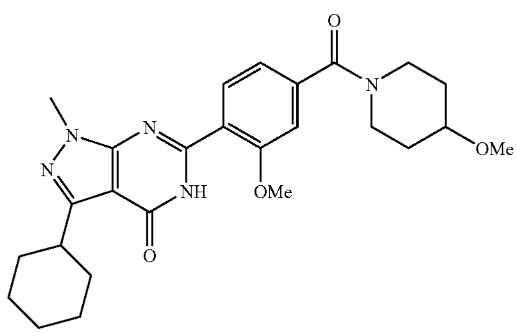 | Colorless solid 202-203.5 (Ethylacetate-Hexane) | CDCl₃ 1.29-2.09(14H, m), 3.02-3.15(1H, m), 3.18-3.32(1H, m), 3.38(3H, s), 3.47-3.70(3H, m), 3.95-4.15(7H, m), 7.11-7.19(2H, m), 8.53(1H, d, J=8.5Hz), 10.68(1H, brs) | 480 |
| 71 | 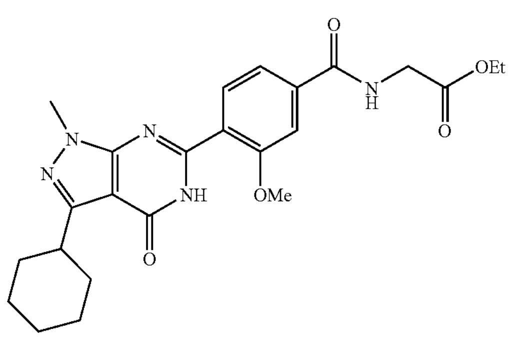 | Colorless solid 219-220 (Ethanol) | CDCl₃ 1.30-1.52(6H, m), 1.70-1.91(5H, m), 1.97-2.09(2H, m), 3.07-3.19(1H, m), 3.99(3H, s), 4.12(3H, s), 4.22-4.35(4H, m), 6.78(1H, t, J=4.6Hz), 7.47(1H, d, J = 8.2Hz), 7.64(1H, s), 8.57(1H, d, J = 8.2Hz), 10.72(1H, brs) | 468 |
| 72 | 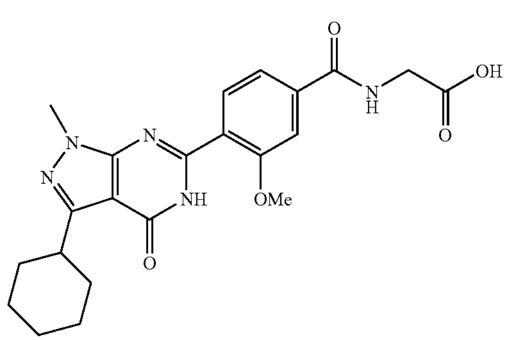 | Colorless solid 267-269 (Ethanol) | DMSO-d₆ 1.20-1.45(3H, m), 1.61-1.84(5H, m), 1.89-2.00(2H, m), 2.91-3.11(1H, m), 3.84(3H, s), 3.92(3H, s), 3.97(2H, d, J=5.7Hz), 7.57-7.68(2H, m), 7.74-7.81(1H, m), 9.02(1H, t, J = 5.7Hz), 11.94(1H, brs) | 440 |

-continued

| Ex. No. | Chemical Structure | Properties Melting Point (° C.) (Solvent for Recrystallization) | $^1$H—NMR | MS(FAB) $(M + 1)^+$ |
|---|---|---|---|---|
| 73 | 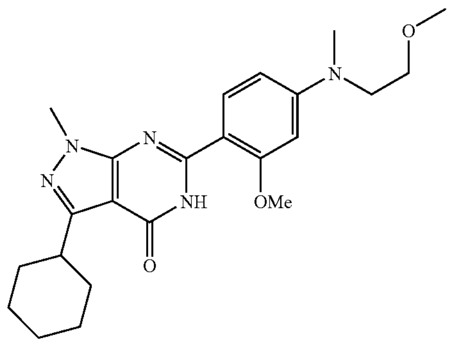 | Faint yellow solid 154-155 (Ethyl acetate-Hexane) | CDCl$_3$ 1.30-1.51(3H, m), 1.68-1.89(5H, m), 1.97-2.08(2H, m), 3.00-3.15(4H, m), 3.37(3H, s), 3.56-3.68(4H, m), 3.94(3H, s), 4.03(3H, s), 6.25(1H, d, J=2.3Hz), 6.47(1H, dd, J=9.1Hz and 2.3Hz), 8.38(1H, d, J=9.1Hz), 10.76(1H, brs) | 426 |
| 74 | 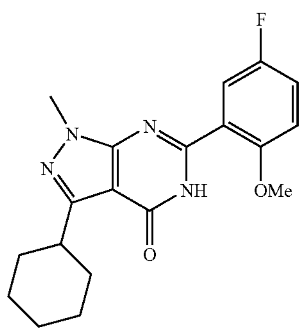 | Colorless solid 211-212 (Hexane-Ethyl acetate) | CDCl$_3$ 1.29-1.53(3H, m), 1.70-1.90(5H, m), 1.96-2.08(2H, m), 3.01-3.14(1H, m), 3.99(3H, s), 4.05(3H, s), 7.04(1H, dd, J=9.2Hz and 4.17Hz), 7.19-7.29(1H, m), 8.25(1H, d, dd, J=9.2Hz and 3.2Hz), 10.81(1H, brs) | 357 |
| 75 | 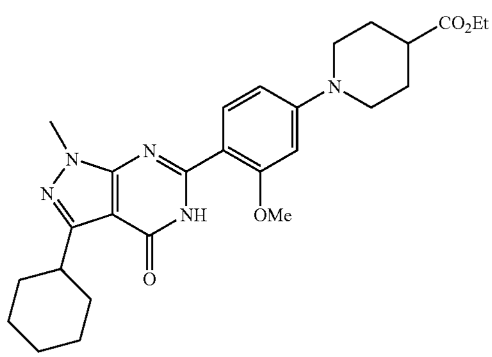 | Pale yellow foam | CDCl$_3$ 1.28(3H, t, J=7.1Hz), 1.27-1.52(3H, m), 1.68-1.91(7H, m), 1.95-2.07(4H, m), 2.50-2.59(1H, m), 2.95-3.11(3H, m), 3.76-3.85(2H, m), 3.95(3H, s), 4.03(3H, s), 4.17(2H, q, J=7.1Hz), 6.42(1H, d. J=2.0Hz), 6.63(1H, dd, J=2.0 and 9.0Hz), 8.38(1H, d, J=9.0Hz), 10.74(1H, brs) | 494 |
| 76 | 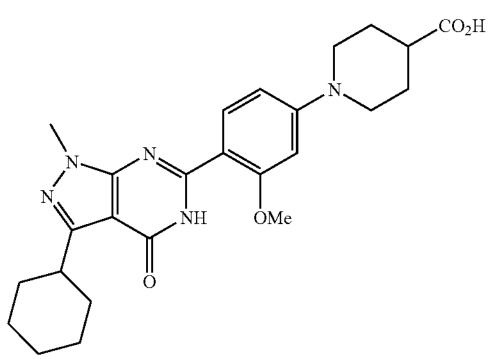 | Faint brown solid 145-149 | CDCl$_3$ 1.26-2.13(14H, m), 2.56-2.67(1H, m), 3.00-3.14(3H, m), 3.79-3.89(2H, m), 3.95(3H, s), 4.03(3H, s), 6.42(1H, d, J=2.0Hz), 6.64(1H, dd, J=2.0 and 9.0Hz), 8.37(1H, d, J=9.0Hz), 10.79(1H, brs) | 466 |

-continued

| Ex. No. | Chemical Structure | Properties Melting Point (° C.) (Solvent for Recrystallization) | $^1$H—NMR | MS(FAB) $(M + 1)^+$ |
|---|---|---|---|---|
| 77 | 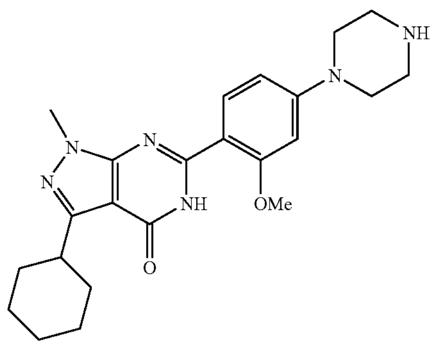 | Faint yellow foam | CDCl$_3$ 1.51-1.75(6H, m), 1.77-1.87(2H, m), 1.92-2.06(4H, m), 3.02-3.08(4H, m), 3.19-3.28(1H, m), 3.31-3.37(4H, m), 3.94(3H, s), 4.03(3H, s), 6.42(1H, d, J=2.1Hz), 6.64(1H, dd, J=2.1 and 9.0Hz), 8.40(1H, d, J=9.0Hz), 10.76(1H, brs) | 437 |
| 78 | MsOH | Colorless crystal 270 (Decomposition) (Ethanol) | DMSO-d$_6$ 1.46-1.98(12H, m), 2.30(3H, s), 3.10-3.19(1H, m), 3.23-3.29(4H, m), 3.53-3.59(4H, m), 3.83(3H, s), 3.95(3H, s), 6.68(1H, d, J=2.0Hz), 6.73(1H, dd, J=2.0 and 8.9Hz), 7.91(1H, d, J=8.9Hz), 8.71(1H, brs), 11.23(1H, brs) | 437 |
| 79 | 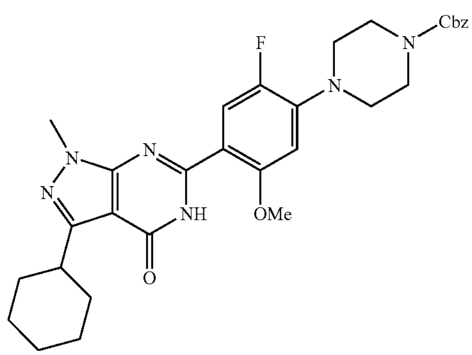 | Colorless foam | CDCl$_3$ 1.25-1.50(3H, m), 1.63-1.87(5H, m), 1.97-2.04(2H, m), 3.01-3.12(1H, m), 3.18-3.25(4H, m), 3.68-3.75(4H, m), 3.96(3H, s), 4.03(3H, s), 4.70(2H, d, J=5.8Hz), 6.47(1H, d, J=6.9Hz), 7.26-7.41(5H, m), 8.21(1H, d, J=14.2Hz), 10.74(1H, brs) | 575 |
| 80 | 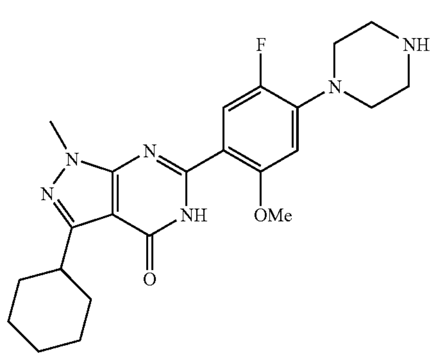 | Colorless solid 203-208 | CDCl$_3$ 1.25-1.54(3H, m), 1.68-1.89(5H, m), 1.98-2.06(2H, m), 3.05-3.13(5H, m), 3.19-3.28(4H, m), 3.96(3H, s), 4.04(3H, s), 6.48(1H, d, J=7.1Hz), 8.19(1H, d, J=14.5Hz), 10.78(1H, brs) | 441 |

-continued
| Ex. No. | Chemical Structure | Properties Melting Point (° C.) (Solvent for Recrystallization) | $^1$H—NMR | MS(FAB) $(M + 1)^+$ |
|---|---|---|---|---|
| 81 | 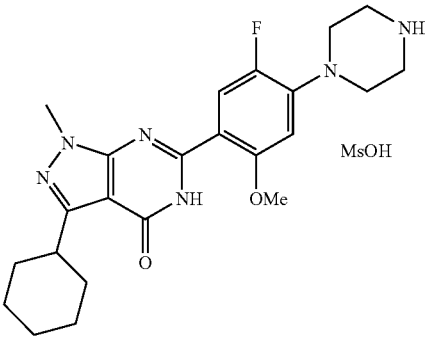 | Colorless solid 228-238 (Methanol-Ether) | DMSO-$d_6$ 1.18-1.43(3H, m), 1.69-1.82(5H, m), 1.87-1.95(2H, m), 2.30(3H, s), 2.89-3.00(1H, m), 3.26-3.32(4H, m), 3.36-3.42(4H, m), 3.84(3H, s), 3.95(3H, s), 6.75(1H, d, J = 7.3Hz), 7.71(1H, d, J=13.6Hz), 8.69(1H, brs), 11.45(1H, brs) | 441 |
| 82 | 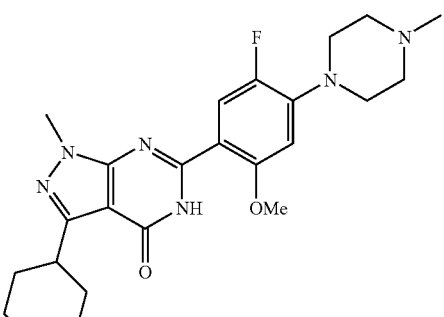 | Pale yellow solid 175-182 | 4CDCl$_3$ 1.25-1.51(3H, m), 1.65-1.89(5H, m), 1.97-2.06(2H, m), 2.37(3H, s), 2.59-2.65(4H, m), 3.03-3.12(1H, m), 3.27-3.34(4H, m), 3.96(3H, s), 4.04(3H, s), 6.48(1H, d, J=7.1Hz), 8.18(1H, d, J=14.5Hz), 10.77(1H, brs) | 455 |

| Ex. No. | Chemical Structure | Properties Melting Point(° C.) (Solvent for Recrystallization) | ¹H—NMR | MS(FAB) (M + 1)⁺ |
|---|---|---|---|---|
| 83 | (structure with dimethylaminoethyl-N-phenyl-OMe substituent, pyrazolopyrimidinone with N-methyl and cyclohexyl) | Faint yellow foam | CDCl₃ 1.20-1.52(3H, m), 1.66-1.86(5H, m), 1.96-2.04(2H, m), 2.50(3H, s), 2.85-2.90(2H, m), 3.03-3.13(1H, m), 3.09(3H, s), 3.55-3.60(2H, m), 3.94(3H, m), 4.03(3H, s), 6.26(1H, d, J=2.2Hz), 6.50(1H, dd, J=2.2 and 9.1Hz), 8.38(1H, d, J=9.1Hz), 10.75(1H, brs) | 425 |
| 84 | (same structure as 83, MsOH salt) | Faint yellow solid 125-140 (Isoprepanol-Ether) | DMSO-d₆ 1.15-1.40(3H, m), 1.57-1.79(5H, m), 1.85-1.93(2H, m), 2.31(3H, s), 2.60-2.65(2H, m), 2.85-2.95(1H, m), 3.03(3H, s), 3.10-3.18(3H, m), 3.66-3.73(2H, m), 3.82(3H, s), 3.98(3H, s), 6.36(1H, d, J=2.0Hz), 6.54(1H, dd, J=2.0 and 9.0Hz), 7.99(1H, d, J=9.0Hz),8.39(2H, brs), 11.07(1H, brs) | 425 |
| 85 | (structure with 4-bromo-2-ethoxyphenyl, pyrazolopyrimidinone with N-methyl and cyclohexyl) | Pale yellow solid 165-175 | CDCl₃ 1.26-1.51(3H, m), 1.64(3H, t, J=7.0Hz), 1.72-1.90(5H, m), 1.98-2.05(2H, m), 3.02-3.12(1H, m), 3.98(3H, s), 4.29(2H, q, J=7.0Hz), 7.21(1H, d, J=1.8Hz), 7.29(1H, dd, J=1.8 and 8.6Hz), 8.40(1H, d, J=8.6Hz), 10.89(1H, brs) | 431 |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 86 | (4-methylpiperazinyl-phenyl-OEt substituted pyrazolopyrimidinone with cyclohexyl and N-methyl) | Pale yellow crystal 185-187 (Ether) | CDCl₃ 1.27-1.68(3H, m), 1.63(3H, t, J=7.0Hz), 1.70-1.88(5H, m), 1.95-2.03(2H, m), 2.37(3H, s), 2.55-2.60(4H, m), 3.00-3.10(1H, m), 3.35-3.40(4H, m), 3.95(3H, s), 4.27(2H, q, J=7.0Hz), 6.42(1H, d, J=2.1Hz), 6.54(1H, dd, J=2.1 and 9.0Hz), 8.42(1H, d, J=9.0Hz), 11.04(1H, brs) | 451 |
| 87 | (same structure) · MsOH | Colorless crystal 166-170 (Isopropanol-Ether) | DMSO-d₆ 1.16-1.38(3H, m), 1.42(3H, t, J=7.0Hz), 1.58-1.80(5H, m), 1.84-1.92(2H, m), 2.29(3H, s), 2.85-2.95(4H, m), 3.03-3.18(4H, m), 3.50-3.56(2H, m), 3.83(3H, s), 4.05-4.11(2H, m), 4.24(2H, q, J=7.0Hz), 6.69(1H, d, J=2.0Hz), 6.74(1H, dd, J=2.0 and 8.9Hz), 8.00(1H, d, J=8.9Hz), 11.28(1H, brs) | 451 |

| Ex. No. | Chemical Structure | Properties Melting Point(° C.) (Solvent for Recrystallization) | ¹H—NMR | MS(FAB) (M + 1)⁺ |
|---|---|---|---|---|
| 88 | 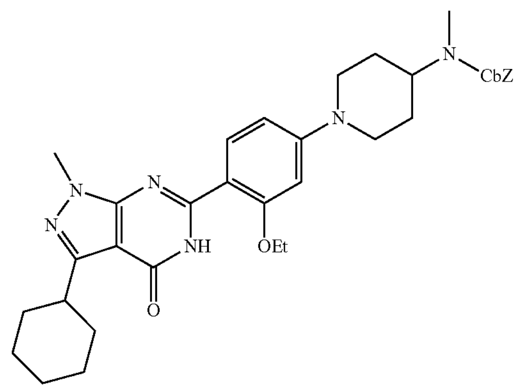 | Faint yellow foam | CDCl₃ 1.27-1.89(15H, m), 1.96-2.05(2H, m), 2.82(3H, brs), 2.90-3.11(3H, m), 3.91-4.00(2H, m), 3.95(3H, s), 4.26(2H, q, J=7.0Hz), 4.25-4.37(1H, m), 5.17(2H, brs), 6.42(1H, d, J=2.0Hz), 6.63(1H, dd, J=2.0 and 9.1Hz), 7.30-7.43(5H, m), 8.41(1H, d, J=9.1Hz), 11.02(1H, brs) | 599 |
| 89 | 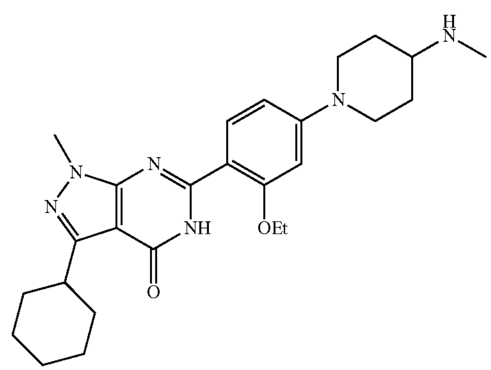 | Pale yellow foam | CDCl₃ 1.28-2.05(17H, m), 2.48(3H, s), 2.59-2.68(1H, m), 2.91-3.09(3H, m), 2.78-2.86(2H, m), 2.98(3H, s), 4.26(2H, q, J=7.0Hz), 6.42(1H, d, J=2.0Hz), 6.64(1H, dd, J=2.0 and 9.1Hz), 8.40(1H, d, J=9.1Hz), 11.04(1H, brs) | 465 |

| Ex. No. | Chemical Structure | Properties Melting Point(° C.) (Solvent for Recrystallization) | ¹H—NMR | MS(FAB) (M + 1)⁺ |
|---|---|---|---|---|
| 90 | 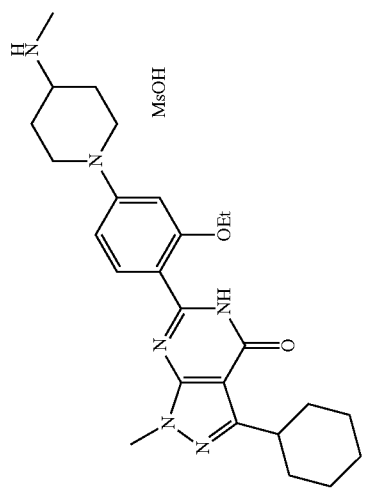 MsOH | Colorless solid 145-150 | DMSO-d₆ 1.19-1.38(3H, m), 1.43(3H, t, J=6.9Hz), 1.45-1.59(2H, m), 1.61-181(5H, m), 1.85-1.92(2H, m), 1.98-2.06(2H, m), 2.28(3H, s), 2.58(3H, brs), 2.85-2.95(3H, m), 3.83(3H, s), 4.00-4.08(2H, m), 4.25(2H, q, J=6.9Hz), 6.62(1H, d, J=2.0Hz), 6.71(1H, dd, J=2.0 and 9.0Hz), 8.03(1H, d, J=9.0Hz), 8.39(2H, brs), 11.21(1H, brs) | 465 |
| 91 | 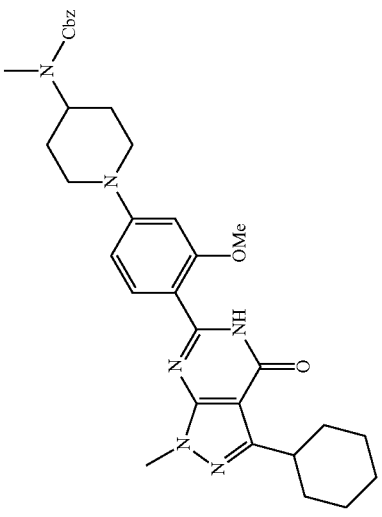 | Faint yellow foam | CDCl₃ 1.21-1.58(3H, m), 1.69-2.10(11H, m), 2.54(3H, s), 2.83(3H, brs), 2.92-3.03(2H, m), 3.88-3.96(2H, m), 4.02(3H, s), 4.25-4.38(1H, m), 4.95-5.05(1H, m), 5.17(2H, brs), 6.45(1H, d, J=2.1Hz), 6.65(1H, dd, J=2.1 and 9.0Hz), 7.31-7.42(5H, m), 8.34(1H, d, J=9.0Hz), 10.80(1H, brs) | 585 |

| Ex. No. | Chemical Structure | Properties Melting Point(° C.) (Solvent for Recrystallization) | ¹H—NMR | MS(FAB) (M + 1)⁺ |
|---|---|---|---|---|
| 92 | (structure: 3-cyclohexyl-1-methyl-6-[4-(4-methylaminopiperidin-1-yl)-2-methoxyphenyl]-pyrazolo-pyrimidinone) | Colorless solid 197-198 (Ether) | CDCl₃ 1.22-1.77(6H, m), 1.85-2.08(8H, m), 2.49(3H, s), 2.54(3H, s), 2.54-2.65(1H, m), 2.90-3.00(2H, m), 3.76-3.95(2H, m), 4.02(3H, s), 4.95-5.06(1H, m), 6.46(1H, d, J=2.1Hz), 6.65(1H, dd, J=2.1 and 8.9Hz),8.34(1H, d, J=8.9Hz), 10.83(1H, brs) | 451 |
| 93 | (structure: 3-cycloheptyl-1-methyl-6-[4-(4-(N-methyl-N-Cbz-amino)piperidin-1-yl)-2-methoxyphenyl]-pyrazolo-pyrimidinone) | Colorless foam | CDCl₃ 1.55-1.87(12H, m), 1.93-2.06(4H, m), 2.83(3H, s), 2.92-3.05(2H, m), 3.20-3.30(1H, m), 3.94(3H, s), 3.95-4.02(2H, m), 4.03(3H, s), 4.23-4.50(1H, m), 5.17(2H, brs), 6.42(1H, d, J=2.0Hz), 6.64(1H, dd, J=2.0 and 9.1Hz), 7.31-7.42(5H, m), 8.39(1H, d, J=9.1Hz), 10.73(1H, brs) | 599 |

| Ex. No. | Chemical Structure | Properties Melting Point(° C.) (Solvent for Recrystallization) | $^1$H—NMR | MS(FAB) (M + 1)$^+$ |
|---|---|---|---|---|
| 94 | (structure: 1-methyl-3-cycloheptyl-pyrazolopyrimidinone with 4-(4-methylaminopiperidin-1-yl)-2-methoxyphenyl) | Pale yellow solid 85-90 | CDCl$_3$ 1.43-1.75(8H, m), 1.78-1.88(2H, m), 1.94-2.07(6H, m), 2.49(3H, s), 2.60-2.70(1H, m), 2.95-3.04(2H, m), 3.19-3.28(1H, m), 3.81-3.89(2H, m), 3.94(3H, s), 4.03(3H, s), 6.42(1H, d, J=2.2Hz), 6.64(1H, dd, J=2.2 and 8.9Hz), 8.39(1H, d, J=8.9Hz), 10.75(1H, brs) | 465 |
| 95 | (structure: same as 94, MsOH salt) | Colorless crystal 238-241 (Ethanol-Diisopropyl ether) | DMSO-d$_6$ 1.45-1.78(10H, m), 1.82-1.95(4H, m), 2.01-2.09(2H, m), 2.29(3H, s), 2.57-2.62(3H, m), 2.87-2.97(2H, m), 3.07-3.17(1H, m), 3.20-3.35(1H, m), 3.81(3H, s), 3.95(3H, s), 4.01-4.10(2H, m), 6.62(1H, d, J=2.0Hz), 6.70(1H, dd, J=2.0 and 8.9Hz),7.93(1H, d, J=8.9Hz), 8.41(2H, brs), 11.11(1H, brs) | 465 |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 96 | (structure with N-Cbz, N-ethyl piperidine, OMe, cyclohexyl pyrazolopyrimidinone) | Colorless foam | CDCl₃, 1.10-1.51(6H, m), 1.69-1.88(9H, m), 1.96-2.04(2H, m), 2.90-3.11(3H, m), 3.16-3.29(2H, m), 3.90-4.00(2H, m), 3.95(3H, s), 4.03(3H, s), 4.14-4.30(1H, m), 5.17(2H, s), 6.42(1H, d, J=1.9Hz), 6.63(1H, dd, J=1.9 and 9.0Hz), 7.28-7.41(5H, m), 7.39(1H, d, J=9.0Hz), 10.73(1H, brs) | 599 |
| 97 | (structure with NH-ethyl piperidine, OMe, cyclohexyl pyrazolopyrimidinone) | Colorless crystal 179-180 (Ether) | CDCl₃, 1.15(3H, t, J=7.1Hz), 1.29-1.62(5H, m), 1.71-1.89(5H, m), 1.97-2.06(4H, m), 2.73(2H, q, J=7.1Hz), 2.70-2.79(1H, m), 2.94-3.13(3H, m), 3.82-3.90(2H, m), 3.95(3H, s), 4.03(3H, s), 6.43(1H, d, J=2.0Hz), 6.64(1H, dd, J=2.0 and 9.0Hz), 8.38(1H, d, J=9.0Hz), 10.75(1H, brs) | 465 |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 98 | (structure with Cbz-N-ethyl piperidine, OMe phenyl, pyrazolopyrimidinone with cyclohexyl and methyl) | Colorless foam | CDCl₃ 1.10-1.19(3H, m), 1.23-1.58(3H, m), 1.62-2.10(11H, m), 2.54(3H, s), 2.89-3.01(2H, m), 3.18-3.39(2H, m), 3.88-4.06(2H, m), 4.02(3H, s), 4.18-4.33(1H, m), 4.97-5.06(1H, m), 5.17(2H, s), 6.44(1H, d, J=1.9Hz), 6.64(1H, dd, J=1.9 and 8.9Hz), 7.29-7.40(5H, m), 8.34(1H, d, J=8.9Hz), 10.81(1H, brs) | 599 |
| 99 | (structure with H-N-ethyl piperidine, OMe phenyl, pyrazolopyrimidinone with cyclohexyl and methyl) | Colorless crystal 184-185.5 (Ether) | CDCl₃ 1.15(3H, t, J=7.1Hz), 1.25-1.61(5H, m), 1.67-1.76(1H, m), 1.86-2.10(8H, m), 2.54(3H, s), 2.70-2.80(3H, m), 2.91-3.00(2H, m), 2.78-2.86(2H, m), 4.02(3H, s), 4.95-5.06(1H, m), 6.45(1H, d, J=2.2Hz), 6.65(1H, dd, J=2.2 and 8.9Hz), 8.33(1H, d, J=8.9Hz), 10.83(1H, brs) | 465 |

-continued
| Ex. No. | Chemical Structure | Properties Melting Point(° C.) (Solvent for Recrystallization) | ¹H—NMR | MS(FAB) (M + 1)⁺ |
|---|---|---|---|---|
| 100 | 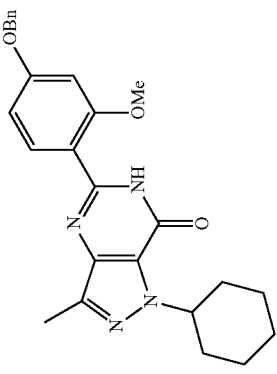 | Colorless solid 191-192 | CDCl₃ 1.23-1.38(1H, m), 1.45-1.59(2H, m), 1.69-1.78(1H, m), 1.85-2.10(6H, m), 2.55(3H, s), 4.00(3H, s), 4.97-5.06(1H, m), 5.15(2H, s), 6.65(1H, d, J=2.0Hz), 6.75(1H, dd, J=2.0 and 8.9Hz), 7.33-7.46(5H, m), 8.42(1H, d, J=8.9Hz), 10.74(1H, brs) | 445 |
| 101 | 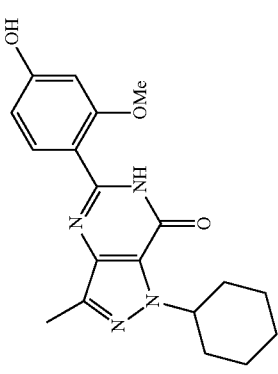 | Colorless solid >270 | DMSO-d₆ 1.14-1.28(1H, m), 1.32-1.45(2H, m), 1.64-1.73(1H, m), 1.79-1.98(6H, m), 2.36(3H, s), 3.80(3H, s), 4.85-4.95(1H, m), 5.15(2H, s), 6.47(1H, dd, J=2.0 and 8.4Hz), 6.51(1H, d, J=2.0Hz), 7.55(1H, d, J=8.4Hz), 10.00(1H, brs), 11.64(1H, brs) | 355 |

| Ex. No. | Chemical Structure | Properties Melting Point(° C.) (Solvent for Recrystallization) | 1H—NMR | MS(FAB) (M + 1)+ |
|---|---|---|---|---|
| 102 | 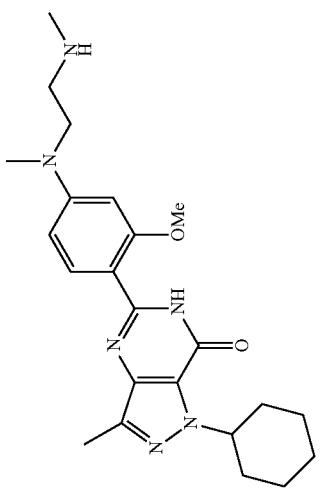 | Faint yellow foam | CDCl3 1.23-1.56(3H, m), 1.68-1.76(1H, m), 1.82-2.10(6H, m), 2.50(3H, s), 2.53(3H, s), 2.84-2.90(2H, m), 3.07(3H, s), 3.55-3.60(2H, m), 4.02(3H, s), 4.95-5.06(1H, m), 6.27(1H, d, J=2.2Hz), 6.50(1H, dd, J=2.2 and 9.0Hz), 8.32(1H, d, J=9.0Hz), 10.84(1H, brs) | 425 |
| 103 | 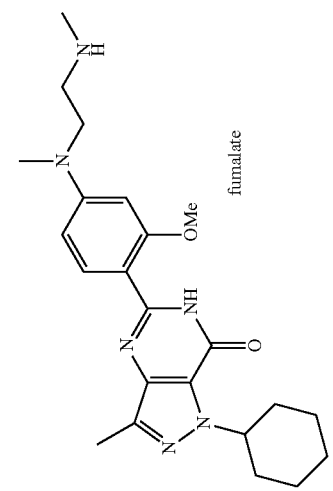 fumalate | Colorless crystal 211-213 (Ethanol) | DMSO-d6 1.15-1.46(3H, m), 1.62-1.71(1H, m), 1.79-1.98(6H, m), 2.37(3H, s), 2.88-2.95(2H, m), 3.00(3H, s), 3.59-3.66(2H, m), 3.91(3H, s), 4.85-4.95(1H, m), 6.35(1H, d, J=1.9Hz), 6.45-6.50(3H, m), 7.73(1H, d, J=8.8Hz) | 425 |
| 104 | 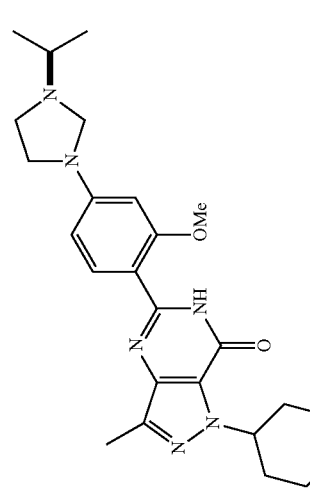 | Faint brown solid 177.5-179 | CDCl3 1.24-1.38(1H, m), 1.44-1.58(2H, m), 1.69-1.78(1H, m), 1.86-2.10(7H, m), 2.21-2.30(1H, m), 2.34(6H, s), 2.54(3H, s), 2.85-2.95(1H, m), 3.20-3.27(1H, m), 3.37-3.45(1H, m), 3.52-3.61(2H, m), 4.03(3H, s), 4.98-5.07(1H, m), 6.05(1H, d, J=2.0Hz), 6.31(1H, dd, J=2.0 and 9.0Hz), 8.34(1H, d, J=9.0Hz), 10.87(1H, brs) | 451 |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 105 | 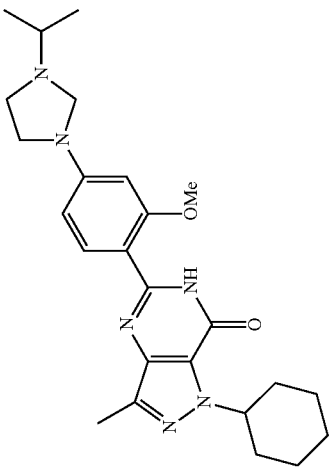 | Faint brown solid 178-181 | CDCl₃ 1.24-1.38(1H, m), 1.44-1.58(2H, m), 1.69-1.78(1H, m), 1.86-2.10(7H, m), 2.21-2.30(1H, m), 2.34(6H, s), 2.54(3H, s), 2.85-2.95(1H, m), 3.20-3.27(1H, m), 3.37-3.45(1H, m), 3.52-3.61(2H, m), 4.03(3H, s), 4.98-5.07(1H, m), 6.05(1H, d, J=2.0Hz), 6.31(1H, dd, J=2.0 and 9.0Hz), 8.34(1H, d, J=9.0Hz), 10.87(1H, brs) | 451 |
| 106 | 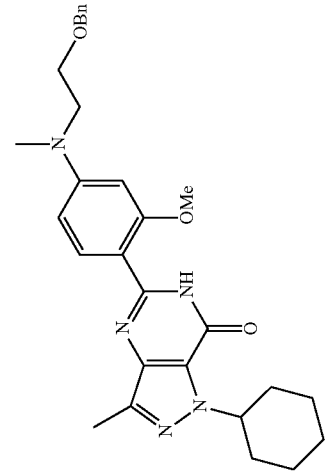 | Colorless viscous solid | CDCl₃ 1.23-1.58(3H, m), 2.69-2.77(1H, m), 1.85-2.10(6H, m), 2.54(3H, s), 3.09(3H, s), 3.61-3.73(4H, m), 3.96(3H, s), 4.53(2H, s), 4.95-5.06(1H, m), 6.26(1H, d, J=2.3Hz), 6.46(1H, dd, J=2.3 and 8.9Hz), 7.26-7.38(5H, m), 8.32(1H, d, J=8.9Hz), 10.85(1H, brs) | 502 |
| 107 | 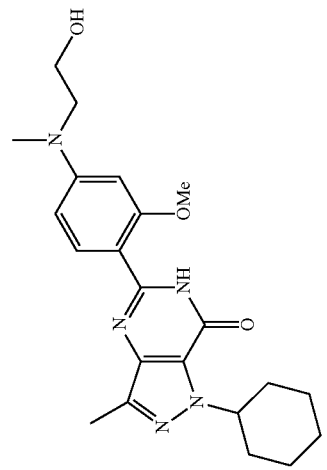 | Colorless solid 155-157 | CDCl₃ 1.24-1.39(1H, m), 1.43-1.61(2H, m), 1.64-1.76(2H, m), 1.85-2.10(6H, m), 2.54(3H, s), 3.10(3H, s), 3.57-3.63(2H, m), 3.85-3.91(2H, m), 4.03(3H, s), 4.96-5.05(1H, m), 6.31(1H, d, J=2.1Hz), 6.51(1H, dd, J=2.1 and 9.0Hz), 8.33(1H, d, J=9.0Hz), 10.84(1H, brs) | 412 |

| Ex. No. | Chemical Structure | Properties Melting Point(° C.) (Solvent for Recrystallization) | ¹H—NMR | MS(FAB) (M + 1)⁺ |
|---|---|---|---|---|
| 108 | (structure with OBn, piperidine, OMe, cyclohexyl pyrazolopyrimidinone) | Colorless solid 140-141.5 | CDCl₃ 1.21-1.59(5H, m), 1.69-1.77(1H, m), 1.86-2.10(9H, m), 1.85-2.10(9H, m), 2.54(3H, s), 2.84-2.95(2H, m), 3.35-3.41(2H, m), 3.82-3.89(2H, m), 4.02(3H, s), 4.53(2H, s), 4.97-5.06(1H, m), 6.44(1H, d, J=2.1Hz), 6.65(1H, dd, J=2.1 and 9.0Hz), 7.28-7.40(5H, m), 8.33(1H, d, J=9.0Hz), 10.84(1H, brs) | 542 |
| 109 | (structure with OH, piperidine, OMe, cyclohexyl pyrazolopyrimidinone) | Colorless crystal 217-218.5 (Ethyl acetate-Ether) | CDCl₃ 1.23-1.58(5H, m), 1.69-2.08(10H, m), 2.54(3H, s), 2.84-2.94(2H, m), 3.54-3.60(2H, m), 3.85-3.93(2H, m), 4.03(3H, s), 4.96-5.06(1H, m), 6.46(1H, d, J=2.1Hz), 6.66(1H, dd, J=2.1 and 8.9Hz), 8.33(1H, d, J=8.9Hz), 10.83(1H, brs) | 452 |

| Ex. No. | Chemical Structure | Properties Melting Point(° C.) (Solvent for Recrystallization) | ¹H—NMR | MS(FAB) (M + 1)⁺ |
|---|---|---|---|---|
| 110 | 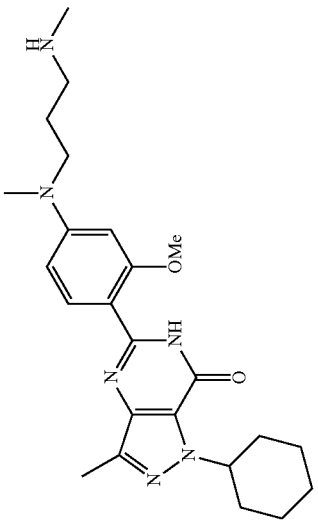 | Faint yellow viscous solid | CDCl₃ 1.21-2.10(12H, m), 2.45(3H, s), 2.54(3H, s), 2.61-2.66(2H, m), 3.03(3H, s), 3.46-3.52(2H, m), 4.02(3H, s), 4.96-5.06(1H, m), 6.25(1H, d, J=2.0Hz), 6.46(1H, dd, J=2.0 and 9.0Hz), 8.32(1H, d, J=9.0Hz), 10.86(1H, brs) | 439 |
| 111 | 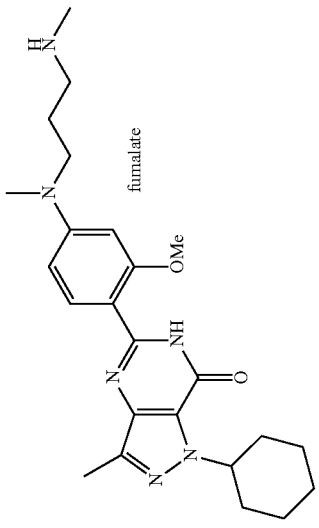 fumalate | Colorless crystal 205-207 (Ethanol-Ether) | DMSO-d₆ 1.14-1.46(3H, m), 1.63-1.71(1H, m), 1.76-1.95(8H, m), 2.36(3H, s), 2.78-2.83(2H, m), 2.98(3H, s), 3.43-3.50(2H, m), 3.91(3H, s), 4.84-4.93(1H, m), 6.31(1H, brs), 6.40-6.47(3H, m), 7.74(1H, d, J=8.8Hz) | 439 |
| 112 | 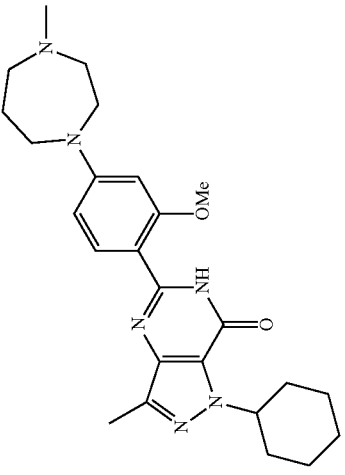 | Faint brown foam | CDCl₃ 1.24-2.10(12H, m), 2.40(3H, s), 2.54(3H, s), 2.55-2.59(2H, m), 2.72-2.76(2H, m), 3.54-3.59(2H, m), 3.61-3.66(2H, m), 4.02(3H, s), 4.95-5.04(1H, m), 6.21(1H, d, J=2.2Hz), 6.46(1H, dd, J=2.2 and 9.0Hz), 8.32(1H, d, J=9.0Hz), 10.84(1H, brs) | 451 |

| Ex. No. | Chemical Structure | Properties Melting Point(° C.) (Solvent for Recrystallization) | ¹H—NMR | MS(FAB) (M + 1)⁺ |
|---|---|---|---|---|
| 113 | 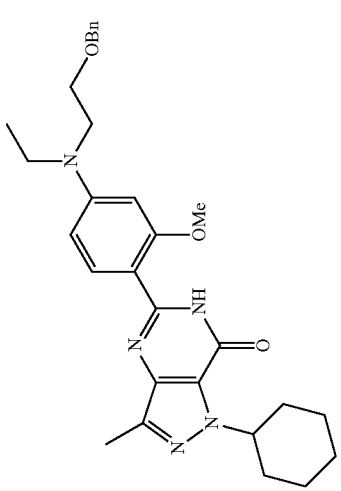 | Faint yellow viscous solid | CDCl₃ 1.21(3H, t, J=7.1Hz), 1.23-1.60(3H, m), 1.68-1.77(1H, m), 1.85-2.08(6H, m), 2.54(3H, s), 3.49(2H, q, J=7.1Hz), 3.57-3.62(2H, m), 3.66-3.71(2H, m), 3.93(3H, s), 4.54(2H, s), 4.95-5.04(1H, m), 6.26(1H, d, J=2.2Hz), 6.44(1H, dd, J=2.2 and 9.1Hz), 7.26-7.38(5H, m), 8.30(1H, d, J=9.1Hz), 10.84(1H, brs) | 516 |
| 114 | 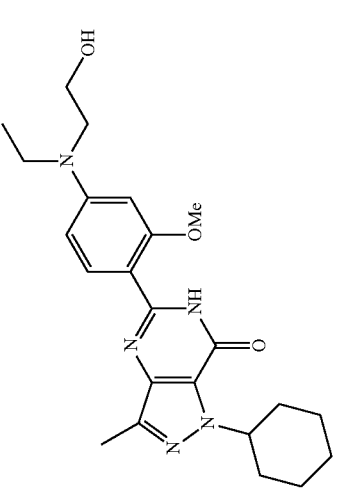 | Colorless viscous solid | CDCl₃ 1.21(3H, t, J=7.1Hz), 1.23-1.36(1H, m), 1.43-1.56(2H, m), 1.68-1.77(1H, m), 1.85-2.09(6H, m), 2.54(3H, s), 3.49(2H, q, J=7.1Hz), 3.52-3.57(2H, m), 3.83-3.88(2H, m), 4.00(3H, s), 4.95-5.05(1H, m), 6.30(1H, brs), 6.47(1H, d, J=9.0Hz), 8.30(1H, d, J=9.0Hz), 10.83(1H, brs) | 426 |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 115 | (structure with N-ethyl-N-(2-hydroxyethyl)amino phenyl, OMe, pyrazolopyrimidinone, cyclohexyl; HCl salt) | Yellow solid 110-114 (Ether) | DMSO-d₆ 1.13(3H, t, J=7.0Hz), 1.16-1.29(1H, m), 1.32-1.47(2H, m), 1.63-1.71(1H, m), 1.80-1.97(6H, m), 2.39(3H, s), 3.42-3.51(4H, m), 3.55-3.61(2H, m), 3.90(3H, s), 4.85-4.95(1H, m), 6.35(1H, brs), 6.42-6.48(1H, m), 7.72(1H, d, J=8.9Hz) | 426 |
| 116 | (structure with Br, OEt phenyl, pyrazolopyrimidinone, cyclohexyl) | Pale yellow crystal 198-200 | CDCl₃ 1.22-1.38(1H, m), 1.42-1.63(2H, m), 1.62(3H, t, J=7.1Hz), 1.86-2.10(6H, m), 2.55(3H, s), 4.28(2H, q, J=7.1Hz), 4.97-5.07(1H, m), 7.19(1H, brs), 7.25-7.31(1H, m), 8.37(1H, d, J=8.5Hz), 10.95(1H, brs) | 431 |
| 117 | (structure with NH-(2-methoxyethyl)amino phenyl, OEt, pyrazolopyrimidinone, cyclohexyl) | Faint yellow solid 184.5-186 | CDCl₃ 1.33-1.50(3H, m), 1.62(3H, t, J=7.0Hz), 1.68-1.86(5H, m), 1.96-2.05(2H, m), 3.00-3.10(1H, m), 3.34-3.40(2H, m), 3.42(3H, s), 3.61-3.66(2H, m), 3.94(3H, s), 4.23(2H, J=7.0Hz), 4.52-4.57(1H, m), 6.17(1H, d, J=1.9Hz), 6.36(1H, dd, J=1.9 and 8.9Hz), 8.37(1H, d, J=8.9Hz), 11.02(1H, brs) | 426 |

| Ex. No. | Chemical Structure | Properties Melting Point(° C.) (Solvent for Recrystallization) | ¹H—NMR | MS(FAB) (M + 1)⁺ |
|---|---|---|---|---|
| 118 | (structure with N-formyl-N-methyl, OEt, pyrazolopyrimidinone, cyclohexyl, methyl) | Colorless solid 120.5-122.5 (Ether) | CDCl₃ 1.22-1.38(1H, m), 1.42-1.58(2H, m), 1.69-2.10(1H, m), 2.55(3H, s), 2.84(1.5H, s), 2.87(1.5H, s), 2.92-3.06(2H, m), 3.47-3.61(0.5H, m), 4.02-4.03(3H, m), 4.45-4.57(0.5H, m), 4.95-5.06(1H, m), 6.45-6.5(1H, m), 6.65-6.70(1H, m), 8.08(0.5H, s), 8.22(0.5H, s), 8.35-8.40(1H, m), 10.78-10.82(1H, m) | 479 |
| 119 | (structure with N-acetyl-N-methylpiperidine, OMe, pyrazolopyrimidinone, cyclohexyl, methyl) | Colorless crystal 204-206 (Ethyl acetate) | CDCl₃ 1.25-1.38(1H, m), 1.43-1.59(2H, m), 1.69-2.10(11H, m), 2.12(1H, s), 2.19(0.9H, s), 2.54(3H, s), 2.84(0.9H, s), 2.87(2.1H, s), 2.91-3.05(2H, m), 3.70-3.80(0.3H, m), 3.89-4.00(2H, m), 4.03(3H, s), 4.69-4.79(0.7H, m), 4.95-5.05(1H, m), 6.45-6.50(1H, m), 4936.65-6.70(1H, m), 8.32-8.39(1H, m), 10.77-10.82(1H, m) | 493 |

| Ex. No. | Chemical Structure | Properties Melting Point(° C.) (Solvent for Recrystallization) | ¹H—NMR | MS(FAB) (M + 1)⁺ |
|---|---|---|---|---|
| 120 | 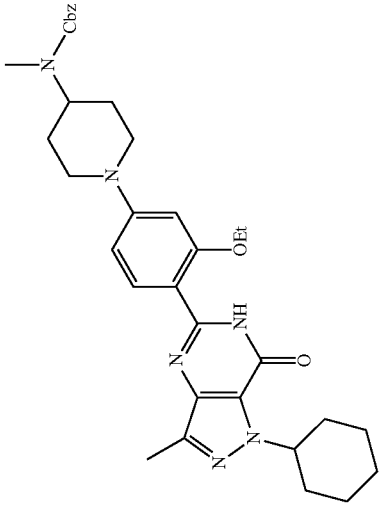 | Faint yellow solid 172-173 | CDCl₃ 1.23-1.56(3H, m), 1.62(3H, t, J=7.0Hz), 1.69-2.08(11H, m), 2.55(3H, s), 2.83(3H, brs), 2.86-3.01(2H, m), 3.87-3.96(2H, m), 4.25(2H, q, J=7.0Hz), 4.23-4.35(1H, m), 4.95-5.05(1H, m), 5.17(2H, s), 6.44(1H, d, J=2.0Hz), 6.65(1H, dd, J=2.0 and 9.0Hz), 7.29-7.40(5H, m), 8.36(1H, d, J9.0Hz), 11.12(1H, brs) | 599 |
| 121 | 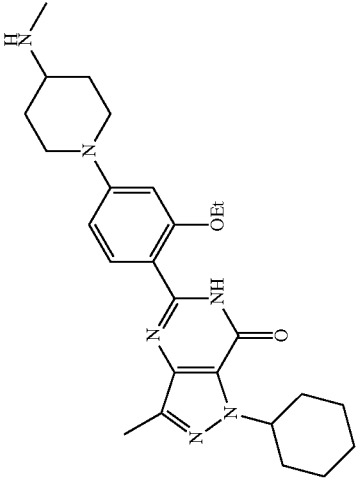 | Faint yellow solid 149-152 (Ether) | CDCl₃ 1.22-1.65(5H, m), 1.61(3H, t, J=7.0Hz), 1.69-1.77(1H, m), 1.87-2.10(8H, m), 2.49(3H, s), 2.55(3H, s), 2.55-2.65(1H, m), 2.88-2.99(2H, m), 3.75-3.85(2H, m), 4.25(2H, q, J=7.0Hz), 4.95-5.05(1H, m), 6.45(1H, d, J=2.0Hz), 6.65(1H, dd, J=2.0 and 9.0Hz), 8.36(1H, d, J=9.0Hz), 11.15(1H, brs) | 465 |

| Ex. No. | Chemical Structure | Properties Melting Point(° C.) (Solvent for Recrystallization) | 1H—NMR | MS(FAB) (M + 1)+ |
|---|---|---|---|---|
| 122 | (structure: 5-[4-(1-methyl-4-hydroxypiperidin-4-yl)-2-methoxyphenyl]-1-cyclohexyl-3-methyl-1H-pyrazolo[3,4-d]pyrimidin-7(6H)-one) | Colorless solid 108-112 | CDCl₃ 1.23-2.50(21H, m), 4.05(3H, s), 4.98-5.07(1H, m), 7.22-7.30(2H, m), 8.42(1H, d, J=8.3Hz), 10.79(1H, brs) | 452 |
| 123 | (structure: 5-[4-(1-methyl-1,2,3,6-tetrahydropyridin-4-yl)-2-methoxyphenyl]-1-cyclohexyl-3-methyl-1H-pyrazolo[3,4-d]pyrimidin-7(6H)-one) | Faint yellow solid 214-217 | CDCl₃ 1.23-1.38(1H, m), 1.44-1.63(2H, m), 1.69-1.76(1H, m), 1.85-2.10(6H, m), 2.44(3H, s), 2.56(3H, s), 2.59-2.72(4H, m), 3.14-3.19(2H, m), 4.06(3H, s), 4.96-5.06(1H, m), 6.20(1H, brs), 7.03-7.06(1H, m), 7.17(1H, dd, J=1.3 and 8.4Hz), 8.41(1H, d, J=8.4Hz), 10.84(1H, brs) | 434 |

| Ex. No. | Chemical Structure | Properties Melting Point(° C.) (Solvent for Recrystallization) | ¹H—NMR | MS(FAB) (M + 1)⁺ |
|---|---|---|---|---|
| 124 | 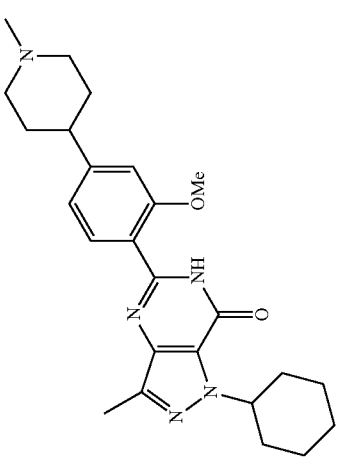 | Colorless solid 214.5-216 | CDCl₃ 1.24-1.39(1H, m), 1.44-1.64(2H, m), 1.69-1.76(1H, m), 1.80-2.13(12H, m), 2.35(3H, s), 2.52-2.62(4H, m), 2.95-3.04(2H, m), 4.03(3H, s), 4.98-5.08(1H, m), 6.91(1H, brs), 7.02(1H, d, J=8.1Hz), 8.37(1H, d, J=8.1Hz), 10.79(1H, brs) | 436 |
| 125 | 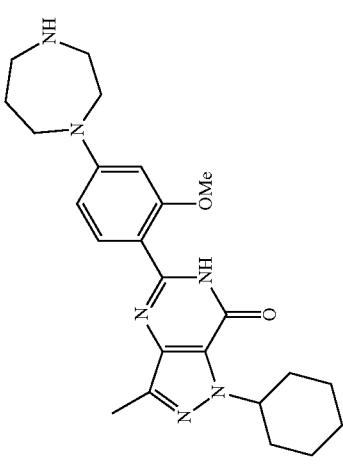 | Faint yellow foamy solid | CDCl₃ 1.23-1.39(1H, m), 1.42-1.58(2H, m), 1.70-2.09(9H, m), 2.54(3H, s), 2.82-2.88(2H, m), 3.04-3.09(2H, m), 3.58-3.68(4H, m), 4.01(3H, s), 4.96-5.06(1H, m), 6.22(1H, d, J=2.2Hz), 6.46(1H, J=2.2 and 8.9Hz), 8.31(1H, d, J=8.9Hz), 10.83(1H, brs) | 437 |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 126 | (structure) | Colorless solid 185.5-187 | CDCl₃ 1.23-1.58(3H, m), 1.68-1.77(1H, m), 1.85-2.12(11H, m), 2.54(3H, s), 3.38-3.51(2H, m), 3.61-3.82(6H, m), 4.02(3H, s), 4.95-5.06(1H, m), 6.24(1H, brs), 6.45-6.51(1H, m), 8.31-8.37(1H m), 10.78(1H, brs) | 478 |
| 127 | (structure) | Pale yellow crystal 138-139.5 (Ethyl acetate) | CDCl₃ 1.09(3H, t, J=7.1Hz), 1.22-1.38(1H, m), 1.44-1.60(2H, m), 1.68-1.75(1H, m), 1.84-2.08(8H, m), 2.54(3H, s), 2.55-2.65(4H, m), 2.75-2.80(2H, m), 3.58(2H, t, J=6.3Hz), 3.61-3.66(2H, m), 4.02(3H, s), 4.94-5.04(1H, m), 6.21(1H, d, J=2.2Hz), 6.46(1H, dd, J=2.2 and 8.9Hz), 8.32(1H, d, J=8.9Hz), 10.84(1H, brs) | 465 |

| Ex. No. | Chemical Structure | Properties Melting Point(° C.) (Solvent for Recrystallization) | ¹H—NMR | MS(FAB) (M + 1)⁺ |
|---|---|---|---|---|
| 128 | (structure with N-Cbz piperidine, F, OMe, cyclohexyl pyrazolopyrimidinone) | Pale yellow foam | CDCl₃ 1.25-1.59(3H, m), 1.69-2.08(11H, m), 2.55(3H, s), 2.80-2.94(5H, m), 3.65-3.72(2H, m), 4.02(3H, s), 4.19-4.33(1H, m), 4.86-5.06(1H, m), 5.17(2H, s), 6.50(1H, d, J=7.0Hz), 7.30-7.41(5H, m), 8.17(1H, d, J=14.2Hz), 10.86(1H, brs) | 603 |
| 129 | (structure with NH-Me piperidine, F, OMe, cyclohexyl pyrazolopyrimidinone) | Colorless crystal 178-179 | CDCl₃ 1.23-1.38(1H, m), 1.43-1.63(3H, m), 1.68-1.77(1H, m), 1.88-2.09(9H, m), 2.49(3H, s), 2.55(3H, s), 2.54-2.63(1H, m), 2.83-2.92(2H, m), 3.58-3.66(2H, m), 4.02(3H, s), 4.95-5.06(1H, m), 6.51(1H, d, J=7.1Hz), 8.16(1H, d, J=14.3Hz), 10.87(1H, brs) | 469 |

-continued

| Ex. No. | Chemical Structure | Properties Melting Point(° C.) (Solvent for Recrystallization) | $^1$H—NMR | MS(FAB) (M + 1)$^+$ |
|---|---|---|---|---|
| 130 | 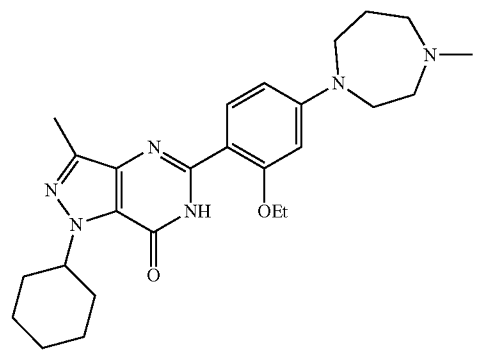 | Faint yellow crystal 146-147 (Ether) | CDCl$_3$ 1.23-1.38(1H, m), 1.42-1.60(2H, m), 1.62(3H, t, J=7.0Hz), 1.66-1.76(1H, m), 1.85-2.11(8H, m), 2.40(3H, s), 2.54(3H, s), 2.55-2.60(2H, m), 2.70-2.75(2H, m), 3.55(2H, t, J=6.3Hz), 3.60-3.65(2H, m), 4.23(2H, q, J=7.0Hz), 4.95-5.05(1H, m), 6.20(1H, d, J=2.2Hz), 6.45(1H, dd, J=2.2 and 9.0Hz), 8.34(1H, d, J=9.0Hz), 11.15(1H, brs) | 465 |
| 131 | 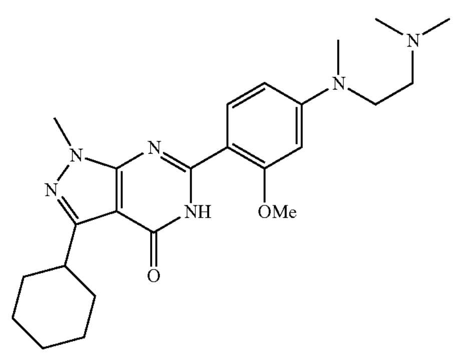 | Light yellow solid 165-166 (Ethyl acetate-Hexane) | CDCl$_3$ 1.28-1.53(3H, m), 1.68-1.90(5H, m), 1.99-2.08(2H, m), 2.31(6H, s), 2.51(2H, t, J=7.5Hz), 3.01-3.13(4H, m), 3.54(2H, t, J=7.5Hz), 3.94(3H, s), 3.95(3H, s), 4.03(3H, s), 6.21(1H, d, J=2.1Hz), 6.45(1H, dd, J=2.1 and 9.1Hz), 8.38(1H, d, J=9.1Hz), 10.74(1H, brs) | 439 |

| Ex. No. | Chemical Structure | Properties Melting Point (° C.) (Solvent for Recrystallization) | ¹H—NMR | MS(FAB) (M + 1)⁺ |
|---|---|---|---|---|
| 132 | 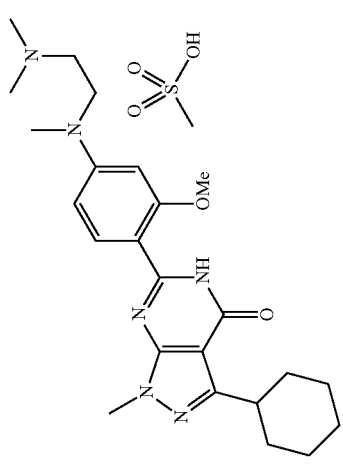 | Colorless solid 207-209 | CDCl₃ 1.29-1.53(3H, m), 1.68-1.90(5H, m), 1.96-2.08(2H, m), 2.85(3H, s), 2.93(6H, s), 3.01-3.18(1H, m), 3.14(3H, s), 3.22(2H, t, J=7.4Hz), 3.94(3H, s), 4.02(2H, t, J=7.4Hz), 4.09(3H, s), 6.38(1H, d, J=2.1Hz), 6.47(1H, dd, J=2.1 and 9.0Hz), 8.42(1H, d, J=9.0Hz), 10.72(1H, brs) | 439 (free) |
| 133 | 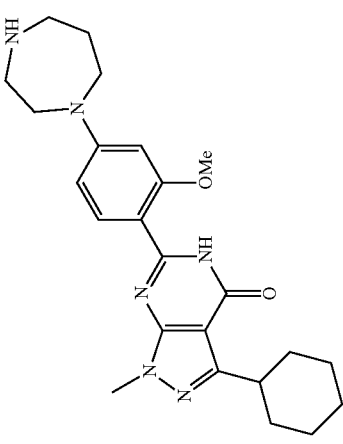 | Light green solid 192.5-193.5 (Ethyl acetate-Hexane) | CDCl₃ 1.30-1.53(3H, m), 1.65-2.08(9H, m), 2.82-2.92(2H, m), 3.01-3.15(3H, m), 3.59-3.73(4H, m), 3.94(3H, s), 4.02(3H, s), 6.22(1H, d, J=2.2Hz), 6.47(1H, dd, J=2.2 and 9.1Hz), 8.37(1H, d, J=9.1Hz), 10.73(1H, brs) | 437 |

| Ex. No. | Chemical Structure | Properties Melting Point(° C.) (Solvent for Recrystallization) | 1H—NMR | MS(FAB) (M + 1)+ |
|---|---|---|---|---|
| 134 | (structure: pyrazolo-pyrimidinone with cyclohexyl, N-methyl pyrazole, phenyl-OMe, homopiperazine-NH; methanesulfonic acid salt) | Colorless solid 255-257.5 | CDCl₃ 1.29-1.53(3H, m), 1.68-1.90(5H, m), 1.97-2.08(2H, m), 2.30-2.41(2H, m), 2.71(3H, s), 3.01-3.13(1H, m), 3.21-3.31(2H, m), 3.39-3.49(2H, m), 3.66-3.75(2H, m), 3.85-3.98(2H, m), 3.95(3H, s), 4.04(3H, s), 6.23(1H, d, J=1.3Hz), 6.46(1H, dd, J=1.3 and 9.0Hz), 8.41(1H, d, J=9.0Hz), 10.68(1H, brs) | 437 (free) |
| 135 | (structure: pyrazolo-pyrimidinone with cyclohexyl, N-methyl pyrazole, phenyl-OMe, N-methyl homopiperazine) | Colorless solid 154.5-157 (Ethyl acetate-Hexane) | CDCl₃ 1.29-1.52(3H, m), 1.70-1.90(5H, m), 1.96-2.11(4H, m), 2.40(3H, s), 2.53-2.62(2H, m), 2.70-2.80(2H, m), 3.00-3.13(1H, m), 3.52-3.71(4H, m), 3.94(3H, s), 4.02(3H, s), 6.20(1H, d, J=2.1Hz), 6.46(1H, dd, J=2.1Hz and 9.1Hz), 8.37(1H, d, J=9.1Hz), 10.74(1H, brs) | 451 |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 136 | 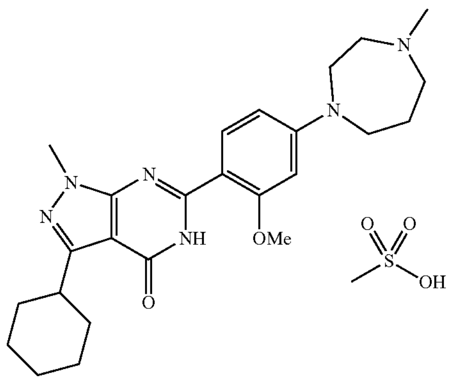 | Light yellow solid 146-150 | CDCl₃ 1.30-1.51(3H, m), 1.61-1.90(5H, m), 1.99-2.10(2H, m), 2.30-2.42(1H, m), 2.71-2.90(1H, m), 2.85(3H, s), 2.96(3H, d, J=4.7), 294-3.15(3H, m), 3.55-3.72(3H, m), 3.80-3.89(1H, m), 3.90-4.00(1H, m), 3.95(3H, s), 4.05-4.19(1H, m), 4.04(3H, s), 6.22(1H, d, J=2.0Hz), 6.45(1H, dd, J=2.0Hz and 9.0Hz), 8.43(1H, d, J=9.0Hz), 10.67(1H, brs), 11.56(1H, brm) | 451 (free) |
| 137 | 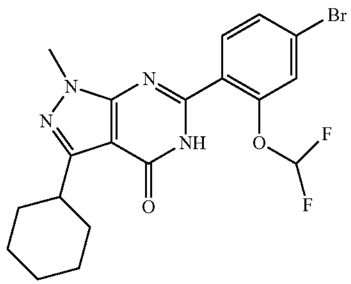 | Colorless solid 232-233 (Ethanol) | CDCl₃ 1.22-1.49(3H, m), 1.65-1.90(5H, m), 1.95-2.05(2H, m), 3.00-3.11(1H, m), 3.97(3H, s), 6.68(1H, t, J=71.8Hz), 7.46-7.51(1H, m), 7.57(1H, dd, J=1.7Hz and 8.5Hz), 8.06(1H, d, J=8.5Hz), 10.33(1H, brs) | 453 |

| Ex. No. | Chemical Structure | Properties Melting Point(° C.) (Solvent for Recrystallization) | ¹H—NMR | MS(FAB) (M + 1)⁺ |
|---|---|---|---|---|
| 138 | (4-methylpiperazinyl phenyl with OCHF₂, linked to pyrazolopyrimidinone with N-methyl and cyclohexyl) | Light yellow solid 262-263.5 (Ethanol) | CDCl₃ 1.28-1.51(3H, m), 1.69-1.90(5H, m), 1.96-2.09(2H, m), 2.37(3H, s), 2.51-2.63(4H, m), 3.00-3.13(1H, m), 3.32-3.44(4H, m), 3.95(3H, s), 6.62(1H, d, J=1.8Hz), 6.64(1H, t, J=72.5Hz), 6.85(1H, dd, J=1.8Hz and 9.0Hz), 8.20(1H, d, J=9.0Hz), 9.85(1H, brs) | 473 |
| 139 | (same as 138 with methanesulfonic acid salt) | Colorless solid 220-222 (Ethyl acetate-Ethanol) | DMSO-d₆ 1.17-1.44(3H, m), 1.59-1.83(5H, m), 1.87-1.97(2H, m), 2.31(3H, s), 2.87(3H, s), 2.90-3.01(1H, m), 3.02-3.25(4H, m), 3.39-3.63(2H, m), 3.82(3H, s), 3.91-4.13(2H, m), 6.80-6.86(1H, m), 6.97-7.02(1H, m), 7.22(1H, t, J=73.8Hz), 7.64(1H, d, J=8.7Hz), 9.70(1H, brs), 11.88(1H, brs) | 473 (free) |
| 140 | (ureido phenyl with OMe, linked to pyrazolopyrimidinone with N-methyl and cyclohexyl) | Yellow solid >300 (Ethanol) | DMSO-d₆ 1.17-1.43(3H, m), 1.59-1.82(5H, m), 1.88-1.97(2H, m), 2.88-3.00(1H, m), 3.84(3H, s), 3.87(3H, s), 6.03(2H, brs)7.00-7.08(1H, m), 7.43-7.49(1H, m), 7.81(1H, d, J=8.6Hz), 8.94(1H, brs), 11.35(1H, brs) | 397 |

| Ex. No. | Chemical Structure | Properties Melting Point(° C.) (Solvent for Recrystallization) | $^1$H—NMR | MS(FAB) (M + 1)$^+$ |
|---|---|---|---|---|
| 141 | 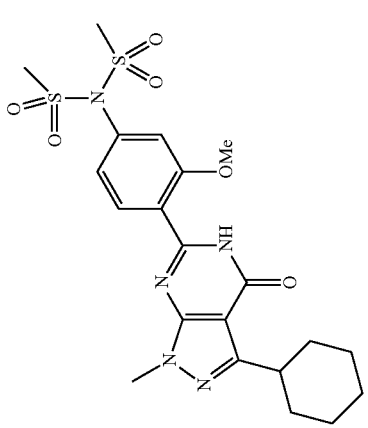 | Light yellow solid 268-270 | CDCl$_3$ 1.29-1.52(3H, m), 1.69-1.90(5H, m), 1.98-2.08(2H, m), 3.03-3.14(1H, m), 3.45(6H, s), 3.98(3H, s), 4.10(3H, s), 7.03(1H, d, J=1.8Hz), 7.17(1H, dd, J=1.8Hz and 8.5Hz), 8.58(1H, d, J=8.5Hz), 10.54(1H, brs) | 510 |
| 142 | 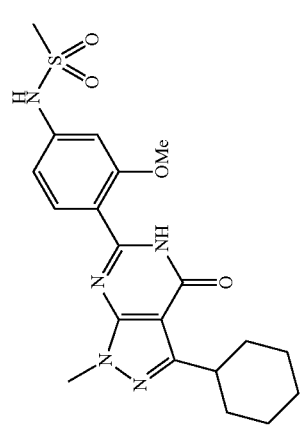 | Colorless solid 286.5-288 (Ethanol) | CDCl$_3$ 1.30-1.51(3H, m), 1.70-1.90(5H, m), 1.99-2.08(2H, m), 3.04-3.15(1H, m), 3.11(3H, s), 3.97(3H, s), 4.07(3H, s), 6.83-6.93(2H, m), 7.04(1H, d, J=1.9Hz), 8.50(1H, d, J=8.6Hz), 10.63(1H, brs) | 432 |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 143 | (structure: 1-methyl-3-cyclohexyl-pyrazolopyrimidinone with 2-methoxyphenyl bearing oxazolidinone) | Colorless solid 262-263.5 (Ethanol) | CDCl₃ 1.28-1.51(3H, m), 1.69-1.89(5H, m), 1.98-2.07(2H, m), 3.02-3.12(1H, m), 3.97(3H, s), 4.09(3H, s), 4.10-4.19(2H, m), 4.51-4.61(2H, m), 6.89(1H, dd, J=2.0Hz and 8.9Hz), 7.92(1H, d, J=2.0Hz), 8.53(1H, d, J=8.9Hz), 10.74(1H, brs) | 424 |
| 144 | (structure: with imidazolidinone) | Light yellow solid 266-269 (Ethyl acetate) | CDCl₃ 1.27-1.51(3H, m), 1.69-1.90(5H, m), 1.98-2.09(2H, m), 3.02-3.15(1H, m), 3.60-3.71(2H, m), 3.97(3H, s), 3.99-4.10(2H, m), 4.04(3H, s), 6.83(1H, dd, J=1.7Hz and 8.8Hz), 7.98(1H, d, J=1.7Hz), 8.46(1H, d, J=8.8Hz), 10.86(1H, brs) | 423 |
| 145 | (structure: with ethyl carbamate) | Light yellow solid 244-246 (Ethanol) | CDCl₃ 1.29-1.52(3H, m), 1.34(3H, t, J=7.1Hz), 1.70-1.90(5H, m), 1.98-2.08(2H, m), 3.02-3.13(1H, m), 3.96(3H, s), 4.07(3H, s), 4.26(2H, q, J=7.1Hz), 6.84(1H, dd, J=1.9Hz and 8.7Hz), 6.88(1H, brs), 7.64(1H, d, J=1.9Hz), 8.45(1H, d, J=8.7Hz), 10.74(1H, brs) | 426 |

| Ex. No. | Chemical Structure | Properties Melting Point(° C.) (Solvent for Recrystallization) | $^1$H—NMR | MS(FAB) (M + 1)$^+$ |
|---|---|---|---|---|
| 146 | 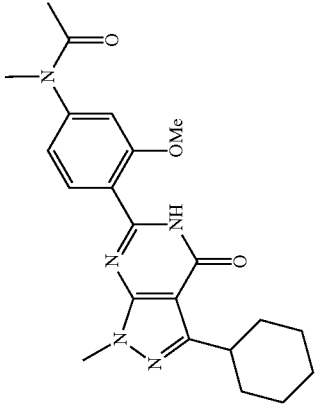 | Colorless solid 236-238 (Ethanol) | CDCl$_3$ 1.28-1.52(3H, m), 1.70-1.91(5H, m), 1.97-2.12(5H, m), 3.04-3.16(1H, m), 3.33(3H, s), 3.99(3H, s), 4.07(3H, s), 6.89-6.97(1H, m), 7.02(1H, dd, J=1.8Hz and 8.4Hz),8.55(1H, d, J=8.4Hz), 10.61(1H, brs) | 410 |
| 147 | 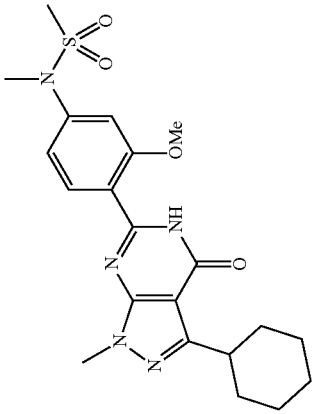 | Colorless solid 237.5-239 | CDCl$_3$ 1.28-1.51(3H, m), 1.70-1.90(5H, m), 1.98-2.07(2H, m), 2.89(3H, s), 3.03-3.13(1H, m), 3.40(3H, s), 3.98(3H, s), 4.08(3H, s), 7.08(1H, dd, J=1.9Hz and 8.6Hz), 7.24(1H, d, J=1.9Hz), 8.52(1H, d, J=8.6Hz), 10.64(1H, brs) | 446 |
| 148 | 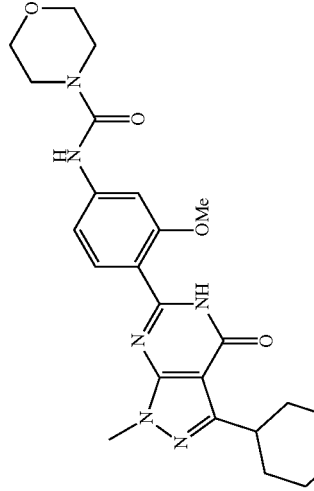 | Colorless solid 214-215 (Ethy acetate-Hexane) | CDCl$_3$ 1.28-1.51(3H, m), 1.69-1.91(5H, m), 1.98-2.09(2H, m), 3.02-3.13(1H, m), 3.49-3.59(4H, m), 3.74-3.83(4H, m), 3.96(3H, s), 4.05(3H, s) 6.65(1H, brs 6.80(1H, dd, J=1.8Hz and 8.7Hz), 7.73(1H, d, J=1.8Hz), 8.43(1H, d, J=8.7Hz), 10.76(1H, brs) | 467 |

| Ex. No. | Chemical Structure | Properties Melting Point(° C.) (Solvent for Recrystallization) | ¹H—NMR | MS(FAB) (M + 1)⁺ |
|---|---|---|---|---|
| 149 | (4-cyclohexyl-2-methyl-pyrazolo[3,4-d]pyrimidin-6-yl)-phenyl with OMe and piperidinyl-NHMe substituents | Colorless solid 172-173 (Ethyl acetate-Hexane) | CDCl₃ 1.28-1.60(5H, m), 1.69-1.90(5H, m), 1.97-2.09(4H, m), 2.48(3H, s), 2.58-2.68(1H, m), 2.93-3.13(3H, m), 3.80-3.89(2H, m), 3.94(3H, s), 4.02(3H, s), 6.43(1H, d, J=2.1Hz), 6.64(1H, dd, J=2.1Hz and 9.1Hz), 8.38(1H, d, J=9.1Hz), 10.74(1H, brs) | 451 |
| 150 | same structure · MeSO₃H | Colorless solid 251-254 (Ethanol) | DMSO-d₆ 1.18-1.42(3H, m), 1.48-1.83(7H, m), 1.88-1.97(2H, m), 2.01-2.11(2H, m), 2.31(3H, s), 2.60(3H, s), 2.86-2.99(3H, m), 3.20-3.33(1H, m), 3.83(3H, s), 3.96(3H, s), 4.02-4.11(2H, m), 6.64(1H, d, J=1.6Hz), 6.71(1H, dd, J=1.6Hz and 8.9Hz), 7.94(1H, d, J=8.9Hz), 8.43(2H, brs), 11.15(1H, brs) | 451 (free) |

| Ex. No. | Chemical Structure | Properties Melting Point(° C.) (Solvent for Recrystallization) | $^1$H—NMR | MS(FAB) (M + 1)$^+$ |
|---|---|---|---|---|
| 151 | 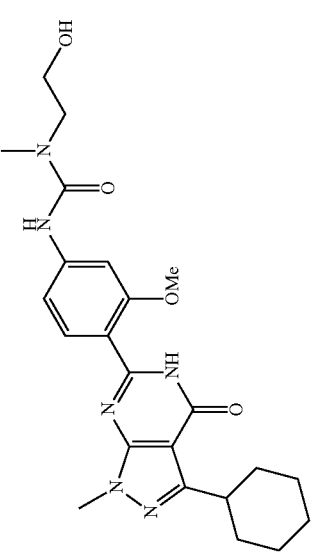 | Colorless solid 119-202 | CDCl$_3$ 1.28-1.51(3H, m), 1.69-1.90(5H, m), 1.97-2.09(2H, m), 3.02(3H, s), 3.03-3.13(1H, m), 3.44-3.58(3H, m), 3.88-3.98(2H, m), 3.94(3H, s), 3.99(3H, s), 6.69(1H, dd, J=1.7Hz and 8.7Hz), 7.60(1H, d, J=1.7Hz), 8.31(1H, d, J=8.7Hz), 8.38(1H, brs), 10.78(1H, brs) | 455 |
| 152 | 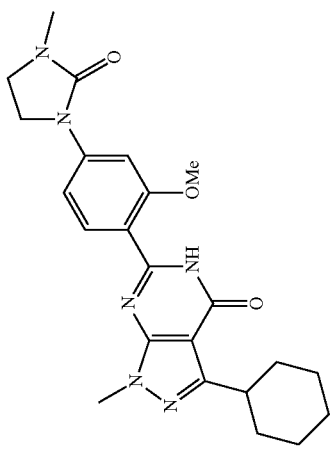 | Colorless solid 238-239.5 (Ethanol) | CDCl$_3$ 1.28-1.51(3H, m), 1.69-1.89(5H, m), 1.98-2.08(2H, m), 2.94(3H, s), 3.02-3.14(1H, m), 3.50-3.60(2H, m), 3.83-3.92(2H, m), 3.96(3H, s), 407(3H, s 6.79(1H, dd, J=2.0Hz and 8.8Hz), 8.09(1H, d, J=2.0Hz), 8.48(1H, d, J=8.8Hz), 10.79(1H, brs) | 437 |

-continued

| Ex. No. | Chemical Structure | Properties Melting Point(° C.) (Solvent for Recrystallization) | 1H—NMR | MS(FAB) (M + 1)+ |
|---|---|---|---|---|
| 153 | 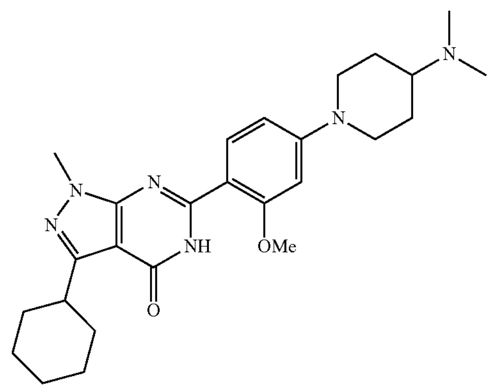 | Colorless solid 173-174.5 (Ethylacetate-Hexane) | CDCl3 1.32-1.52(3H, m), 1.57-1.67(2H, m), 1.70-1.88(5H, m), 1.91-2.08(4H, m), 2.29-2.42(1H, m), 2.32(6H, s), 2.85-2.98(2H, m), 3.01-3.12(1H, m), 3.87-3.99(2H, m), 3.95(3H, s), 4.03(3H, s), 6.43(1H, d, J=2.0Hz), 6.54(1H, dd, J=2.0Hz and 9.0Hz), 8.38(1H, d, J=9.0Hz), 10.85(1H, brs) | 465 |
| 154 | 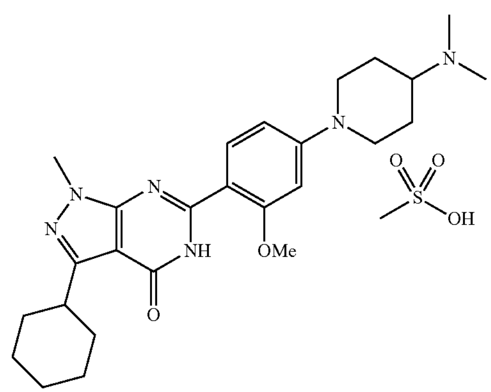 | Colorless solid 243-246 (Ethanol-Ethyl acetate) | DMSO-d6 1.17-1.42(3H, m), 1.58-1.82(7H, m), 1.87-1.97(2H, m), 2.02-2.14(2H, m), 2.30(3H, s), 2.78(6H, s), 2.81-2.99(3H, m), 3.32-3.46(1H, m), 3.83(3H, s), 3.96(3H, s), 4.08-4.19(2H, m), 6.61-6.66(1H, m), 6.70-6.79(1H, m), 7.90-7.99(1H, m), 9.41(1H, brs), 11.15(1H, brs) | 465 (free) |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 155 | 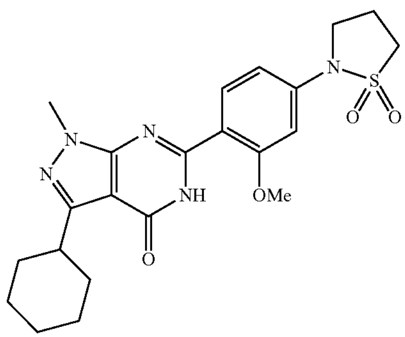 | Light yellow solid 287.5-289 (Ethyl acetate) | CDCl₃ 1.30-1.51(3H, m), 1.70-1.92(5H, m), 1.97-2.10(2H, m), 2.54-2.67(2H, m), 3.02-3.15(1H, m), 3.45(2H, t, d=7.4Hz), 3.87(2H, t, J=6.5Hz), 3.96(3H, s), 4.07(3H, s), 6.82(1H, dd, J=2.0Hz and 8.8Hz), 7.07(1H, d, J=2.0), 8.51(1H, d, J=8.8Hz), 10.68(1H, BRS) | 458 |
| 156 | 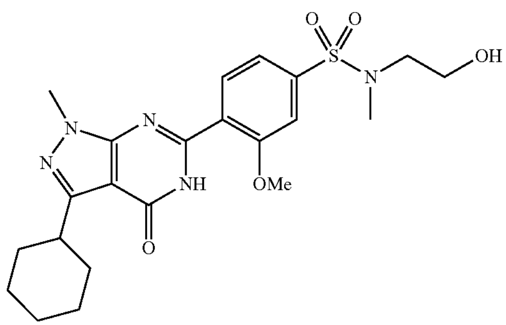 | Light yellow solid 199-203 (Ethyl acetate-Hexane) | CDCl₃ 1.31-1.52(3H, m), 1.70-1.91(5H, m), 1.95-2.10(3H, m), 2.92(3H, s), 3.04-3.18(1H, m), 3.27(2H, t, J=5.2Hz), 3.82(2H, q, J=5.2Hz), 4.00(3H, s), 4.14(3H, s), 7.50-7.62(2H, m), 8.62-8.70(1H, m), 10.58(1H, brs) | 476 |
| 157 | 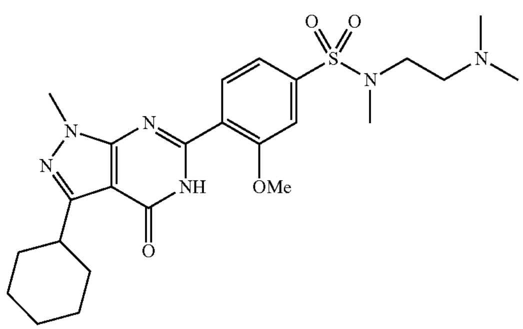 | Light yellow solid 182-183 (Ethyl acetate-Hexane) | CDCl₃ 1.30-1.52(3H, m), 1.70-1.90(5H, m), 1.99-2.08(2H, m), 2.26(6H, s), 2.51(2H, t, J=6.9Hz), 2.87(3H, s), 3.04-3.17(1H, m), 3.21(2H, t, J=6.8Hz), 4.00(3H, s), 4.13(3H, s), 7.49-7.60(2H, m), 8.60-8.69(1H, m), 10.59(1H, brs) | 503 |

| Ex. No. | Chemical Structure | Properties Melting Point(° C.) (Solvent for Recrystallization) | ¹H—NMR | MS(FAB) (M + 1)⁺ |
|---|---|---|---|---|
| 158 | 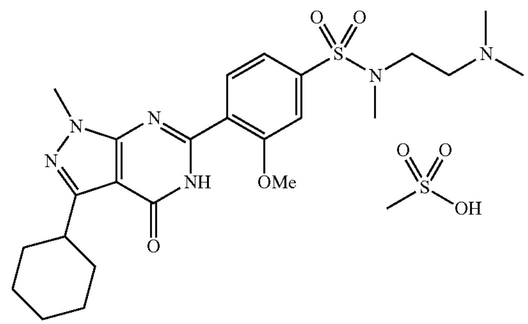 | Colorless solid 234-237.5 (Ethyl acetate-Ethanol) | DMSO-d₆ 1.19-1.43(3H, m), 1.60-1.82(5H, m), 1.88-1.98(2H, m), 2.30(3H, s), 2.78(3H, s), 2.87(6H, s), 2.90-3.02(1H, m), 3.30-3.45(4H, m), 3.84(3H, s), 3.95(3H, s), 7.41-7.46(1H, m), 7.52-7.59(1H, m), 7.85-7.90(1H, m), 9.36(1H, brs), 12.09(1H, brs) | 503 |
| 159 | 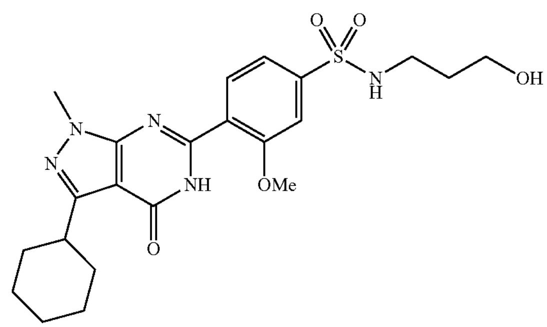 | Yellow solid 208-209.5 (Ethanol) | CDCl₃ 1.32-1.51(3H, m), 1.63-1.91(8H, m), 1.98-2.07(2H, m), 3.06-3.17(1H, m), 3.21(2H, q, J=6.0Hz), 3.79(2H, q, J=5.2Hz), 4.00(3H, s), 4.13(3H, s), 5.26(1H, t, J=6.0), 7.55-7.59(1H, m), 7.60-7.66(1H, m), 8.61-8.69(1H, m), 10.61(1H, brs) | 476 |
| 160 | 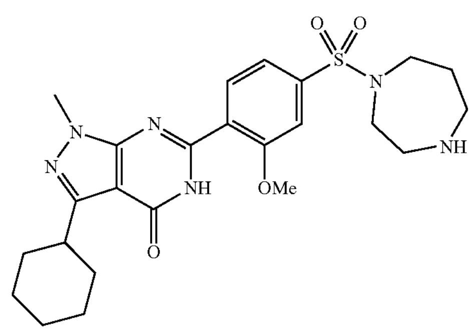 | Colorless solid 159-160.5 (Ethanol) | CDCl₃ 1.32-1.92(10H, m), 1.98-2.09(2H, m), 2.90-3.02(4H, m), 3.05-3.16(1H, m), 3.32-3.49(4H, m), 3.99(3H, s), 4.13(3H, s), 7.50-7.61(2H, m), 8.61-8.69(1H, m), 10.60(1H, brs) | 501 |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 161 | (structure: 1-methyl-3-cyclohexyl-pyrazolopyrimidinone with 2-OMe-phenyl bearing 4-(1,4-diazepan-1-ylsulfonyl); methanesulfonic acid) | Colorless solid 152-154 (Ethanol) | DMSO-d₈ 1.20-1.44(3H, m), 1.60-1.85(5H, m), 1.88-2.02(4H, m), 2.31(3H, s), 2.93-3.03(1H, m), 3.15-3.28(4H, m), 3.35-3.44(2H, m), 3.53-3.60(2H, m), 3.83(3H, s), 3.94(3H, s), 7.41-7.46(1H, m), 7.50-7.56(1H, m), 7.82-7.89(1H, m), 8.68(1H, brs), 12.07(1H, brs) | 501 (free) |
| 162 | (structure: 1-methyl-3-cyclohexyl-pyrazolopyrimidinone with 2-OMe-phenyl bearing 4-(4-methyl-1,4-diazepan-1-ylsulfonyl); methanesulfonic acid) | Colorless solid 192.5-194 (Ethanol) | CDCl₃ 1.29-1.51(3H, m), 1.70-1.92(7H, m), 1.96-2.07(2H, m), 2.36(3H, s), 2.59-2.71(4H, m), 3.05-3.16(1H, m), 3.39-3.50(4H, m), 3.99(3H, s), 4.13(3H, s), 7.47-7.57(2H, m), 8.60-8.68(1H, m), 10.58(1H, brs) | 515 |
| 163 | (structure: 1-methyl-3-cyclohexyl-pyrazolopyrimidinone with 2-OMe-phenyl bearing 4-(4-methyl-1,4-diazepan-1-ylsulfonyl); methanesulfonic acid) | Colorless solid 201-203.5 (Ethyl acetate-Isopropanol) | DMSO-d₈ 1.21-1.44(3H, m), 1.60-1.81(5H, m), 1.86-2.20(4H, m), 2.30(3H, s), 2.85(3H, s), 2.90-3.02(1H, m), 3.12-3.61(8H, m), 3.83(3H, s), 3.94(3H, s), 7.41-7.47(1H, m), 7.50-7.56(1H, m), 7.80-7.89(1H, m), 9.52(1H, brs), 12.06(1H, brs) | 515 |

-continued

| Ex. No. | Chemical Structure | Properties Melting Point(° C.) (Solvent for Recrystallization) | ¹H—NMR | MS(FAB) (M + 1)⁺ |
|---|---|---|---|---|
| 164 | (structure with 3-hydroxypyrrolidinyl sulfonyl, OMe, pyrazolopyrimidinone, cyclohexyl) | Colorless solid 246-247 (Ethanol) | CDCl₃ 1.28-1.51(3H, m), 1.69-2.09(10H, m), 3.02-3.13(1H, m), 3.29-3.56(4H, m), 3.97(3H, s), 4.13(3H, s), 4.41-4.49(1H, m), 7.53(1H, d, J=1.2Hz), 7.60(1H, dd, J=1.2Hz and 8.4Hz), 8.63(1H, d, J=8.4Hz), 10.59(1H, brs) | 488 |
| 165 | (structure with thiomorpholinyl sulfonyl, OMe, pyrazolopyrimidinone, cyclohexyl) | Colorless solid 226-227.5 (Ethanol) | CDCl₃ 1.29-1.52(3H, m), 1.69-1.90(5H, m), 1.98-2.09(2H, m), 2.70-2.80(4H, m), 3.04-3.15(1H, m), 3.39-3.50(4H, m), 4.00(3H, s), 4.14(3H, s), 7.43(1H, d, J=1.2Hz), 7.50(1H, dd, J=1.2Hz and 8.4Hz), 8.66(1H, d, J=8.4Hz), 10.56(1H, brs) | 504 |
| 166 | (structure with 1,4-dioxa-8-azaspiro[4.5]decyl sulfonyl, OMe, pyrazolopyrimidinone, cyclohexyl) | Colorless solid 270.5-272 (Ethanol-Ethyl acetate) | CDCl₃ 1.30-1.52(3H, m), 1.69-1.91(9H, m), 1.98-2.08(2H, m), 3.04-3.17(1H, m), 3.20-3.30(4H, m), 3.91(4H, s), 4.00(3H, s), 4.12(3H, s), 7.44(1H, d, J=1.0Hz), 7.52(1H, dd, J=1.0Hz and 8.2Hz), 8.64(1H, d, J=8.2Hz), 10.57(1H, brs) | 544 |

| Ex. No. | Chemical Structure | Properties Melting Point(° C.) (Solvent for Recrystallization) | ¹H—NMR | MS(FAB) (M + 1)⁺ |
|---|---|---|---|---|
| 167 | 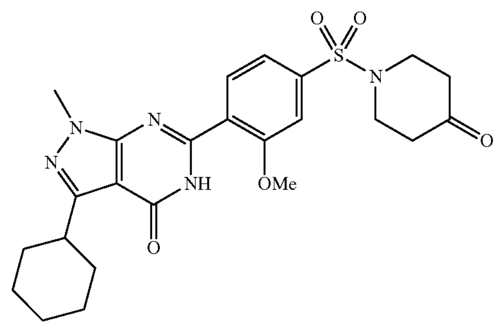 | Colorless solid 249-251 (Ethanol) | CDCl₃ 1.29-1.52(3H, m), 1.69-1.90(5H, m), 1.96-2.07(2H, m), 2.59(4H, t, J=6.1Hz), 3.05-3.18(1H, m), 3.50(4H, t, J=6.1Hz), 3.99(3H, s), 4.14(3H, s), 7.48(1H, d, J=1.2Hz), 7.55(1H, dd, J=1.2Hz and 8.3Hz), 8.67(1H, d, J=8.3Hz), 10.54(1H, brs) | 500 |
| 168 | 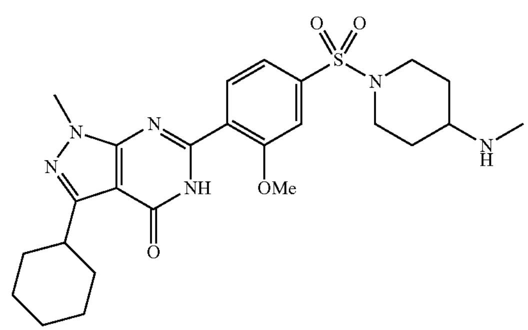 | Colorless solid 241.5-242.5 (Ethanol) | CDCl₃ 1.29-1.65(5H, m), 1.71-2.07(9H, m), 2.36-2.47(1H, m), 2.38(3H, s), 2.62-2.71(2H, m), 3.03-3.18(1H, m), 3.61-3.70(2H, m), 4.00(3H, s), 4.13(3H, s), 7.43-7.48(1H, m), 7.51-7.57(1H, m), 8.62-8.68(1H, m), 10.54(1H, brs) | 515 |

-continued
| Ex. No. | Chemical Structure | Properties Melting Point(° C.) (Solvent for Recrystallization) ¹H—NMR | MS(FAB) (M + 1)⁺ |
|---|---|---|---|
| 169 | 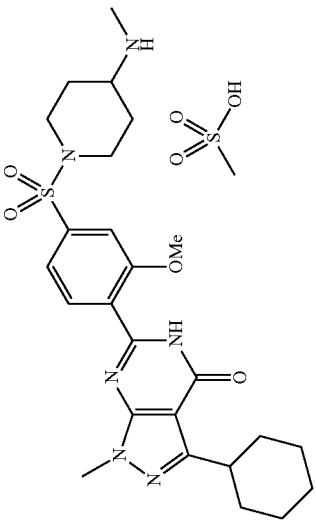 | Colorless solid 212-215 (Ethyl acetate-Ethanol) DMSO-d₆ 1.18-1.41(3H, m), 1.47-1.82(7H, m), 1.87-1.96(2H, m), 2.00-2.10(2H, m), 2.30(3H, s), 2.39-2.60(2H, m), 2.52(3H, s), 2.90-3.08(2H, m), 3.70-3.85(2H, m), 3.82(3H, s), 3.93(3H, s), 7.34-7.40(1H, m), 7.41-7.50(1H, m), 7.79-7.88(1H, m), 8.46(1H, brs), 12.06(1H, brs) | 515 |
| 170 | 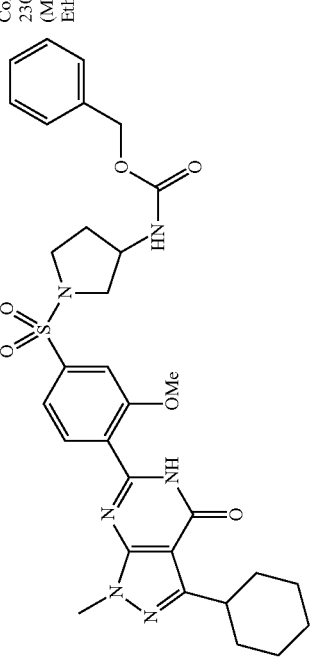 | Colorless solid 230-232 (Methanol-Ethanol) CDCl₃ 1.30-1.52(3H, m), 1.70-1.92(6H, m), 1.99-2.20(3H, m), 3.05-3.18(1H, m), 3.29-3.39(2H, m), 3.41-3.56(2H, m), 3.98(3H, s), 4.08-4.23(1H, m), 4.13(3H, s), 4.69(1H, brs), 4.97-5.14(2H, m), 7.21-7.39(5H, m), 7.46-7.61(2H, m), 8.60-8.70(1H, m), 10.56(1H, brs) | 621 |

| Ex. No. | Chemical Structure | Properties Melting Point(° C.) (Solvent for Recrystallization) | ¹H-NMR | MS(FAB) (M + 1)⁺ |
|---|---|---|---|---|
| 171 | 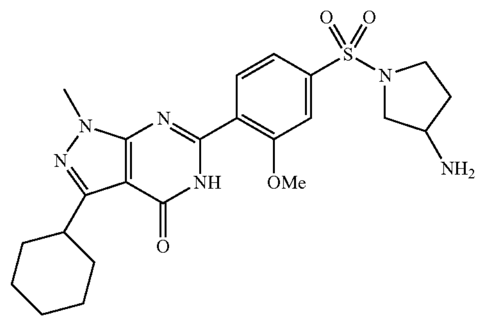 | Colorless solid 239-240 (Ethanol) | CDCl₃ 1.30-1.93(9H, m), 1.99-2.14(3H, m), 2.99-3.17(2H, m), 3.32-3.61(4H, m), 4.00(3H, s), 4.14(3H, s), 7.53-7.68(2H, m), 8.64-8.71(1H, m), 10.60(1H, brs) | 487 |
| 172 | 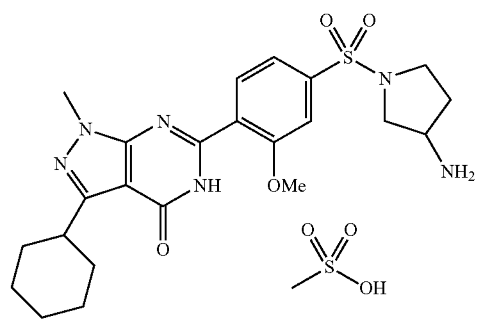 | Colorless solid 205-209 | DMSO-d₆ 1.17-1.47(3H, m), 1.60-2.00(8H, m), 2.02-2.19(1H, m), 2.30(3H, s), 2.90-3.01(1H, m), 3.18-3.51(4H, m), 3.70-3.80(1H, m), 3.82(3H, s), 3.94(3H, s), 7.39-7.48(1H, m), 7.50-7.60(1H, m), 7.81-7.91(1H, m), 8.00(3H, brs), 12.08(1H, brs) | 487 |
| 173 | 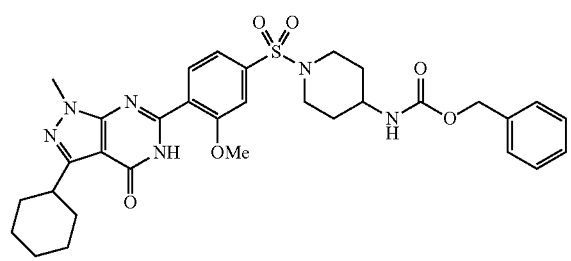 | Colorless solid 223-226 | CDCl₃ 1.30-1.63(5H, m), 1.71-1.91(5H, m), 1.99-2.11(4H, m), 2.56-2.69(2H, m), 3.05-3.18(1H, m), 3.48-3.60(1H, m), 3.68-3.81(2H, m), 4.00(3H, s), 4.13(3H, s), 4.64(1H, brs), 5.07(2H, s), 7.28-7.41(5H, m), 7.43(1H, d, J=1.0), 7.50(1H, dd, J=1.0Hz and 8.3Hz), 8.65(1H, d, J=8.3Hz), 10.57(1H, brs) | 635 |

| Ex. No. | Chemical Structure | Properties Melting Point(° C.) (Solvent for Recrystallization) | ¹H-NMR | MS(FAB) (M + 1)⁺ |
|---|---|---|---|---|
| 174 | 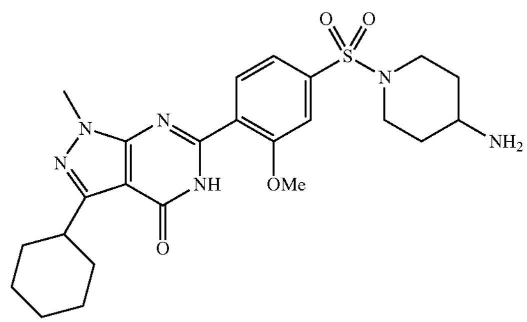 | Colorless solid 196-197.5 (Ethanol) | CDCl₃ 1.29-1.96(12H, m), 1.99-2.10(2H, m), 2.53-2.65(2H, m), 2.70-2.80(1H, m), 3.07-3.18(1H, m), 3.68-3.78(2H, m), 4.00(3H, s), 4.13(3H, s), 7.45(1H, d, J=1.4), 7.52(1H, dd, J=1.4Hz and 8.3Hz), 8.64(1H, d, J=8.3Hz), 10.58 (1H, brs) | 501 |
| 175 | 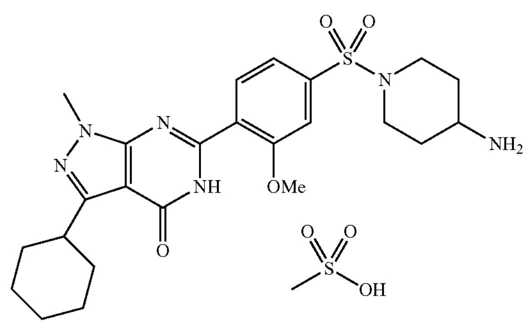 | Colorless solid 135-140 (Ethanol) | DMSO-d₆ 1.19-1.43(3H, m), 1.50-1.84(7H, m), 1.88-2.04(4H, m), 2.30(3H, s), 2.44-2.59(2H, m), 2.92-3.01(1H, m), 3.05-3.16(1H, m), 3.67-3.78(2H, m), 3.82(3H, s), 3.93(3H, s), 7.39-7.48(1H, m), 7.41-7.49(1H, m), 7.70-8.00(4H, m), 12.05(1H, brs) | 501 (free) |
| 176 | 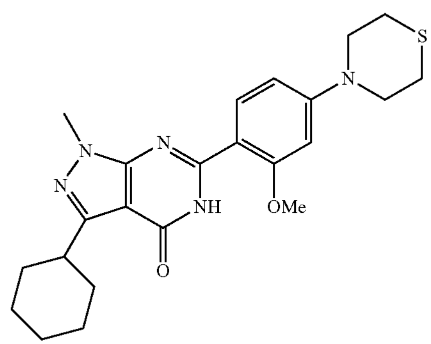 | Light yellow solid 132.5-135 (Ethanol) | CDCl₃ 1.29-1.52(3H, m), 1.69-1.90(5H, m), 1.97-2.08(2H, m), 2.70-2.79(4H, m), 3.01-3.12(1H, m), 3.73-3.83(4H, m), 3.95(3H, s), 4.03(3H, s), 6.38(1H, d, J=2.1), 6.59(1H, dd, J=2.1Hz and 8.9Hz), 8.40(1H, d, J=8.9Hz), 10.71 (1H, brs) | 440 |

| Ex. No. | Chemical Structure | Properties Melting Point(° C.) (Solvent for Recrystallization) | ¹H-NMR | MS(FAB) (M + 1)⁺ |
|---|---|---|---|---|
| 177 | (4-bromophenyl pyrazolopyrimidinone with cyclohexyl and N-methyl) | Colorless solid 267-269 (Ethanol) | CDCl₃ 1.21-1.35(1H, m), 1.39-1.51(2H, m), 1.70-1.93(5H, m), 2.00-2.10(2H, m), 3.05-3.17(1H, m), 4.01(3H, s), 7.65-7.72(2H, m), 8.11-8.19(2H, m), 12.03(1H, brs) | 387 |
| 178 | (4-(4-methylpiperazin-1-yl)phenyl pyrazolopyrimidinone with cyclohexyl and N-methyl) | Colorless solid 275-278 (Ethanol-Ethyl acetate) | CDCl₃ 1.27-1.52(3H, m), 1.69-1.92(5H, m), 2.01-2.11(2H, m), 2.37(3H, s), 2.58(4H, t, J=5.0Hz), 3.09-3.19(1H, m), 3.38(4H, t, J=5.0Hz), 3.98(3H, s), 6.95-7.04(2H, m), 8.11-8.19(2H, m), 11.00(1H, brs) | 407 |
| 179 | (same as 178, methanesulfonic acid salt) | Colorless solid >300 (Ethanol-Water) | DMSO-d₆ 1.17-1.41(3H, m), 1.54-1.80(5H, m), 1.86-1.96(2H, m), 2.32(3H, s), 2.86(3H, s), 2.89-2.99(1H, m), 3.01-3.27(4H, m), 3.40-3.63(2H, m), 3.85(3H, s), 3.92-4.20(2H, m), 7.07-7.17(2H, m), 8.08-8.18(2H, m), 9.68(1H, brs), 11.92(1H, brs) | 407 (free) |

| Ex. No. | Chemical Structure | Properties Melting Point(° C.) (Solvent for Recrystallization) | ¹H-NMR | MS(FAB) (M + 1)⁺ |
|---|---|---|---|---|
| 180 | (structure: 4-aminophenyl-substituted pyrazolopyrimidinone with cyclohexyl and N-methyl) | Colorless solid 229-330 (Ethanol) | CDCl₃ 1.20-1.44(3H, m), 1.51-1.65(2H, m), 1.69-1.77(1H, m), 1.80-1.89(2H, m), 1.91-2.01(2H, m), 2.65-2.77(1H, m), 3.73(3H, s), 4.16(2H, brs), 6.68-6.76(2H, m), 7.70-7.79(2H, m), 7.84(1H, brs) | 324 |
| 181 | (structure: 4-chlorosulfonylphenyl-substituted pyrazolopyrimidinone with cyclohexyl and N-methyl) | Yellow solid 182-187 | CDCl₃ 1.20-1.45(3H, m), 1.49-1.64(2H, m), 1.69-2.02(5H, m), 2.64-2.81(1H, m), 3.76(3H, s), 8.14-8.28(4H, m), 8.94(1H, brs) | 407 |
| 182 | (structure: 4-(4-hydroxypiperidin-1-ylsulfonyl)phenyl-substituted pyrazolopyrimidinone with cyclohexyl and N-methyl) | Light yellow solid 188-193 (Ethyl acetate-Hexane) | CDCl₃ 1.21-1.45(3H, m), 1.59-1.79(5H, m), 1.80-2.01(6H, m), 2.68-2.80(1H, m), 2.91-3.01(2H, m), 3.24-3.33(2H, m), 3.76(3H, s), 3.78-3.86(1H, m), 7.82-7.89(2H, m), 8.02-8.09(2H, m), 8.63(1H, brs) | 472 |

| Ex. No. | Chemical Structure | Properties Melting Point(° C.) (Solvent for Recrystallization) | ¹H-NMR | MS(FAB) (M + 1)⁺ |
|---|---|---|---|---|
| 183 | 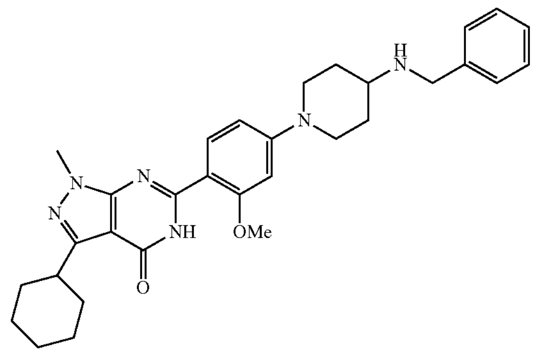 | Colorless solid 161-162 (Ethanol) | CDCl₃ 1.30-1.64(5H, m), 1.72-1.90(5H, m), 1.98-2.10(4H, m), 2.77-2.85(1H, m), 2.96-3.12(3H, m), 3.79-3.90(2H, m), 3.87(2H, s), 3.95(3H, s), 4.03(3H, s), 6.43(1H, d, J=2.1), 6.64(1H, dd, J=2.1Hz and 9.1Hz), 7.23-7.39(5H, m), 8.38(1H, d, J=9.1Hz), 10.74(1H, brs) | 527 |
| 184 | 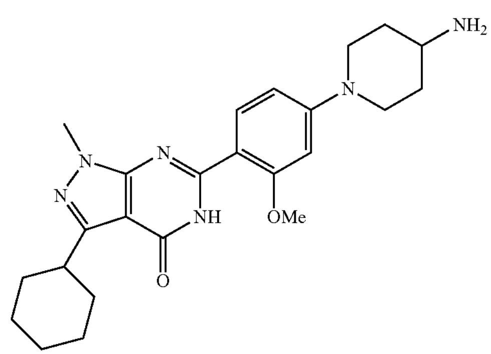 | Light yellow solid 152-155 (Ethyl acetate-Hexane) | CDCl₃ 1.28-1.65(5H, m), 1.69-1.89(5H, m), 1.90-2.08(4H, m), 2.89-3.12(4H, m), 3.79-3.89(2H, m), 3.95(3H, s), 4.03(3H, s), 6.43(1H, d, J=2.2), 6.65(1H, dd, J=2.2Hz and 9.0Hz), 8.38(1H, d, J=9.0Hz), 10.74(1H, brs) | 437 |

| Ex. No. | Chemical Structure | Properties Melting Point(° C.) (Solvent for Recrystallization) | $^1$H-NMR | MS(FAB) (M + 1)$^+$ |
|---|---|---|---|---|
| 185 | 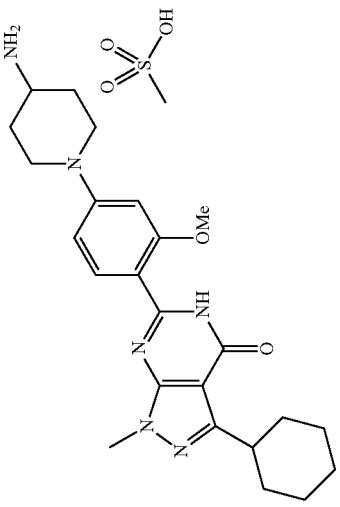 | Yellow brown solid 124-127 (Isopropanol-Ethyl acetate) | DMSO-d$_6$ 1.15-1.41(3H, m), 1.49-1.82(7H, m), 1.86-2.01(4H, m), 2.30(3H, s), 2.85-3.00(3H, m), 3.22-3.36(1H, m), 3.82(3H, s), 3.94(3H, s), 3.98-4.07(2H, m), 6.62(1H, d, J=1.8), 6.76(1H, dd, J=1.8Hz and 8.9Hz), 7.83(3H, brs), 7.93(1H, d, J=8.9Hz), 11.12(1H, brs) | 437 |
| 186 | 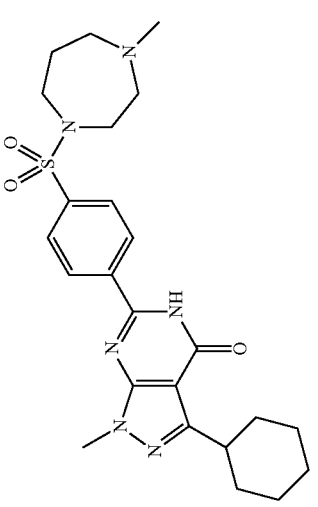 | Colorless solid 181.5-182.5 (Ethanol) | CDCl$_3$ 1.22-1.46(3H, m), 1.53-1.66(2H, m), 1.71-1.79(1H, m), 1.81-1.91(4H, m), 1.94-2.02(2H, m), 2.34(3H, s), 2.55-2.68(4H, m), 2.70-2.80(1H, m), 3.36-3.48(4H, m), 3.76(3H, s), 3.85-3.91(2H, m), 8.00-8.08(2H, m) | 485 |

| Ex. No. | Chemical Structure | Properties Melting Point(° C.) (Solvent for Recrystallization) | ¹H-NMR | MS(FAB) (M + 1)⁺ |
|---|---|---|---|---|
| 187 | 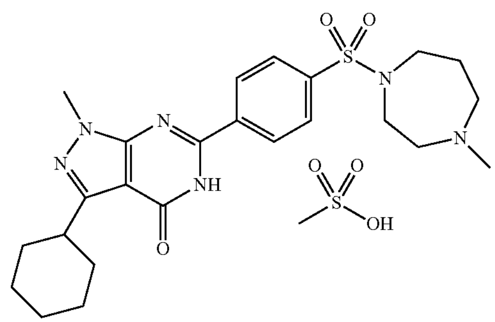 | Colorless solid 124-127 | DMSO-d₆ 1.13-1.28(1H, m), 1.29-1.42(2H, m), 1.45-1.59(2H, m), 1.64-1.72(1H, m), 1.73-1.81(2H, m), 1.85-2.01(3H, m), 2.06-2.18(1H, m), 2.31(3H, s), 2.62-2.73(1H, m), 2.83(3H, d, J=4.5Hz), 3.14-3.59(5H, m), 3.69(3H, s), 3.71-3.95(3H, m), 7.99-8.07(2H, m), 8.19-8.27(2H, m), 9.44-9.58(1H, brs), 11.10(1H, brs) | 485 (free) |
| 188 | 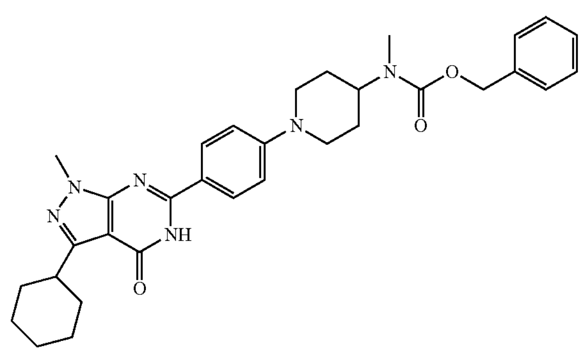 | Colorless solid 225.5-226.5 (Ethanol) | CDCl₃ 1.29-1.54(3H, m), 1.70-1.92(9H, m), 2.01-2.12(2H, m), 2.82(3H, s), 2.90-3.06(2H, m), 3.10-3.20(1H, m), 3.91-4.07(2H, m), 3.98(3H, s), 4.20-4.41(1H, m), 7.27(2H, m), 6.96-7.05(2H, m), 7.29-7.45(5H, m), 8.09-8.20(2H, m), 10.69-10.87(1H, brm) | 555 |

| Ex. No. | Chemical Structure | Properties Melting Point(° C.) (Solvent for Recrystallization) | ¹H-NMR | MS(FAB) (M + 1)⁺ |
|---|---|---|---|---|
| 189 | 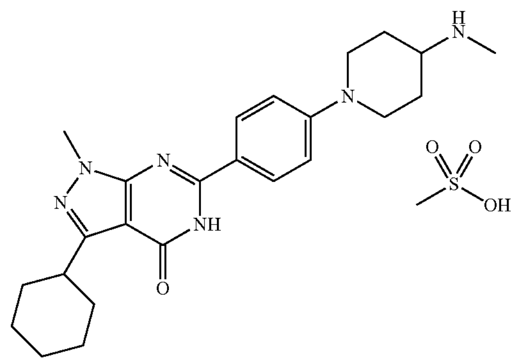 | Colorless solid >300 (Decomposition) (Ethanol-Water) | DMSO-d₆ 1.17-2.11(14H, m), 2.30(3H, s), 2.58(3H, s), 2.80-3.04(3H, m), 3.16-3.29(1H, m), 3.84(3H, m), 3.96-4.13(2H, m), 6.98-7.14(2H, m), 8.01-8.18(2H, m), 8.42(2H, brs), 11.85(1H, brs) | 421 |
| 190 | 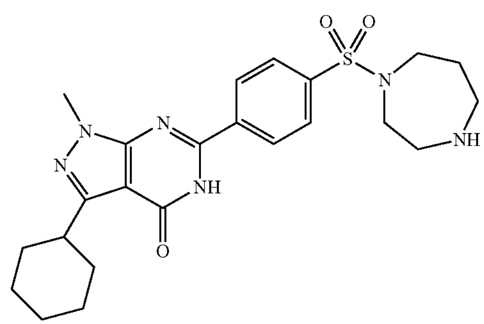 | Colorless solid 113-118 | CDCl₃ 1.21-1.45(3H, m), 1.52-1.67(2H, m), 1.70-1.79(1H, m), 1.81-1.90(4H, m), 1.92-2.04(2H, m), 2.68-2.80(1H, m), 2.89-3.04(4H, m), 3.32-3.46(4H, m), 3.76(3H, s), 7.88-7.94(2H, m), 8.02-8.10(2H, m) | 471 |

| Ex. No. | Chemical Structure | Properties Melting Point(° C.) (Solvent for Recrystallization) | ¹H-NMR | MS(FAB) (M + 1)⁺ |
|---|---|---|---|---|
| 191 | 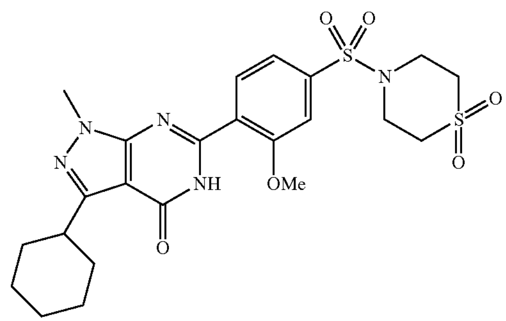 | Colorless solid 260-261 (Ethanol-Toluene) | CDCl₃ 1.28-1.51(3H, m), 1.69-1.90(5H, m), 1.97-2.07(2H, m), 3.04-3.34(5H, m), 3.69-3.82(4H, m), 4.00(3H, s), 4.15(3H, s), 7.45(1H, d, J=1.4Hz), 7.53(1H, dd, J=1.4Hz and 8.3Hz), 8.68(1H, d, J=8.3Hz), 10.52(1H, brs) | 536 |
| 192 | 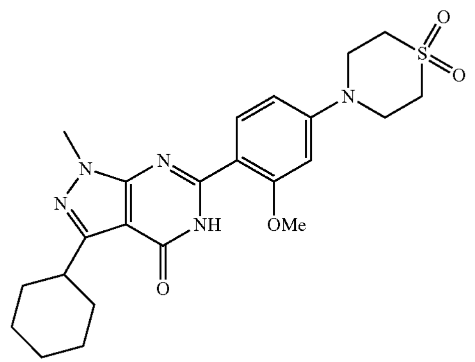 | Colorless solid >300 (Ethanol-Toluene) | CDCl₃ 1.28-1.52(3H, m), 1.70-1.91(5H, m), 1.97-2.09(2H, m), 3.01-3.22(5H, m), 3.96(3H, s), 3.98-4.03(4H, m), 4.05(3H, s), 6.46(1H, d, J=2.1Hz), 6.65(1H, dd, J=2.1Hz and 8.9Hz), 8.46(1H, d, J=8.9Hz), 10.62(1H, brs) | 472 |
| 193 | 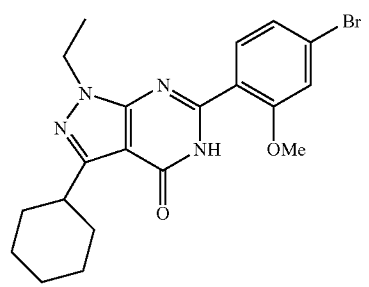 | Colorless solid 230-231 (Ethanol) | CDCl₃ 1.29-1.54(3H, m), 1.51(3H, t, J=7.3Hz), 1.69-1.89(5H, m), 1.96-2.05(2H, m), 3.01-3.12(1H, m), 4.06(3H, s), 4.39(2H, q, J=7.3Hz), 7.23(1H, d, J=1.5Hz), 7.30(1H, dd, J=1.5Hz and 8.5Hz), 8.36(1H, d, J=8.5Hz), 10.57(1H, brs) | 431 |

| Ex. No. | Chemical Structure | Properties Melting Point(° C.) (Solvent for Recrystallization) | ¹H-NMR | MS(FAB) (M + 1)⁺ |
|---|---|---|---|---|
| 194 | 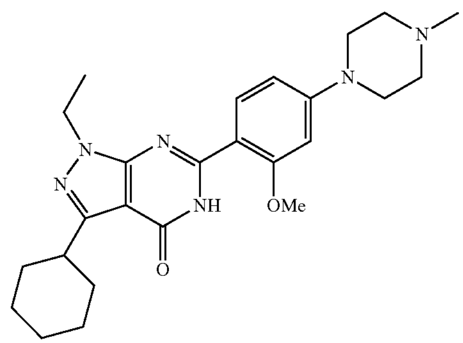 | Colorless solid 218-220 (Ethanol) | CDCl₃ 1.29-1.52(3H, m), 1.50(3H, t, J=7.2Hz), 1.69-1.89(5H, m), 1.96-2.05(2H, m), 2.37(3H, s), 2.54-2.62(4H, m), 3.01-3.12(1H, m), 3.33-3.42(4H, m), 4.03(3H, s), 4.37(2H, q, J=7.2Hz), 6.43(1H, d, J=2.2Hz), 6.65(1H, dd, J=2.2Hz and 8.9Hz), 8.39(1H, d, J=8.9Hz), 10.71(1H, brs) | 451 |
| 195 | 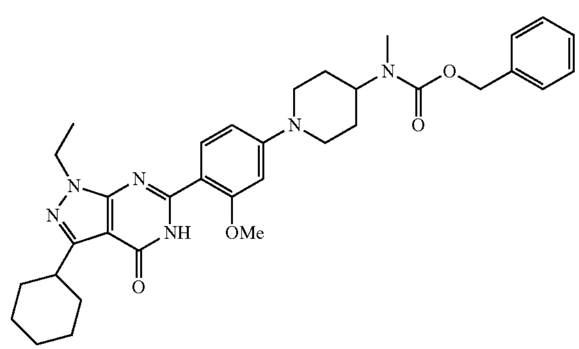 | Colorless solid 136-137.5 (Ethyl acetate-Ethanol) | CDCl₃ 1.30-1.52(3H, m), 1.50(3H, t, J=7.2Hz), 1.69-1.90(9H, m), 1.97-2.05(2H, m), 2.83(3H, s), 2.90-3.11(3H, m), 3.91-4.00(2H, m), 4.03(3H, s), 4.28-4.40(1H, m), 4.37(2H, q, J=7.2Hz), 5.17(2H, s), 6.43(1H, d, J=2.0Hz), 6.64(1H, dd, J=2.0Hz and 8.9Hz), 7.30-7.43(5H, m), 8.38(1H, d, J=8.9Hz), 10.71(1H, brs) | 599 |

-continued

| Ex. No. | Chemical Structure | Properties Melting Point(° C.) (Solvent for Recrystallization) | ¹H-NMR | MS(FAB) (M + 1)⁺ |
|---|---|---|---|---|
| 196 | (structure with piperidine-NH, OMe, pyrazolopyrimidinone, N-ethyl, cyclohexyl) | Colorless solid 176-177 (Ethyl Acetate) | CDCl₃ 1.30-1.58(5H, m), 1.50(3H, t, J=7.2Hz), 1.63-1.91(5H, m), 1.96-2.10(4H, m), 2.50(3H, s), 2.61-2.72(1H, m), 2.92-3.12(3H, m), 3.80-3.90(2H, m), 4.03(3H, s), 4.37(2H, q, J=7.2Hz), 6.43(1H, d, J=1.9Hz), 6.64(1H, dd, J=1.9Hz and 9.0Hz), 8.37(1H, d, J=9.0Hz), 10.72(1H, brs) | 465 |
| 197 | (structure with SO₂Cl, OMe, pyrrolopyrimidinone, methyl, cyclohexyl) | Light yellow solid 235 (Decomposition) | CDCl₃ 1.23-1.39(1H, m), 1.43-1.60(2H, m), 1.70-1.80(1H, m), 1.88-2.12(6H, m), 2.57(3H, s), 4.18(3H, s), 4.97-5.10(1H, m), 7.67(1H, d, J=1.6Hz), 7.81(1H, dd, J=1.6Hz and 8.5Hz), 8.71(1H, d, J=8.5Hz), 10.67(1H, brs) | 437 |

| Ex. No. | Chemical Structure | Properties Melting Point(° C.) (Solvent for Recrystallization) | 1H-NMR | MS(FAB) (M + 1)+ |
|---|---|---|---|---|
| 198 | 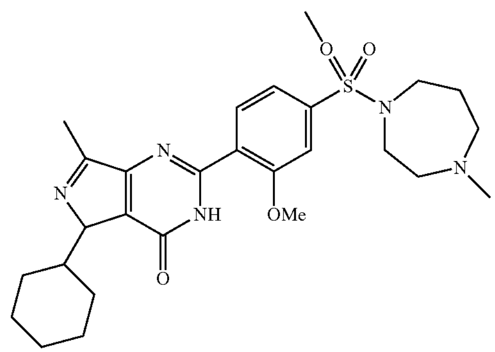 | Colorless solid 191-192 (Ethanol) | CDCl₃ 1.22-1.39(1H, m), 1.43-1.65(2H, m), 1.70-1.80(1H, m), 1.84-2.13(8H, m), 2.36(3H, s), 2.56(3H, s), 2.59-2.74(4H, m), 3.3.39-3.52(4H, m), 4.12(3H, s), 4.99-5.10(1H, m), 7.47(1H, d, J=1.3Hz), 7.52(1H, dd, J=1.3Hz and 8.3Hz), 8.60(1H, d, J=8.3Hz), 10.65(1H, brs) | 515 |
| 199 | 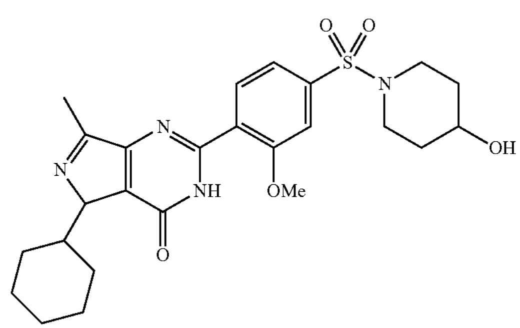 | Colorless solid 227-228.5 (Ethanol) | CDCl₃ 1.21-1.38(1H, m), 1.41(1H, d, J=3.9Hz), 1.42-1.61(2H, m), 1.65-1.80(3H, m), 1.89-2.11(8H, m), 2.56(3H, s), 2.94-3.08(2H, m), 3.29-3.41(2H, m), 3.79-3.89(1H, m), 4.12(3H, s), 4.98-5.10(1H, m), 7.40-7.46(1H, m), 7.49-7.55(1H, m), 8.61(1H, d, J=8.3Hz), 10.63(1H, brs) | 502 |

-continued

| Ex. No. | Chemical Structure | Properties Melting Point(° C.) (Solvent for Recrystallization) | ¹H-NMR | MS(FAB) (M + 1)⁺ |
|---|---|---|---|---|
| 200 | (structure with sulfonamide-NH-CH₂CH₂OH, OMe, pyrrolopyrimidinone with methyl and cyclohexyl) | Colorless solid 220.5-222 (Ethyl acetate) | CDCl₃ 1.26-1.40(1H, m), 1.43-1.62(2H, m), 1.71-1.79(1H, m), 1.84(1H, t, J=5.0Hz), 1.88-2.11(6H, m), 2.56(3H, s), 3.12-3.21(2H, m), 3.70-3.79(2H, m), 4.13(3H, s), 4.98-5.13(2H, m), 7.57(1H, d, J=1.5Hz), 7.62(1H, dd, J=1.5Hz and 8.3Hz), 8.61(1H, d, J=8.3Hz), 10.66(1H, brs) | 462 |
| 201 | (structure with sulfonamide-NHMe, OMe, pyrrolopyrimidinone with methyl and cyclohexyl) | Colorless solid 259-260 (Ethanol) | CDCl₃ 1.23-1.39(1H, m), 1.43-1.59(2H, m), 1.70-1.80(1H, m), 1.89-2.11(6H, m), 2.57(3H, s), 2.74(3H, d, J=5.2Hz), 4.13(3H, s), 4.48(1H, q, J=5.2Hz), 4.99-5.09(1H, m), 7.55(1H, d, J=1.5Hz), 7.60(1H, dd, J=1.5Hz and 8.4Hz), 8.62(1H, d, J=8.4Hz), 10.66(1H, brs) | 432 |
| 202 | (structure with homopiperazinyl sulfonyl, OMe, pyrrolopyrimidinone with methyl and cyclohexyl) | Colorless solid 180-181 (Ethyl acetate) | CDCl₃ 1.25-1.39(1H, m), 1.41-1.62(2H, m), 1.70-1.79(1H, m), 1.81-2.10(8H, m), 2.56(3H, s), 2.90-3.03(4H, m), 3.33-3.48(4H, m), 4.12(3H, s), 4.99-5.10(1H, m), 7.49(1H, d, J=1.4Hz), 7.53(1H, dd, J=1.4Hz and 8.2Hz), 8.60(1H, d, J=8.2Hz), 10.66(1H, brs) | 501 |

| Ex. No. | Chemical Structure | Properties Melting Point(° C.) (Solvent for Recrystallization) | ¹H-NMR | MS(FAB) (M + 1)⁺ |
|---|---|---|---|---|
| 203 | 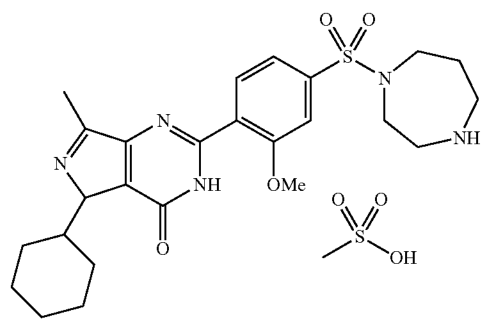 | Colorless solid 151-154 | DMSO-d₆ 1.17-1.29(1H, m), 1.31-1.48(2H, m), 1.63-1.73(1H, m), 1.80-2.00(8H, m), 2.29(3H, s), 2.37(3H, s), 3.13-3.25(4H, m), 3.33-3.41(2H, m), 3.50-3.59(2H, m), 3.91(3H, s), 4.89-5.00(1H, m), 7.41(1H, d, J=1.3Hz), 7.48(1H, dd, J=1.3Hz and 8.0Hz), 7.77(1H, d, J=8.0Hz), 8.66(1H, brs), 12.28(1H, brs) | 501 (free) |
| 204 | 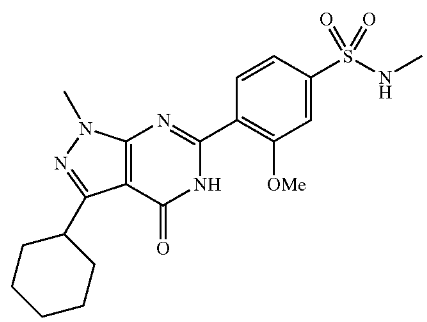 | Colorless solid 242-243 (Ethanol) | CDCl₃ 1.29-1.51(3H, m), 1.70-1.91(5H, m), 1.98-2.08(2H, m), 2.75(3H, d, J=5.2Hz), 3.05-3.17(1H, m), 4.00(3H, s), 4.14(3H, s), 4.59(1H, q, J=5.2Hz), 7.58(1H, d, J=1.4Hz), 7.62(1H, dd, J=1.4Hz and 8.4Hz), 8.65(1H, d, J=8.4Hz), 10.61(1H, brs) | 432 |
| 205 | 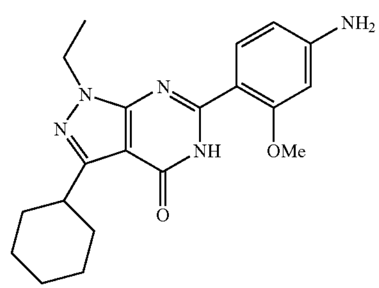 | Light yellow solid 222.5-223.5 (Ethanol) | CDCl₃ 1.30-1.55(3H, m), 1.49(3H, t, J=7.3Hz), 1.69-1.89(5H, m), 1.96-2.05(2H, m), 3.00-3.11(1H, m), 4.00(3H, s), 4.13(2H, brs), 4.36(2H, q, J=7.3Hz), 6.28(1H, d, J=2.0Hz), 6.42(1H, dd, J=2.0Hz and 8.6Hz), 8.33(1H, d, J=8.6Hz), 10.68(1H, brs) | 368 |

-continued

| Ex. No. | Chemical Structure | Properties Melting Point(° C.) (Solvent for Recrystallization) | ¹H-NMR | MS(FAB) (M + 1)⁺ |
|---|---|---|---|---|
| 206 | 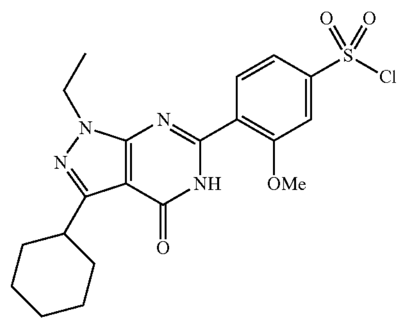 | Orange solid 175.5-179 | CDCl₃ 1.28-1.59(3H, m), 1.53(3H, t, J=7.2Hz), 1.70-1.90(5H, m), 1.97-2.09(2H, m), 3.03-3.17(1H, m), 4.19(3H, s), 4.43(2H, q, J=7.2Hz), 7.69(1H, d, J=1.7Hz), 7.83(1H, dd, J=1.7Hz and 8.4Hz), 8.72(1H, d, J=8.4Hz), 10.57(1H, brs) | 451 |
| 207 | 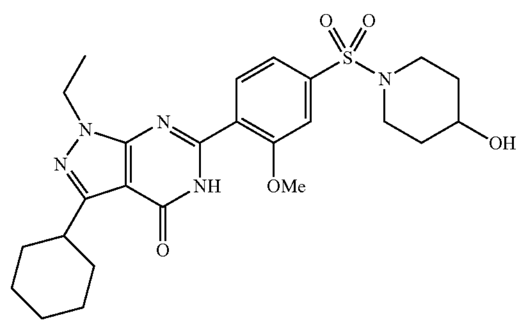 | Colorless solid 192-193.5 (Ethanol) | CDCl₃ 1.29-1.57(4H, m), 1.52(3H, t, J=7.2Hz), 1.66-1.90(5H, m), 1.93-2.07(2H, m), 2.98-3.14(3H, m), 3.31-3.40(2H, m), 3.80-3.90(1H, m), 4.13(3H, s), 4.41(2H, q, J=7.2Hz), 7.45(1H, d, J=1.3Hz), 7.52(1H, dd, J=1.3Hz and 8.3Hz), 8.63(1H, d, J=8.3Hz), 10.55(1H, brs) | 516 |
| 208 | 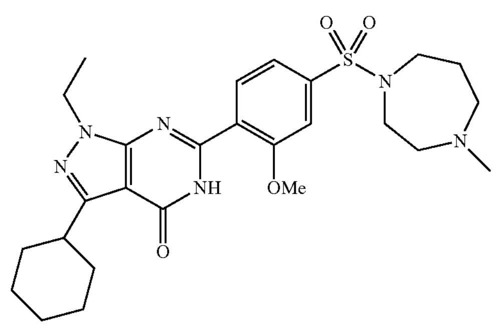 | Light yellow solid 163.5-165 (Ethyl acetate-Hexane) | CDCl₃ 1.30-1.54(3H, m), 1.52(3H, t, J=7.2Hz), 1.70-1.91(7H, m), 1.97-2.06(2H, m), 2.36(3H, s), 2.59-2.71(4H, m), 3.02-3.14(1H, m), 3.40-3.50(4H, m), 4.13(3H, s), 4.41(2H, q, J=7.2Hz), 7.48(1H, d, J=1.4Hz), 7.53(1H, dd, J=1.4Hz and 8.3Hz), 8.62(1H, d, J=8.3Hz), 10.57(1H, brs) | 529 |

| Ex. No. | Chemical Structure | Properties Melting Point(° C.) (Solvent for Recrystallization) | ¹H-NMR | MS(FAB) (M + 1)⁺ |
|---|---|---|---|---|
| 209 | 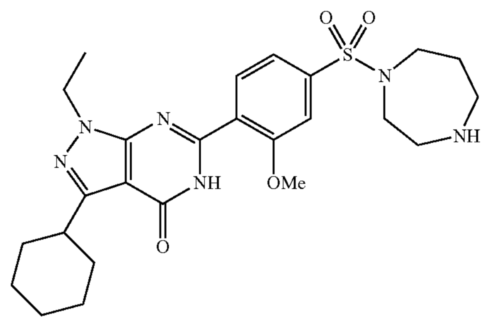 | Orange solid 179-185 (Ethyl acetate-Hexane) | CDCl₃ 1.29-1.57(3H, m), 1.51(3H, t, J=7.2Hz), 1.70-2.07(9H, m), 2.92-3.12(5H, m), 3.36-3.49(4H, m), 4.13(3H, s), 4.40(2H, q, J=7.2Hz), 7.50(1H, d, J=1.3Hz), 7.54(1H, dd, J=1.4Hz and 8.2Hz), 8.61(1H, d, J=8.2Hz), 10.58(1H, brs) | 515 |
| 210-1 | 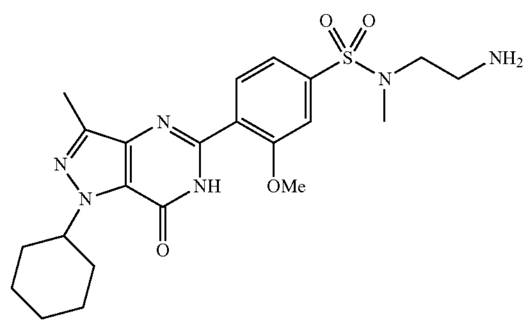 | Colorless solid 115-118 (Ethyl acetate-Hexane) | CDCl₃ 1.23-1.39(1H, m), 1.43-1.80(3H, m), 1.87-2.10(6H, m), 2.56(3H, s), 2.83(3H, s), 2.86-2.93(2H, m), 3.08-3.17(2H, m), 4.13(3H, s), 4.99-5.10(1H, m), 7.48(1H, d, J=1.4Hz), 7.53(1H, dd, J=1.4Hz and 8.3Hz), 8.62(1H, d, J=8.3Hz), 10.62(1H, brs) | 475 |
| 210-2 | 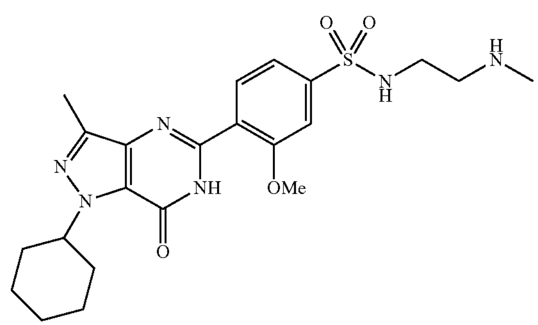 | Colorless solid 143.5-145 (Ethyl acetate-Hexane) | CDCl₃ 1.26-1.39(1H, m), 1.44-1.58(2H, m), 1.70-1.78(1H, m), 1.89-2.10(6H, m), 2.32(3H, s), 2.57(3H, s), 2.67-2.72(2H, m), 3.01-3.09(2H, m), 4.13(3H, s), 4.99-5.09(1H, m), 7.57(1H, d, J=1.3Hz), 7.61(1H, dd, J=1.3Hz and 8.3Hz), 8.61(1H, d, J=8.3Hz) | 475 |

| Ex. No. | Chemical Structure | Properties Melting Point(° C.) (Solvent for Recrystallization) | ¹H-NMR | MS(FAB) (M + 1)⁺ |
|---|---|---|---|---|
| 211 | 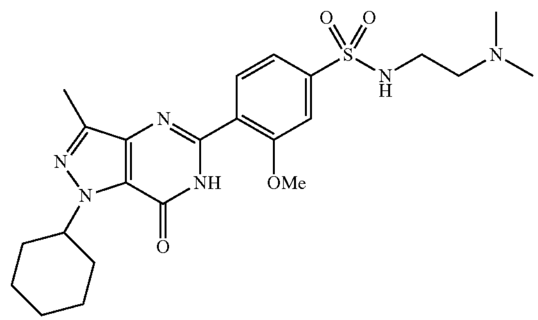 | Colorless solid 182-183 (Ethanol) | CDCl₃ 1.22-1.39(1H, m), 1.42-1.60(2H, m), 1.70-1.80(1H, m), 1.89-2.09(6H, m), 2.11(6H, s), 2.32-2.40(2H, m), 2.57(3H, s), 2.99-3.07(2H, m), 4.13(3H, s), 4.99-5.09(1H, m), 7.57(1H, d, J=1.5Hz), 7.62(1H, dd, J=1.5Hz and 8.3Hz), 8.62(1H, d, J=8.3Hz), 10.69(1H, brs) | 489 |
| 212 | 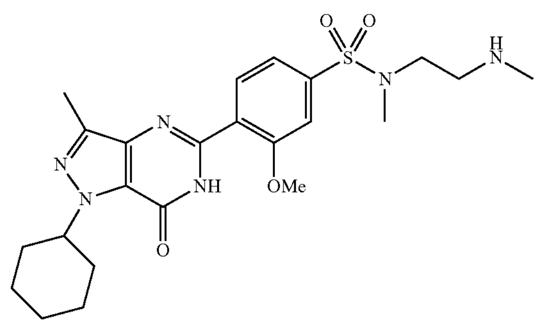 | Colorless solid 198-199.5 (Ethanol) | CDCl₃ 1.25-1.39(1H, m), 1.43-1.59(2H, m), 1.70-1.80(1H, m), 1.87-2.10(6H, m), 2.48(3H, s), 2.56(3H, s), 2.80(2H, t, J=6.1Hz), 2.84(3H, s), 3.18(2H, t, J=6.1Hz), 4.12(3H, s), 4.99-5.09(1H, m), 7.48(1H, d, J=1.3Hz), 7.54(1H, dd, J=1.3Hz and 8.6Hz), 8.61(1H, d, J=8.6Hz) | 489 |
| 213 | 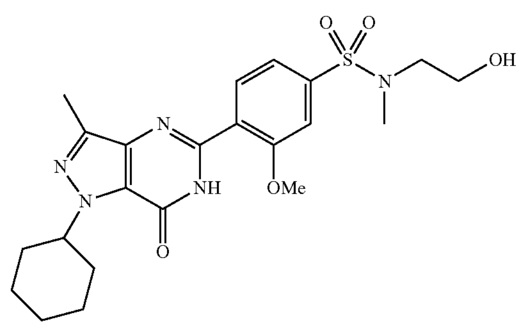 | Colorless solid 183-184 (Ethanol) | CDCl₃ 1.22-1.39(1H, m), 1.42-1.60(2H, m), 1.70-1.79(1H, m), 1.88-2.10(7H, m), 2.56(3H, s), 2.91(3H, s), 3.21-3.28(2H, m), 3.78-3.94(2H, m), 4.13(3H, s), 4.99-5.09(1H, m), 7.49(1H, d, J=1.4Hz), 7.55(1H, dd, J=1.4Hz and 8.3Hz), 8.62(1H, d, J=8.3Hz), 10.64(1H, brs) | 476 |

| Ex. No. | Chemical Structure | Properties Melting Point(° C.) (Solvent for Recrystallization) | ¹H-NMR | MS(FAB) (M + 1)⁺ |
|---|---|---|---|---|
| 214 | 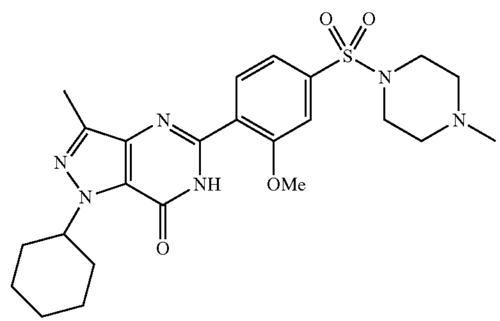 | Colorless solid 188-189 (Ethanol) | CDCl₃ 1.22-1.40(1H, m), 1.44-1.61(2H, m), 1.70-1.79(1H, m), 1.88-2.11(7H, m), 2.28(3H, s), 2.43-2.52(4H, m), 2.57(3H, s), 3.06-3.19(4H, m), 4.12(3H, s), 4.99-5.09(1H, m), 7.41(1H, d, J=1.4Hz), 7.50(1H, dd, J=1.4Hz and 8.2Hz), 8.63(1H, d, J=8.2Hz), 10.65(1H, brs) | 501 |
| 215 | 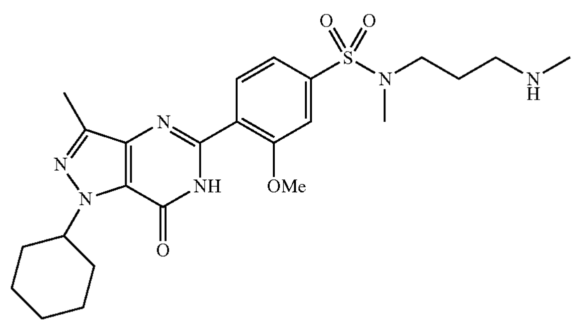 | Colorless solid 177.5-178.5 (Ethanol) | CDCl₃ 1.22-1.38(1H, m), 1.43-1.59(2H, m), 1.70-1.80(3H, m), 1.88-2.10(6H, m), 2.44(3H, s), 2.56(3H, s), 2.67(2H, t, J=6.8Hz), 2.80(3H, s), 3.14(2H, t, J=6.8Hz), 4.12(3H, s), 4.99-5.09(1H, m), 7.46(1H, d, J=1.4Hz), 7.52(1H, dd, J=1.4Hz and 8.3Hz), 8.61(1H, d, J=8.3Hz) | 503 |
| 216 | 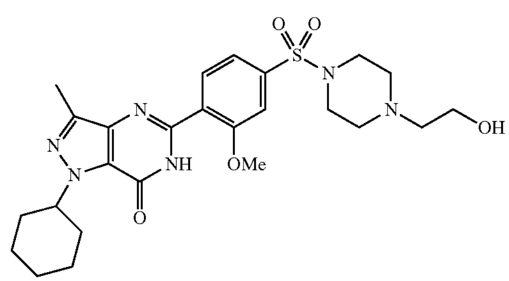 | Colorless solid 129-133 (Ethanol) | CDCl₃ 1.24-1.39(1H, m), 1.43-1.62(2H, m), 1.71-1.79(1H, m), 1.89-2.11(6H, m), 2.23-2.31(1H, bm), 2.51-2.69(6H, m), 2.56(3H, s), 3.06-3.18(4H, m), 3.58-3.62(2H, m), 4.13(3H, s), 4.99-5.09(1H, m), 7.42(1H, d, J=1.4Hz), 7.51(1H, dd, J=1.4Hz and 8.2Hz), 8.63(1H, d, J=8.2Hz), 10.63(1H, brs) | 531 |

-continued

| Ex. No. | Chemical Structure | Properties Melting Point(° C.) (Solvent for Recrystallization) | ¹H-NMR | MS(FAB) (M + 1)⁺ |
|---|---|---|---|---|
| 217 | (structure with piperazine-NH sulfonyl, OMe, cyclohexyl pyrazolopyrimidinone) | Colorless solid 220-222 (Ethanol) | CDCl₃ 1.25-1.39(1H, m), 1.44-1.60(2H, m), 1.70-1.80(1H, m), 1.90-2.11(6H, m), 2.57(3H, s), 2.90-2.99(4H, m), 3.02-3.11(4H, m), 4.12(3H, s), 4.99-5.10(1H, m), 7.41(1H, d, J=1.4Hz), 7.50(1H, dd, J=1.4Hz and 8.4Hz), 8.63(1H, d, J=8.4Hz), 10.65(1H, brs) | 487 |
| 218 | (structure with N-ethylpiperazine sulfonyl, OMe, cyclohexyl pyrazolopyrimidinone) | Colorless solid 235-236 (Ethanol) | CDCl₃ 1.04(3H, t, J=7.2Hz), 1.24-1.39(1H, m), 1.43-1.60(2H, m), 1.70-1.80(1H, m), 1.89-2.11(6H, m), 2.41(2H, q, J=7.2Hz), 2.48-2.60(4H, m), 2.56(3H, s), 3.07-3.19(4H, m), 4.12(3H, s), 4.99-5.09(1H, m), 7.41(1H, d, J=1.4Hz), 7.51(1H, dd, J=1.4Hz and 8.3Hz), 8.63(1H, d, J=8.3Hz), 10.66(1H, brs) | 515 |
| 219 | (structure with N-benzylpiperidinyl-NH sulfonyl, OMe, cyclohexyl pyrazolopyrimidinone) | Colorless solid 201.5-203 (Ethanol) | CDCl₃ 1.26-1.39(1H, m), 1.43-1.62(4H, m), 1.71-1.82(3H, m), 1.88-2.11(8H, m), 2.56(3H, s), 2.69-2.78(2H, m), 3.19-3.30(1H, m), 3.45(2H, s), 4.12(3H, s), 4.53(1H, brd, J=7.9Hz), 4.99-5.09(1H, m), 7.21-7.32(5H, m), 7.56(1H, d, J=1.4Hz), 7.61(1H, dd, J=1.4Hz and 8.3Hz), 8.60(1H, d, J=8.3Hz), 10.67(1H, brs) | 591 |

| Ex. No. | Chemical Structure | Properties Melting Point(° C.) (Solvent for Recrystallization) | ¹H-NMR | MS(FAB) (M + 1)⁺ |
|---|---|---|---|---|
| 220 | 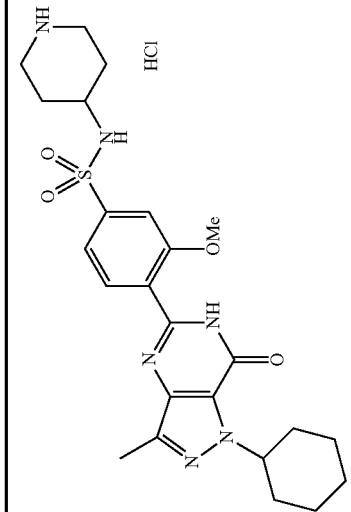 | Colorless solid 165-168.5 (Ethanol) | DMSO-d₆ 1.20-1.30(1H, m), 1.33-1.49(2H, m), 1.52-1.99(11H, m), 2.37(3H, s), 2.83-2.95(2H, m), 3.11-3.21(2H, m), 3.29-3.41(1H, m), 3.88(3H, s), 4.89-5.01(1H, m), 7.48-7.52(2H, m), 7.73(1H, d, J=7.8Hz), 8.15(1H, brd, J=7.2Hz) | 501 (free) |
| 221 | 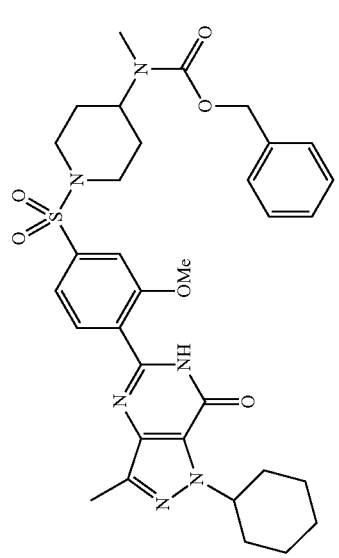 | Colorless solid 200-201 (Ethanol) | CDCl₃ 1.23-1.39(1H, m), 1.41-1.60(2H, m), 1.70-2.11(11H, m), 2.34-2.50(2H, m), 2.55(3H, s), 2.81(3H, s), 3.80-4.07(3H, m), 4.12(3H, s), 4.99-5.09(1H, m), 5.11(2H, s), 7.24-7.39(5H, m), 7.42(1H, d, J=1.3Hz), 7.50(1H, dd, J=1.3Hz and 8.3Hz), 8.63(1H, d, J=8.3Hz), 10.64(1H, brs) | 649 |

| Ex. No. | Chemical Structure | Properties Melting Point(° C.) (Solvent for Recrystallization) | ¹H-NMR | MS(FAB) (M + 1)⁺ |
|---|---|---|---|---|
| 222 | (structure with sulfonyl-piperidine-NHMe, OMe, pyrazolopyrimidinone, cyclohexyl) | Colorless solid 247.5-248.5 | CDCl₃ 1.23-1.81(6H, m), 1.88-2.11(8H, m), 2.33-2.44(1H, m), 2.38(3H, s), 2.57(3H, s), 2.59-2.69(2H, m), 3.61-3.71(2H, m), 4.12(3H, s), 5.00-5.09(1H, m), 7.43(1H, d, J=1.3Hz), 7.51(1H, dd, J=1.3Hz and 8.3Hz), 8.61(1H, d, J=8.3Hz) | 515 |
| 223 | (structure with N-benzyl-piperidine-NH, OMe, pyrazolopyrimidinone, cyclohexyl) | Colorless solid 231-233 | CDCl₃ 1.22-1.39(1H, m), 1.42-1.61(4H, m), 1.70-1.78(1H, m), 1.87-2.11(8H, m), 2.15-2.28(2H, m), 2.53(3H, s), 2.81-2.92(2H, m), 3.31-3.45(1H, m), 3.55(2H, s), 3.94-4.06(1H, m), 3.98(3H, s), 4.94-5.07(1H, m), 6.14(1H, d, J=2.0Hz), 6.34(1H, dd, J=2.0Hz and 8.8Hz), 7.22-7.39(5H, m), 8.29(1H, d, J=8.8Hz), 10.79(1H, brs) | 527 |
| 224 | (structure with piperidine-NH, OMe, pyrazolopyrimidinone, cyclohexyl) | Colorless solid 237-238.5 (Ethanol) | CDCl₃ 1.23-1.79(6H, m), 1.86-2.15(8H, m), 2.54(3H, s), 2.79-2.82(2H, m), 3.10-3.21(2H, m), 3.40-3.51(1H, m), 3.93-4.05(1H, m), 3.99(3H, s), 4.96-5.07(1H, m), 6.16(1H, d, J=1.8Hz), 6.36(1H, dd, J=1.8Hz and 8.8Hz), 8.30(1H, d, J=8.8Hz), 10.80(1H, brs) | 437 |

| Ex. No. | Chemical Structure | Properties Melting Point(° C.) (Solvent for Recrystallization) | ¹H-NMR | MS(FAB) (M + 1)⁺ |
|---|---|---|---|---|
| 225 | (structure with methoxyethylamino, OMe, pyrazolopyrimidinone, cyclohexyl, methyl) | Colorless solid 165.5-167 (Ethanol) | CDCl₃ 1.23-1.39(1H, m), 1.42-1.58(2H, m), 1.69-1.78(1H, m), 1.85-2.11(6H, m), 2.54(3H, s), 3.33-3.40(2H, m), 3.42(3H, s), 3.60-3.68(2H, m), 4.00(3H, s), 4.47(1H, brt, J=5.1Hz), 4.97-5.08(1H, m), 6.20(1H, d, J=2.1Hz), 6.38(1H, dd, J=2.1Hz and 8.7Hz), 8.31(1H, d, J=8.7Hz), 10.81(1H, brs) | 412 |
| 226 | (structure with methyl acrylate, OMe, pyrazolopyrimidinone, cyclohexyl, methyl) | Light yellow solid 202-204 | CDCl₃ 1.23-1.39(1H, m), 1.42-1.59(2H, m), 1.70-1.79(1H, m), 1.88-2.10(6H, m), 2.56(3H, s), 3.84(3H, s), 4.09(3H, s), 5.00-5.09(1H, m), 6.53(1H, d, J=16.1Hz), 7.16(1H, d, J=0.8Hz), 7.32(1H, dd, J=0.8Hz and 8.2Hz), 7.70(1H, d, J=16.1Hz), 8.51(1H, d, J=8.2Hz), 10.80(1H, brs) | 423 |
| 227 | (structure with acrylic acid, OMe, pyrazolopyrimidinone, cyclohexyl, methyl) | Colorless solid >300 | DMSO-d₆ 1.13-1.30(1H, m), 1.32-1.49(2H, m), 1.62-1.72(1H, m), 1.79-1.99(6H, m), 2.37(3H, s), 3.88(3H, s), 4.89-5.00(1H, m), 6.69(1H, d, J=16.1Hz), 7.32-7.40(1H, m), 7.48-7.51(1H, m), 7.60-7.69(2H, m), 12.04(1H, brs), 12.45(1H, brs) | 409 |

| Ex. No. | Chemical Structure | Properties Melting Point(° C.) (Solvent for Recrystallization) | ¹H-NMR | MS(FAB) (M + 1)⁺ |
|---|---|---|---|---|
| 228 | (structure with methyl ester, OMe, pyrazolopyrimidinone, cyclohexyl) | Colorless solid 139-140 (Ethanol) | CDCl₃ 1.25-1.39(1H, m), 1.43-1.59(2H, m), 1.70-1.79(1H, m), 1.88-2.10(6H, m), 2.55(3H, s), 2.68(2H, t, J=7.6Hz), 3.02(2H, t, J=7.6Hz), 3.69(3H, s), 4.04(3H, s), 4.99-5.09(1H, m), 6.90(1H, d, J=0.7Hz), 6.99(1H, dd, J=0.7Hz and 8.1Hz), 8.37(1H, d, J=8.1Hz), 10.78(1H, brs) | 425 |
| 229 | (structure with carboxylic acid, OMe, pyrazolopyrimidinone, cyclohexyl) | Colorless solid 290-295 | DMSO-d₆ 1.15-1.29(1H, m), 1.31-1.48(2H, m), 1.62-1.72(1H, m), 1.80-2.00(6H, m), 2.36(3H, s), 2.59(2H, t, J=7.6Hz), 2.88(2H, t, J=7.6Hz), 3.82(3H, s), 4.89-4.98(1H, m), 6.90-6.95(1H, m), 7.03-7.08(1H, m), 7.52(1H, d, J=7.7Hz), 11.91(1H, brs), 12.13(1H, brs) | 411 |
| 230 | (structure with dimethylaminoethylamino, OMe, pyrazolopyrimidinone, cyclohexyl) | Colorless solid 168-169.5 (Ethanol) | CDCl₃ 1.23-1.39(1H, m), 1.42-1.59(2H, m), 1.69-1.77(1H, m), 1.85-2.10(6H, m), 2.28(6H, s), 2.54(3H, s), 2.55-2.62(2H, m), 3.18-3.26(2H, m), 4.00(3H, s), 4.80(1H, brt, J=4.5Hz), 4.96-5.08(1H, m), 6.19(1H, d, J=2.0Hz), 6.37(1H, dd, J=2.0Hz and 8.7Hz), 8.31(1H, d, J=8.7Hz), 10.83(1H, brs) | 425 |

-continued

| Ex. No. | Chemical Structure | Properties Melting Point(° C.) (Solvent for Recrystallization) | ¹H-NMR | MS(FAB) (M + 1)⁺ |
|---|---|---|---|---|
| 231 | 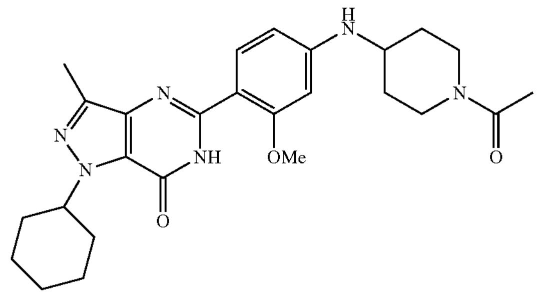 | Colorless solid 230-231.5 (Ethanol) | CDCl₃ 1.21-1.64(5H, m), 1.69-1.78(1H, m), 1.85-2.21(8H, m), 2.13(3H, s), 2.54(3H, s), 2.83-2.96(1H, m), 3.19-3.31(1H, m), 3.53-3.66(1H, m), 3.80-3.89(1H, m), 3.95-4.02(1H, m), 3.99(3H, s), 4.48-4.57(1H, m), 4.93-5.07(1H, m), 6.17(1H, d, J=1.9Hz), 6.37(1H, dd, J=1.9Hz and 8.7Hz), 8.31(1H, d, J≦8.7Hz), 10.76(1H, brs) | 479 |
| 232 | 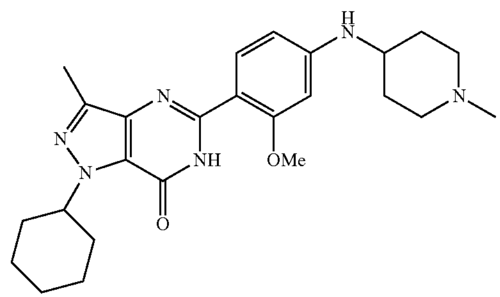 | Colorless solid 247-249 (Ethanol) | CDCl₃ 1.23-1.39(1H, m), 1.42-1.65(4H, m), 1.69-1.78(1H, m), 1.87-2.22(10H, m), 2.32(3H, s), 2.53(3H, s), 2.79-2.89(2H, m), 3.32-3.42(1H, m), 3.96-4.02(1H, m), 3.99(3H, s), 4.96-5.07(1H, m), 6.15(1H, d, J=2.0Hz), 6.35(1H, dd, J=2.0Hz and 8.8Hz), 8.30(1H, d, J=8.8Hz), 10.79(1H, brs) | 451 |
| 233 | 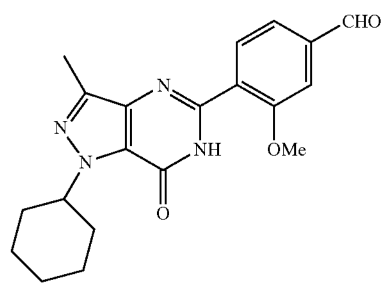 | Light yellow solid 213-215.5 (Ethyl acetate) | CDCl₃ 1.23-1.39(1H, m), 1.44-1.60(2H, m), 1.70-1.79(1H, m), 1.88-2.11(6H, m), 2.58(3H, s), 4.14(3H, s), 4.99-5.10(1H, m), 7.59(1H, d, J=1.1Hz), 7.64(1H, dd, J=1.1Hz and 8.0Hz), 8.68(1H, d, J=8.0Hz), 10.07(1H, s), 10.79(1H, brs) | 367 |

| Ex. No. | Chemical Structure | Properties Melting Point(° C.) (Solvent for Recrystallization) | ¹H-NMR | MS(FAB) (M + 1)⁺ |
|---|---|---|---|---|
| 234 | (structure with N-methylpiperazine, OMe, cyclohexyl-pyrazolopyrimidinone) | Colorless solid 170-171 | CDCl₃ 1.22-1.39(1H, m), 1.42-1.58(2H, m), 1.69-1.79(1H, m), 1.86-2.11(6H, m), 2.30(3H, s), 2.32-2.67(8H, m), 2.56(3H, s), 3.56(2H, s), 40.5(3H, s), 4.99-5.09(1H, m), 7.04-7012(2H, m), 8.38(1H, d, J=7.9Hz), 10.80(1H, brs) | 451 |
| 235 | (structure with morpholine, OMe, cyclohexyl-pyrazolopyrimidinone) | Colorless solid 190-192 (Ethanol) | CDCl₃ 1.25-1.39(1H, m), 1.43-1.61(2H, m), 170-1.79(1H, m), 1.87-2.10(6H, m), 2.42-2.51(4H, m), 2.56(3H, s), 3.55(2H, s), 3.70-3.78(4H, m), 4.05(3H, s), 4.99-5.08(1H, m), 7.08-7.13(2H, m), 8.39(1H, d, J=7.9Hz), 10.79(1H, brs) | 438 |
| 236 | (structure with 4-hydroxypiperidine, OMe, cyclohexyl-pyrazolopyrimidinone) | Colorless solid 227-228.5 (Ethanol) | CDCl₃ 1.22-1.38(1H, m), 1.40-1.68(4H, m), 1.70-1.78(1H, m), 1.86-2.10(8H, m), 2.13-2.25(2H, m), 2.56(3H, s), 2.71-2.81(2H, m), 3.55(2H, s), 3.70-3.80(1H, m), 4.05(3H, s), 4.99-5.09(1H, m), 7.05-7.11(2H, m), 8.38(1H, d, J=8.3Hz), 10.81(1H, brs) | 452 |

| Ex. No. | Chemical Structure | Properties Melting Point(° C.) (Solvent for Recrystallization) | ¹H-NMR | MS(FAB) (M + 1)⁺ |
|---|---|---|---|---|
| 237 | (structure with methoxyethylamino-methyl, OMe, pyrazolopyrimidinone, cyclohexyl) | Colorless solid 104-105 | CDCl₃ 1.23-1.39(1H, m), 1.43-1.59(2H, m), 1.70-1.80(1H, m), 1.87-2.10(6H, m), 2.56(3H, s), 2.83(2H, t, J=5.1Hz), 3.38(3H, s), 3.54(2H, t, J=5.1Hz), 3.89(2H, s), 4.06(3H, s), 4.99-5.09(1H, m), 7.06-7.12(2H, m), 8.40(1H, d, J=8.0Hz), 10.83(1H, brs) | 426 |
| 238 | (structure with piperidine-ethyl ester, OMe, pyrazolopyrimidinone, cyclohexyl) | Colorless solid 117-118 (Ether-Hexane) | CDCl₃ 1.21-1.39(1H, m), 1.26(3H, t, J=7.1Hz), 1.42-1.61(2H, m), 1.69-2.12(13H, m), 2.27-2.37(1H, m), 2.56(3H, s), 2.80-2.90(2H, m), 3.53(2H, s), 4.05(3H, s), 4.14(2H, q, J=7.1Hz), 4.99-5.09(1H, m), 7.04-7.12(2H, m), 8.37(1H, d, J=8.0Hz), 10.80(1H, brs) | 508 |
| 239 | (structure with piperidine-carboxylic acid, OMe, pyrazolopyrimidinone, cyclohexyl) | Colorless solid 160-164 | CDCl₃ 1.23-1.39(1H, m), 1.41-1.58(2H, m), 1.70-1.80(1H, m), 1.87-2.23(10H, m), 2.45-2.58(1H, m), 2.54(3H, s), 2.60-2.80(2H, m), 3.20-3.30(2H, m), 4.01(2H, s), 4.07(3H, s), 4.98-5.09(1H, m), 7.05-7.12(1H, m), 7.57-7.67(1H, m), 8.34(1H, d, J=8.0Hz), 10.93(1H, brs) | 480 |

| Ex. No. | Chemical Structure | Properties Melting Point(° C.) (Solvent for Recrystallization) | $^1$H-NMR | MS(FAB) $(M + 1)^+$ |
|---|---|---|---|---|
| 240 | 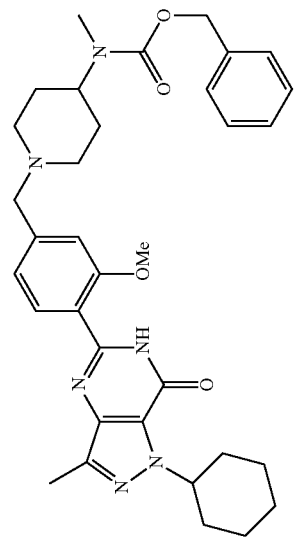 | Colorless solid 143-144 | CDCl$_3$ 1.23-1.40(1H, m), 1.44-1.68(4H, m), 1.70-1.84(3H, m), 1.88-2.19(8H, m), 2.56(3H, s), 2.85(3H, s), 2.90-2.99(2H, m), 3.54(2H, s), 3.98-4.14(1H, m), 4.05(3H, s), 4.98-5.09(1H, m), 5.15(2H, s), 7.02-7.12(2H, m), 7.29-7.42(5H, m), 8.38(1H, d, J=8.1Hz), 10.80(1H, brs) | 599 |
| 241 | 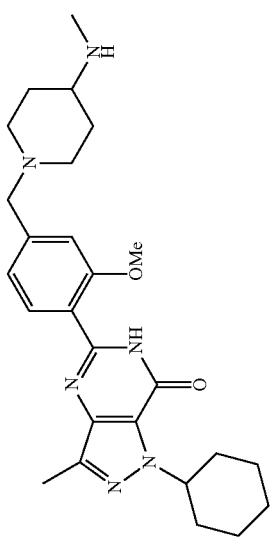 | Colorless solid 177-180 (Ethyl acetate-Hexane) | CDCl$_3$ 1.26-2.12(16H, m), 2.34-2.46(1H, m), 2.44(3H, s), 2.56(3H, s), 2.80-2.90(2H, m), 3.55(2H, s), 4.04(3H, s), 4.98-5.10(1H, m), 7.04-7.11(2H, m), 8.37(1H, d, J=7.9Hz) | 465 |

| Ex. No. | Chemical Structure | Properties Melting Point(° C.) (Solvent for Recrystallization) | ¹H-NMR | MS(FAB) (M + 1)⁺ |
|---|---|---|---|---|
| 242 | 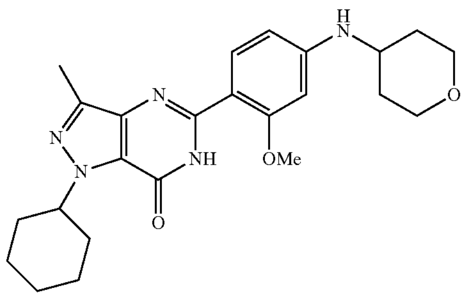 | Colorless solid 244.5-245.5 (Ethanol) | CDCl₃ 1.23-1.39(1H, m), 1.43-1.62(4H, m), 1.69-1.78(1H, m), 1.87-2.11(8H, m), 2.54(3H, s), 3.50-3.66(3H, m), 3.97-4.08(3H, m), 3.99(3H, s), 4.97-5.06(1H, m), 6.17(1H, d, J=2.0Hz), 6.37(1H, dd, J=2.0Hz and 8.8Hz), 8.30(1H, d, J=8.8Hz), 10.78(1H, brs) | 438 |
| 243 | 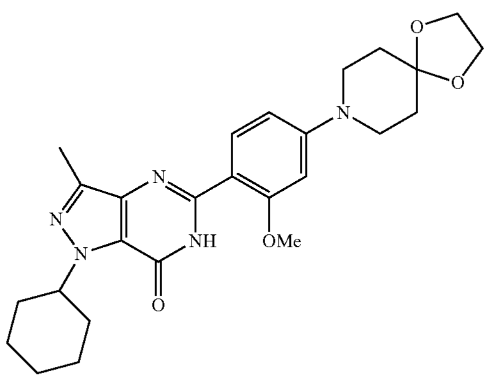 | Colorless solid 230-231.5 (Ethanol) | CDCl₃ 1.23-1.39(1H, m), 1.42-1.60(4H, m), 1.69-1.78(1H, m), 1.81-2.11(10H, m), 2.54(3H, s), 3.45-3.52(4H, m), 4.01(4H, s), 4.02(3H, s), 4.97-5.07(1H, m), 6.47(1H, d, J=2.2Hz), 6.67(1H, dd, J=2.2Hz and 9.0Hz), 8.34(1H, d, J=9.0Hz), 10.82(1H, brs) | 480 |

| Ex. No. | Chemical Structure | Properties Melting Point(° C.) (Solvent for Recrystallization) | ¹H-NMR | MS(FAB) (M + 1)⁺ |
|---|---|---|---|---|
| 244 | 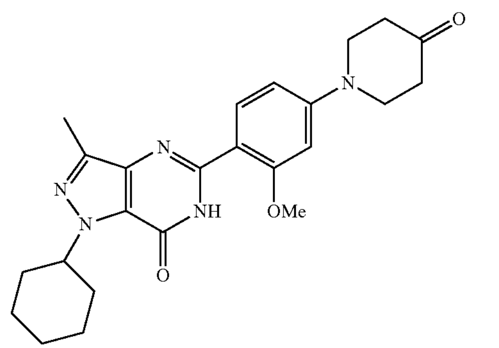 | Colorless solid 206-207 (Ethyl acetate) | CDCl₃ 1.23-1.39(1H, m), 1.42-1.59(2H, m), 1.69-1.78(1H, m), 1.87-2.11(6H, m), 2.55(3H, s), 2.59-2.67(4H, m), 3.71-3.80(4H, m), 4.05(3H, s), 4.97-5.08(1H, m), 6.48(1H, d, J=2.2Hz), 6.69(1H, dd, J=2.2Hz and 9.0Hz), 8.40(1H, d, J=9.0Hz), 10.78(1H, brs) | 436 |
| 245 | 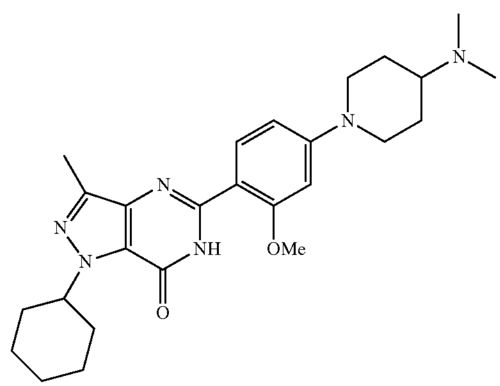 | Colorless solid 218-219 (Ethanol) | CDCl₃ 1.23-1.39(1H, m), 1.42-1.78(5H, m), 1.85-2.10(8H, m), 2.30-2.40(1H, m), 2.32(6H, s), 2.54(3H, s), 2.82-2.93(2H, m), 3.82-3.92(2H, m), 4.02(3H, s), 4.95-5.08(1H, m), 6.46(1H, d, J=2.0Hz), 6.66(1H, dd, J=2.2Hz and 9.0Hz), 8.34(1H, d, J=9.0Hz), 10.83(1H, brs) | 465 |

| Ex. No. | Chemical Structure | Properties Melting Point(° C.) (Solvent for Recrystallization) | ¹H-NMR | MS(FAB) (M + 1)⁺ |
|---|---|---|---|---|
| 246 | (structure with benzyl-NH-piperidine, OMe, pyrazolopyrimidinone, cyclohexyl) | Colorless solid 174.5-175.5 (Ethanol) | CDCl₃ 1.23-1.39(1H, m), 1.42-1.79(5H, m), 1.88-2.10(8H, m), 2.54(3H, s), 2.72-2.83(1H, m), 2.81-3.02(2H, m), 3.77-3.86(2H, m), 3.87(2H, s), 4.02(3H, s), 4.98-5.09(1H, m), 6.45(1H, d, J=2.1Hz), 6.65(1H, dd, J=2.1Hz and 9.1Hz), 7.23-7.40(5H, m), 8.34(1H, d, J=9.1Hz), 10.84(1H, brs) | 527 |
| 247 | (structure with NH₂-piperidine, OMe, pyrazolopyrimidinone, cyclohexyl) | Colorless solid 218-219.5 (Ethyl acetate) | CDCl₃ 1.23-1.38(1H, m), 1.40-1.78(5H, m), 1.86-2.10(8H, m), 2.54(3H, s), 2.88-3.00(3H, m), 3.77-3.86(2H, m), 4.02(3H, m), 4.97-5.08(1H, m), 6.45(1H, d, J=2.2Hz), 6.66(1H, dd, J=2.2 and 8.9Hz), 8.34(1H, d, J=8.9Hz), 10.83(1H, brs) | 437 |

| Ex. No. | Chemical Structure | Properties Melting Point(° C.) (Solvent for Recrystallization) | ¹H-NMR | MS(FAB) (M + 1)⁺ |
|---|---|---|---|---|
| 248 | 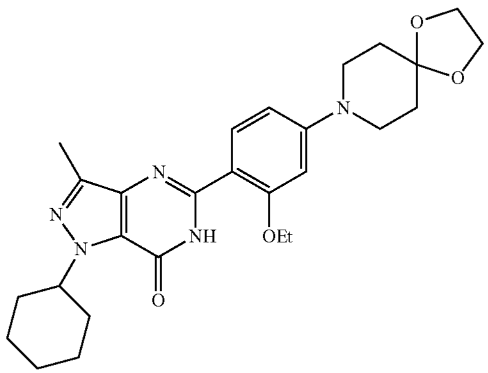 | Colorless solid 144-146 (Ethanol) | CDCl₃ 1.23-1.36(1H, m), 1.41-1.54(2H, m), 1.61(3H, t, J=7.0Hz), 1.68-1.77(1H, m), 1.80-2.10(10H, m), 2.54(3H, s), 3.42-3.50(4H, m), 4.01(4H, s), 4.26(2H, q, J=7.0Hz), 4.96-5.06(1H, m), 6.46(1H, d, J=2.2Hz), 6.66(1H, dd, J=2.2 and 8.9Hz), 8.36(1H, d, J=8.9Hz), 11.13(1H, brs) | 494 |
| 249 | 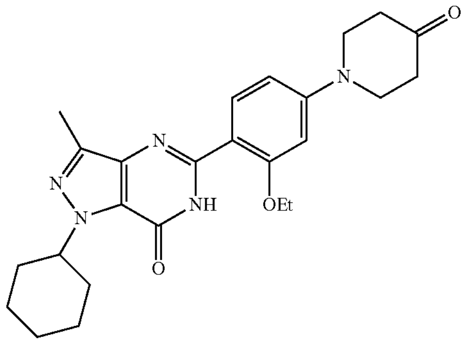 | Colorless solid 230-231.5 (Ethyl acetate) | CDCl₃ 1.22-1.38(1H, m), 1.40-1.58(2H, m), 1.63(3H, t, J=6.9Hz), 1.69-1.78(1H, m), 1.85-2.11(6H, m), 2.55(3H, s), 2.60(4H, t, J=6.1Hz), 3.74(4H, t, J=6.1Hz), 4.28(2H, q, J=6.9Hz), 4.96-5.08(1H, m), 6.48(1H, d, J=2.3Hz), 6.69(1H, dd, J=2.3 and 8.9Hz), 8.42(1H, d, J=8.9Hz), 11.09(1H, brs) | 450 |

| Ex. No. | Chemical Structure | Properties Melting Point(° C.) (Solvent for Recrystallization) | ¹H-NMR | MS(FAB) (M + 1)⁺ |
|---|---|---|---|---|
| 250 | 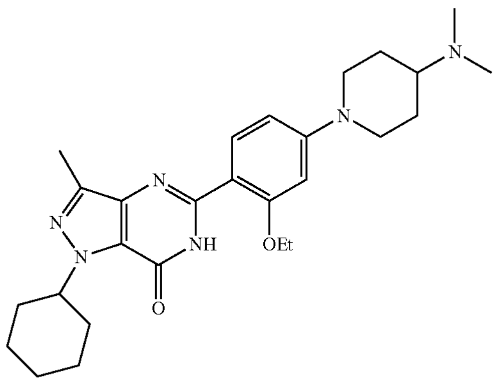 | Colorless solid 147-149 | CDCl₃ 1.23-1.38(1H, m), 1.41-1.55(2H, m), 1.62(3H, t, J=6.9Hz), 1.64-2.11(11H, m), 2.41(6H, s), 2.48-2.59(1H, m), 2.54(3H, s), 2.82-2.93(2H, m), 3.84-3.93(2H, m), 4.26(2H, q, J=6.9Hz), 4.96-5.08(1H, m), 6.45(1H, d, J=2.2Hz), 6.65(1H, dd, J=2.2 and 9.0Hz), 8.37(1H, d, J=9.0Hz), 11.13(1H, brs) | 479 |
| 251 | 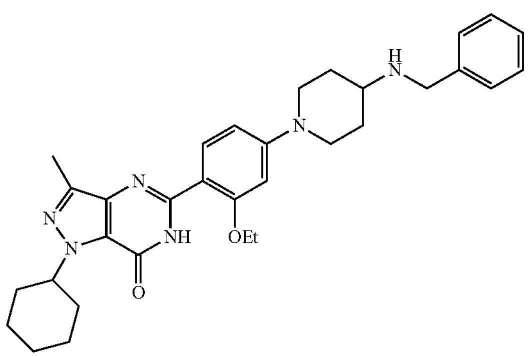 | Colorless solid 166-167.5 (Ethanol) | CDCl₃ 1.22-1.38(1H, m), 1.41-1.63(4H, m), 1.61(3H, t, J=6.9Hz), 1.69-1.77(1H, m), 1.82-2.11(8H, m), 2.55(3H, s), 2.71-2.80(1H, m), 2.88-2.99(2H, m), 3.71-3.81(2H, m), 3.87(2H, s), 4.26(2H, q, J=6.9Hz), 4.96-5.07(1H, m), 6.44(1H, d, J=2.1Hz), 6.65(1H, dd, J=2.1 and 9.0Hz), 7.21-7.39(5H, m), 8.36(1H, d, J=9.0Hz), 11.15(1H, brs) | 541 |

| | | | |
|---|---|---|---|
| 252 | 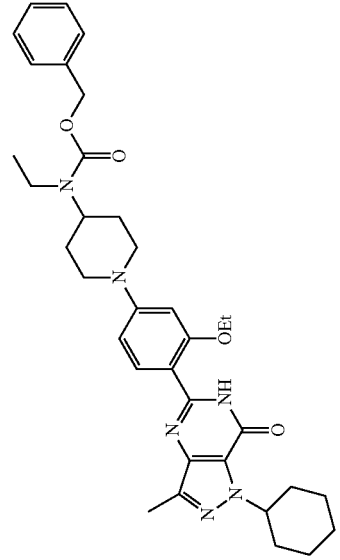 | Colorless solid 138.5-140 (Ether-Hexane) | CDCl₃ 1.10-1.19(3H, m), 1.22-1.39(1H, m), 1.41-1.55(2H, m), 1.62(3H, t, J=6.9Hz), 1.69-1.77(1H, m), 1.79-2.11(10H, m), 2.55(3H, s), 2.87-3.00(2H, m), 3.17-3.31(2H, m), 3.87-3.97(2H, m), 4.19-4.31(1H, m), 4.25(2H, q, J=6.9Hz), 4.96-5.07(1H, m), 5.17(2H, s), 6.44(1H, d, J=1.9Hz), 6.65(1H, dd, J=1.9Hz and 9.0Hz), 7.28-7.40(5H, m), 8.36(1H, d, J=9.0Hz), 11.12(1H, brs) | 613 |
| 253 | 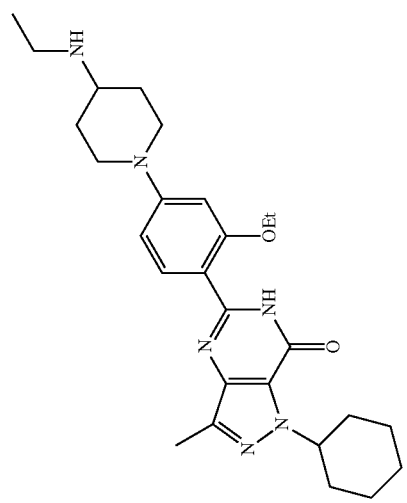 | Colorless solid 160-161.5 (Ethanol) | CDCl₃ 1.15(3H, t, J=7.1Hz), 1.22-1.57(5H, m), 1.61(3H, t, J=7.0Hz), 1.68-1.78(1H, m), 1.82-2.10(8H, m), 2.54(3H, s), 2.66-2.77(1H, m), 2.73(2H, q, J=7.1Hz), 2.89-2.99(2H, m), 3.75-3.85(2H, m), 4.26(2H, q, J=7.0Hz), 4.96-5.08(1H, m), 6.45(1H, d, J=2.2Hz), 6.65(1H, dd, J=2.2Hz and 9.0Hz), 8.36(1H, d, J=9.0Hz), 11.15(1H, brs) | 479 |
| 254 | 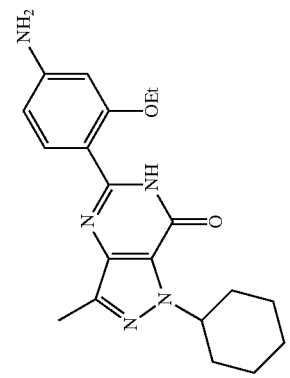 | Yellow solid 206-207.5 (Ethanol) | CDCl₃ 1.22-1.38(1H, m), 1.41-1.54(2H, m), 1.60(3H, t, J=6.9Hz), 1.69-1.79(1H, m), 1.88-2.12(6H, m), 2.54(3H, s), 4.02(2H, brs), 4.21(2H, q, J=6.9Hz), 4.97-5.08(1H, m), 6.26(1H, d, J=2.1Hz), 6.42(1H, dd, J=2.2 and 8.5Hz), 8.31(1H, d, J=8.5Hz), 11.09(1H, brs) | 368 |

| | Structure | Appearance mp (°C) (recrystallization solvent) | NMR | MS |
|---|---|---|---|---|
| 255 | [structure with SO₂Cl, OEt, cyclohexyl-pyrazolopyrimidinone] | Yellow solid 205-207 | CDCl₃ 1.26-1.40(1H, m), 1.41-1.80(3H, m), 1.68(3H, t, J=7.0Hz), 1.89-2.11(6H, m), 2.57(3H, s), 4.42(2H, q, J=7.0Hz), 4.96-5.09(1H, m), 7.65(1H, d, J=1.7Hz), 7.79(1H, dd, J=1.7 and 8.4Hz), 8.75(1H, d, J=8.4Hz), 10.91(1H, brs) | 451 |
| 256 | [structure with N-methyl-homopiperazinyl sulfonyl, OEt, cyclohexyl-pyrazolopyrimidinone] | Colorless solid 189.5-191 (Ethanol) | CDCl₃ 1.23-1.39(1H, m), 1.42-1.56(2H, m), 1.64(3H, t, J=7.0Hz), 1.69-1.79(1H, m), 1.83-2.11(8H, m), 2.36(3H, s), 2.57(3H, s), 2.59-2.70(4H, m), 3.39-3.49(4H, m), 4.36(2H, q, J=7.0Hz), 4.98-5.10(1H, m), 7.45(1H, d, J=1.3Hz), 7.51(1H, dd, J=1.3 and 8.4Hz), 8.64(1H, d, J=8.4Hz), 10.95(1H, brs) | 529 |
| 257 | [structure with 4-hydroxypiperidinyl sulfonyl, OEt, cyclohexyl-pyrazolopyrimidinone] | Colorless solid 252-253.5 (Ethanol) | CDCl₃ 1.23-1.40(2H, m), 1.42-1.59(2H, m), 1.62-1.79(3H, m), 1.65(3H, t, J=7.0Hz), 1.88-2.11(8H, m), 2.57(3H, s), 2.94-3.02(2H, m), 3.29-3.39(2H, m), 3.79-3.88(1H, m), 4.36(2H, q, J=7.0Hz), 4.98-5.09(1H, m), 7.41(1H, d, J=1.4Hz), 7.49(1H, dd, J=1.4 and 8.2Hz), 8.65(1H, d, J=8.2Hz), 10.92(1H, brs) | 516 |

| # | Structure | Appearance / mp (solvent) | NMR | MS |
|---|---|---|---|---|
| 258 | (4-hydroxypiperidin-1-yl-phenyl-OMe substituted pyrazolopyrimidinone, N-cyclohexyl) | Colorless solid 213.5-215 (Ethanol) | CDCl₃ 1.23-1.38(1H, m), 1.43-1.61(3H, m), 1.64-1.79(3H, m), 1.84-2.11(8H, m), 2.54(3H, s), 3.05-3.16(2H, m), 3.66-3.75(2H, m), 3.90-3.99(1H, m), 4.02(3H, s), 4.97-5.06(1H, m), 6.46(1H, d, J=2.2Hz), 6.66(1H, dd, J=2.2 and 9.0Hz), 8.35(1H, d, J=9.0Hz), 10.82(1H, brs) | 438 |
| 259 | (cyanovinyl-phenyl-OMe substituted pyrazolopyrimidinone, N-cyclohexyl) | Light green solid >300 (Ethanol) | CDCl₃ 1.22-1.39(1H, m), 1.43-1.59(2H, m), 1.70-1.79(1H, m), 1.88-2.11(6H, m), 2.56(3H, s), 4.10(3H, s), 4.99-5.10(1H, m), 5.99(1H, d, J=16.7Hz), 7.07(1H, d, J=1.2Hz), 7.26(1H, dd, J=1.2Hz and 8.3Hz), 7.43(1H, d, J=16.7Hz), 8.54(1H, d, J=8.3Hz), 10.74(1H, brs) | 390 |
| 260 | (4-aminopiperidin-1-yl-phenyl-OEt substituted pyrazolopyrimidinone, N-cyclohexyl) | Colorless solid 185-188 | CDCl₃ 1.22-1.38(1H, m), 1.39-1.57(4H, m), 1.62(3H, t, J=7.0Hz), 1.68-1.78(1H, m), 1.84-2.10(8H, m), 2.55(3H, s), 2.87-3.00(3H, m), 3.75-3.84(2H, m), 4.27(2H, q, J=7.0Hz), 4.96-5.08(1H, m), 6.45(1H, d, J=2.1Hz), 6.66(1H, dd, J=2.2 and 8.9Hz), 8.36(1H, d, J=8.9Hz), 11.14(1H, brs) | 451 |

| | | | |
|---|---|---|---|
| 261 | 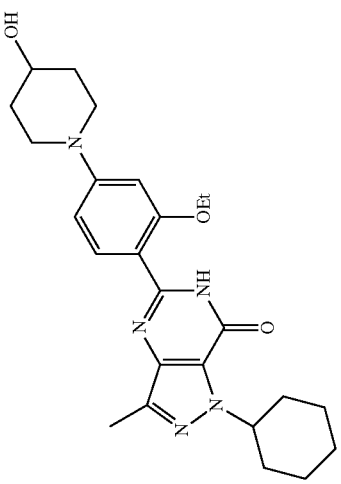 | Colorless solid 208-210 (EtOH) | CDCl₃ 1.22-1.38(1H, m), 1.41-1.78(6H, m), 1.62 3H, t, J=7.0Hz), 1.88-2.10(8H, m), 2.55(3H, s), 3.04-3.15(2H, m), 3.63-3.73(2H, m), 3.89-3.99(1H, m), 4.26(2H, q, J=7.0Hz), 4.95-5.06(1H, m), 6.46(1H, d, J=2.3Hz), 6.66(1H, dd, J=2.3 and 9.0Hz), 8.37(1H, d, J=9.0Hz), 11.14(1H, brs) | 452 |
| 262 | 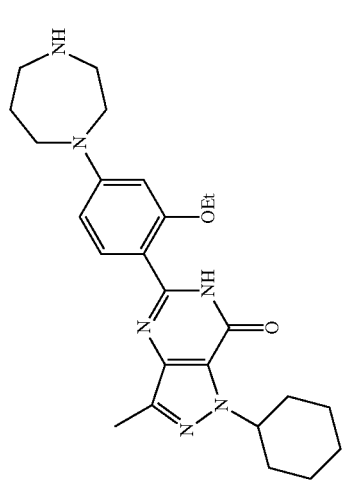 | Faint brown crystal 172-176 (Ethyl acetate) | CDCl₃ 1.20-1.58(3H, m), 1.60(3H, t, J=7.0Hz), 1.65-1.73(1H, m), 1.83-2.08(8H, m), 2.52(3H, s), 2.80-2.85(2H, m), 3.01-3.06(2H, m), 3.56-3.68(4H, m), 4.23(2H, q, J=7.0Hz), 4.93-5.02(1H, m), 6.20(1H, d, J=2.3Hz), 6.45(1H, dd, J=2.3 and 9.1Hz), 8.32(1H, d, J=9.1Hz), 11.12(1H, brs) | 451 |
| 263 | 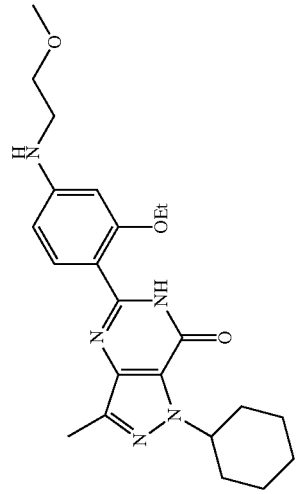 | Colorless solid 141-142 (Ethanol) | CDCl₃ 1.20-1.36(1H, m), 1.40-1.52(2H, m), 1.59(3H, t, J=7.0Hz), 1.65-1.74(1H, m), 1.81-2.09(6H, m), 2.52(3H, s), 3.30-3.37(2H, m), 3.40(3H, s), 3.60-3.64(2H, m), 4.21(2H, q, J=7.0Hz), 4.42(1H, brt, J=5.4Hz), 4.93-5.04(1H, m), 6.17(1H, d, J=2.0Hz), 6.36(1H, dd, J=2.0 and 8.8Hz), 8.31(1H, d, J=8.8Hz), 11.10(1H, brs) | 426 |

| | | | |
|---|---|---|---|
| 264 | 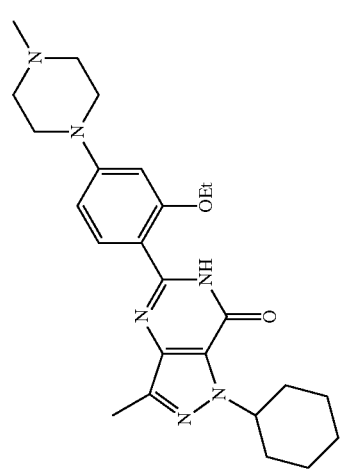 | Light yellow solid 207-208 (Ethanol) | CDCl₃ 1.20-1.37(1H, m), 1.40-1.54(2H, m), 1.56(3H, t, J=7.0Hz), 1.66-1.76(1H, m), 1.82-2.10(6H, m), 2.35(3H, s), 2.53(3H, s), 2.54-2.60(4H, m), 3.29-3.38(4H, m), 4.25(2H, q, J=7.0Hz), 4.94-5.05(1H, m), 6.43(1H, d, J=2.1Hz), 6.64(1H, dd, J=2.1 and 9.0Hz), 8.36(1H, d, J=9.0Hz), 11.12(1H, brs) | 451 |
| 265 | 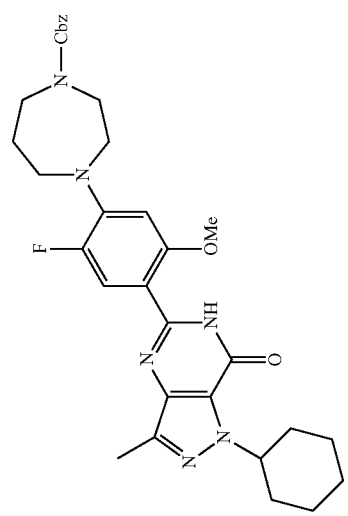 | Colorless foam | CDCl₃ 1.21-1.35(1H, m), 1.41-1.59(2H, m), 1.67-1.75(1H, m), 1.85-2.09(8H, m), 2.53(3H, s), 3.47-3.75(8H, m), 3.94 and 3.95(total 3H, each s), 4.95-5.05(1H, m), 5.09(2H, d, J=21.2Hz), 6.33(1H, dd, J=7.4 and 13.1Hz), 7.21-7.33(5H, m), 8.11(1H, d, J=15.8Hz), 10.82(1H, brs) | 589 |
| 266 | 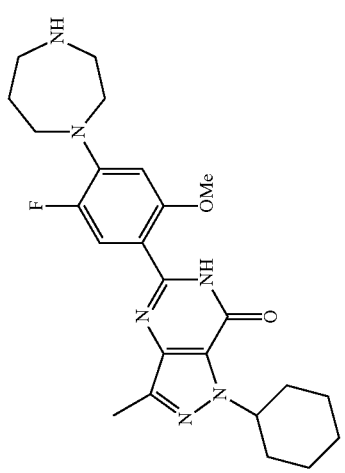 | Colorless crystal 154-157 (Ethyl acetate-Ether) | CDCl₃ 1.21-1.35(1H, m), 1.41-1.56(2H, m), 1.67-1.74(1H, m), 1.85-2.08(8H, m), 2.52(3H, s), 2.90-2.95(2H, m), 3.06-3.11(2H, m), 3.55-3.63(4H, m), 3.98(3H, s), 4.95-5.05(1H, m), 6.33(1H, d, J=7.5Hz), 8.10(1H, d, J=15.9Hz), 10.85(1H, brs) | 455 |

| | | | | |
|---|---|---|---|---|
| 267 | 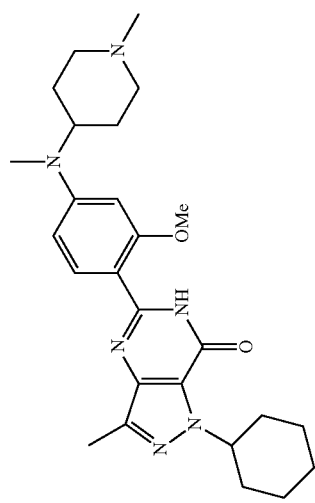 | Colorless solid 151-153.5 | CDCl₃ 1.21-1.38(1H, m), 1.41-1.57(2H, m), 1.67-1.81(3H, m), 1.82-2.09(8H, m), 2.12-2.28(2H, m), 2.39(3H, s), 2.52(3H, s), 2.89(3H, s), 3.00-3.11(2H, m), 3.63-3.75(2H, m), 4.01(3H, s), 4.94-5.04(1H, m), 6.25(1H, d, J=2.2Hz), 6.51(1H, dd, J=2.2 and 9.1Hz), 8.32(1H, d, J=9.1Hz), 10.82(1H, brs) | 465 |
| 268 | 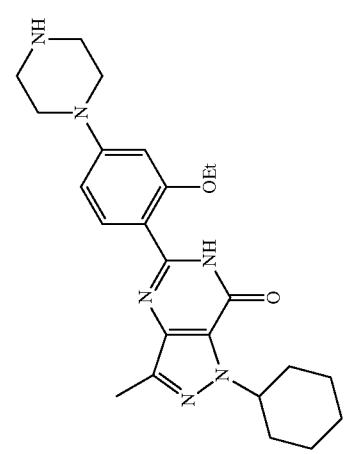 | Colorless solid 202-204 (Ethanol) | CDCl₃ 1.21-1.37(1H, m), 1.40-1.55(2H, m), 1.60(3H, t, J=7.0Hz), 1.65-1.75(1H, m), 1.82-2.10(6H, m), 2.53(3H, s), 3.00-3.09(4H, m), 3.21-3.30(4H, m), 4.25(2H, q, J=7.0Hz), 4.94-5.04(1H, m), 6.43(1H, d, J=2.2Hz), 6.64(1H, dd, J=2.2 and 8.9Hz), 8.37(1H, d, J=8.9Hz), 11.13(1H, brs) | 437 |
| 269 | 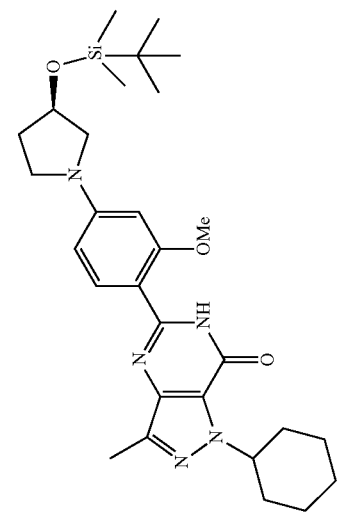 | Colorless foam | CDCl₃ 0.10(3H, s), 0.11(3H, s), 0.90(9H, s), 1.23-1.38(1H, m), 1.41-1.58(2H, m), 1.68-1.77(1H, m), 1.83-2.19(8H, s), 2.54(3H, s), 3.19-3.27(1H, m), 3.39-3.46(1H, m), 3.50-3.60(2H, m), 4.03(3H, s), 4.53-4.60(1H, m), 4.95-5.06(1H, m), 6.05(1H, d, J=1.9Hz), 6.30(1H, dd, J=1.9 and 8.9Hz), 8.34(1H, d, J=8.9Hz), 10.87(1H, brs), | 538 |

| | | | |
|---|---|---|---|
| 270 | 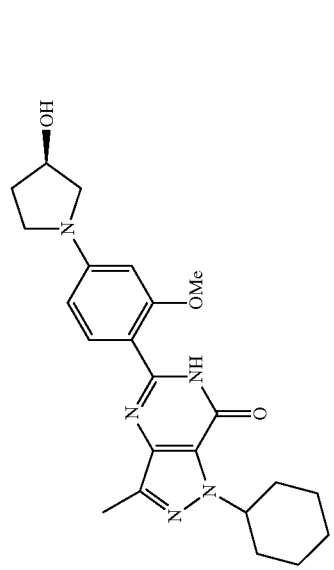 | Colorless solid 203.5-205 (Ethanol) | CDCl₃ 1.20-1.35(1H, m), 1.40-1.54(2H, m), 1.66-1.75(1H, m), 1.83-2.23(9H, m), 2.52(3H, s), 3.30-3.38(1H, m), 3.40-3.49(1H, m), 3.51-3.61(2H, m), 3.98(3H, s), 4.61-4.69(1H, m), 4.93-5.03(1H, m), 6.03(1H, d, J=2.0Hz), 6.29(1H, dd, J=2.0Hz and 9.0Hz), 8.33(1H, d, J=9.0Hz), 10.86(1H, brs) | 424 |
| 271 | 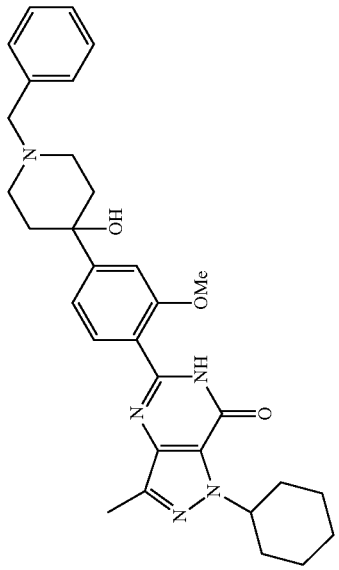 | Colorless solid | CDCl₃ 1.21-1.36(1H, m), 1.42-1.61(2H, m), 1.67-1.75(3H, m), 1.85-2.08(6H, m), 2.12-2.23(2H, m), 2.45-2.50(2H, m), 2.54(3H, s), 2.80-2.87(2H, m), 3.58-3.63(2H, m), 4.04(3H, s), 4.97-5.07(1H, m), 7.20-7.38(7H, m), 8.39(1H, d, J=8.4Hz), 10.79(1H, brs) | 528 |
| 272 | 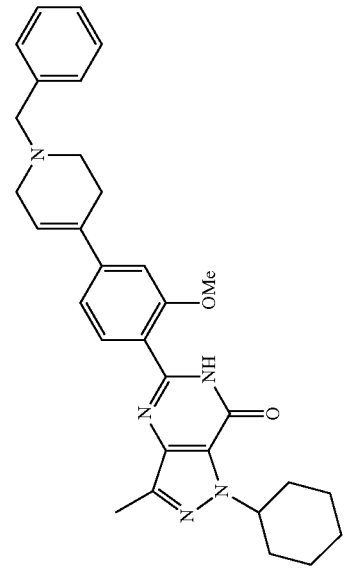 | Pale yellow solid 188-193 (Decomposition) | CDCl₃ 1.21-1.36(1H, m), 1.40-1.57(2H, m), 1.68-1.75(1H, m), 1.85-2.08(6H, m), 2.53(3H, s), 2.56-2.62(2H, m), 2.71-2.77(2H, m), 3.19-3.24(2H, m), 3.63-3.67(2H, m), 4.03(3H, s), 4.95-5.07(1H, m), 6.17-6.21(1H, s), 7.01(1H, s), 7.14-7.18(1H, m), 7.25-7.40(5H, m), 8.38(1H, d, J=8.4Hz), 10.81(1H, brs) | 510 |

| | | -continued | | |
|---|---|---|---|---|
| 273 | 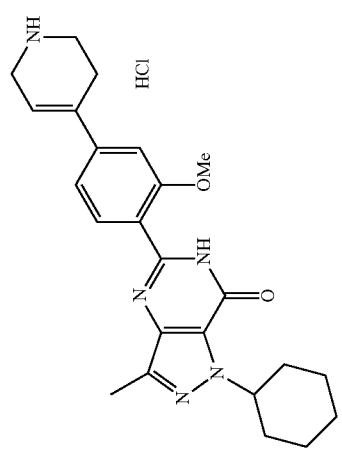 | Colorless solid | DMSO-d₆ 1.14-1.28(1H, m), 1.31-1.45(2H, m), 1.62-1.69(1H, m), 1.78-1.96(6H, m), 2.35(3H, s), 2.68-2.75(2H, m), 3.26-3.36(2H, m), 3.74-3.79(2H, m), 3.88(3H, s), 4.85-4.96(1H, m), 6.32-6.36(1H, m), 7.12-7.16(2H, m), 7.60(1H, d, J=8.5Hz), 9.01(2H, brs), 11.97(1H, brs) | 420 |
| 274 | 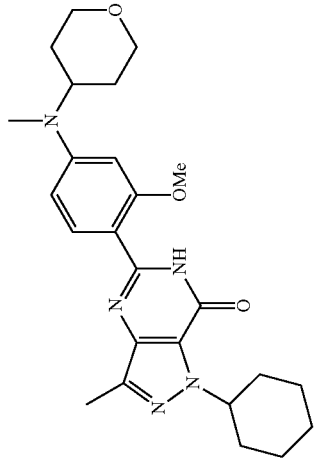 | Colorless solid 179-181 (Ethanol) | CDCl₃ 1.21-1.36(1H, m), 1.41-1.59(2H, m), 1.65-1.76(3H, m), 1.81-2.09(8H, m), 2.52(3H, s), 2.89(3H, s), 3.46-3.57(2H, m), 3.86-3.95(1H, m), 4.02(3H, s), 4.04-4.13(2H, m), 4.92-5.05(1H, m), 6.27(1H, d, J=2.2Hz), 6.55(1H, dd, J=2.2 and 8.9Hz), 8.33(1H, d, J=8.9Hz), 10.82(1H, brs) | 452 |
| 275 | 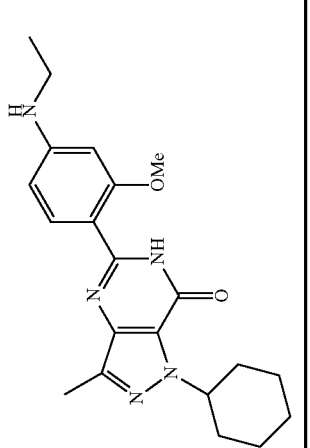 | Colorless solid 208.5-210.5 (Ethanol) | CDCl₃ 1.21-1.37(1H, m), 1.29(3H, t, J=7.1Hz), 1.41-1.54(2H, m), 1.68-1.77(1H, m), 1.82-2.09(6H, m), 2.52(3H, s), 3.19-3.29(2H, m), 3.95-4.06(1H, m), 3.98(3H, s), 4.93-5.02(1H, m), 6.14(1H, d, J=2.0Hz), 6.34(1H, dd, J=2.0 and 8.7Hz), 8.28(1H, d, J=8.7Hz), 10.80(1H, brs) | 382 |

| Production Ex. No. | Chemical Structure | Properties Melting Point(° C.) (Solvent for Recrystallization) | ¹H-NMR | MS(FAB) (M + 1)⁺ |
|---|---|---|---|---|
| 1 | (3-methyl-1-cyclohexyl-pyrazol-5(4H)-one) | Colorless solid 147.6-150.4 | CDCl₃ 1.21-1.36(1H, m), 1.39-1.52(2H, m), 1.71-1.98(7H, m), 2.09(3H, s), 3.20(2H, s), 3.95-4.02(1H, m) | 181 |
| 2 | (4-nitro-5-chloro-3-methyl-1-cyclohexyl-pyrazole) | Colorless solid 104.8-105.2 (Hexane) | CDCl₃ 1.22-1.50(3H, m), 1.70-1.79(1H, m), 1.88-2.01(6H, m), 2.54(3H, s), 4.23-4.33(1H, m) | 244 |
| 3 | (4-nitro-5-cyano-3-methyl-1-cyclohexyl-pyrazole) | Colorless solid 109.0-110.2 (Hexane-Ethyl acetate) | CDCl₃ 1.22-1.37(1H, m), 1.39-1.54(2H, m), 1.72-1.82(1H, m), 1.91-2.10(6H, m), 2.58(3H, s), 4.32-4.43(1H, m) | 235 |
| 4 | (4-amino-5-cyano-3-methyl-1-cyclohexyl-pyrazole) | Light yellow solid 85.5-87.0 (Hexane) | CDCl₃ 1.18-1.31(1H, m), 1.32-1.48(2H, m), 1.66-1.75(1H, m), 1.79-2.03(6H, m), 2.16(3H, s), 3.33(2H, brs), 4.02-4.14(1H, m) | 205 |

-continued
| | | | |
|---|---|---|---|
| 5 | 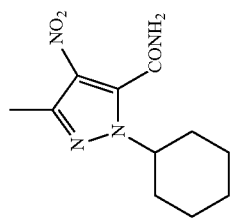 | Colorless solid 148.1-149.0 (Ethyl acetate-Hexane) | CDCl₃ 1.19-1.48(3H, m), 1.64-1.77(1H, m), 1.84-2.07(6H, m), 2.52(3H, s), 4.41-4.54(1H, m), 6.04(1H, brs), 6.77(1H, brs) | 253 |
| 6 | 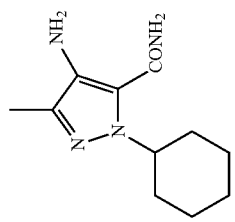 | Colorless solid 193-194 (Ethyl acetate) | CDCl₃ 1.18-1.31(1H, m), 1.38-1.52(2H, m), 1.63-1.74(1H, m), 1.79-2.01(6H, m), 2.21(3H, s), 2.80(2H, s), 5.18-5.29(1H, m) | 223 |
| 7 | 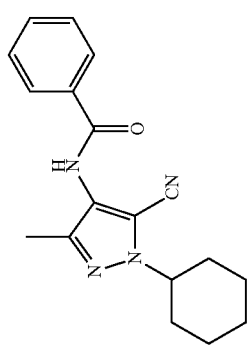 | Colorless solid 187.5-188.5 (Ethanol) | CDCl₃ 1.20-1.32(1H, m), 1.35-1.51(2H, m), 1.70-1.80(1H, m), 1.88-2.12(6H, m), 2.26(3H, s), 4.22-4.33(1H, m), 7.46-7.64(4H, m), 7.88-7.93(2H, m) | 309 |
| 8 | 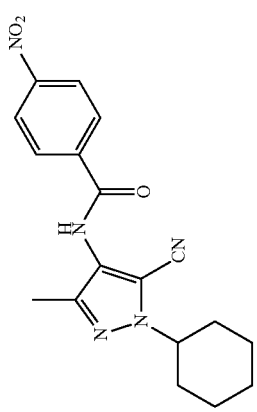 | Colorless solid 214.2-216.1 (Ethanol) | CDCl₃ 1.21-1.33(1H, m), 1.37-1.52(2H, m), 1.70-1.80(1H, m), 1.85-2.11(6H, m), 2.27(3H, s), 4.22-4.34(1H, m), 7.61(1H, brs), 8.02-8.11(2H, m), 8.32-8.40(2H, m) | 354 |

| | | | |
|---|---|---|---|
| 9 | 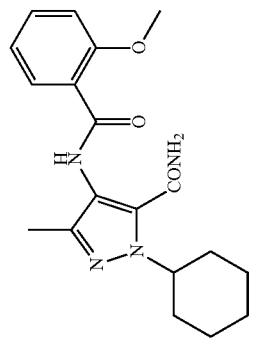 | Colorless solid 239.8-241.0 (Ethyl acetate-Ethanol) | CDCl₃ 1.20-1.33(1H, m), 1.35-1.50(2H, m), 1.62-1.73(1H, m), 1.81-2.09(6H, m), 2.21(3H, s), 4.04(3H, s), 4.71-4.83(1H, m), 5.54(1H, brs), 7.05-7.10(1H, m), 7.11-7.19(1H, m), 7.51-7.59(1H, m), 7.87(1H, brs), 8.21-8.28(1H, m), 9.20(1H, brs) | 357 |
| 10 | 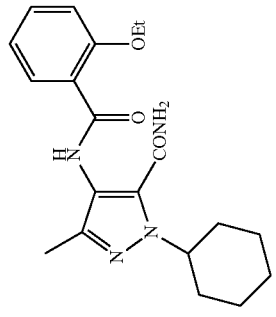 | Colorless solid 163-164 | CDCl₃ 1.20-1.33(1H, m), 1.35-1.50(2H, m), 1.55(3H, t, J=7.0Hz), 1.65-1.75(1H, m), 1.83-1.98(4H, m), 2.01-2.09(2H, m), 2.22(3H, s), 4.30(2H, q, J=7.0Hz), 4.73-4.82(1H, m), 5.57(1H, brs), 7.01-7.07(1H, m), 7.09-7.16(1H, m), 7.48-7.53(1H, m), 7.98(1H, brs), 8.23-8.27(1H, m), 9.45(1H, s) | 371 |
| 11 | 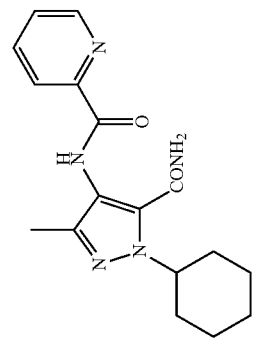 | Colorless solid 209-211 (Ethyl acetate) | CDCl₃ 1.20-1.34(1H, m), 1.37-1.51(2H, m), 1.65-1.74(1H, m), 1.82-2.11(6H, m), 2.22(3H, s), 4.72-4.83(1H, m), 5.57(1H, brs), 7.50-7.56(1H, m), 7.61(1H, brs), 7.89-7.97(1H, m), 8.21-8.28(1H, m), 8.62-8.69(1H, m), 9.46(1H, brs) | 328 |

| | | | |
|---|---|---|---|
| 12 | 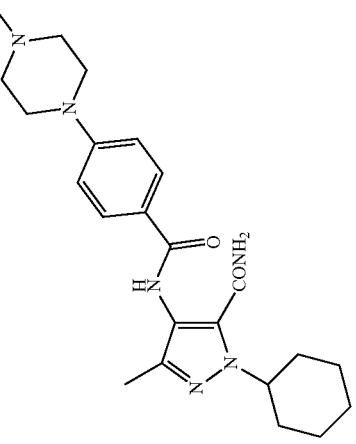 | Colorless solid 262-263.5 (Ethanol-Ethyl acetate) | CDCl₃ 1.18-1.30(1H, m), 1.32-1.49(2H, m), 1.63-1.73(1H, m), 1.80-2.07(6H, m), 2.19(3H, s), 2.36(3H, s), 2.53-2.61(4H, m), 3.31-3.39(4H, m), 4.66-4.78(1H, m), 6.90-6.97(2H, m), 7.36(1H, brs), 7.78-7.84(2H, m) | 425 |
| 13 | 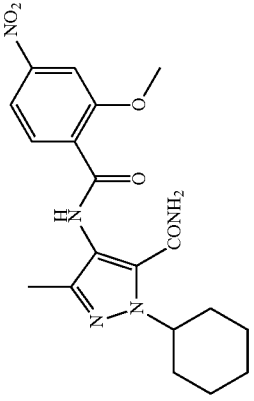 | Colorless solid 248.2-250 (Ethanol-Ethyl acetate) | CDCl₃ 1.20-1.31(1H, m), 1.35-1.50(2H, m), 1.65-1.73(1H, m), 1.82-2.09(6H, m), 2.21(3H, s), 4.17(3H, s), 4.68-4.78(1H, m), 5.57(1H, brs), 7.51(1H, brs), 7.90-8.02(2H, m), 8.41-8.48(1H, m), 9.07(1H, brs) | 402 |
| 14 | 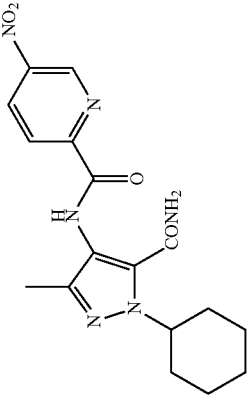 | Colorless solid 260-262 | DMSO-d₆ 1.13-1.25(1H, m), 1.28-1.41(2H, m), 1.61-1.71(1H, m), 1.73—1.95(6H, m), 2.04(3H, s), 4.57-4.68(1H, m), 7.66(1H, m), 7.72(1H, brs), 8.31-8.37(1H, m), 8.79-8.84(1H, m), 9.41-9.45(1H, m), 10.38(1H, brs) | 373 |

| | | -continued | | |
|---|---|---|---|---|
| 15 | 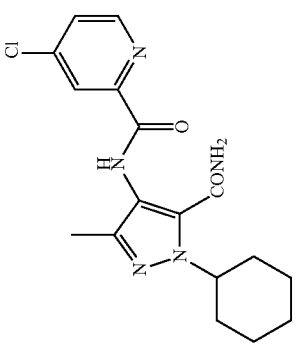 | Colorless solid 182.2-183.1 (Ethyl acetate-Hexane) | CDCl₃ 1.20-1.32(1H, m), 1.35-1.50(2H, m), 1.67-1.73(1H, m), 1.82-2.11(6H, m), 2.21(3H, s), 4.70-4.82(1H, m), 7.52-7.56(1H, m), 8.25-8.27(1H, m), 8.52-8.58(1H, m), 9.35(1H, brs) | 362 |
| 16 | 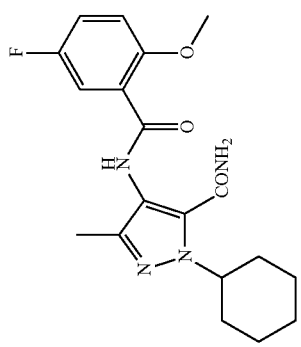 | Colorless solid 251-252 (Hexane-Ethyl acetate) | CDCl₃ 1.20-1.33(1H, m), 1.36-1.50(2H, m), 1.65-1.74(1H, m), 1.82-1.97(4H, m), 1.99-2.09(2H, m), 2.21(3H, s), 4.03(3H, s), 4.69-4.81(1H, m), 5.56(1H, brs), 6.99-7.07(1H, m), 7.21-7.29(1H, m), 7.75(1H, brs), 7.91-7.99(1H, m), 9.25(1H, brs) | 375 |
| 17 | 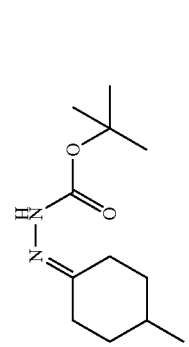 | Colorless solid 110.5-112 | CDCl₃ 0.95(3H, d, J=6.6Hz), 1.07-1.30(2H, m), 1.50(9H, m), 1.59-1.74(1H, m), 1.80-1.93(3H, m), 2.15-2.27(1H, m), 2.52-2.61 (2H, m), 7.48(1H, brs) | 227 |
| 18 | 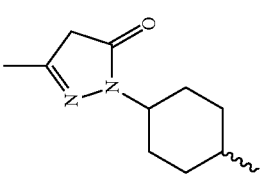 | Colorless solid 137.1-138.0 (Ethyl acetate) | CDCl₃ 0.90(2H, d, J=6.5Hz), 1.02(1H, d, J=7.1Hz), 1.03-1.13(1.3H, m), 1.33-1.46(0.7H, m), 1.50-1.81(6H, m), 1.84-1.99(1H, m), 2.09(3H, m), 3.18(0.7H, s), 3.19(1.3H, s), 3.91-4.03(1H, m) | 195 |

| | | | |
|---|---|---|---|
| 19 | 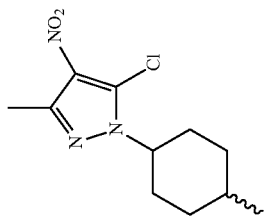 | Colorless solid 62.9-64.2 (Hexane) | CDCl₃ 0.96(2H, d, J=6.5Hz), 1.07(1H, d, J=7.1Hz), 1.04-1.21(1.3H, m), 1.44-1.57(0.7H, m), 1.63-1.77(2.7H, m), 1.83-2.03(4.3H, m), 2.07-2.21(1H, m), 2.54(2H, s), 2.55(1H, s), 4.20-4.35(1H, m) | 258 |
| 20 | 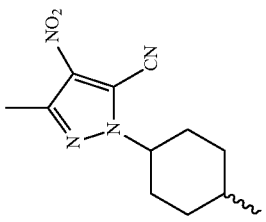 | Colorless solid 99.0-110.0 (Hexane-Ethyl acetate) | CDCl₃ 0.97(2H, d, J=6.5Hz), 1.07(1H, d, J=7.1Hz), 1.11-1.28(1.3H, m), 1.45-1.58(0.7H, m), 1.65-1.74(1.3H, m), 1.79-2.10(5H, m), 2.13-2.28(0.7H, m), 2.58(2H, s), 2.59(1H, s), 4.30-4.48(1H, m) | 249 |
| 21 | 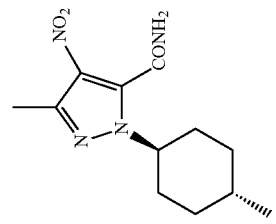 | Colorless solid 182.2-184.5 (Hexane-Ethyl acetate) | CDCl₃ 0.93(3H, d, J=6.5Hz), 1.02-1.18(2H, m), 1.40-1.53(1H, m), 1.78-1.88(2H, m), 1.91-2.07(4H, m), 2.52(3H, s), 4.39-4.51(1H, m), 6.05(1H, brs), 6.77(1H, brs) | 267 |

| | | | | |
|---|---|---|---|---|
| 22 | [structure: 3-methyl-4-nitro-1-(trans-4-methylcyclohexyl)-1H-pyrazole-5-carboxamide] | Colorless solid 161.0-162.2 (Hexane-Ethyl acetate) | CDCl₃ 1.06(3H, d, J=7.1Hz), 1.59-1.68(4H, m), 1.71-1.81(2H, m), 1.89-2.00(1H, m), 2.09-2.13(2H, m), 2.53(3H, s), 4.43-4.55(1H, m), 6.08(1H, brs), 6.76(1H, brs) | 267 |
| 23 | [structure: 4-amino-3-methyl-1-(trans-4-methylcyclohexyl)-1H-pyrazole-5-carboxamide] | Colorless solid 171.4-173.2 (Hexane-Ethyl acetate) | CDCl₃ 0.92(3H, d, J=6.5Hz), 1.10-1.22(2H, m), 1.41-1.51(1H, m), 1.73-1.83(2H, m), 1.85-1.99(4H, m), 2.21(3H, s), 2.80(2H, brs), 5.15-5.27(1H, m) | 237 |
| 24 | [structure: 4-amino-3-methyl-1-(cis-4-methylcyclohexyl)-1H-pyrazole-5-carboxamide] | Colorless solid 130.7-131.9 (Hexane-Ethyl acetate) | CDCl₃ 1.05(3H, d, J=7.2Hz), 1.54-1.81(6H, m), 1.88-1.98(1H, m), 2.00-2.13(2H, m), 2.22(3H, s), 2.82(2H, brs), 5.11-5.23(1H, m) | 237 |

-continued
| | | | | |
|---|---|---|---|---|
| 25 | 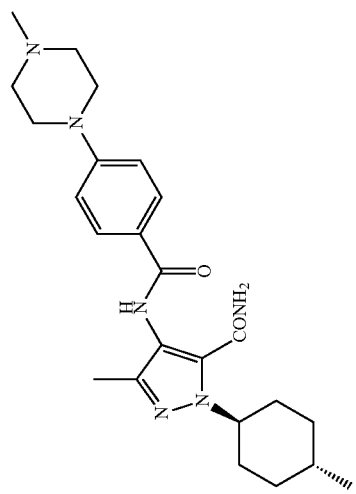 | Colorless solid 228-242 (Ethyl acetate-Ethanol) | CDCl₃ 0.91(3H, d, J=6.5Hz), 1.04-1.20(2H, m), 1.41-1.53(1H, m), 1.74-1.86(2H, m), 1.88-2.05(4H, m), 2.19(3H, s), 2.36(3H, s), 2.52-2.63(4H, m), 3.34-3.43(4H, m), 4.62-4.75(1H, m), 6.89-6.98(2H, m), 7.38(1H, brs), 7.79-7.86(2H, m) | 439 |
| 26 | 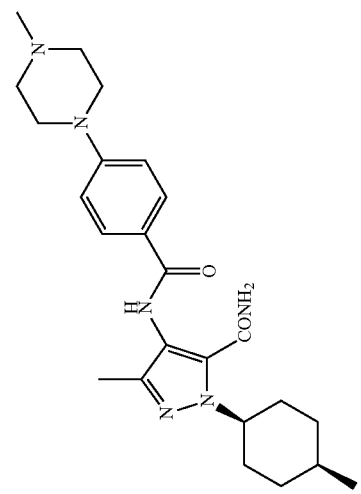 | Colorless solid 279-281 (Ethyl acetate-Ethanol) | CDCl₃ 1.05(3H, d, J=7.1Hz), 1.57-1.85(6H, m), 1.88-1.99(1H, m), 2.07-2.18(2H, m), 2.19(3H, s), 2.36(3H, s), 2.53-2.62(4H, m), 3.32-3.41(4H, m), 4.67-4.76(1H, m), 6.90-6.98(2H, m), 7.39(1H, brs), 7.80-7.86(2H, m) | 439 |
| 27 | 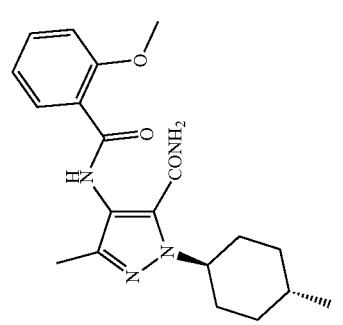 | Colorless solid 250-251.5 (Ethyl acetate-Ethanol) | CDCl₃ 0.92(3H, d, J=6.5Hz), 1.08-1.21(2H, m), 1.41-1.58(1H, m), 1.77-1.88(2H, m), 1.91-2.10(4H, m), 2.21(3H, s), 4.04(3H, s), 4.70-4.81(1H, m), 5.57(1H, brs), 7.05-7.10(1H, m), 7.12-7.19(1H, m), 7.52-7.61(1H, m), 7.88(1H, brs), 8.23-8.29(1H, m), 9.21(1H, brs) | 371 |

| | Structure | Form / mp (solvent) | NMR | MS |
|---|---|---|---|---|
| 28 | (2-methoxybenzamide-pyrazole-CONH2, 3-methyl, N-(4-methylcyclohexyl)) | Colorless solid 243.5-244.8 (Ethyl acetate-Ethanol) | CDCl₃ 1.07(3H, d, J=7.2Hz), 1.58-1.75(4H, m), 1.77-1.86(2H, m), 1.88-1.99(1H, m), 2.09-2.20(2H, m), 2.21(3H, s), 4.04(3H, s), 4.72-4.82(1H, m), 5.56(1H, brs), 7.04-7.09(1H, m), 7.11-7.19(1H, m), 7.52-7.60(1H, m), 7.88(1H, brs), 8.23-8.30(1H, m), 9.21(1H, brs) | 371 |
| 29 | (NC)₂C=C(OH)(cyclohexyl) | Pale yellow solid 124-129 (Diisopropyl ether) | CDCl₃ 1.12-1.41(3H, m), 1.45-1.58(2H, m), 1.68-1.89(5H, m), 2.77-2.86(1H, m) | 177 |
| 30 | (NC)₂C=C(OMe)(cyclohexyl) | Pale yellow solid 58-59 | CDCl₃ 1.12-1.51(5H, m), 1.66-1.85(5H, m), 2.77-2.86(1H, m), 4.34(1H, s) | 191 |
| 31 | 5-amino-4-cyano-1-methyl-3-cyclohexylpyrazole | Colorless solid 139-141 | CDCl₃ 1.20-1.41(3H, m), 1.48-1.62(2H, m), 1.65-1.73(1H, m), 1.77-1.85(2H, m), 1.88-1.97(2H, m), 2.57-2.66(1H, m), 3.58(3H, s), 4.13(2H, br-s) | 205 |

-continued

| | Structure | | Solid/mp | NMR | MS |
|---|---|---|---|---|---|
| 32 | pyrazole with NH2, CONH2, N-Me, cyclohexyl | | Colorless solid 172-173.5 | CDCl₃ 1.20-1.40(3H, m), 1.52-1.66(2H, m), 1.71-1.78(1H, m), 1.83—1.92(2H, m), 1.98-2.06(2H, m), 2.54-2.63(1H, m), 3.56(3H, s), 5.30(2H, br-s), 5.41 (2H, br-s) | 223 |
| 33 | EtO₂C-C₆H₄-N(piperidine)-OH | | Faint brown solid 97-100 | CDCl₃ 1.35(3H, t, J=7.1Hz), 1.58-1.70(2H, m), 1.95-2.05(2H, m), 3.03-3.14(2H, m), 3.66-3.75(2H, m), 3.85-3.95(1H, m), 4.32(2H, q, J=7.1Hz), 6.83-6.91(2H, m), 7.87-7.95(2H, m) | 250 |
| 34 | HO₂C-C₆H₄-N(piperidine)-OH·HCl | | Faint brown solid 238-243 (Decomposition) | DMSO-d₆ 1.35-1.47(2H, m), 1.75-1.83(2H, m), 2.98-3.07(2H, m), 3.64-3.73(3H, m), 6.92-6.98(2H, m), 7.71-7.77(2H, m) | 222(Free) |

-continued

| | | | |
|---|---|---|---|
| 35 | [structure: CO2Me, OH, phenyl-O-CH2CH2-OMe] | Colorless oil | CDCl3 3.45(3H, s), 3.75(2H, t, J=4.6Hz), 3.91(3H, s), 4.14(2H, t, J=4.6Hz), 6.45-6.51(2H, m), 7.71-7.77(1H, m), 10.95(1H, s) | 226 |
| 36 | [structure: CO2Me, OMe, phenyl-O-CH2CH2-OMe] | Colorless oil | CDCl3 3.46(3H, s), 3.76(2H, t, J=4.6Hz), 3.85(3H, s), 3.88(3H, s), 4.17(2H, t, J=4.6Hz), 6.47-6.52(1H, m), 6.55-6.58(1H, m), 7.82-7.86(1H, m) | 241 |
| 37 | [structure: CO2Me, OMe, phenyl-O-CH2CH2-OMe] | Colorless oil 105-107 | CDCl3 3.46(3H, s), 3.77(2H, t, J=4.5Hz), 4.03(3H, s), 4.20(2H, t, J=4.5Hz), 6.60-6.67(2H, m), 8.01-8.07(1H, m) | 227 |

-continued
| | | | | |
|---|---|---|---|---|
| 38 | 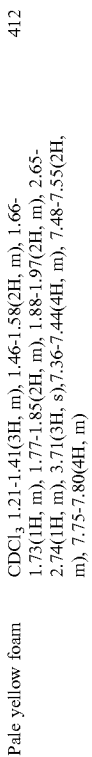 | Pale yellow foam | CDCl₃ 1.21-1.41(3H, m), 1.46-1.58(2H, m), 1.66-1.73(1H, m), 1.77-1.85(2H, m), 1.88-1.97(2H, m), 2.65-2.74(1H, m), 3.71(3H, s),7.36-7.44(4H, m), 7.48-7.55(2H, m), 7.75-7.80(4H, m) | 412 |
| 39 | 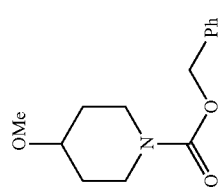 | Colorless oil | CDCl₃ 1.50-1.63(2H, m), 1.79-1.92(2H, m), 3.18-3.26(2H, m), 3.35(3H, s), 3.36-3.42(1H, m), 3.76-3.85(2H, m), 5.12(2H, brs), 7.29-7.38(5H, s) | 250 |
| 40 | 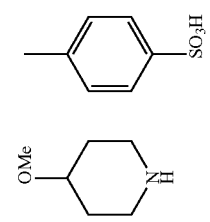 | Colorless oil | DMSO-d₆ 1.58-1.69(2H, m), 1.87-1.96(2H, m), 2.29(3H, s), 2.91-3.00(2H, m), 3.08-3.18(2H, m), 3.25(3H, s), 3.38-3.46(1H, m), 7.11 (2H, d, J=8.0Hz), 7.48(2H, d, J=8.0Hz) 8.15-8.45(2H, m) | 116(free) |
| 41 | 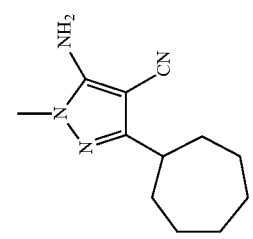 | Colorless oil 135-136 (Toluene-Diisopropyl ether) | CDCl₃ 1.47-1.71(6H, m), 1.72-1.84(4H, m), 1.92-2.00(2H, m), 2.75-2.83(1H, m), 3.57(3H, s), 4.14(2H, brs) | 219 |
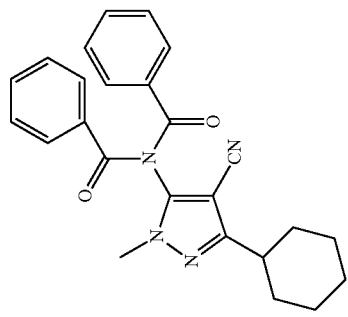

| | Structure | # | Appearance / mp | NMR | MS |
|---|---|---|---|---|---|
| 42 | (pyrazole with NH2, CONH2, N-methyl, cycloheptyl) | | Faint yellow solid 134-135 | CDCl3 1.45-1.71(6H, m), 1.75-1.87(4H, m), 2.00-2.08(2H, m), 2.75-2.83(1H, m), 3.55(3H, s), 5.29(2H, brs), 5.37 (2H, brs) | 237 |
| 43 | (methyl 2,5-difluoro-4-(4-benzylpiperazin-1-yl)benzoate) | | Pale yellow oil | CDCl3 2.57-2.64(4H, m), 3.21-3.28(4H, m), 3.57(2H, s), 3.88(3H, s), 6.56(1H, dd, J=6.5 and 12.7Hz), 7.25-7.37(5H, m), 7.55(1H, dd, J=6.8 and 13.6Hz), | 347 |
| 44 | (methyl 2-methoxy-5-fluoro-4-(4-benzylpiperazin-1-yl)benzoate) | | Pale yellow oil | CDCl3 2.61-2.69(4H, m), 3.21-3.29(4H, m), 3.58(2H, s), 3.84(3H, s), 3.87(3H, s), 6.41(1H, d, J=7.1Hz), 7.28-7.41(5H, m), 7.54(1H, d, J=13.7Hz) | 359 |

| | | | | |
|---|---|---|---|---|
| 45 | 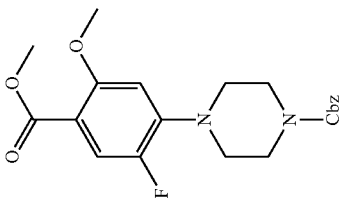 | Colorless crystal 118-120 | CDCl₃ 3.10-3.22(4H, m), 3.62-3.71(4H, m), 3.85(3H, s), 3.87(3H, s), 5.17(2H, s), 6.41(1H, d, J=7.0Hz), 7.28-7.39(5H, m), 7.56(1H, d, J=13.5Hz) | 403 |
| 46 | 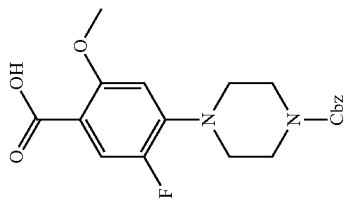 | Colorless crystal 122-126 | CDCl₃ 3.19-3.25(4H, m), 3.67-3.74(4H, m), 4.04(3H, s), 5.17(2H, s), 6.43(1H, d, J=6.7Hz), 7.30-7.41(5H, m), 7.79(1H, d, J=13.3Hz) | 389 |
| 47 | 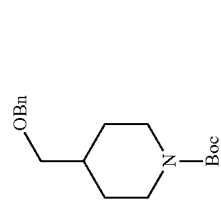 | Colorless oil | CDCl₃ 1.10-1.30(2H, m), 1.46(9H, s), 2.70-2.85(3H, m), 2.65-2.76(2H, m), 3.32(2H, d, J=6.2Hz), 4.03-4.14(2H, m), 4.51(2H, s), 7.29-7.41(5H, m) | 306 |

| | | -continued | |
|---|---|---|---|
| 48 | [structure: 4-(benzyloxymethyl)piperidine HCl] | Colorless crystal 155-158 | DMSO-d₆ 1.31-1.45(2H, m), 1.72-1.90(3H, m), 2.73-2.88(2H, m), 3.16-3.23(2H, m), 3.28(2H, d, J=6.2Hz), 4.45(2H, s), 7.22-7.37(5H, m), 8.78(1H, brs), 9.11(1H, brs) | 206 |
| 49 | [structure: 2-(benzyloxy)-N-ethylethanamine] | Colorless oil | CDCl₃ 1.12(3H, t, J=7.1Hz), 2.66(2H, q, J=7.1Hz), 2.82(2H, t, J=5.2Hz), 3.61(2H, t, J=5.2Hz), 4.54(2H, s), 7.25-7.38(5H, m) | 180 |
| 50 | [structure: 2-(benzyloxy)-N-ethylethanamine HCl] | Colorless solid 99-102 | DMSO-d₆ 1.19(3H, t, J=7.2Hz), 2.95(2H, q, J=7.0Hz), 3.12(2H, t, J=5.2Hz), 3.69(2H, t, J=5.2Hz), 4.54(2H, s), 7.28-7.41(5H, m), 8.74(2H, brs) | 180 |
| 51 | [structure: methyl 2,5-difluoro-4-(4-(N-methyl-Cbz-amino)piperidin-1-yl)benzoate] | Colorless oil | CDCl₃ 1.75-1.82(2H, m), 1.84-1.97(2H, m), 2.82-2.92(2H, m), 2.86(3H, s), 3.66-3.74(2H, m), 3.89(3H, s), 4.19-4.32(1H, m), 5.17(2H, s), 6.59(1H, dd, J=7.1 and 12.6Hz), 7.30-7.41(5H, m), 7.57(1H, dd, J=6.7 and 13.3Hz) | 419 |

-continued
| | | | |
|---|---|---|---|
| 52 | 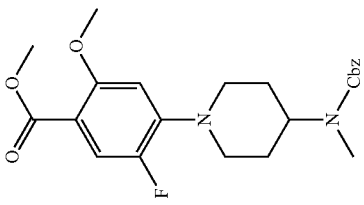 | Colorless crystal 91.5-92.5 | CDCl₃ 1.74-1.82(2H, m), 1.85-1.99(2H, m), 2.80-2.91(2H, m), 2.87(3H, s), 3.64-3.71(2H, m), 3.85(3H, s), 3.89(3H, s), 4.19-4.32(1H, m), 5.17(2H, s), 6.43(1H, d, J=7.1Hz), 7.29-7.42(5H, m), 7.55(1H, d, J=13.6Hz) | 431 |
| 53 | 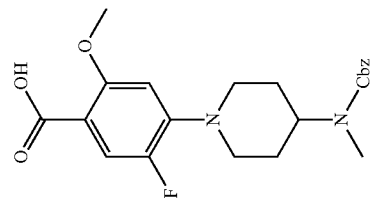 | Colorless foam | CDCl₃ 1.75-1.83(2H, m), 1.85-1.99(2H, m), 2.87(3H, s), 2.85-2.95(2H, m), 3.70-3.77(2H, m), 4.04(3H, s), 4.19-4.32(1H, m), 5.17(2H, s), 6.45(1H, d, J=6.7Hz), 7.30-7.42(5H, m), 7.78(1H, d, J=13.4Hz), 10.52(1H, brs) | 417 |
| 54 | 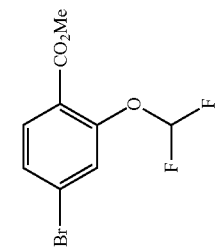 | Colorless solid 64-65 (Hexane) | CDCl₃ 3.92(3H, s), 6.57(1H, t, J=74.1Hz), 7.43-7.52(2H, m), 7.79(1H, d, J=8.3Hz) | 281 |

| # | Structure | Appearance / mp | NMR | MS |
|---|---|---|---|---|
| 55 | 4-bromo-2-(difluoromethoxy)benzoic acid (CO₂H, OCHF₂, Br-phenyl) | Colorless solid 124-129 | CDCl₃ 6.60(1H, t, J=73.6Hz), 7.45-7.67(2H, m), 7.92(1H, d, J=8.3) | 267 |
| 56 | 5-amino-1-ethyl-3-cyclohexyl-1H-pyrazole-4-carbonitrile | Colorless solid 166-167 (Ethyl acetate-Hexane) | CDCl₃ 1.20-1.42(6H, m), 1.49-1.63(2H, m), 1.66-1.73(1H, m), 1.75-1.85(2H, m), 1.88-1.98(2H, m), 2.57-2.68(1H, m), 3.89(2H, q, J=7.3Hz), 4.14(2H, brs) | 219 |
| 57 | 5-amino-1-ethyl-3-cyclohexyl-1H-pyrazole-4-carboxamide | Colorless solid 127.5-128.5 (Ethyl acetate-Hexane) | CDCl₃ 1.22-1.43(6H, m), 1.52-1.68(2H, m), 1.71-1.78(1H, m), 1.81-1.91(2H, m), 1.97-2.07(2H, m), 2.52-2.63(1H, m), 3.89(2H, q, J=7.3Hz), 5.30(2H, brs), 5.38(2H, brs) | 237 |
| 58 | methyl 2-fluoro-4-(thiomorpholin-4-yl)benzoate | Colorless solid 78-80 | CDCl₃ 2.65-2.73(4H, m), 3.72-3.81(4H, m), 3.88(3H, s), 6.46(1H, dd, J=2.5Hz and 14.7Hz), 6.57(1H, dd, J=2.5Hz and 9.0Hz), 7.83(1H, dd, J=8.8Hz and 9.0Hz) | 256 |

-continued
| | | | |
|---|---|---|---|
| 59 | 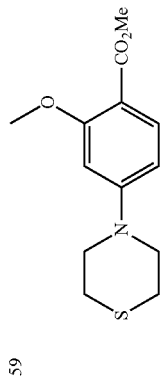 | Colorless oil | CDCl₃ 2.69-2.76(4H, m), 3.69-3.79(4H, m), 3.84(3H, s), 3.89(3H, s), 6.32(1H, d, J=2.1Hz), 6.41(1H, dd, J=2.1Hz and 8.9Hz), 7.80(1H, d, J=8.9Hz) | 268 |
| 60 | 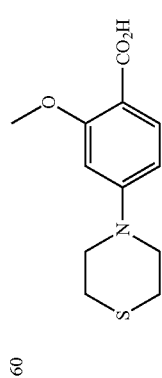 | Colorless solid 154-155 | CDCl₃ 2.69-2.76(4H, m), 3.74-3.82(4H, m), 4.04(3H, s), 6.32(1H, d, J=2.2Hz), 6.53(1H, dd, J=2.2Hz and 9.0Hz), 8.02(1H, d, J=9.0Hz), 10.45(1H, brs) | 254 |
| 61 | 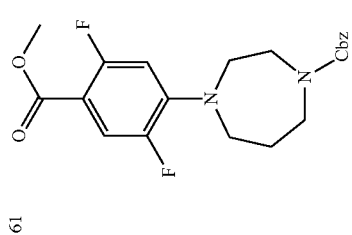 | Colorless oil | CDCl₃ 1.88-2.03(2H, m), 3.42-3.70(8H, m), 3.86(3H, s), 5.10(2H, d, J=17.1Hz), 6.36-6.46(1H, m), 7.23-7.36(5H, m), 7.45-7.56(1H, m) | 405 |

| | | | |
|---|---|---|---|
| 62 | 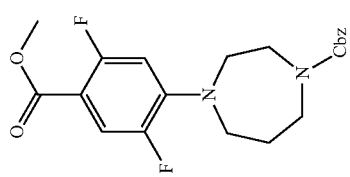 | Colorless oil | CDCl₃ 1.88-2.05(2H, m), 3.42-3.72(8H, m), 3.82(3H, s), 3.84(3H, s), 5.10(2H, s), 6.23-6.31(1H, m), 7.24-7.36(5H, m), 7.53(1H, dd, J=2.3 and 15.2Hz) 417 |
| 63 | 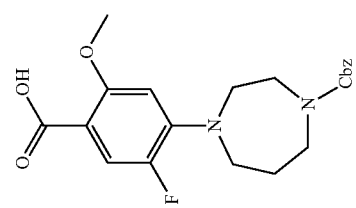 | Colorless viscous solid | CDCl₃ 1.87-1.95(1H, m), 1.98-2.05(1H, m), 3.45-3.75(8H, m), 3.95(3H, s), 3.96(3H, s), 5.08(2H, d, J=19.0Hz), 6.25(1H, dd, J=7.0 and 16.2Hz), 7.21-7.35(5H, m), 7.71(1H, d, J=15.1Hz) 403 |

Example 236

1-Cyclohexyl-5-{4-[(4-hydroxy-1-piperidinyl)methyl]-2-methoxyphenyl}-3-methyl-1,6-dihydro-7H-pyrazolo[4,3-d]pyrimidin-7-one The same reaction procedure as in Example 234 was performed, except that 4-hydroxypiperidine was used in place of N-methylpiperazine. In this manner, 65 mg (88%) of the captioned compound was obtained.

Example 237

1-Cyclohexyl-5-(2-methoxy-4-{[(2-methoxyethyl)amino]methyl}phenyl)-3-methyl-1,6-dihydro-7H-pyrazolo[4,3-d]pyrimidin-7-one The same reaction procedure as in Example 234 was performed, except that methoxyethylamine was used in place of N-methylpiperazine. In this manner, 66 mg (95%) of the captioned compound was obtained.

Example 238

Ethyl 1-[4-(1-cyclohexyl-3-methyl-7-oxo-6,7-dihydro-1H-pyrazolo[4,3-d]pyrimidin-5-yl)-3-methoxybenzyl]-4-piperidinecarboxylate The same reaction procedure as in Example 234 was performed, except that ethyl isonipecotate was used in place of N-methylpiperazine. In this manner, 57 mg (69%) of the captioned compound was obtained.

Example 239

1-[4-(1-Cyclohexyl-3-methyl-7-oxo-6,7-dihydro-1H-pyrazolo[4,3-d]pyrimidin-5-yl)-3-methoxybenzyl]-4-piperidinecarboxylic acid To a 1 ml ethanol solution of 43 mg (0.0848 mmol) of the compound obtained in Example 238, 1 ml of a 1M aqueous solution of sodium hydroxide was added, and the mixture was stirred at room temperature for 2 hours. Then, the reaction mixture was distilled under reduced pressure, and the residue was dissolved in water. Acetic acid was added, and precipitated solids were collected by filtration to obtain 21 mg (52%) of the captioned compound.

Example 240

Benzyl 1-[4-(1-cyclohexyl-3-methyl-7-oxo-6,7-dihydro-1H-pyrazolo[4,3-d]pyrimidin-5-yl)-3-methoxybenzyl]-4-piperidinyl(methyl)carbamate The same reaction procedure as in Example 234 was performed, except that benzyl methyl(4-piperidinyl)carbamate monohydrochloride was used in place of N-methylpiperazine. In this manner, 92.5 mg (64%) of the captioned compound was obtained.

Example 241

1-Cyclohexyl-5-(2-methoxy-4-{[4-(methylamino)-1-piperidinyl]methyl}phenyl)-3-methyl-1,6-dihydro-7H-pyrazolo[4,3-d]pyrimidin-7-one The same reaction procedure as in Example 36 was performed, except that the compound obtained in Example 240 was used in place of the compound obtained in Example 35. In this manner, 52 mg (quant.) of the captioned compound was obtained.

Example 242

1-Cyclohexyl-5-[2-methoxy-4-(tetrahydro-2H-pyran-4-ylamino)phenyl]-3-methyl-1,6-dihydro-7H-pyrazolo[4,3-d]pyrimidin-7-one To a 5 ml 1,2-dichloroethane solution of 250 mg (0.71 mmol) of the compound obtained in Example 9, 25 μl of acetic acid and 66 μl (0.71 mmol) of tetrahydro-4H-pyran-4-one were added, and the mixture was stirred for 30 minutes. Then, 226 mg (1.07 mmol) of sodium triacetoxyborohydride was added, and the mixture was stirred at room temperature for 20 hours. Further, 32 μl (0.35 mmol) of tetrahydro-4H-pyran-4-one and 100 mg (0.45 mmol) of sodium triacetoxyborohydride were added. The mixture was stirred at 60° C. for 6 hours and then stirred at room temperature for 20 hours. Then, a saturated aqueous solution of sodium hydrogen carbonate was added to the reaction mixture, and the mixture was extracted with dichloromethane. The organic layer was washed with water and a saturated aqueous solution of sodium chloride, and dried over anhydrous sodium sulfate, whereafter the solvent was distilled off under reduced pressure. The residue was purified by silica gel column chromatography (ethyl acetate/hexane=2/1) to obtain 151 mg (49%) of the captioned compound.

Example 243

1-Cyclohexyl-5-[4-(1,4-dioxa-8-azaspiro[4,5]deca-8-yl)-2-methoxyphenyl]-3-methyl-1,6-dihydro-7H-pyrazolo[4,3-d]pyrimidin-7-one The same reaction procedure as in Example 16 was performed, except that 1,4-dioxa-8-azaspiro[4,5]decane was used in place of N-methylpiperazine. In this manner, 459 mg (80%) of the captioned compound was obtained.

Example 244

1-Cyclohexyl-5-[2-methoxy-4-(4-oxo-1-piperidinyl)phenyl]-3-methyl-1,6-dihydro-7H-pyrazolo[4,3-d]pyrimidin-7-one The same reaction procedure as in Example 30 was performed, except that the compound obtained in Example 243 was used in place of the compound obtained in Example 29. In this manner, 399 mg (quant.) of the captioned compound was obtained.

Example 245

1-Cyclohexyl-5-{4-[4-(dimethylamino)-1-piperidinyl]-2-methoxyphenyl}-3-methyl-1,6-dihydro-7H-pyrazolo[4,3-d]pyrimidin-7-one The same reaction procedure as in Example 234 was performed, except that the compound obtained in Example 244 was used in place of the compound obtained in Example 233, and dimethylamine monohydrochloride was used in place of N-methylpiperazine. In this manner, 32.9 mg (42%) of the captioned compound was obtained.

Example 246

5-{4-[4-(Benzylamino)-1-piperidinyl]-2-methoxyphenyl}-1-cyclohexyl-3-methyl-1,6-dihydro-7H-pyrazolo[4,3-d]pyrimidin-7-one The same reaction procedure as in Example 234 was performed, except that the compound obtained in Example 244 was used in place of the compound obtained in Example 233, and benzylamine was used in place of N-methylpiperazine. In this manner, 115 mg (91%) of the captioned compound was obtained.

Example 247

5-[4-(4-Amino-1-piperidinyl)-2-methoxyphenyl]-1-cyclohexyl-3-methyl-1,6-dihydro-7H-pyrazolo[4,3-d]pyrimidin-7-one The same reaction procedure as in Example 36 was performed, except that the compound obtained in Example 246 was used in place of the compound obtained in Example 35. In this manner, 70 mg (84%) of the captioned compound was obtained.

Example 248

1-Cyclohexyl-5-[4-(1,4-dioxa-8-azaspiro[4,5]deca-8-yl)-2-ethoxyphenyl]-3-methyl-1,6-dihydro-7H-pyrazolo[4,3-d]pyrimidin-7-one The same reaction procedure as in Example 16 was performed, except that the compound obtained in Example 116 was used in place of the compound obtained in Example 15, and 1,4-dioxa-8-azaspiro[4,5]decane was used in place of N-methylpiperazine. In this manner, 416 mg (70%) of the captioned compound was obtained.

Example 249

1-Cyclohexyl-5-[2-ethoxy-4-(4-oxo-1-piperidinyl)phenyl]-3-methyl-1,6-dihydro-7H-pyrazolo[4,3-d]pyrimidin-7-one The same reaction procedure as in Example 30 was performed, except that the compound obtained in Example 248 was used in place of the compound obtained in Example 29. In this manner, 160 mg (40%) of the captioned compound was obtained.

Example 250

1-Cyclohexyl-5-{4-[4-(dimethylamino)-1-piperidinyl]-2-ethoxyphenyl}-3-methyl-1,6-dihydro-7H-pyrazolo[4,3-d]pyrimidin-7-one The same reaction procedure as in Example 234 was performed, except that the compound obtained in Example 249 was used in place of the compound obtained in Example 233, and dimethylamine monohydrochloride was used in place of N-methylpiperazine. In this manner, 46 mg (78%) of the captioned compound was obtained.

Example 251

5-{4-[4-(Benzylamino)-1-piperidinyl]-2-ethoxyphenyl}-1-cyclohexyl-3-methyl-1,6-dihydro-7H-pyrazolo[4,3-d]pyrimidin-7-one The same reaction procedure as in Example 234 was performed, except that the compound obtained in Example 249 was used in place of the compound obtained in Example 233, and benzylamine was used in place of N-methylpiperazine. In this manner, 86 mg (quant.) of the captioned compound was obtained.

Example 252

Benzyl 1-[4-(1-cyclohexyl-3-methyl-7-oxo-6,7-dihydro-1H-pyrazolo[4,3-d]pyrimidin-5-yl)-3-ethoxyphenyl]-4-piperidinyl(ethyl)carbamate The same reaction procedure as in Example 16 was performed, except that the compound obtained in Example 116 was used in place of the compound obtained in Example 15, and benzyl ethyl(4-piperidinyl)carbamate monohydrochloride was used in place of N-methylpiperazine. In this manner, 134 mg (47%) of the captioned compound was obtained.

Example 253

1-Cyclohexyl-5-{2-ethoxy-4-[4-(ethylamino)-1-piperidinyl]phenyl}-3-methyl-1,6-dihydro-7H-pyrazolo[4,3-d]pyrimidin-7-one The same reaction procedure as in Example 36 was performed, except that the compound obtained in Example 252 was used in place of the compound obtained in Example 35. In this manner, 61 mg (69%) of the captioned compound was obtained.

Example 254

5-(4-amino-2-ethoxyphenyl)-1-cyclohexyl-3-methyl-1,6-dihydro-7H-pyrazolo[4,3-d]pyrimidin-7-one The same reaction procedure as in Example 205 was performed, except that 2-ethoxy-4-nitrobenzoic acid was used in place of 2-methoxy-4-nitrobenzoic acid, and the compound obtained in Production Example 6 was used in place of the compound obtained in Production Example 57. In this manner, 1.19 g (65%) of the captioned compound was obtained.

Example 255

4-(1-Cyclohexyl-3-methyl-7-oxo-6,7-dihydro-1H-pyrazolo[4,3-d]pyrimidin-5-yl)-3-ethoxybenzenesulfonyl chloride The same reaction procedure as in Example 48 was performed, except that the compound obtained in Example 254 was used in place of the compound obtained in Example 44. In this manner, 1.05 g (91%) of the captioned compound was obtained.

Example 256

1-Cyclohexyl-5-{2-ethoxy-4-[(4-methyl-1,4-diazepan-1-yl)sulfonyl]phenyl}-3-methyl-1,6-dihydro-7H-pyrazolo[4,3-d]pyrimidin-7-one The same reaction procedure as in Example 49 was performed, except that the compound obtained in Example 255 was used in place of the compound obtained in Example 48, and N-methyl-1,4-diazacycloheptane was used in place of N-methylpiperazine. In this manner, 145 mg (83%) of the captioned compound was obtained.

Example 257

1-Cyclohexyl-5-{2-ethoxy-4-[(4-hydroxy-1-piperidinyl)sulfonyl]phenyl}-3-methyl-1,6-dihydro-7H-pyrazolo[4,3-d]pyrimidin-7-one The same reaction procedure as in Example 49 was performed, except that the compound obtained in Example 255 was used in place of the compound obtained in Example 48, and N-hydroxypiperidine was used in place of N-methylpiperazine. In this manner, 147 mg (86%) of the captioned compound was obtained.

Example 258

1-Cyclohexyl-5-[4-(4-hydroxy-1-piperidinyl)-2-methoxyphenyl]-3-methyl-1,6-dihydro-7H-pyrazolo[4,3-d]pyrimidin-7-one The same reaction procedure as in Example 31 was performed, except that the compound obtained in Example 244 was used in place of the compound obtained in Example 30. In this manner, 115 mg (quant.) of the captioned compound was obtained.

Example 259

(2E)-3-[4-(1-cyclohexyl-3-methyl-7-oxo-6,7-dihydro-1H-pyrazolo[4,3-d]pyrimidin-5-yl)-3-methoxyphenyl]-2-propenenitrile The same reaction procedure as in Example 226 was performed, except that acrylonitrile was used in place of methyl acrylate. In this manner, 89 mg (48%) of the captioned compound was obtained.

Example 260

5-[4-(4-Amino-1-piperidinyl)-2-ethoxyphenyl]-1-cyclohexyl-3-methyl-1,6-dihydro-7H-pyrazolo[4,3-d]pyrimidin-7-one The same reaction procedure as in Example 36 was performed, except that the compound obtained in Example 251 was used in place of the compound obtained in Example 35. In this manner, 29 mg (50%) of the captioned compound was obtained.

Example 261

1-Cyclohexyl-5-[2-ethoxy-4-(4-hydroxy-1-piperidinyl)phenyl]-3-methyl-1,6-dihydro-7H-pyrazolo[4,3-d]pyrimidin-7-one The same reaction procedure as in Example 31 was performed, except that the compound obtained in Example 249 was used in place of the compound obtained in Example 30. In this manner, 117 mg (89%) of the captioned compound was obtained.

Example 262

1-Cyclohexyl-5-[4-(1,4-diazepan-1-yl)-2-ethoxyphenyl]-3-methyl-1,6-dihydro-7H-pyrazolo[4,3-d]pyrimidin-7-one The same reaction procedure as in Example 16 was performed, except that the compound obtained in Example 116 was used in place of the compound obtained in Example 15, and homopiperazine was used in place of N-methylpiperazine. In this manner, 97 mg (62%) of the captioned compound was obtained.

Example 263

1-Cyclohexyl-5-{2-ethoxy-4-[(2-methoxyethyl)amino]phenyl}-3-methyl-1,6-dihydro-7H-pyrazolo[4,3-d]pyrimidin-7-one The same reaction procedure as in Example 16 was performed, except that the compound obtained in Example 116 was used in place of the compound obtained in Example 15, and methoxyethylamine was used in place of N-methylpiperazine. In this manner, 55 mg (37%) of the captioned compound was obtained.

Example 264

1-Cyclohexyl-5-[2-ethoxy-4-(4-methyl-1-piperazinyl)phenyl]-3-methyl-1,6-dihydro-7H-pyrazolo[4,3-d]pyrimidin-7-one The same reaction procedure as in Example 16 was performed, except that the compound obtained in Example 116 was used in place of the compound obtained in Example 15. In this manner, 115 mg (73%) of the captioned compound was obtained.

Example 265

Benzyl 4-[4-(1-cyclohexyl-3-methyl-7-oxo-6,7-dihydro-1H-pyrazolo[4,3-d]pyrimidin-5-yl)-2-fluoro-5-methoxyphenyl]-1,4-diazepane-1-carboxylate The same reaction procedure as in Example 14 was performed, except that the compound obtained in Production Example 63 was used in place of the compound obtained in Production Example 34. In this manner, 152 mg (38%) of the captioned compound was obtained.

Example 266

1-Cyclohexyl-5-[4-(1,4-diazepan-1-yl)-5-fluoro-2-methoxyphenyl]-3-methyl-1,6-dihydro-7H-pyrazolo[4,3-d]pyrimidin-7-one The same reaction procedure as in Example 36 was performed, except that the compound obtained in Example 265 was used in place of the compound obtained in Example 35. In this manner, 181 mg (76%) of the captioned compound was obtained.

Example 267

1-Cyclohexyl-5-{2-methoxy-4-[methyl(1-methyl-4-piperidinyl)amino]phenyl}-3-methyl-1,6-dihydro-7H-pyrazolo[4,3-d]pyrimidin-7-one The same reaction procedure as in Example 16 was performed, except that 1-methyl-4-(methylamino)piperidine was used in place of N-methylpiperazine. In this manner, 181 mg (quant.) of the captioned compound was obtained.

Example 268

1-Cyclohexyl-5-[2-ethoxy-4-(1-piperazinyl)phenyl]-3-methyl-1,6-dihydro-7H-pyrazolo[4,3-d]pyrimidin-7-one The same reaction procedure as in Example 16 was performed, except that the compound obtained in Example 116 was used in place of the compound obtained in Example

Example 269

5-[4-((3R)-3-{[tert-butyl(dimethyl)silyl]oxy}pyrrolidinyl)-2-methoxyphenyl]-1-cyclohexyl-3-methyl-1,6-dihydro-7H-pyrazolo[4,3-d]pyrimidin-7-one The same reaction procedure as in Example 16 was performed, except that (3R)-3-{[tert-butyl(dimethyl)silyl]oxy}pyrrolidine was used in place of N-methylpiperazine. In this manner, 263 mg (82%) of the captioned compound was obtained.

Example 270

1-Cyclohexyl-5-{4-[(3R)-3-hydroxypyrrolidinyl]-2-methoxyphenyl}-3-methyl-1,6-dihydro-7H-pyrazolo[4,3-d]pyrimidin-7-one To a 3 ml tetrahydrofuran solution of 243 mg (0.452 mmol) of the compound obtained in Example 269, 0.54 ml of tetrabutylammonium fluoride (1.0M tetrahydrofuran solution 0.54 mmoml) was added, and the mixture was stirred at room temperature for 2 hours. Then, water was added to the reaction mixture, and the mixture was extracted with dichloromethane. The organic layer was washed with water and a saturated aqueous solution of sodium chloride, and dried over anhydrous sodium sulfate, whereafter the solvent was distilled off under reduced pressure. The residue was purified by silica gel column chromatography (dichloromethane/methanol=30/1~20/1) to obtain 191 mg (quant.) of the captioned compound.

Example 271

5-[4-(1-Benzyl-4-hydroxy-4-piperidinyl)-2-methoxyphenyl]-1-cyclohexyl-3-methyl-1,6-dihydro-7H-pyrazolo[4,3-d]pyrimidin-7-one The same reaction procedure as in Example 122 was performed, except that 1-benzyl-4-piperidone was used in place of 1-methyl-4-piperidone. In this manner, 162 mg (43%) of the captioned compound was obtained.

Example 272

5-[4-(1-Benzyl-1,2,3,6-tetrahydro-4-pyridinyl)-2-methoxyphenyl]-1-cyclohexyl-3-methyl-1,6-dihydro-7H-pyrazolo[4,3-d]pyrimidin-7-one The same reaction procedure as in Example 123 was performed, except that the compound obtained in Example 271 was used in place of the compound obtained in Example 122. In this manner, 92 mg (68%) of the captioned compound was obtained.

Example 273

1-Cyclohexyl-5-[2-methoxy-4-(1,2,3,6-tetrahydro-4-pyridinyl)phenyl]-3-methyl-1,6-dihydro-7H-pyrazolo[4,3-d]pyrimidin-7-one monohydrochloride To a 10 ml 1,2-dichloroethane solution of 80 mg (0.16 mmol) of the compound obtained in Example 272, 25.4 μl (0.24 mmol) of 1-chloroethyl chloroformate was added, and the mixture was heated under reflux for 40 minutes. Then, the reaction mixture was returned to room temperature, and concentrated under reduced pressure. Methanol (10 ml) was added to the residue, and the mixture was heated under reflux for 20 minutes. The reaction mixture was returned to room temperature, and concentrated under reduced pressure. Precipitated solids were washed with methanol/ether=1/4 to obtain 43 mg (60%) of the captioned compound.

Example 274

1-Cyclohexyl-5-{2-methoxy-4-(methyl(tetrahydro-2H-pyran-4-yl)amino)phenyl}-3-methyl-1,6-dihydro-7H-pyrazolo[4,3-d]pyrimidin-7-one The same reaction procedure as in Example 16 was performed, except that N-methyltetrahydro-2H-pyran-4-amine hydrochloride was used in place of N-methylpiperazine. In this manner, 124 mg (76%) of the captioned compound was obtained.

Example 275

1-Cyclohexyl-5-[4-(ethylamino)-2-methoxyphenyl]-3-methyl-1,6-dihydro-7H-pyrazolo[4,3-d]pyrimidin-7-one In the reactions of Example 242, 58 mg (21%) of the captioned compound was obtained as a by-product.

INDUSTRIAL APPLICABILITY

The pyrazolopyrimidinone derivatives of the present invention have the action of selectively inhibiting PDE7, thereby increasing the intracellular cAMP level and inhibiting the activation of T cells. Thus, they are useful for prevention and treatment of various allergic diseases and inflammatory or immunological diseases. Since they selectively inhibit PDE7, moreover, they exert minimal influence on other PDE's. Thus, they are expected to decrease side effects when used as pharmaceuticals.

We claim:

1. A compound of the formula (IA) or (IB), or a salt thereof:

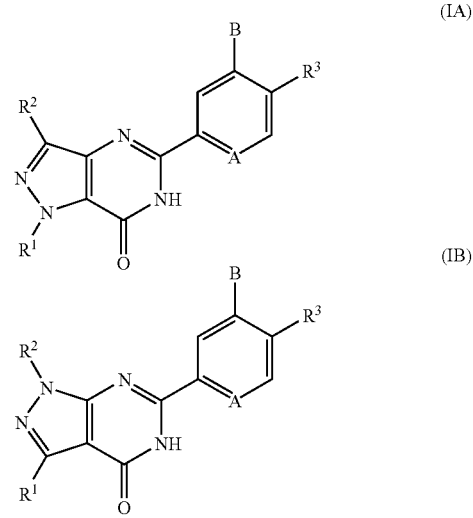

where A represents N or $CR^4$,

B represents a hydrogen atom or a halogen atom, $R^1$ represents optionally substituted $C_{3-7}$ cycloalkyl or tert-butyl, $R^2$ represents hydrogen, methyl or ethyl, $R^3$ represents a hydrogen, nitro, cyano or halogen atom, $NR^5R^6$, $C(=X)R^7$, $SO_2NR^5R^6$, $OR^8$, $NR^8CONR^5R^6$, $NR^8SO_2R^9$, a heteroaryl group, or optionally substituted $C_{1\sim3}$ alkyl, $R^4$ represents hydrogen, or $C_{1\sim3}$ alkoxy substituted, if desired, by one or more fluorine atoms, $R^5$ and $R^6$ are the same or different, and represent a hydrogen atom, optionally substituted $C_{1\sim6}$ alkyl, or optionally substituted acyl or, together with the nitrogen atom which they are bound to, form azetidinyl, pyrrolidinyl, piperidinyl, morpholino, thiomorpholino, piperazinyl or homopiperazinyl, each of these groups being optionally substituted by optionally substituted $C_{1\sim4}$ alkyl, OH, $C_{1\sim3}$ alkoxy, $CO_2H$, or $NR^{10}R^{11}$, wherein $R^{10}$ and $R^{11}$ are the same or different, and represent a hydrogen atom, optionally substituted $C_{1\sim6}$ alkyl, or optionally substituted acyl or, together with the nitrogen atom which they are bound to, form azetidinyl, pyrrolidinyl, piperidinyl, morpholino, thiomorpholino, piperazinyl or homopiperazinyl, each of these groups being optionally substituted by optionally substituted $C_{1\sim4}$ alkyl, OH, $C_{1\sim3}$ alkoxy, $CO_2H$, $R^7$ represents optionally substituted $C_{1\sim6}$ alkyl, OH, $OR^8$, or $NR^5R^6$, $R^8$ represents hydrogen or an optionally substituted $C_{1\sim6}$ alkyl group, $R^9$ represents an optionally substituted $C_{1\sim6}$ alkyl group, and X represents O, S or NH.

2. A compound according to claim 1, which is formula (IA).

3. A compound according to claim 1, which is formula (IB).

4. A compound according to claim 1, wherein $R^1$ is $C_{5\sim7}$ cycloalkyl.

5. A compound according to claim 4, wherein the $C_{5\sim7}$ cycloalkyl is cyclopentyl, cyclohexyl or cycloheptyl.

6. A compound according to claim 1, wherein A is $CR^4$.

7. A compound according to claim 6, wherein $R^4$ is methoxy or ethoxy.

8. A compound according to claim 1, wherein B is hydrogen or fluorine.

9. A compound according to claim 1, wherein $R^2$ is methyl.

10. A compound according to claim 1, wherein $R^3$ is a substituent other than hydrogen.

11. A compound according to claim 10, wherein
$R^3$ is a $NR^5R^6$, $C(=X)R^7$, $SO_2NR^5R^6$, $OR^8$, $NR^8CONR^5R^6$, $NR^8SO_2R^9$, or a heteroaryl group, $R^5$ and $R^6$ are groups which, together with the nitrogen atom which they are bound to, form azetidinyl, pyrrolidinyl, piperidinyl, morpholino, thiomorpholino, piperazinyl or homopiperazinyl, these groups further being optionally substituted by optionally substituted $C_{1\sim4}$ alkyl, OH, $C_{1\sim3}$ alkoxy, $CO_2H$, or $NR^{10}R^{11}$, $R^{10}$ and $R^{11}$ are groups which, together with the nitrogen atom which they are bound to, form azetidinyl, pyrrolidinyl, piperidinyl, morpholino, thiomorpholino, piperazinyl or homopiperazinyl, these groups further being optionally substituted by optionally substituted $C_{1\sim4}$ alkyl, OH, $C_{1\sim3}$ alkoxy, $CO_2H$, $R^7$ is an optionally substituted linear or branched $C_{1\sim6}$ alkyl, OH, $OR^8$, or $NR^5R^6$, where $R^5$ and $R^6$ are as defined earlier, $R^8$ is hydrogen or an optionally substituted linear or branched $C_{1\sim6}$ alkyl group $R^9$ is an optionally substituted $C_{1\sim3}$ alkyl group, X is O or S, and the heteroaryl group is an optionally substituted pyrrole, furyl, thienyl, imidazolyl, thiazolyl, pyridyl, pyrazyl, indolyl, quinolyl, isoquinolyl, or tetrazolyl.

12. A compound of the formula (IA') or (IB'), or a salt thereof:

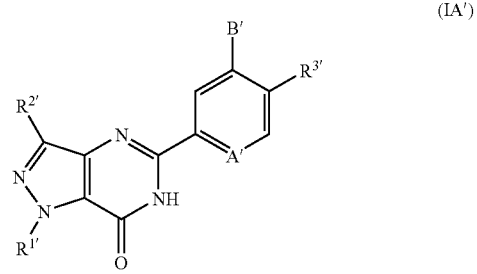

(IA')

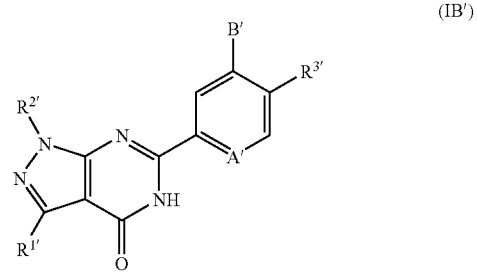

(IB')

where A' represents N or $CR^{4'}$,

B' represents a hydrogen atom or a halogen atom, $R^{1'}$ represents optionally substituted $C_{3\sim7}$ cycloalkyl or tert-butyl, $R^{2'}$ represents hydrogen, methyl or ethyl, $R^{3'}$ represents $NR^{5'}R^{6'}$, $C(=O)R^{7'}$, $SO_2NR^{5'}R^{6'}$, $OR^{8'}$, $NR^{8'}CONR^{5'}R^{6'}$, $NR^{8'}CO_2R^{9'}$, $NR^{8'}SO_2R^{9'}$, optionally substituted $C_{1\sim6}$ alkyl, optionally substituted $C_{1\sim6}$ alkenyl, or optionally substituted saturated or unsaturated heterocycloalkyl, $R^{4'}$ represents hydrogen or $C_{1\sim3}$ alkoxy which may be substituted by one or more fluorine atoms, $R^{5'}$ and $R^{6'}$ are the same or different, and represent a hydrogen atom, optionally substituted $C_{1\sim6}$ alkyl, or optionally substituted heterocycloalkyl or, together with the nitrogen atom which they are bonded to, form azetidinyl, pyrrolidinyl, piperidinyl, thiomorpholino, piperazinyl or homopiperazinyl, each of these groups being further substituted by $NR^{9'}C(=O)R^{7'}$, an oxo group, or $C(=O)R^{7'}$, $R^{7'}$ represents hydrogen, optionally substituted $C_{1\sim6}$ alkyl, OH, $OR^{8'}$, $R^{8'}$ represents hydrogen, an optionally substituted $C_{1\sim6}$ alkyl group, or optionally substituted heterocycloalkyl, and $R^{9'}$ represents an optionally substituted $C_{1\sim6}$ alkyl group.

13. A compound according to claim 12, which is formula (IA').

14. A compound according to claim 12, which is formula (IB').

15. A compound according to claim 12, wherein $R^{1'}$ is cyclopentyl, cyclohexyl or cycloheptyl.

16. A compound according to claim 12, wherein A' is $CR^{4'}$ and $R^{4'}$ is methoxy or ethoxy.

17. A compound according to claim 12, wherein $R^{2'}$ is methyl.

18. A pharmaceutical composition comprising a compound according to claim 1 or 12 as an active ingredient.

19. A compound according to claim 15, wherein A' is CR4' and $R^{4'}$ is methoxy or ethoxy.

20. A compound according to claim 15, wherein $R^{2'}$ is methyl.

21. A compound according to claim 16, wherein $R^{2'}$ is methyl.

22. A method of inhibiting PDE7 comprising administering at least one compound according to claim 1 or 12 to a patient.

23. A method according to claim 22, comprising administering said at least one compound to said patient orally.

24. A method according to claim 23, comprising administering said at least one compound in a capsule, tablet, granule, fine granule, syrup, or dry syrup.

25. A method according to claim 23, comprising administering said at least one compound in a daily dose, for adults, of 0.1 to 1,000 mg.

26. A method according to claim 25, wherein said daily dose is between 0.1 and 500 mg.

27. A method according to claim 26, wherein said daily dose is between 1 and 100 mg.

28. A method according to claim 22, comprising administering said at least one compound to a patient parenterally.

29. A method according to claim 28, comprising administering said at least one compound to said patient by injection, suppository, transnasally, percutaneously, or transdermally.

* * * * *